(12) United States Patent
Smet et al.

(10) Patent No.: US 12,396,897 B2
(45) Date of Patent: Aug. 26, 2025

(54) ABSORBENT ARTICLE WITH CHANNELS AND METHOD FOR MANUFACTURING THEREOF

(71) Applicant: Drylock Technologies NV, Zele (BE)

(72) Inventors: Steven Smet, Zele (BE); Werner Van Ingelgem, Zele (BE); Tom Derycke, Zele (BE)

(73) Assignee: Drylock Technologies NV, Zele (BE)

( * ) Notice: Subject to any disclaimer, the term of this patent is extended or adjusted under 35 U.S.C. 154(b) by 562 days.

(21) Appl. No.: 16/645,977

(22) PCT Filed: Sep. 4, 2018

(86) PCT No.: PCT/EP2018/073665
§ 371 (c)(1),
(2) Date: Mar. 10, 2020

(87) PCT Pub. No.: WO2019/048397
PCT Pub. Date: Mar. 14, 2019

(65) Prior Publication Data
US 2020/0276059 A1 Sep. 3, 2020

(30) Foreign Application Priority Data

Sep. 11, 2017 (EP) .................................. 17190395
Oct. 11, 2017 (EP) .................................. 17195872

(51) Int. Cl.
*A61F 13/15* (2006.01)
*A61F 13/532* (2006.01)
*A61F 13/539* (2006.01)

(52) U.S. Cl.
CPC .. *A61F 13/15634* (2013.01); *A61F 13/15699* (2013.01); *A61F 13/5323* (2013.01);
(Continued)

(58) Field of Classification Search
CPC .......... A61F 13/15634; A61F 13/15699; A61F 13/5323; A61F 13/539; A61F 2013/15878; A61F 2013/1591; A61F 13/00987
See application file for complete search history.

(56) References Cited

U.S. PATENT DOCUMENTS 3,444,732 A * 5/1969 McKinley ............... B29C 65/18
156/64
3,826,701 A * 7/1974 Miller .................. B29C 66/1122
156/308.2
(Continued)

FOREIGN PATENT DOCUMENTS

EP        2905000 A1   8/2015
WO   WO-2012170798 A1  12/2012

OTHER PUBLICATIONS

"International Application Serial No. PCT/EP2018/073665, International Search Report dated Oct. 24, 2018", (Oct. 24, 2018), 3 pgs.
(Continued)

*Primary Examiner* — George R Koch
*Assistant Examiner* — Christopher C Caillouet
(74) *Attorney, Agent, or Firm* — Schwegman Lundberg & Woessner, P.A.

(57) ABSTRACT

An absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet, wherein the absorbent core is provided with at least one attachment zone between the top core wrap sheet and the back core wrap sheet, wherein a first binder is arranged in a first area between the top core wrap sheet and the back core wrap sheet at a distance from the at least one attachment zone, on one of the top core wrap sheet and the back core
(Continued)

wrap sheet and a second binder is arranged in a second area between the top core wrap sheet and the back core wrap sheet, on the other of the top core wrap sheet and the back core wrap sheet.

15 Claims, 79 Drawing Sheets

(52) U.S. Cl.
CPC .. *A61F 13/539* (2013.01); *A61F 2013/15878* (2013.01); *A61F 2013/1591* (2013.01)

(56) References Cited

U.S. PATENT DOCUMENTS

| | | | | |
|---|---|---|---|---|
| 3,925,139 | A | * 12/1975 | Simmons | B29C 66/91313 340/657 |
| 2007/0246147 | A1 | 10/2007 | Venturino et al. | |

OTHER PUBLICATIONS

"International Application Serial No. PCT/EP2018/073665, Written Opinion dated Oct. 24, 2018", (Oct. 24, 2018), 6 pgs.

\* cited by examiner

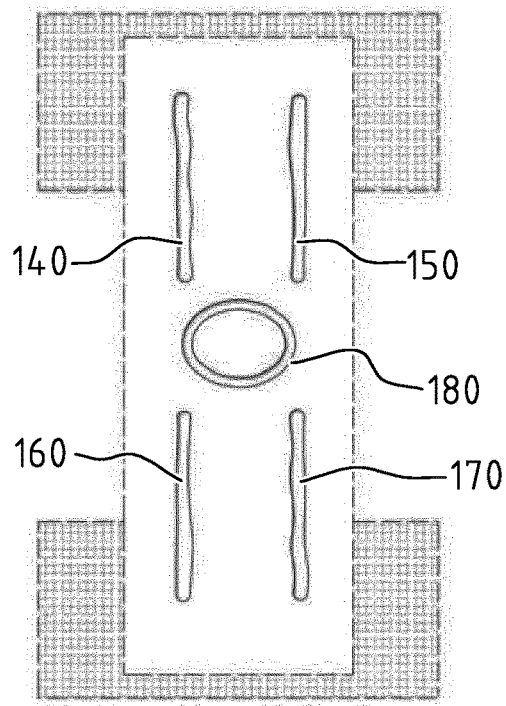
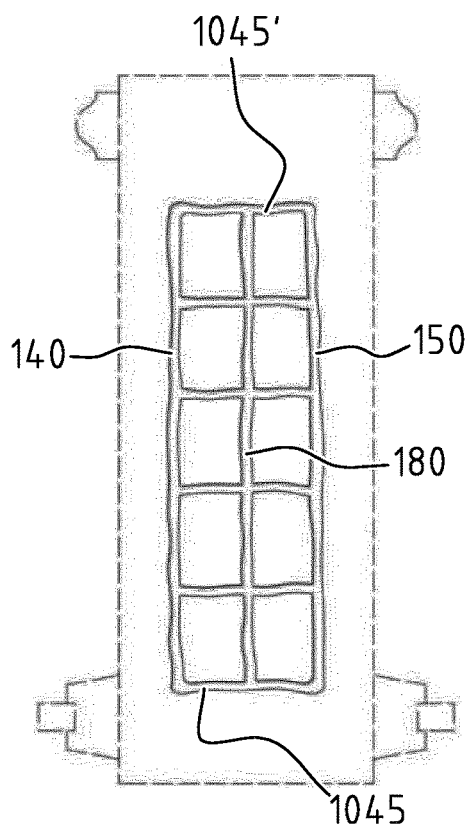
FIG. 18A  FIG. 18B
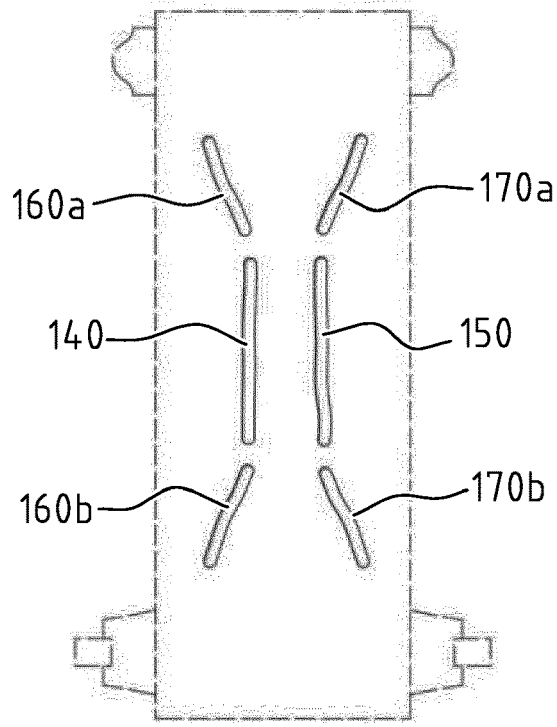
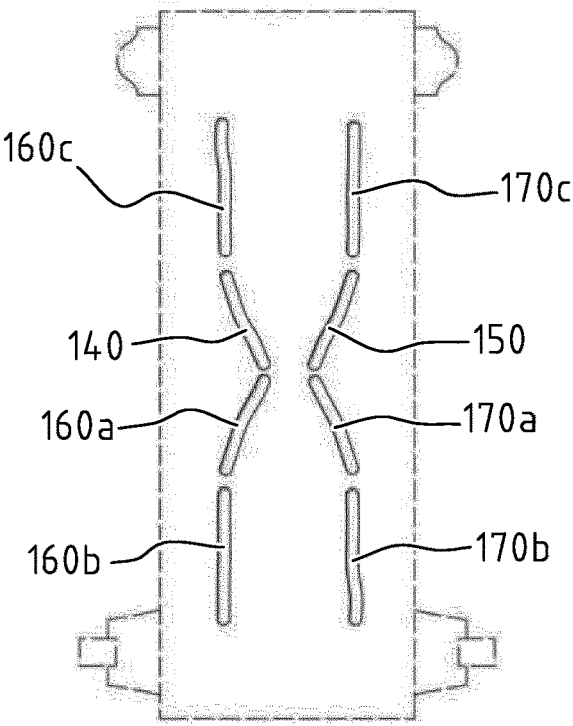
FIG. 18C  FIG. 18D

ABSORBENT ARTICLE WITH CHANNELS AND METHOD FOR MANUFACTURING THEREOF

PRIORITY APPLICATIONS

This application is a U.S. National Stage Filing under 35 U.S.C. 371 from International Application No. PCT/EP2018/073665, filed on Sep. 4, 2018, and published as WO2019/048397 on Mar. 14, 2019, which claims the benefit of priority to European Application No. 17195872.1, filed on Oct. 11, 2017 and to European Application No. 17190395.8, filed on Sep. 11, 2017; the benefit of priority of each of which is hereby claimed herein, and which applications and publication are hereby incorporated herein by reference in their entirety.

TECHNICAL FIELD

The present invention pertains to the technical field of absorbent articles, more preferably disposable personal care articles such as diapers, baby pants, adult incontinent garments, and the like, and to absorbent structures for use in such absorbent articles. More specifically the present invention relates to an absorbent structure comprising an absorbent core between a topsheet and a backsheet. The present invention also relates to a method and apparatus for manufacturing such an absorbent article.

BACKGROUND

Absorbent articles such as diapers, baby pants, adult incontinent garments and the like, typically comprise an absorbent core, positioned in between a liquid permeable or pervious, hydrophilic or semi hydrophilic topsheet and a liquid impermeable or impervious backsheet. The absorbent core comprises absorbent material that is able to absorb fluid and liquid bodily excretions of the user of the absorbent article.

The absorbent material of the absorbent core may be an absorbent particulate polymer material which is dispersed in a matrix of cellulose fibers or fluff pulp in order to prevent the particulate material from aggregating, as well as to prevent gel blocking. Gel blocking can occur when the absorbent particulate polymer material absorbs liquid, as they tend to typically swell and form a gel structure. This gel structure often blocks the further transfer of liquid into the remaining absorbent core. As a result, the liquid may be unable to reach the remaining absorbent particulate polymer material and the efficiency of the overall absorbent article decreases significantly. Existing fluff pulp materials are not suited to cope with rapid, subsequent insults of fluid since they possess limited distribution capacities. Moreover existing fluff pulp materials exhibit a limited capacity of overall liquid intake. Furthermore, existing absorbent cores containing fluff pulp have a limited wet integrity, which leads to the shape and fit of the absorbent article being deformed when e.g. an absorbent article is being worn by a baby which moves around.

In recent years, there has been a strong demand for more flexible, thinner, light-weight, absorbent articles to resolve various problems associated with manufacturing, marketing, design, fit, wearing comfort, distribution, garbage disposal, material and energy consumption, transport and storage costs and the like. This lead to the search for and the development and production of absorbent articles of which the absorbent cores contains little to no cellulose fibers or fluff pulp, as the latter tend to be quite bulky, thus rendering generally more thick absorbent cores which reduces the overall wearing comfort of the user of the absorbent article.

Hence, various absorbent cores containing little to no cellulose fibers or fluff pulp were developed in the past few years to try and overcome the above drawbacks, whereby the relative high amounts of absorbent polymer materials necessary to replace the absorption, distribution and retention capacity of the excluded cellulose fibers and/or fluff pulp were loaded, distributed and immobilized within these new absorbent cores according to several techniques. However given the ability and capacity of the absorbent core to absorb, transport and retain fluid and liquids is heavily dependent upon the form, position and/or manner wherein these absorbent polymer materials are incorporated within the absorbent core several drawback remained unsolved. In general the substantially heterogeneously distributed absorbent cores having non-continuous compartments and/or clusters of absorbent polymer material have in general proven to be better in coping with the above mentioned problems, nevertheless they also proved to remain unsatisfactory within most of the available absorbent articles. Especially problematic however, were the substantially homogenously distributed absorbent structures having continuous layers of absorbent polymer particulate material given they exhibit a substantially homogenous swollen absorbent polymer material area for second, third and next liquid insults wherein the dry and/or wetted absorbent polymer material layer may actually act as a liquid barrier. These problems and complications are especially prevalent within very flexible, thin, lightweight absorbent structures wherein high amounts of absorbent polymer material are distributed within the absorbent core of the absorbent article. Adding even more, thicker and larger overlying acquisition and dispersing layers did not at all resolve the above cited absorption, distribution and retention problems and moreover made the absorbent articles commercially unviable, environmentally unsustainable and more difficult to manufacture, store and transport.

Furthermore an existing problem which has been associated with such absorbent cores containing no or little cellulose fibers or fluff pulp is related to the migration, loss and leakage of the absorbent particulate polymer material from the absorbent article during dry and/or wet state, which leads to irritation, skin problems and overall discomfort for the user. This again is also especially true in the more homogenously distributed absorbent structures given their immobilization and liquid distribution properties remain unsatisfactory to date. This lack of effective and efficient immobilization and liquid distribution lead to dysfunctional absorbent articles due to lowered uptake capacity, gel blocking, enhanced rewet values, leakages and the creation of ruptures and/or pinholes through the liquid pervious topsheet and/or liquid impervious backsheet of such absorbent articles.

Absorbent cores generally have a high absorbent capacity and the absorbent core may expand several times its weight and volume. These increases may cause the absorbent article to deform and/or to sag in the crotch region as they become saturated with liquid. This may cause leaks to occur via a longitudinal and/or transversal edge of the absorbent article.

SUMMARY

The object of embodiments of the invention is to provide an absorbent article of the type stated in the preamble, with improved liquid distribution and absorption capacities.

According to a first aspect of the invention there is provided an absorbent article comprising a liquid pervious topsheet, a liquid impervious backsheet, and an absorbent core comprising an absorbent material between a top core wrap sheet and a back core wrap sheet. Said absorbent core is positioned in between said topsheet and said backsheet, and the absorbent core is provided with at least one attachment zone between the top core wrap sheet and the back core wrap sheet. A first binder is arranged in a first area between the top core wrap sheet and the back core wrap sheet at a distance from the at least one attachment zone, on one of the top core wrap sheet and the back core wrap sheet, and a second binder is arranged in a second area between the top core wrap sheet and the back core wrap sheet, on the other of the top core wrap sheet and the back core wrap sheet.

Embodiments are based inter alia on the inventive insight that, by providing at least one attachment zone in the absorbent core, a corresponding at least one liquid distribution zone is created in the absorbent core upon wetting such that liquid can be distributed and absorbed in an improved manner. Indeed, liquid can flow in the plurality of attachment zones and can be absorbed by the absorbent core through the side walls of the plurality of attachment zones, in addition to liquid being absorbed through the top surface of the absorbent core. Advantageously, as will be discussed later on, the at least one attachment zone is embodied as a plurality of channels.

In a preferred embodiment, the first area is substantially complementary to the second area. The second area preferably includes the at least one attachment zone.

The first binder may be different from the second binder, or may be the same as the second binder, wherein a transition zone may be distinguishable between the first area and the second area. The first binder may, additionally or alternatively, be arranged as a layer having a first thickness and the second binder may then be arranged as a layer having a second thickness which is different from the first thickness, preferably higher than the first thickness.

The attachment between the top core wrap sheet and the back core wrap sheet in the at least one attachment zone may be a permanent attachment; in which case the absorbent core is configured such that, in a wetted state of the absorbent material, the absorbent material extends over the at least one attachment zone. Alternately, in said at least one attachment zone said top core wrap sheet may be attached to said back core wrap sheet through a semi-permanent attachment configured to release after having been in contact with liquid.

A position and/or shape of one or more attachment zones of the at least one attachment zone may be indicated by means of a distinguishable color and/or colored pattern. The distinguishable color and/or colored pattern may be provided on at least one of the topsheet, the top core wrap sheet, the backsheet and the back core wrap sheet. Alternately or additionally, the position and/or shape of one or more of the plurality of attachment zones may be indicated by means of a printed ink layer.

Outside of the at least one attachment zone the absorbent core may have a maximum thickness, wherein the at least one attachment zone extends through at least 90% of the maximum thickness of the absorbent core, more preferably through 100% of the thickness of the absorbent core, such that in the at least one attachment zone substantially no absorbent material is present between the top core wrap sheet and the back core wrap sheet.

The attachment between the top core wrap sheet and the back core wrap sheet may be any one of the following or a combination thereof: pressure bonding, thermal bonding, sonic bonding, chemical bonding, adhesive.

The absorbent material may comprise cellulosic fluff pulp, or may be substantially fluffless. In the at least one attachment zone, preferably substantially no absorbent material is present.

In a second aspect of the invention, there is provided a method for manufacturing an absorbent article, said method comprising: applying a first binder in a first area on a first side of first sheet material; applying a second binder in a second area on a first side of second sheet material; applying an absorbent material on the first side of the first sheet material; attaching the first sheet material to the second sheet material with the first sides facing each other, such that at least one attachment zone is formed. In this method, one of the first sheet material and the second sheet material is a top core wrap sheet material and the other is a back core wrap sheet material; and the first area is arranged at a distance from the intended position of the at least one attachment zone.

Embodiments are based inter alea on the inventive insight that the attachment between the top core wrap sheet and the back core wrap sheet should be sufficiently strong, especially in cases where a significant amount of liquid is absorbed. Therefore, it may be desirable to additionally use a binder, such as glue, to strengthen the bond between the top and back core wrap sheets.

Furthermore, it is based on the inventive insight that it is not desirable to apply this binder to the entire surface area of one of the wrap sheets, since this may lead to the absorbent material and/or binder contaminating the at least one attachments zone, and therefore hindering the formation of at least one liquid distribution zone. By applying a first binder in areas of a wrap sheet substantially where absorbent material should be present, and applying a second binder on the other wrap sheet substantially where absorbent material should not be present, contamination can be prevented.

Preferably, the first area and the second area are substantially complementary after the step of attaching the wrap sheets to each other. Also preferably, substantially the entire surface of the absorbent article is provided with binder on either the first sheet material or the second sheet material.

The method may further include guiding the first and/or second sheet material along a rotating member while the first and/or second binder is applied. The attaching may be performed by applying pressure and heat on the top core wrap sheet material and/or the back core wrap sheet material in the area(s) where substantially no absorbent material is present. Additionally or alternately, the attaching is performed by a rotating The binder applied on at least one portion of the first sheet material may be different from, preferably less strong than, the binder applied on the at least one portion of the second sheet material. Additionally or alternatively, the binder may be applied on at least one portion of the first sheet material as a first layer having a first thickness, and on the at least one portion of the second sheet material as a second layer having a second thickness which is different from, preferably higher than, the first thickness.

According to a third aspect of the invention, there is provided an absorbent article manufactured according to the above-described method.

According to a fourth aspect of the invention, there is provided an apparatus for manufacturing an absorbent article, said apparatus comprising a first rotating member for guiding a first sheet material along a surface thereof, a first means for applying a first binder to at least one portion of the first sheet material, a second rotating member for guiding a second sheet material along a surface thereof, a second means for applying a second binder to at least one portion of the second sheet material, an application unit configured for applying an absorbent material on said first sheet material on the rotating member such that the at least one portion on which the first binder has been applied is covered with absorbent material and substantially no absorbent material is present on areas in which the first binder was not applied; a sheet feed unit configured for applying the second sheet material on top of the absorbent material on the first sheet material, wherein one of said first and second sheet material is a top core wrap sheet material, and the other one is a back core wrap sheet material; and an attachment unit configured for attaching said first sheet material to said second sheet material at least in the areas where substantially no absorbent material is present, wherein the at least one portion of the first sheet material on which the first binder is applied is arranged at a distance from the intended position of at least one attachment zone.

The portion of the first sheet material to which the first binder is applied and the portion of the second sheet material to which the second binder is applied are preferably substantially complementary in the resulting absorbent article.

The attaching unit may be a rotating member which is provided with at least a first sealing element dimensioned for applying pressure and heat on the top core wrap sheet material and/or the back core wrap sheet material in the area where substantially no absorbent material is present in order to create the at least one attachment zone. The first binder may be different from the second binder. Additionally or alternately, the first means may be configured to apply the first binder with a first thickness and the second means is configured to apply the second binder with a second thickness which is different from the first thickness, preferably higher than the first thickness.

In preferred embodiments, the at least one attachment zone is embodied as a plurality of substantially longitudinal sections, such that wetting of the absorbent material leads to the creation of a first and second channel at the first and second attachment zone, respectively. These embodiments will be described in more detail below.

In a first preferred embodiment of the invention, there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone, said first and second attachment zone extending next to each other from a crotch region in the direction of the first and/or second transverse edge. In the first and second attachment zone any one of the following conditions is fulfilled: the top core wrap sheet is attached to said back core wrap sheet along an attachment which extends, seen in a transverse direction of the absorbent core, over a transverse distance which is at least 1 mm, preferably at least 2 mm, more preferably at least 3 mm, and most preferably at least 4 mm; the top core wrap sheet is attached to said back core wrap sheet along a discontinuous attachment at a plurality of locations at a distance of each other, seen in the transverse direction of the absorbent core, preferably over a transverse distance which is at least 1 mm, preferably at least 2 mm, more preferably at least 3 mm, and most preferably at least 4 mm. Upon wetting of the absorbent material of the absorbent article, any one of the above described conditions leads to the creation of a first and second channel at the first and second attachment zone, respectively.

Because the first and second attachment zones extend in the direction of the first and/or second transverse edge as do the created first and second channel, liquid can be distributed adequately. Both the plurality of attachments zones, before swelling of the absorbent material, and the plurality of created channels, during and after swelling of the absorbent material, allow for a more rapid distribution of liquid, especially towards the transverse edges of the absorbent core. In addition to a fast and adequate distribution of liquid in the longitudinal direction, the presence of the plurality of attachment zones and/or the creation of the corresponding plurality of channels leads to a more rapid and efficient distribution of liquid in both the transverse direction of the absorbent core and in the depth direction of the absorbent core. Furthermore, overall liquid intake by the absorbent core is faster as a result. By giving the attachment zones a sufficient width, depth and/or length a quantity of liquid can be held temporarily whilst the absorption takes place. Because the liquid is distributed quickly, this effect is established not only during a first liquid insult, but also during an eventual second liquid insult, a third liquid insult and a fourth liquid insult. Further, the first and second attachment zones allow the absorbent core to swell in the shape of a tub while the first and second channels are formed. Indeed, a portion of the absorbent core between the first longitudinal edge and the first attachment zone will be allowed to rotate inward and upward and a portion of the absorbent core between the second longitudinal edge and the second attachment zone will be allowed to rotate inward and upward, which is made possible thanks to the sufficiently wide first and second attachment zone.

Preferably, the first attachment zone and the attachment zone are substantially parallel and extend in a longitudinal direction of the absorbent core. In an alternative embodiment an angle between the first attachment zone and a longitudinal direction of the absorbent core and an angle between the second attachment zone and the longitudinal direction of the absorbent core is smaller than 5°. In that manner appropriate first and second channels and an appropriate tub-shape of the absorbent product can be obtained upon wetting of the absorbent material.

In an exemplary embodiment, the attachment between the top core wrap sheet and the back core wrap sheet in the first and the second attachment zone is a permanent attachment, and the absorbent core is configured such that, in a wetted state of the absorbent material, the absorbent material extends over the first and second attachment zone. In that matter, the absorbent material bulges over the first and second attachment zone, thereby causing a tension in the absorbent core which causes the absorbent core, which is in a substantially flat state when dry, to curl up to form a tub shaped and/or cup shaped absorbent core including the first and second channel.

Preferably, the plurality of attachment zones cover together at least 30%, preferably at least 40%, preferably at least 50%, more preferably at least 60%, more preferably at least 70%, more preferably 80% and more preferably at least 90% of a total length of the absorbent core. The covered length may be realized with the first and second attachment zone alone, or with a combination of a first and second attachment zone and one or more additional attachment zones. For example, first and second adjacent longitudinal attachment zones together with third and fourth adjacent longitudinal attachment zones may extend over at least 30%, preferably at least 40%, preferably at least 50%, more preferably at least 60%, more preferably at least 70%, more preferably 80% and more preferably at least 90% of a total length of the absorbent core. This will allow a good distribution over the entire absorbent core as well as a good formation of the channels and the tub-shape upon swelling of the absorbent core.

According to a second preferred embodiment, there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone, said first and second attachment zone each extending from a crotch region in the direction of the first and/or second transverse edge. Preferably, the first channel is arranged adjacent to the second channel, seen in a transverse direction of the absorbent core. In the first and second attachment zone the top core wrap sheet is attached to the back core wrap sheet through a semi-permanent attachment configured to release after having been in contact with liquid.

Embodiments are based inter alia on the inventive insight that, by providing a plurality of attachment zones in the absorbent core, in combination with semi-permanent attachments, the absorbent core can swell in an improved manner, resulting in an improved liquid absorption. Indeed, when liquid flows in the attachments zones, the attachments are released and the absorbent core can "fill" or "overlap" the attachment zones and/or channels, wherein a portion of the absorbent core between the first longitudinal edge and the first channel will be allowed to rotate inward and upward and a portion of the absorbent core between the second longitudinal edge and the second channel will be allowed to rotate inward and upward, which is made possible thanks to the first and second channel and the swelling underneath the released top core wrap sheet.

In an exemplary embodiment of the second preferred embodiment, the top core wrap sheet is attached to the back core wrap sheet along a continuous or discontinuous attachment which extends, seen in a transverse direction of the absorbent core, over a transverse distance which is at least 1 mm, preferably at least 2 mm, more preferably at least 3 mm, and most preferably at least 4 mm.

In an exemplary embodiment of the second preferred embodiment, the semi-permanent attachment is configured to release after having been in contact with urine for a period of time, e.g. a period of time is smaller than 30 s.

In a third preferred embodiment, there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone located a distance of each other, said first and second attachment zone each extending from a crotch region in the direction of the first and/or second transverse edge. A position and/or shape of one or more attachment zones of the plurality of attachment zone is indicated by means of a distinguishable color and/or colored pattern.

Such embodiments have the advantage that, on the one hand the attachment zones result in an improved liquid distribution and absorption of the liquid, and on the other hand, the color and/or pattern allows a user to easily distinguish a front and a rear portion of the absorbent article. Indeed, by giving e.g. the first attachment zone a color and/or pattern which is different from the color and/or pattern of the second attachment zone, a user can remember easily e.g. which color has to be on the left or right side. The person skilled in the art understands that many color and/or pattern variants are possible which will allow a user to easily recognize a front and a rear portion. In addition to or alternative to allow a user to easily recognize the correct orientation of the absorbent article, the color and/or pattern which indicate the position and/or shape of the attachment zones may be utilized to provide more information to a user about the absorbent article by linking a particular color and/or pattern of the visual indication to a certain characteristic of the absorbent article such as size, type (e.g. diaper versus pants), etc.

Preferably, the position of one or more of the plurality of attachment zones is indicated by means of a printed ink layer.

In exemplary embodiments the distinguishable color and/or colored pattern is provided on at least one of the topsheet, the top core wrap sheet, the backsheet and the back core wrap sheet. The color and/or colored pattern may be provided on either side of the topsheet, the top core wrap sheet, the backsheet and/or the back core wrap sheet. In addition or alternatively, the color and/or colored pattern is provided on an acquisition and/or a distribution layer of the absorbent article.

According to a fourth preferred embodiment of the invention, there is provided an absorbent article comprising a liquid pervious topsheet, a liquid impervious backsheet, and an absorbent core comprising an absorbent material between a top core wrap sheet and a back core wrap sheet, the absorbent core being positioned in between said topsheet and said backsheet. The absorbent core has a first and second longitudinal edge and a first and second transverse edge. The absorbent core is provided with at least a first attachment zone. In the first attachment zone any one of the following conditions is fulfilled: the top core wrap sheet is attached to the back core wrap sheet along an attachment which extends, seen in a transverse and/or longitudinal direction of the absorbent core, over a transverse and/or longitudinal distance which is at least 1 mm, preferably at least 2 mm, more preferably at least 3 mm, most preferably at least 4 mm; the top core wrap sheet is attached to the back core wrap sheet along a discontinuous attachment at a plurality of locations at a distance of each other, seen in the transverse and/or longitudinal direction of the absorbent core. Upon wetting of the absorbent material, a first channel is created at said first attachment zone.

According to an exemplary embodiment, the first attachment zone extends from a crotch region in the direction of the first and/or second transverse edge.

According to an alternative embodiment, the first attachment zone extends in the transversal direction of the absorbent core in between the first and second longitudinal edge.

Preferably, the absorbent core is provided with at least a second attachment zone. The at least one second attachment zone extends in the transversal direction of the absorbent core in between the first and second longitudinal edge.

It is clear to the skilled person that following embodiments may correspond with either one of the above described first, second, third and fourth preferred embodiments.

Preferably, outside of the plurality of attachment zones the absorbent core has a maximum thickness; wherein the first and second attachment zone extend through at least 90% of the maximum thickness of the absorbent core, more preferably through 100% of the thickness of the absorbent core such that in the first and second attachment zone substantially no absorbent material is present between the top core wrap sheet and the back core wrap sheet.

According to an exemplary embodiment the first attachment zone and the second attachment zone are arranged symmetrically with respect to a longitudinal center line of the absorbent core extending between the first and second transverse edge.

Preferably, the attachment between the top core wrap sheet and the back core wrap sheet is any one of the following or a combination thereof: pressure bonding, thermal bonding, sonic bonding, chemical bonding, adhesive.

Preferably, the plurality of attachment zones further comprises a third and a fourth attachment zone located at a distance of each other, the third and fourth attachment zone each extending in the direction of the first and/or second transverse edge.

Preferably, the distance between the first and the second attachment zone is different from the distance between the third and the fourth attachment zone.

According to an exemplary embodiment, the absorbent core has a front portion extending at one side of a transverse crotch line and a rear portion extending at the other side of the transverse crotch line. The first and second attachment zone extend at least in the front portion of the absorbent core; and the third and fourth attachment zone extend at least in the rear portion of the absorbent core.

Preferably, the distance between the first and the second attachment zone is smaller than the distance between the third and the fourth attachment zone.

Preferably, the first attachment zone is connected to the third attachment zone through a first transverse attachment zone, and the second attachment zone is connected to the fourth attachment zone through a second transverse attachment zone.

Preferably, the first and the second attachment zone extend in a longitudinal direction of the absorbent core over a length which is longer than the length of the third and fourth attachment zone, and the first and the second attachment zone are located between the third and fourth attachment zone.

In an exemplary embodiment, the third attachment zone and the fourth attachment zone are arranged symmetrically with respect to a longitudinal center line of the absorbent core extending between the first and second transverse edge.

Preferably the distance between the first and the second attachment zone is between 10 mm and 50 mm, preferably between 15 mm and 30 mm.

According to an exemplary embodiment, the length of the first and the second attachment zone is larger than 60 mm, preferably larger than 70 mm.

According to an embodiment, the absorbent material comprises cellulosic fluff pulp.

According to an alternative embodiment, the absorbent material is substantially fluffless.

Preferably substantially no absorbent material is present in the first and second attachment zone.

According to exemplary embodiment, the first and second attachment zone each have a bottom and a top, wherein the top core wrap sheet is attached to the back core wrap sheet at said bottom, at said top, or between said bottom and said top.

According to an exemplary embodiment, the absorbent article further comprises at least one transversal attachment zone extending from an end portion of the first attachment zone to a corresponding end portion of the second attachment zone, wherein upon wetting of the absorbent material, a third channel is created at said transversal attachment zone, thus connecting the first and second channels.

According to another preferred embodiment of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone, said first and second attachment zone extending next to each other from a crotch region in the direction of the first and/or second transverse edge. A first binder is arranged in a first area between the top core wrap sheet and the back core wrap sheet at a distance from the first and second attachment zone, and a second binder is arranged in a second area between the top core wrap sheet and the back core wrap sheet. Preferably, the first area is substantially complementary to the second area. Preferably, the second area includes the first and second attachment zone.

According to yet another preferred embodiment of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with at least a first attachment zone extending from a crotch region in the direction of the first and/or second transverse edge. A first binder is arranged in a first area between the top core wrap sheet and the back core wrap sheet at a distance from the first attachment zone, and a second binder is arranged in a second area between the top core wrap sheet and the back core wrap sheet. Preferably, the first area is substantially complementary to the second area. Preferably, the second area includes the first and second attachment zone.

According to an exemplary embodiment the first binder is different from the second binder.

According to another exemplary embodiment the first binder is the same as the second binder; and a transition zone is distinguishable between the first area and the second area.

According to an exemplary embodiment the first binder is arranged as a layer having a first thickness and the second binder is arranged as a layer having a second thickness which is different from the first thickness, preferably higher than the first thickness.

According to an exemplary embodiment the first area comprises a plurality of longitudinal stripes; and/or the second area comprises a plurality of longitudinal stripes.

According to an embodiment, a first binder is applied to at least one portion of the back core wrap sheet at a distance from the intended position of the first and/or second attachment zones before the absorbent material is applied, and a second binder is applied to at least one portion of the top core wrap sheet before it is applied on top of the absorbent material on the back core wrap sheet.

According to an alternative embodiment, a first binder is applied to at least one portion of the top core wrap sheet at a distance from the intended position of the first and/or second attachment zones before the absorbent material is applied, and a second binder is applied to at least one portion of the back core wrap sheet before it is applied on top of the absorbent material on the back core wrap sheet. Preferably, the at least one portion of the top core wrap sheet and the at least one portion of the back core wrap sheet are chosen such that in the application and attachment of the top core wrap sheet to the back core wrap sheet the plurality of portions are complementary, wherein preferably substantially the entire surface of the absorbent article is provided with binder on either the top core wrap sheet or the back core wrap sheet. According to an embodiment the first and second binder are the same binder. In alternative embodiments, the first and second binder are mutually different binders, such as different glues. It is clear to the skilled person that the first and second binder may be applied in either layers with the same thickness, or layers with a different thickness.

The skilled person understands that an absorbent article as described above, more in particular in view of the application of binder, can be distinguished from absorbent articles which are manufactured otherwise. More in particular, the above described application of binder, such as glue, is distinguishable in an absorbent article by examining the present bonds within the particular absorbent article by means of any one of the following: color analysis, UV analysis, chemical analysis, and the like. In other words, by examining the absorbent article, the skilled person can determine which type of binder has been used, where the particular binder has been applied, how many layers of binder have been applied, etc.

The skilled person will understand that the hereinabove described technical considerations and advantages for absorbent article embodiments also apply to the below described method embodiments, mutatis mutandis.

According to a fifth preferred embodiment, there is provided a method for manufacturing an absorbent article, said method comprising the steps of:
  guiding a first sheet material along a rotating member, wherein a surface of said rotating member is provided with a pattern with suction zones and non-suction zones; wherein said non-suction zones comprise at least a first and a second elongate zone extending in a circumferential direction of the rotating member;
  applying an absorbent material on said first sheet material on the rotating member such that the suction zones are covered with absorbent material and substantially no absorbent material is present on the non-suction zones;
  applying a second sheet material on top of the absorbent material on the first sheet material; wherein one of said first and second sheet material is a top core wrap sheet material, and the other one is a back core wrap sheet material;
  attaching said first sheet material to said second sheet material at least in the areas where substantially no absorbent material is present, and such that at least a first and a second attachment zone are formed.

Preferably, the attaching is done by applying pressure and heat on the top core wrap sheet material and/or the back core wrap sheet material in the areas where substantially no absorbent material is present.

Preferably, a binder is applied to at least one portion of the first sheet material at a distance from the intended position of the first and second attachment zones, before the absorbent material is applied on said first sheet material and a binder is applied to at least one portion of the second sheet material before it is applied on top of the absorbent material on the first sheet material. Preferably, the at least one portion of the first sheet material and the at least one portion of the second sheet material are chosen such that in the application and attachment of the first sheet material to the second sheet material the plurality of portions are complementary, wherein preferably substantially the entire surface of the absorbent article is provided with binder on either the first sheet material or the second sheet material.

According to a further embodiment, the attaching is done by a rotating member which is provided with at least a first and a second seal rib dimensioned for applying pressure and heat on the top core wrap sheet material and/or the back core wrap sheet material in the areas where substantially no absorbent material is present in order to create the first and second attachment zone, respectively.

Additionally, there is provided a method for manufacturing an absorbent article, said method comprising:
a. guiding a first sheet material along a conveying or rotating member, wherein a surface of said conveying member is provided with a pattern with at least one suction zone and non-suction zone; wherein said at least one non-suction zone comprises at least a first zone extending in a conveying direction of the conveying member;
b. applying an absorbent material on said first sheet material on the rotating member such that the at least one suction zone is covered with absorbent material and substantially no absorbent material is present on the at least one non-suction zone;
c. applying a second sheet material on top of the absorbent material on the first sheet material; wherein one of said first and second sheet material is a top core wrap sheet material, and the other one is a back core wrap sheet material;
d. attaching said first sheet material to said second sheet material at least in the areas where substantially no absorbent material is present, and such that at least at least a first attachment zone is formed.

The attaching may be done by applying pressure and heat on the top core wrap sheet material and/or the back core wrap sheet material in the areas where substantially no absorbent material is present.

The attaching may be done by a rotating member which is provided with at least a first seal rib dimensioned for applying pressure and heat on the top core wrap sheet material and/or the back core wrap sheet material in the areas where substantially no absorbent material is present in order to create the first attachment zone.

A first binder may be applied to at least one portion of the first sheet material at a distance from the intended position of the first attachment zone, prior to step b, and a second binder may be applied to at least one portion of the second sheet material prior to step c. Preferably, the at least one portion of the first sheet material and the at least one portion of the second sheet material are chosen such that in the application and attachment of the first sheet material to the second sheet material the plurality of portions are complementary, wherein preferably substantially the entire surface of the absorbent article is provided with binder on either the first sheet material or the second sheet material.

The first binder applied on at least one portion of the first sheet material may be different from, preferably less strong than, the second binder applied on the at least one portion of the second sheet material.

The binder may be applied on at least one portion of the first sheet material as a first layer having a first thickness, and on the at least one portion of the second sheet material as a second layer having a second thickness which is different from, preferably higher than, the first thickness.

The binder may be applied on the first sheet material as a plurality of parallel first longitudinal stripes and on the second sheet material as a plurality of parallel second longitudinal stripes, wherein preferably a second longitudinal stripe thereof is located in between two first longitudinal stripes of the plurality of first longitudinal stripes.

It is clear to the skilled person that an absorbent article which is manufactured according to any one of the method embodiments as described above can be distinguished from absorbent articles which are manufactured according to another method. More in particular, the above described manner of applying layers of binder, such as glue, is distinguishable in an absorbent article end product by examining the bonds within the particular absorbent article by means of any one of the following: color analysis, UV analysis, chemical analysis, and the like. In other words, by examining the absorbent article end product, the skilled person can determine which type of binder has been used, where the particular binder has been applied, how many layers of binder have been applied, etc.

BRIEF DESCRIPTION OF FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which:

FIG. 10E shows a cross section of an insert placed at a non-suction zone of the exemplary embodiment of FIG. 10;

FIG. 10F shows a top view indicating how inserts may be positioned in order to create non-suction zones for the exemplary embodiment of FIG. 10;

FIG. 10G shows a cross section of the absorbent core when the second sheet 120 is being applied;

FIG. 10H shows a cross section of the absorbent core before attaching the first sheet 110 to the second sheet 120;

FIGS. 18A-18G illustrate yet other exemplary embodiments of an absorbent core according to the invention;

DESCRIPTION OF EMBODIMENTS

Figure 1A:
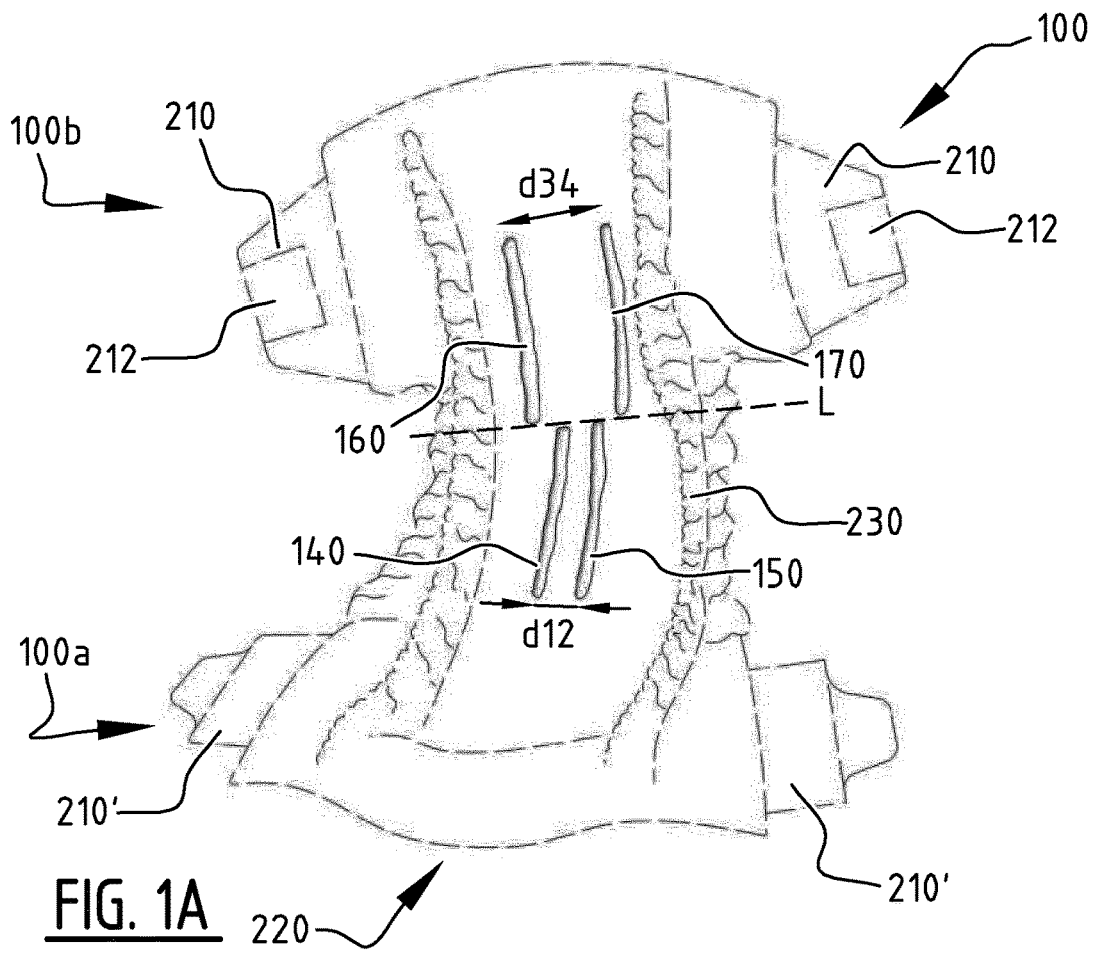
FIG. 1A is a perspective view of an exemplary embodiment of a diaper.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit $g/cm^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of a joint determined in dry state conditions, immediately after drying under specified conditions or after a period of conditioning in the standard laboratory atmosphere.

"Essentially cellulose free" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

Note that while in the exemplary embodiments described the at least one attachment zone is embodied as a plurality of channels, other configurations are not excluded and will be within the purview of the skilled person.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The same or similar features and components are indicated with the same reference numerals throughout the figures.

Figure 1B:
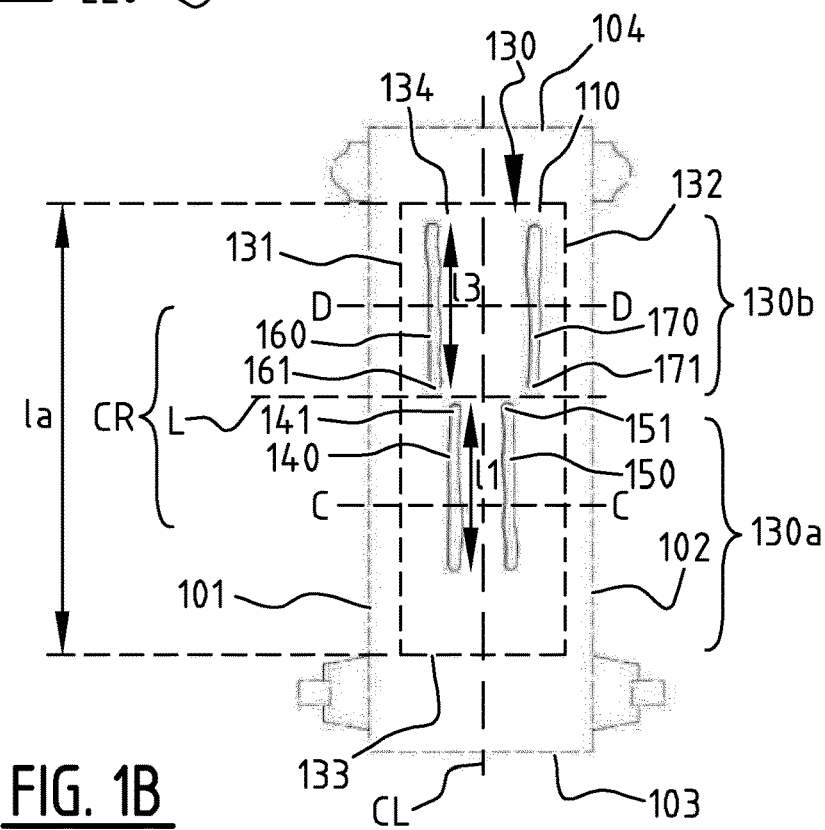
FIG. 1B is a top plan view of the diaper of FIG. 1A.

FIGS. 1A, 1B, 1C and 1D illustrate an exemplary embodiment of an absorbent article, here a diaper. FIG. 1B shows the absorbent article in its flat out, un-contracted state with the wearer side facing the viewer. The skilled person understands that the absorbent article may also be a pant or an adult incontinence garment or the like. The absorbent article 100 comprises a liquid pervious topsheet, a liquid impervious backsheet, and an absorbent core 130 positioned in between the topsheet and the backsheet. The absorbent core 130 comprises absorbent material 105 between a top core wrap sheet 110 and a back core wrap sheet 120. Absorbent core 130 has a first and second longitudinal edge 131, 132 and a first and second transverse edge 133, 134.

The absorbent core 130 is provided with a plurality of attachment zones 145, 155, 165, 175 comprising at least a first attachment zone 145 and a second attachment zone 155. The first and second attachment zones extend next to each other from the crotch region CR in the direction of the first and/or second transverse edge 133, 134. In first and second attachment zone 145, 155 the top core wrap sheet 110 is attached to the back core wrap sheet 120
- along an attachment which extends, seen in a transverse direction of the absorbent core, over a transverse distance which is at least 1 mm, preferably at least 2 mm, more preferably at least 3 mm, most preferably at least 4 mm; and/or
- along a discontinuous attachment at a plurality of locations at a distance of each other, seen in the transverse direction of the absorbent core. In that manner, upon wetting of the absorbent material, a first and second channel 140, 150 are created at said first and second attachment zone 145, 155, respectively.

Absorbent article 100 is provided at said top core wrap sheet with at least a first and a second attachment zone 145, 155 located a distance d12 of each other. In that manner a first and second channel 140, 150 formed upon wetting, each extend from a crotch region CR in the direction of the first transverse edge 133. Preferably the distance d12 is between 10 mm and 50 mm, more preferably between 15 and 30 mm.

Preferably, the length of the first and second channel is substantially the same, more preferably the length l1 of the first channel and the length l2 of the second channel is between 60 mm and 140 mm, more preferably between 75 mm and 125 mm. Preferably, the distance between the first attachment zone 145 and the first longitudinal side 131 is between 20 and 30 mm, and the distance between the second attachment zone 155 and the second longitudinal side 132 is between 20 and 30 mm. Preferably, the distance between the first/second attachment zone 145, 155 and the transverse edge 133 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second attachment zone 145, 155 (and hence first and second channel 140, 150) may be diverging slightly outwardly in the direction of first transverse edge 133. Preferably first channel 140 and second channel 150 are arranged symmetrically with respect to a longitudinal center line CL of absorbent core 130.

Absorbent article 100 is further provided with a third and a fourth channel 160, 170 located at a distance d34 of each other. Third and fourth channel 160, 170 each extend from crotch region CR in the direction of second transverse edge 134. The distance d12 between first and second channel 140, 150 is different from the distance d34 between third and fourth channel 160, 170. Preferably the distance d34 is between 25 mm and 80 mm, more preferably between 35 mm and 55 mm. Preferably, the length of the third and fourth channel 160, 170 is substantially the same, more preferably the length l3 of the third channel and the length l4 of the fourth channel is between 30 mm and 130 mm, more preferably between 30 mm and 70 mm. Preferably, the distance between the third attachment zone 165/third channel 160 and the first longitudinal side 131 is between 20 and 30 mm, and the distance between the fourth attachment zone 175 and the second longitudinal side 132 is between 20 and 30 mm. Preferably, the distance between the third/fourth attachment zone 165, 175 and the transverse edge 134 is between 30 mm and 100 mm, more preferably between 40 mm and 75 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of second transverse edge 134. Preferably third channel 160 and fourth channel 170 are arranged symmetrically with respect to a longitudinal center line CL of absorbent core 130.

Preferably, the distance between an end point 141 of first channel 140 and an end point 161 of third channel 160 is smaller than 25 mm, more preferably smaller than 20 mm. Similarly, preferably, the distance between an end point 151 of second channel 150 and an end point 171 of fourth channel 170 is smaller than 25 mm, more preferably smaller than 20 mm. More preferably, endpoints 141, 151, 161 and 171 are located on substantially the same transverse line L functioning as a fold line along which the diaper can be folded in two.

Figure 1C:
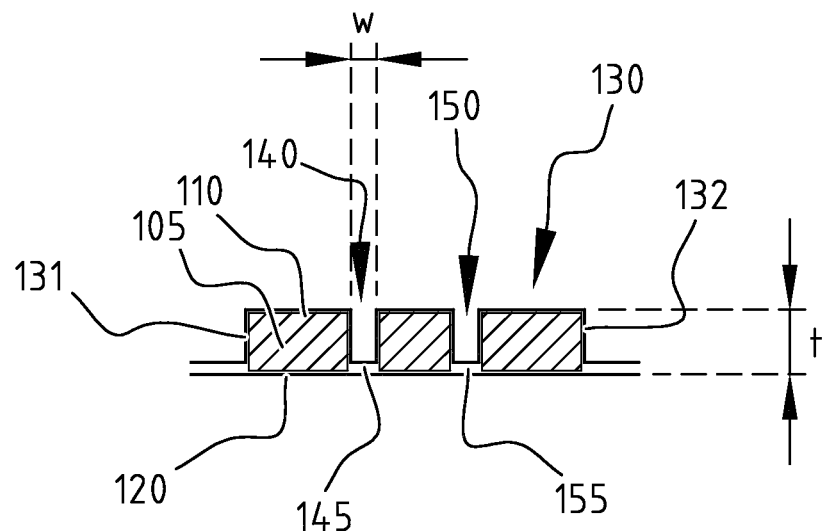
FIG. 1C is a schematic cross-section along line C-C of FIG. 1B.
Figure 1D:
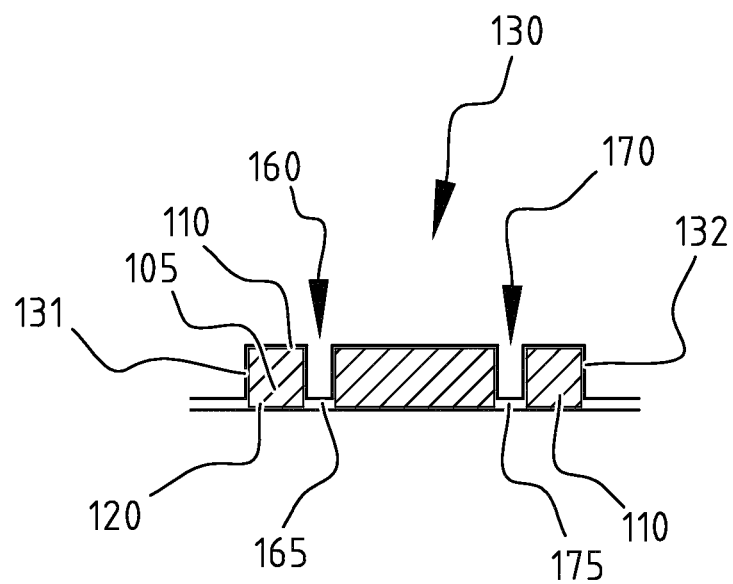
FIG. 1D is a schematic cross-section along line D-D of FIG. 1B.

First, second, third and fourth channel 140, 150, 160, 170 each have a bottom which forms the attachment zone 145, 155, 165, 175, see FIG. 1C and FIG. 1D. At bottom 145, 155, 165, 175 top core wrap sheet 110 is attached to back core wrap sheet 120. The width w of the bottom, seen in a transverse direction of absorbent core 130, is preferably larger than 2 mm, more preferably larger than 3 mm and even more preferable larger than 4 mm. To that end the attachment between top core wrap sheet 110 and the back core wrap sheet 120 may be an attachment extending over a transverse distance which is at least 2 mm, preferably at least 3 mm, more preferably at least 4 mm; and/or the attachment may be a discontinuous attachment in a plurality of locations at a distance of each other, seen in a transverse direction of absorbent core 130. Preferably the attachment at the bottom between the top core wrap sheet and the back core wrap sheet is realized by any one of the following or a combination thereof: pressure bonding, thermobonding, sonic bonding, chemical bonding, adhesive, mechanical bonding.

Outside of the plurality of channels 140, 150, 160, 170, absorbent core 130 has a maximum thickness t. Preferably, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present that between top core wrap sheet 110 and back core wrap sheet 120. It is noted that the channel 140, 150, 160, 170 may be located below and/or above the attachment zones 145, 155, 165, 175, as will be explained in more detail below with reference to FIG. 14.

In a possible embodiment the attachment 145, 155, 165, 175 between top core wrap sheet 110 and back core wrap sheet 120, here at a bottom of each channel 140, 150, 160, 170, is a semi-permanent attachment configured to release after having been in contact with urine for a predetermined period of time, wherein said predetermined period of time is preferably smaller than 30 s.

Figure 9A:
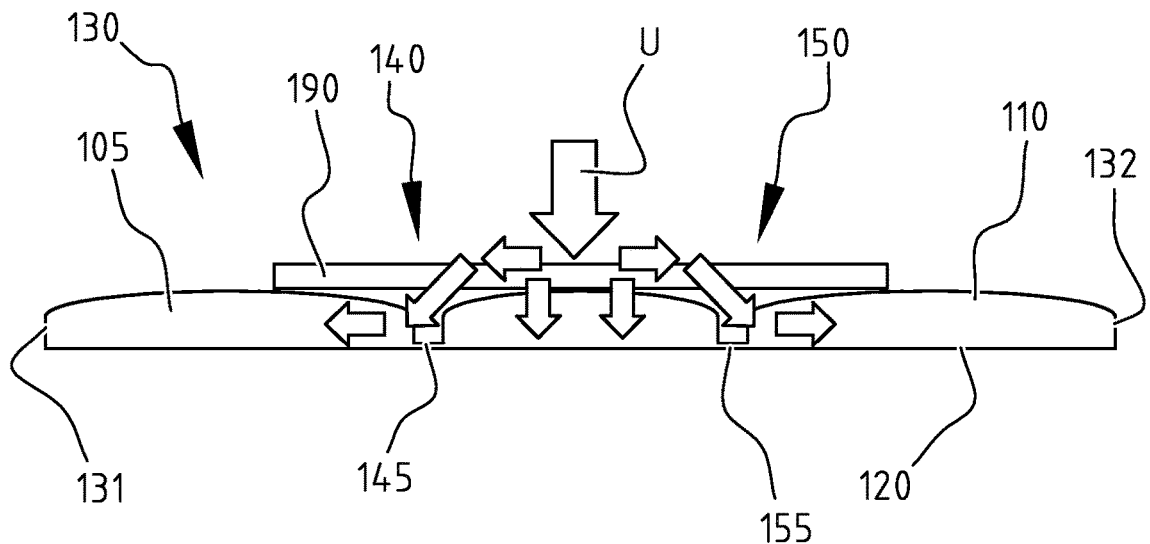
FIGS. 9A and 9B are cross-sectional views illustrating the effect of liquid being absorbed by the absorbent core of an exemplary embodiment of an absorbent article.
Figure 9B:
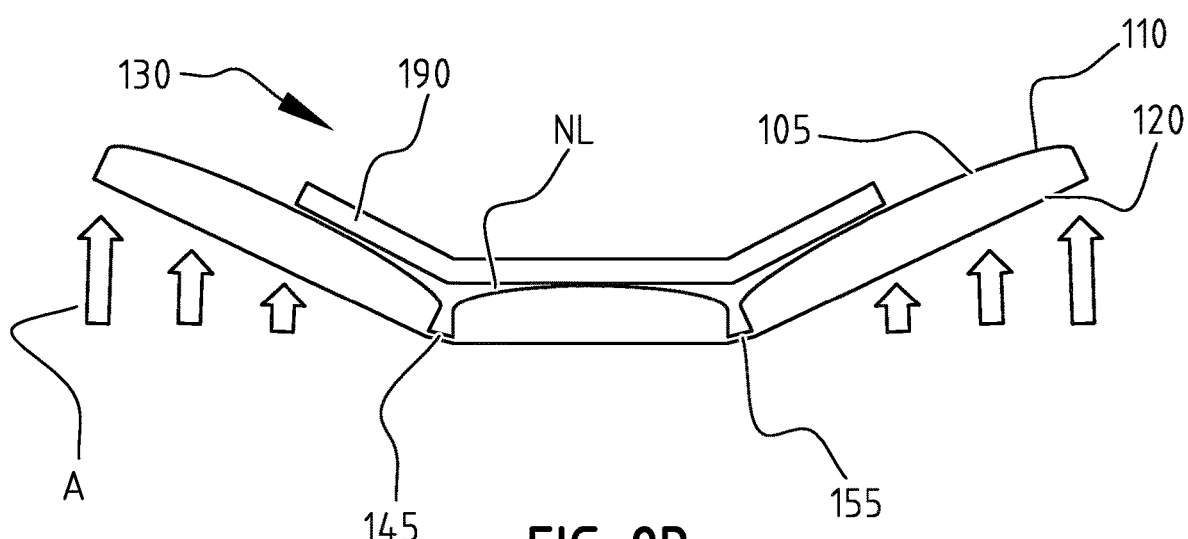

In another possible embodiment the attachment 145, 155, 165, 175 between top core wrap sheet 110 and back core wrap sheet 120, here at the bottom of each channel 140, 150, 160, 170, is a permanent attachment; and absorbent core 130 is configured such that, in a wetted state of absorbent core 130, the absorbent material extends over bottom 145, 155, 165, 175 of channel 140, 150, 160, 170. This is illustrated in FIGS. 9A and 9B for first and second channels 140, 150. Channels 140, 150, 160, 170 guide urine U or any other aqueous liquid through the side walls of channels 140, 150, 160, 170 into absorbent core 130. Those side walls create an additional path along which the liquid can flow into absorbent core 130 and enhance the diffusion of the liquid into absorbent core 130. Also, because of the swelling of the core material of absorbent core 130, the outer bands of absorbent core 130 will rotate around channels 140, 150, 160, 170 as indicated by arrows A in FIG. 9B. In that manner the diaper takes the shape of a tub or cup, such that any liquid NL which would not yet be absorbed by the absorbent material 105 is maintained in the tub shape. This results in a better protection against leakage and a diaper fitting perfectly to the body. Hence the diaper of FIGS. 1A-1D will create more freedom of movement for the wearer of a wetted diaper.

It is clear to the skilled person that the attachment zones may be provided by means of continuous attachments in the transversal direction of the absorbent core and/or continuous attachments in the longitudinal direction of the absorbent core and/or discontinuous attachments in the transversal direction of the absorbent core and/or discontinuous attachments in the longitudinal direction of the absorbent core.

Absorbent core 130 has a front portion 130a extending at one side of a transverse crotch line which corresponds in this embodiment with fold line L, and a rear portion 130b extending at the other side of the transverse crotch line L. First and second channel 140, 150 extend at least in front portion 130a of absorbent core 130, and third and fourth channel 160, 170 extend at least in rear portion 130b of the absorbent core 130. Preferably the distance d12 between first and second channel 140, 150 in front portion 130a is smaller than the distance d34 between third and fourth channel 160, 170 in rear portion 130b.

The plurality of channels 140, 150, 160, 170 together cover at least 60%, preferably at least 70% of the length la of absorbent core 130; indeed, in the embodiment of FIG. 1A-1D the channels cover a length equal to l1+l3 which is more than 60% of the length la of absorbent core 130.

The plurality of channels 140, 150, 160, 170 may be indicated with a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. As the sheets may be partially transparent, the print may be arranged on a sheet in between the topsheet and the backsheet, as long as it is visible through the topsheet and/or the backsheet. Preferably the print is visible when looking at the topsheet of the diaper. For example, a topsheet area above first and second channels 140, 150 may be printed with an ink of a first color and a topsheet area above third and fourth channels 160, 170 may be printed with the same color or with a different color. In that manner a user will be able to easily recognize the front and rear portion of a diaper, and will recognize more easily how to put on the diaper.

The chassis of the diaper 100 in FIGS. 1A-1D comprises a liquid pervious topsheet (not shown in FIGS. 1C and 1D, but the topsheet is a layer above top core wrap sheet 110) and liquid impervious backsheet (not shown in FIGS. 1C and 1D, but the backsheet is a layer below back core wrap sheet 110). The topsheet may be attached to the top core wrap sheet 110, e.g. in the attachment zones 140, 150, 160, 170. Also, the backsheet may be attached to the back core wrap sheet 120, e.g. in the attachment zones 140, 150, 160, 170. Preferably the chassis further includes side panels or ears 210, elasticized leg cuffs 230 and elastic waist elements (not shown). A front end portion of diaper 100 is configured as a front waist region 100a. The opposite rear end portion is configured as a back waist region 100b of diaper 100. An intermediate portion of diaper 100 is configured as crotch region CR, which extends longitudinally between first and second waist regions 100a and 100b. Waist regions 100a and 100b may include elastic waist elements such that they gather about the waist of the wearer to provide improved fit and containment. Crotch region CR is that portion of diaper 100 which, when the diaper 100 is worn, is generally positioned between the wearer's legs. The periphery of diaper 100 is defined by the outer edges of the diaper 100 in which longitudinal edges 101, 102 run generally parallel to a longitudinal axis of diaper 100 and transverse end edges 103, 104 run between the longitudinal edges 101, 102 generally parallel to a transverse axis of diaper 100. The chassis also comprises a fastening system, which may include at least one fastening or securing member 212 and at least one landing zone 220. The various components within diaper 100 may be bound, joined or secured by any method known in the art, for example by adhesives in uniform continuous layers, patterned layers or arrays of separate lines, spirals or spots. Top core wrap sheet, topsheet, back core wrap sheet, backsheet, absorbent material and other components may be assembled in a variety of well-known configurations and are well known in the art.

Backsheet covers absorbent core 130 and preferably extends beyond the absorbent core 130 toward longitudinal edges 101, 102 and end edges 103, 104 of diaper 100 and may be joined with top sheet. Backsheet prevents bodily exudates absorbed by the absorbent core 130 and contained within diaper 100 from soiling other external articles that may contact the wearer, such as bed sheets and undergarments. In preferred embodiments, backsheet is substantially impervious to bodily exudates and comprises a laminate of a nonwoven and a thin plastic film such as a thermoplastic film. Backsheet may comprise breathable materials that permit vapor to escape from diaper 100 while still preventing bodily exudates from passing through backsheet. It may be semi-rigid, non-elastic and can be made fully or partially elasticized and include backing.

The top sheet which is located above the top core wrap sheet 110, is preferably soft, exhibits good strikethroughs and has a reduced tendency to rewet from the liquid absorbent material. Top sheet may be semi-rigid and non-elastic, or may be fully or partially elasticized. Topsheet is intended to be placed in close proximity to the skin of the wearer when diaper 100 is worn. Topsheet permits bodily exudates to rapidly penetrate it so as to flow more quickly toward absorbent core 130 via a top surface thereof and via the plurality of channels 140, 150, 160, 170, preferably not allowing such bodily exudates to flow back through topsheet. Topsheet may be constructed from any one of a wide range of liquid and vapor permeable, preferably hydrophilic, materials. The upper and lower surface of topsheet may be treated differently. Topsheet may include e.g. a surfactant on the upper surface so as to facilitate liquid transfer there through, especially at a central zone or area of topsheet located over absorbent core 130, and/or a hydrophobic agent on the lower surface to minimize the liquid contained within absorbent core 130 from contact wetting topsheet thereby reducing rewet values. Topsheet may be coated with a substance having rash preventing or rash reducing properties. Preferably, topsheet covers substantially the entire wearer facing area of diaper 100, including substantially all of front waist region 100a, back waist region 100b, and crotch region CR. Optionally, side panels 210, 210' and/or waist feature layers of the inner region may be formed from the same single topsheet material. Alternatively, topsheet may be formed from multiple different materials which vary across of topsheet. Such a multiple piece design allows for creation of preferred properties and different zones of the topsheet.

Absorbent core 130 may comprise any absorbent material that is generally compressible, conformable, non-irritating to the wearer's skin, and capable of absorbing and retaining bodily exudates. Absorbent core 130 may comprise a wide variety of liquid absorbent materials commonly used in absorbent articles. Preferably, absorbent core 130 comprises fluff material, typically cellulosic fluff pulp. However, in other embodiments, absorbent core 130 may be substantially fluffless and comprise superabsorbent polymers. Also, absorbent core 130 may comprise a combination of cellulosic fluff pulp and superabsorbent polymers. Absorbent core 130 may be configured to extend substantially the full length and/or width of diaper 100. However, as in the embodiment of FIGS. 1A-1D, preferably absorbent structure 130 is not coextensive with the entire diaper 100 and is limited to certain regions of diaper 100 including crotch region CR. In various embodiments, the absorbent core 300 extends to the edges of diaper 100 but the absorbent material is concentrated in the crotch region CR or another target zone of the diaper 100. In FIGS. 1A-1D, absorbent core 130 is shown as having a substantially rectangular configuration, however, absorbent core 130 may be shaped differently, such as, elliptical, dogbane shaped, T-shaped or I-shaped. More in particular the width of the front portion 130*a* may be smaller than the width of the rear portion 130*b* of the absorbent core.

Examples of commonly occurring absorbent materials used for absorbent core 130 are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride.

Diaper 100 may also utilize a pair of containment walls or cuffs 230. Each cuff 230 is a longitudinally extending wall structure preferably positioned on each side of absorbent core 130 and spaced laterally from the center line CL. Preferably, cuffs 230 are attached, for example, by adhesive or sonic bonding to the lower structure. Preferably, cuffs 230 are equipped with elastic members. When released or otherwise allowed relaxing, the elastic members retract inwardly. When diaper 100 is worn, the elastic members function to contract cuffs 230 about the buttocks and the thighs of the wearer in a manner, which forms a seal between diaper 100, the buttocks and the thighs.

The waist regions 100*a* and 100*b* each comprise a central region and a pair of side panels or ears 210, 210' which typically comprise the outer lateral portions of the waist regions. These side panels 210, 210' may be unitary with the chassis or may be attached or joined thereto by any means know in the art. Preferably, the side panels 210 positioned in the back waist region 100*b* are flexible, extensible and/or elastic in at least the lateral direction. In another embodiment the side panels 210 are non-elastic, semi-rigid, rigid and/or stiff. In order to keep diaper 100 in place about the wearer, preferably at least a portion of the back waist region 100*b* is attached by fastening or securing members 212 to at least a portion of the front waist region 100*a*. The fastening or securing members 212 may be e.g. adhesive, mechanical fasteners, hook and loop features, conceivable strings and/or combinations thereof. The fastening or securing members 212 may also be co-adhesive such that they adhere to each other but not other materials. Preferably the materials making up the fastening or securing members 212 are flexible, extensible and/or elastic, allowing them to better conform to the shape and movements of the body and thus, to reduce the likelihood that the fastening system will irritate or injure the wearer's skin. Alternatively, the absorbent article may be pants and the like. In this configuration, the absorbent article may or may not have fastening members.

Diaper 100 may also employ additional layers, such as an acquisition layer and/or dispersion layer situated between topsheet and absorbent core 130, and/or coverstock layers, and/or other layers situated between absorbent core 130 and backsheet. An acquisition layer and/or dispersion layer serves to slow down the flow so that the liquid has adequate time to be absorbed by absorbent core 130. FIGS. 9A and 9B show an acquisition layer 190 above top core wrap layer 110.

Diaper 100 may also include such other features, components and elements as are known in the art including waistbands, waist cap features, elastics and the like to provide better fit, containment and aesthetic characteristics. These features may be assembled in a variety of well-known configurations and are well known in the art.

Figure 2A:
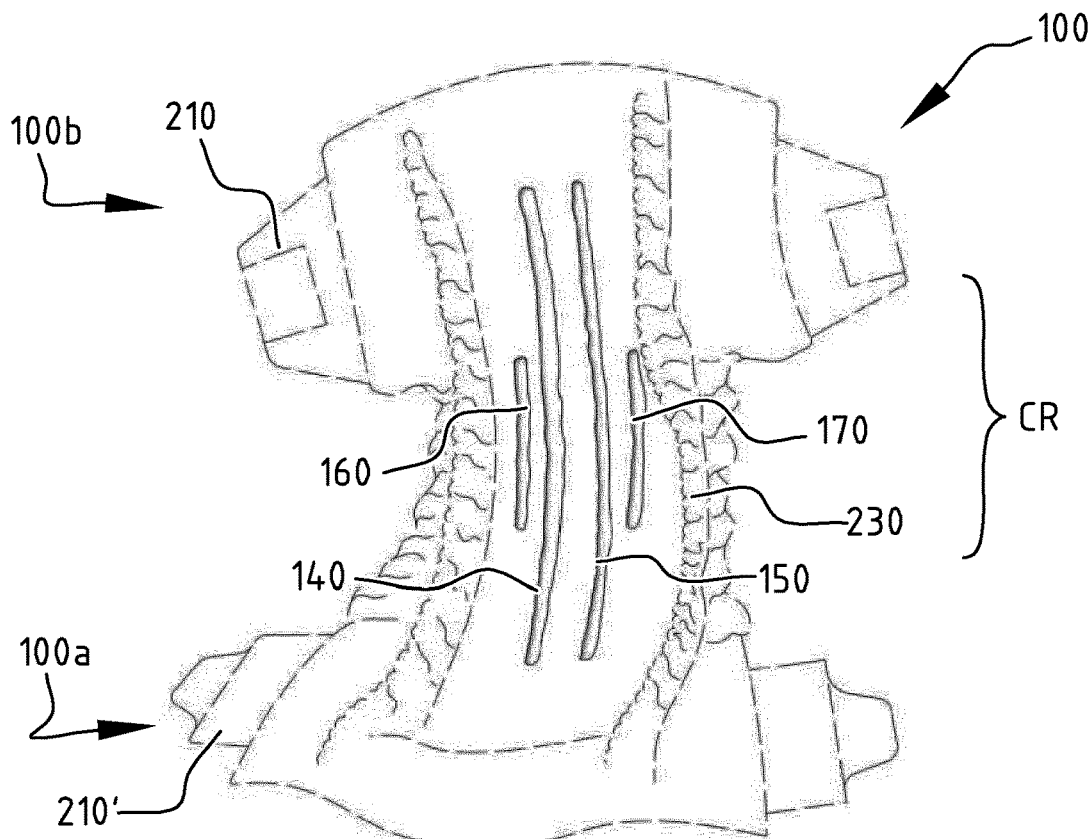
FIG. 2A is a perspective view of an exemplary embodiment of a diaper.
Figure 2B:
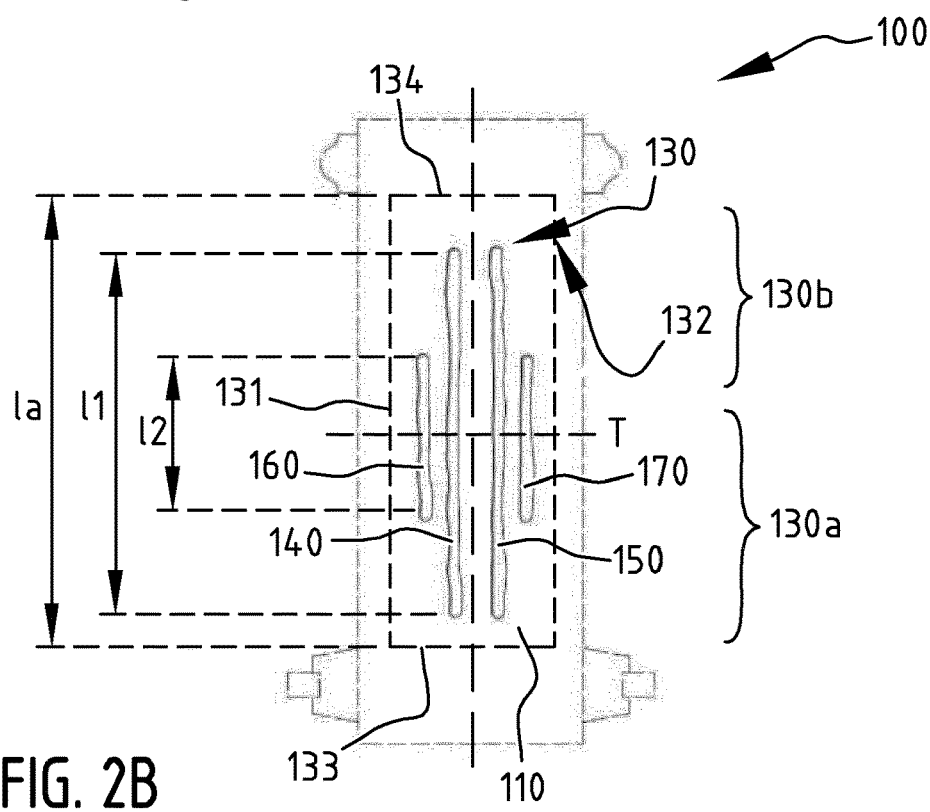
FIG. 2B is a top plan view of the diaper of FIG. 2A.

FIGS. 2A and 2B illustrate another exemplary embodiment of a diaper 100. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided at the top core wrap sheet 110 with a first and a second attachment zone 145, 155 for creating a first and second channel 140, 150 located a distance d12 of each other. First and second channel 140, 150 each extend from a crotch region CR in the direction of the first transverse edge 133 and the second transverse edge 134. In this embodiment, preferably, first and second channel extend over more than 80% of the length of absorbent core 130. Preferably the distance d12 is between 10 mm and 50 mm, more preferably between 15 and 30 mm. Preferably, the length of the first and second channel is substantially the same, more preferably the length 11 of the first channel and the length 12 of the second channel is between 100 mm and 300 mm, more preferably between 100 mm and 250 mm. Preferably, the distance between the first/second attachment zone 145, 155 and the transverse edge 133 is between 50 and 125 mm, more preferably between 75 and 115 mm, and the distance between the first/second attachment zone 145, 155 and the transverse edge 134 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

Absorbent article 100 is further provided with a third and a fourth channel 160, 170 located a distance d34 of each other. Third and fourth channel 160, 170 each extend from crotch region CR in the direction of first and second transverse edge 134. The distance d12 between first and second channel 140, 150 is different from the distance d34 between third and fourth channel 160, 170. Preferably the distance d34 is between 25 mm and 85 mm, more preferably between 35 mm and 55 mm. Preferably, the length of the third and fourth channel 160, 170 is substantially the same, more preferably the length 13 of the third channel and the length 14 of the fourth channel is between 50 mm and 150 mm, more preferably between 60 mm and 140 mm. Preferably, the distance between the third attachment zone 165 and the first longitudinal side 131 is between 10 and 30 mm, and the distance between the second attachment zone 175 and the second longitudinal side 132 is between 10 and 30 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of first transverse edge 133 and second transverse edge 134. Preferably third channel 160 and fourth channel 170 are arranged symmetrically with respect to a longitudinal center line CL of absorbent core 130.

In this embodiment, first, second, third and fourth channel 140, 150, 160, 170 each have a bottom 145, 155, 165, 175, similar to the bottom illustrated in FIG. 1C and FIG. 1D for the first embodiment of FIGS. 1A-1D. At bottom 145, 155, 165, 175 top core wrap sheet 110 is attached to back core wrap sheet 120 as described previously. Outside of the plurality of channels 140, 150, 160, 170, absorbent core 130 has a maximum thickness t. Preferably, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present that between top core wrap sheet 110 and back core wrap sheet 120.

Absorbent core 130 has a front portion 130a extending at one side of a transverse crotch line T, and a rear portion 130b extending at the other side of the transverse crotch line T. First, second, third and fourth channel 140, 150, 160, 170 each extend both in front portion 130a and rear portion 130b of absorbent core 130. Preferably the distance d12 between first and second channel 140, 150 is smaller than the distance d34 between third and fourth channel 160, 170, and the length l1 of first and second channel 140, 150 is bigger than the length l3 of third and fourth channel 160, 170. Such a channel pattern has the advantage that liquid can be distributed over substantially the entire absorbent core 130, and that any leakage risks in various positions of the wearer can be reduced.

The plurality of channels 140, 150, 160, 170 together cover at least 60%, preferably at least 70% of the length la of absorbent core 130; indeed, in the embodiment of FIGS. 1A-1D the channels cover a length equal to l1 which is more than 70% of the length la of absorbent core 130.

The plurality of channels 140, 150, 160, 170 may be indicated in a color and/or with a pattern which is different from the color and/or pattern of topsheet. More in particular the area of the channels may comprise a print allowing a user to visually distinguish the channels. For example, an area of the topsheet above front portions of channels 140, 150, 160, 170 may be printed with an ink of a first color and an area of the topsheet above rear portions the channels 140, 150, 160, 170 may be printed with a different color. In that manner a user will be able to easily recognize the front and rear portion of a diaper, and will recognize more easily how to put on the diaper.

Topsheet, backsheet and absorbent core 130 may have the same features as described above in connection with FIGS. 1A-1D.

Figure 3:
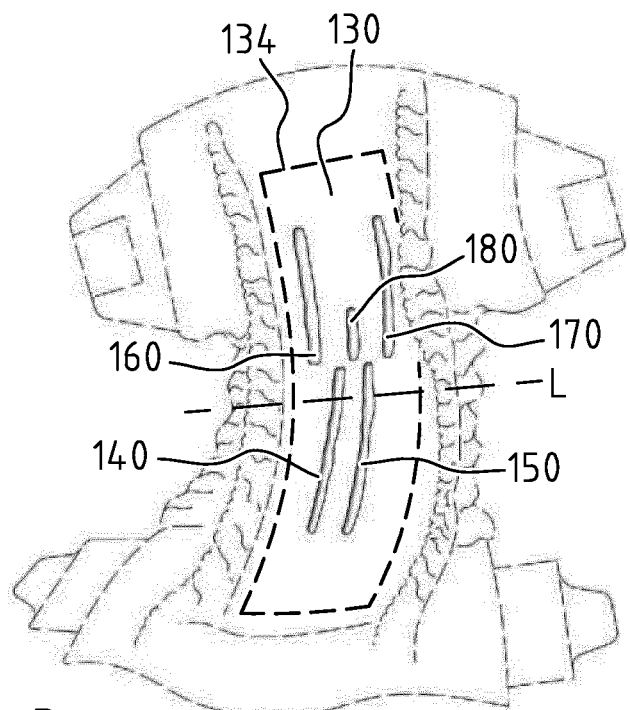
FIGS. 3-8 are perspective view of other exemplary embodiments of a diaper.

FIG. 3 illustrates a variant of diaper 100 of FIGS. 1A-1D. The features and characteristics are similar with this difference that a fifth channel 180 is provided in top core wrap sheet 110, in between third and fourth channel 160, 170 and extending along a longitudinal center line of diaper 100. Further, the first and second channels are slightly longer and extend over transverse fold line L in the direction of second transverse edge 134. The third and fourth channel are slightly shorter compared to the embodiment of FIGS. 1A-1D. By the additional channel 180 the distribution of the liquid can be further improved, especially for larger absorbent articles.

Figure 4:
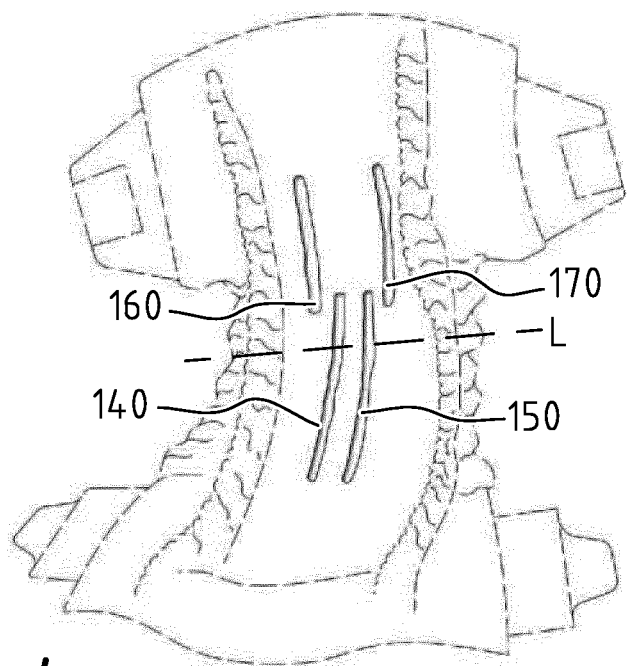

FIG. 4 illustrates a further variant of diaper 100 of FIGS. 1A-1D. The features and characteristics are similar with this difference that the first and second channels are slightly longer and extend over transverse fold line L in the direction of second transverse edge 134, in between third and fourth channel 160, 170. Depending on the shape and size of the absorbent article, the distribution of the liquid and the creation of the cup/tub shape can be further improved by this additional length.

Figure 5:
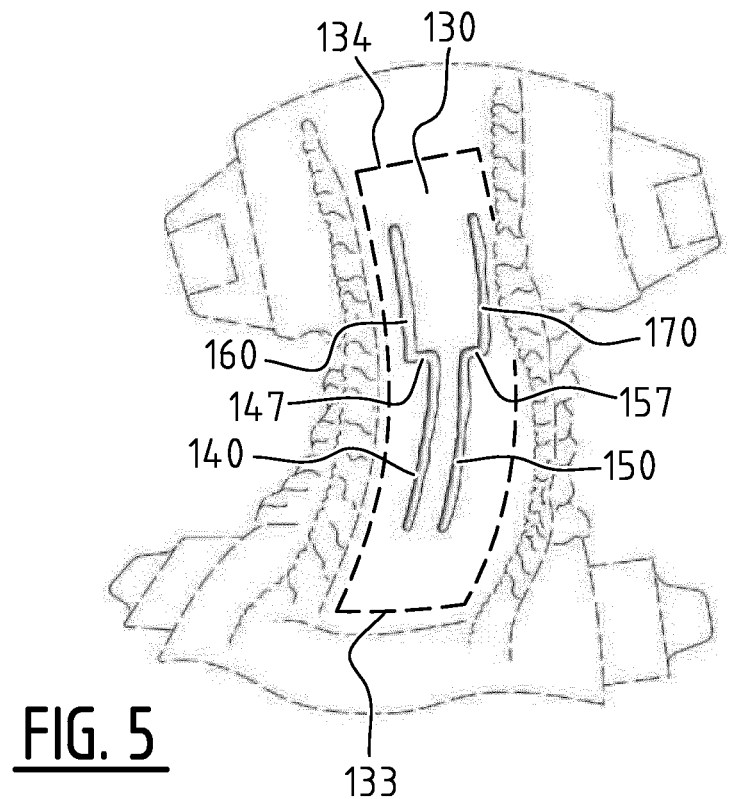

FIG. 5 illustrates a variant of diaper 100 of FIG. 4. The features and characteristics are similar with this difference that first channel 140 is connected to third channel 160 through a first transverse channel portion 147 and that second channel 150 is connected to fourth channel 170 through a second transverse channel portion 157. In that manner any liquid can flow from the first channel 140 to the third channel 160 and vice versa, and liquid can flow from the second channel 150 to the fourth channel 170 and vice versa, resulting in an even better distribution of the liquid. Also, channel portions 147, 157 may help in creating the tub shape upon wetting of the absorbent core 130. Preferably first and second channel 140, 150 extend in a longitudinal direction of absorbent core 130 over a length which is longer than the length of third and fourth channel 160, 170, wherein third and fourth channel extend between crotch region CR and second transverse edge 134 and first and second channel extend between crotch region CR and first transverse edge 133.

Figure 6:
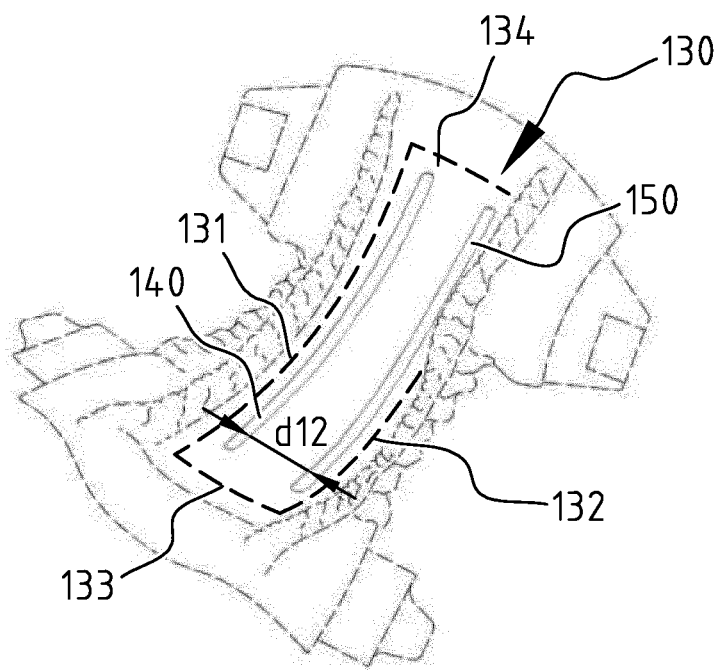

FIG. 6 illustrates another more basic exemplary embodiment of a diaper 100 according to the invention. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided with a first and a second attachment zone for creating a first and a second channel 140, 150 located a distance d12 of each other, upon wetting of the diaper 100. First and second channel 140, 150 each extend from a crotch region CR in the direction of the first transverse edge 133 and the second transverse edge 134. In this embodiment, preferably, first and second channel extend over more than 80% of the length of absorbent core 130. Preferably the distance d12 is between 10 mm and 90 mm, more preferably between 20 mm and 80 mm, even more preferably between 30 mm and 50 mm. Preferably, the length of the first and second channel is substantially the same, more preferably the length l1 of the first channel and the length l2 of the second channel is between 100 mm and 350 mm, more preferably between 150 mm and 300 mm. Preferably, the distance between the first channel 140 and the first longitudinal side 131 is between 10 mm and 30 mm, and the distance between the second channel 150 and the second longitudinal side 132 is between 10 mm and 30 mm. Preferably, the distance between the first/second channel 140, 150 and the transverse edges 133, 134 is between 20 mm and 100 mm, more preferably between 30 mm and 75 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

First and second channel 140, 150 may each have a bottom 145, 155, similar to the bottom illustrated in FIG. 1C for the first embodiment of FIGS. 1A-1D. However, it is noted that the channels 140, 150, 160, 170 may be located below and/or above the attachment zones 145, 155, 165, 175, as will be explained in more detail below with reference to FIG. 14.

At the attachment zones 145, 155, 165, 175 top core wrap sheet 110 is attached to back core wrap sheet 120 as described previously. Outside of the plurality of channels 140, 150, 160, 170 absorbent core 130 has a maximum thickness t. Preferably, in the unwetted state, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present between top core wrap sheet 110 and back core wrap sheet 120.

The areas of the channels 140 and/or 150 and/or 160 and/or 170 may be indicated in a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. Preferably the print is visible when looking at the topsheet of the diaper.

For example, a front portion of the channel 140 and/or 150 and/or 160 and/or 170 may be indicated with an ink of a first color and a rear portion the channels 140 and/or 150 and/or 160 and/or 170 may be indicated with a different color. In that manner a user will be able to easily recognize the front and rear portion of a diaper. Indeed, the user will know that the first color has to be on the left and the second color on the right. Hence he will recognize more easily how to put on the diaper.

Topsheet, backsheet and absorbent core 130 may have the same features as described above in connection with FIGS. 1A-1D.

Figure 7:
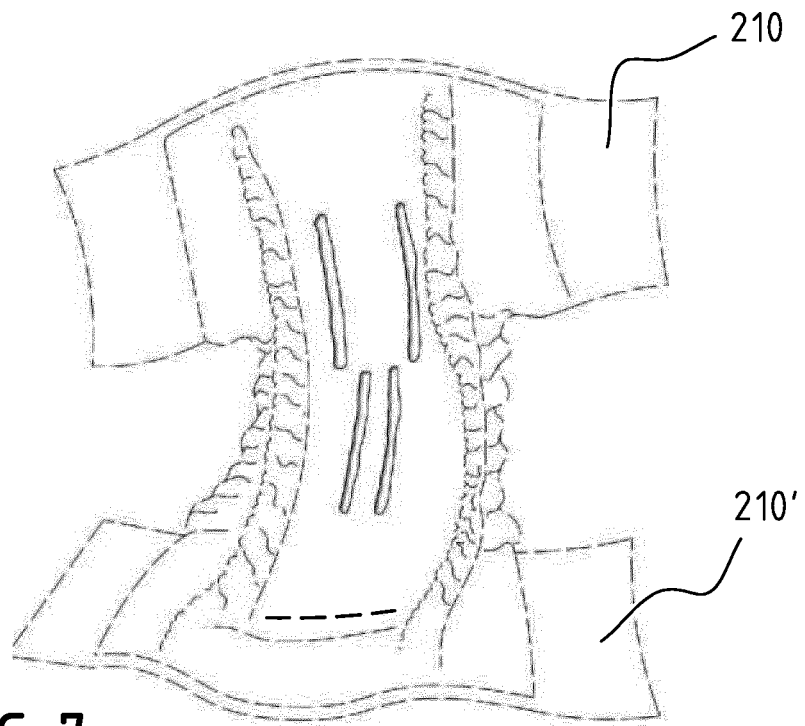
Figure 8:
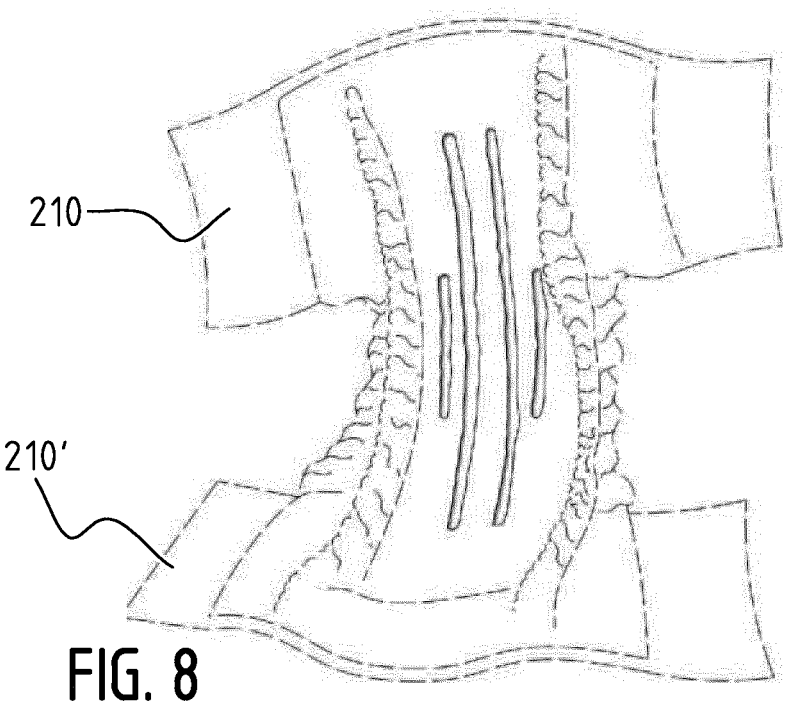

FIGS. 7 and 8 illustrate baby pants variants of the baby diaper embodiments of FIGS. 1A and 2A. In the embodiments of FIGS. 7 and 8 the side panels 210, 210' are larger compared to the embodiments of FIGS. 1A and 2A. It is clear to the skilled person that any embodiment described in view of baby diapers, is applicable in a similar manner to baby pants, mutatis mutandis.

Figure 10:
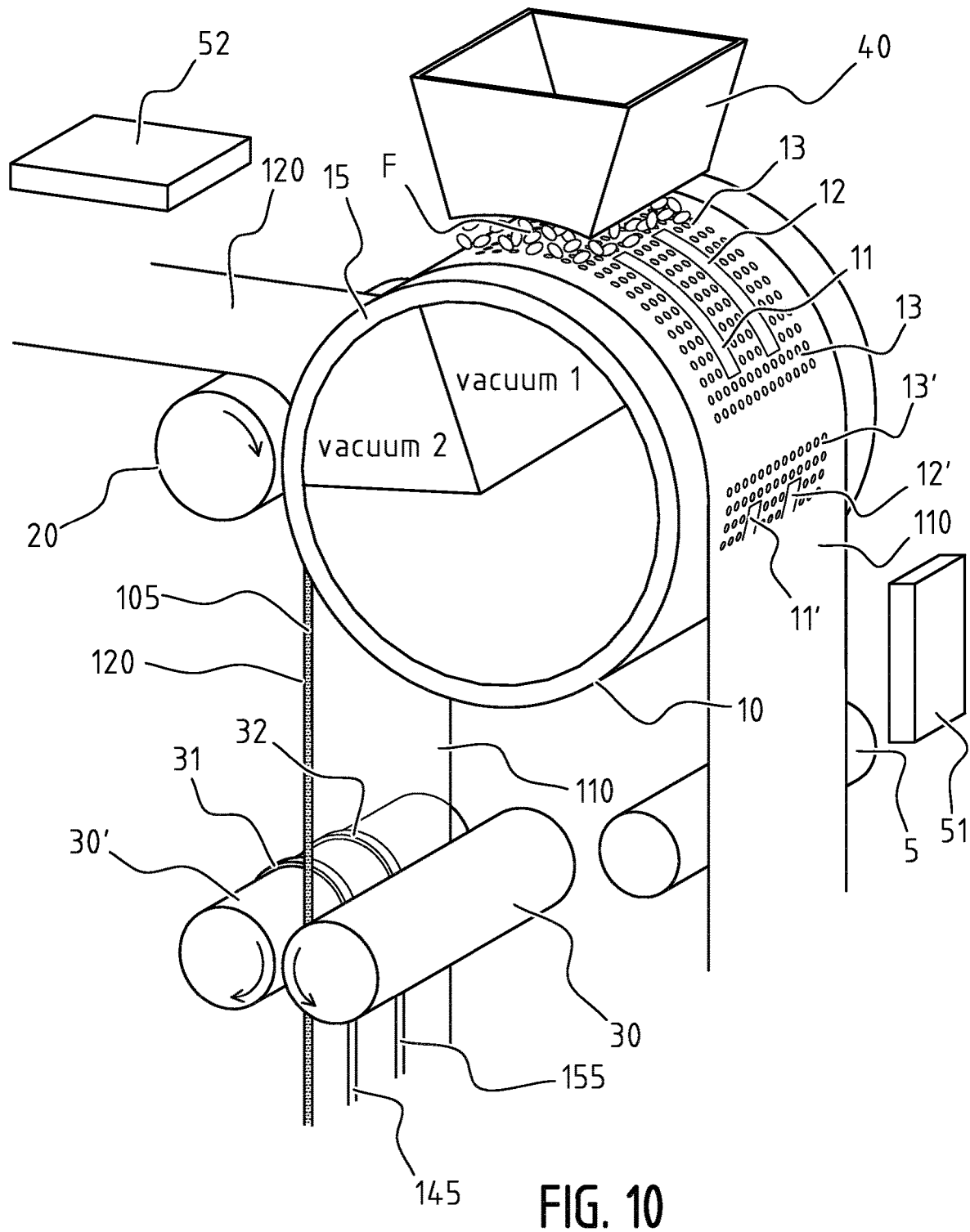
FIG. 10 illustrates schematically an exemplary embodiment of a method and apparatus for manufacturing an absorbent article.

FIG. 10 illustrates an embodiment of a method for manufacturing an absorbent article according to the invention. In this embodiment, the attachment zone takes the form of a plurality of channels. The method comprises in a first step guiding a first sheet material 110 along an optional guide roller 5, and further along a rotating member 10. Binder may be applied to a first area on a first side of the first sheet material by a first means 51, preferably before it arrives at the rotating member 10. In a further step an absorbent material F is applied via a hopper 40 on said first sheet material 110 on the rotating member 10 such that the zones on which the first binder was applied 13, 13' are covered with absorbent material and substantially no absorbent material is present on the areas where the first binder was not applied 11, 12; 11', 12'. Separately from this process, a second binder is applied by means 52 to a second area on a first side of the second sheet material, wherein preferably the area to which the second binder is applied is chosen such that it will substantially complementary to the area to which the first binder is applied after assembly of the first and second sheet materials. In a further step the second sheet material 120 is applied on top of the absorbent material on the first sheet material 110, e.g. using a further rotating member 20.

One of said first and second sheet material is a top core wrap sheet material, and the other one is a back core wrap sheet material. In the illustrated embodiment it is assumed that the first sheet material 110 is the top core wrap sheet material. In a further step the first sheet material 110 is attached to the second sheet material 120 at least in the areas where substantially no absorbent material is present, and such that at least a first and a second liquid distribution zones, which in the example take the form of channels 140, 150, are formed in said top core wrap sheet material 110.

The attaching may be done by applying pressure and heat on the top core wrap sheet material 110 and/or on the back core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat on the top core wrap sheet material 110 in the areas where substantially no absorbent material is present in order to create the first and second channel 140, 150, respectively.

An example of the application of the first and second binders and the assembling of the absorbent core is shown in FIGS. 10A-10D.

In particular, taking as an example the possible manufacturing process for the embodiment of FIGS. 1A and 1B, while the first sheet material 110 is being guided along an optional guide roller and further along a rotating member a binder, such as glue, may first be applied to the first sheet material, but only in substantially parallel stripes which do not overlap with the intended locations of the attachment zones 140, 150, 160, 170. Note that in this embodiment, the first sheet material forms the bottom core wrap, but in other embodiments this can also be the top core wrap. The skilled person will be aware of various method of binder/glue application, such as spraying, contact application and so on.

Figure 10A:
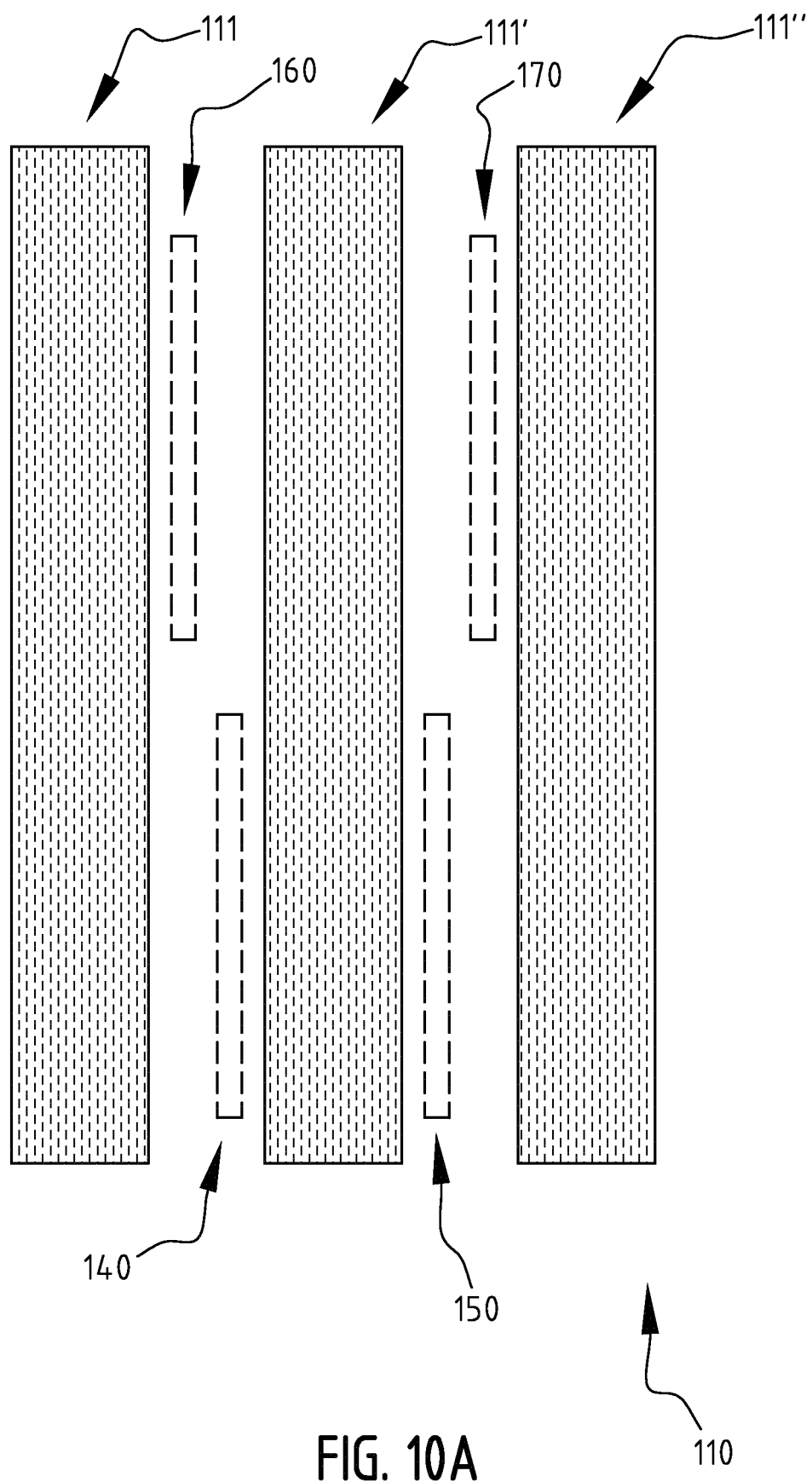
FIGS. 10A-10D illustrate a method for manufacturing an absorbent article, wherein 10A shows glue application to the bottom core wrap, 10B shows glue application to the top core wrap, 10C shows the combined bottom and top core wraps, and 10D shows the absorbent article after the manufacturing steps.

FIG. 10A shows a possible pattern for the application of glue to the first sheet material, which will be the back core wrap. In particular, in this example there are three stripes 111, 111', 111", but a different number of substantially parallel stripes, either continuous, intermittent and/or discontinuous in the longitudinal direction, may also be chosen depending on the shape and locations of the attachment zones 140, 150, 160, 170, which preferably cover a substantial portion of the surface of the bottom core wrap while not overlapping with the intended location of the attachment zones, and preferably while keeping some distance from the intended location of the attachment zones. Although, FIG. 10A illustrates an application pattern of stripes, it is clear to the skilled person that the application pattern can be adapted and tuned depending on the intended shape, configuration and location of the one or more attachment zones. Moreover, the skilled person will know how to best adapt the binder application zones on the first and second sheet materials 110, 120 for other configurations of attachments zones, such as the ones described in the present application. Preferably, the application of the glue to the bottom core wrap takes place while the bottom core wrap is moved towards the rotating number, and before the absorbent material is added to it. In such a way, the sheet material on the rotating member is already provided with binder, and may subsequently have absorbent material attached thereto via the hopper.

Please note that the dotted line indicating the intended location of the attachment zones is there for illustrative purposes only: it does not correspond to anything on the first sheet material 110.

Figure 10B:
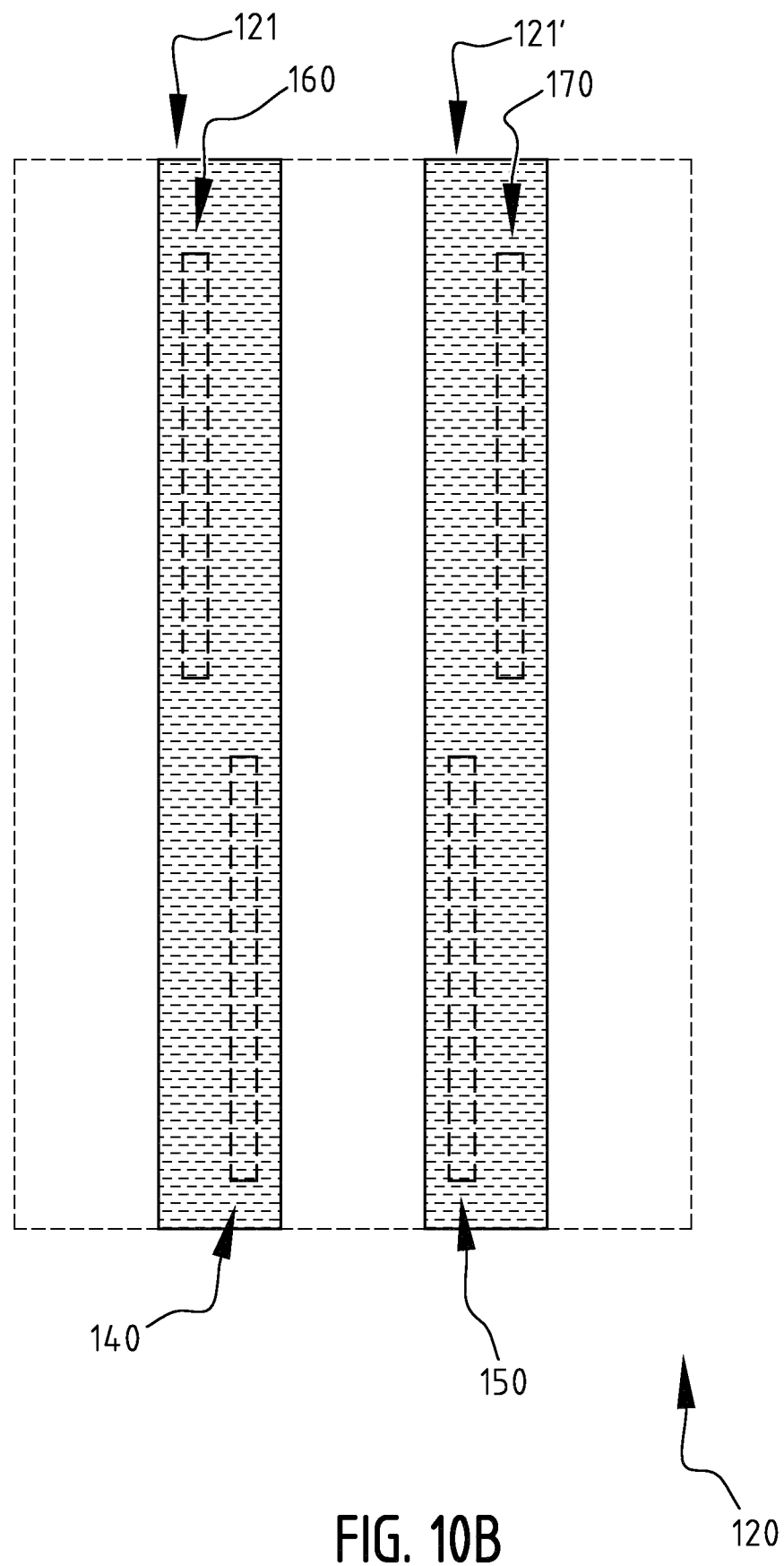

FIG. 10B shows application of glue to the second sheet material 120, which in this case will become the top core wrap. In this case too the application of the binder preferably happens along substantially parallel stripes 121, 121', which preferably are complementary to the stripes on the first sheet material 110. Preferably, the application of glue to the top core wrap sheet happens at a distance from hopper 40, to minimize the chance of contamination, i.e. absorbent material sticking to the areas that are to become attachment zones 140, 150, 160, 170. For instance, the binder may be applied before or while the sheet material is guided along further rotating member 20. Note that here, too, the dotted lines merely indicate the intended position of the attachment zones 140, 150, 160, 170; they do not indicate any interruption or change in the binder application. As before, the skilled person will be aware of various method of binder/glue application, such as spraying, contact application and so on.

Figure 10C:
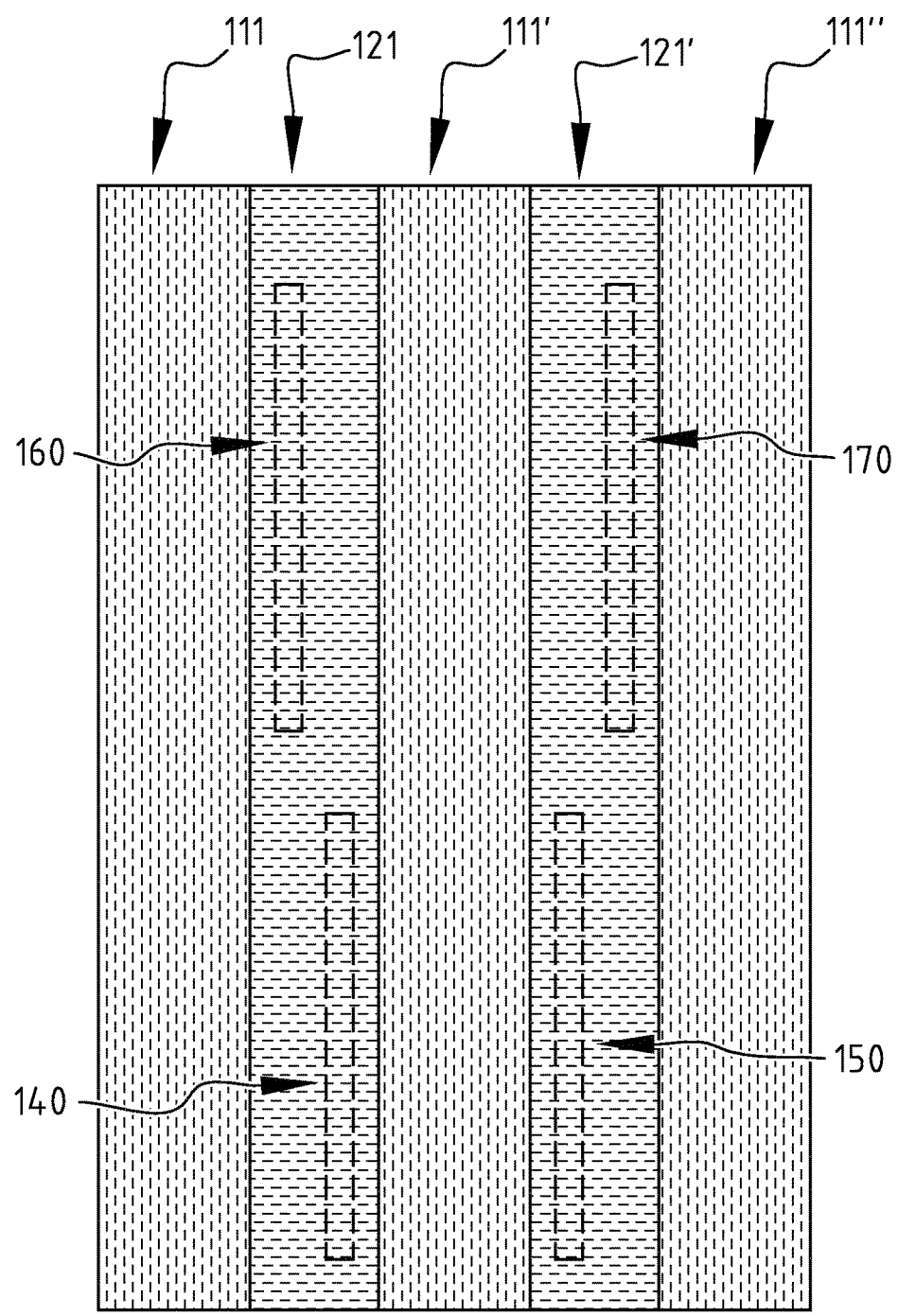

FIG. 10C shows the result. after the second sheet material 120, which here is the top core wrap sheet, is applied on top of the absorbent material on the first sheet material 110, e.g. using a further rotating member 20. Note that the pattern fill indicates the presence of binder, and not the presence of absorbent material, since the absorbent material will not be present in the areas indicated by the dotted lines. These areas will be bonded together in a fourth step such as described above, such that channels 140, 150, 160 and 170 are formed in said back core wrap sheet materials 110 and/or 120, for instance by applying pressure and heat on the back core wrap sheet material 110 and/or on the top core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat in between the core wrap sheet materials 110 and 120 in the areas where substantially no absorbent material is present in order to create the channels 140, 150, 160 and 170.

Figure 10D:
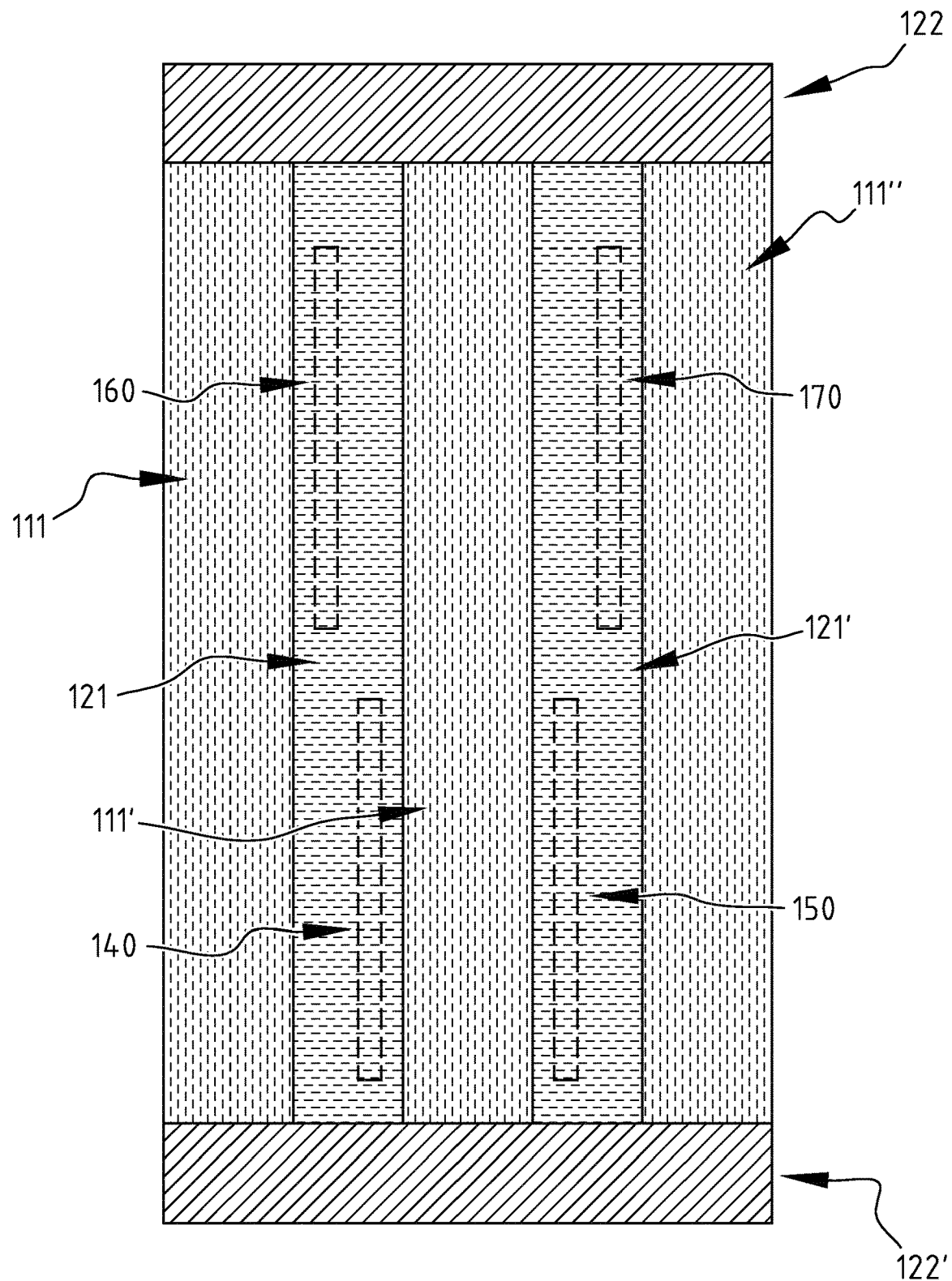

Finally, FIG. 10D shows the absorbent article resulting from the above-described method, in which a further step has taken place of traversal sealing in bands 122, 122' by chemical, thermal or physical binding such as for in stance glue, heat and/or pressure, which prevents the core from opening up and the front and the back. Note that this step of transversal sealing may also take place prior to the fourth step.

The above-described method may yield an absorbent article with higher dry and especially wet integrity and which avoids unwanted migration of absorbent material, while avoiding the risk of contamination in the attachment zones 140, 150, 160 and 170 which may impede the formation of channels. The skilled person will understand that this method is not limited to this particular configuration of attachment zones and will know how to best adapt the binder application zones on the first and second sheet materials 110, 120 for other configurations, such as the ones described in the present application. More in particular the skilled person understands that the method is also useful for absorbent cores with only one attachment zone or with more than two attachment zones.

Figure 10E:
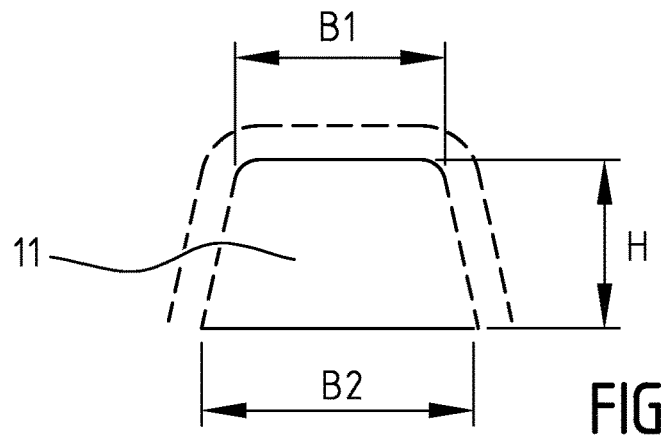
FIG. 10E-10H illustrate elements relating to the exemplary method in which suction is used.
Figure 10F:
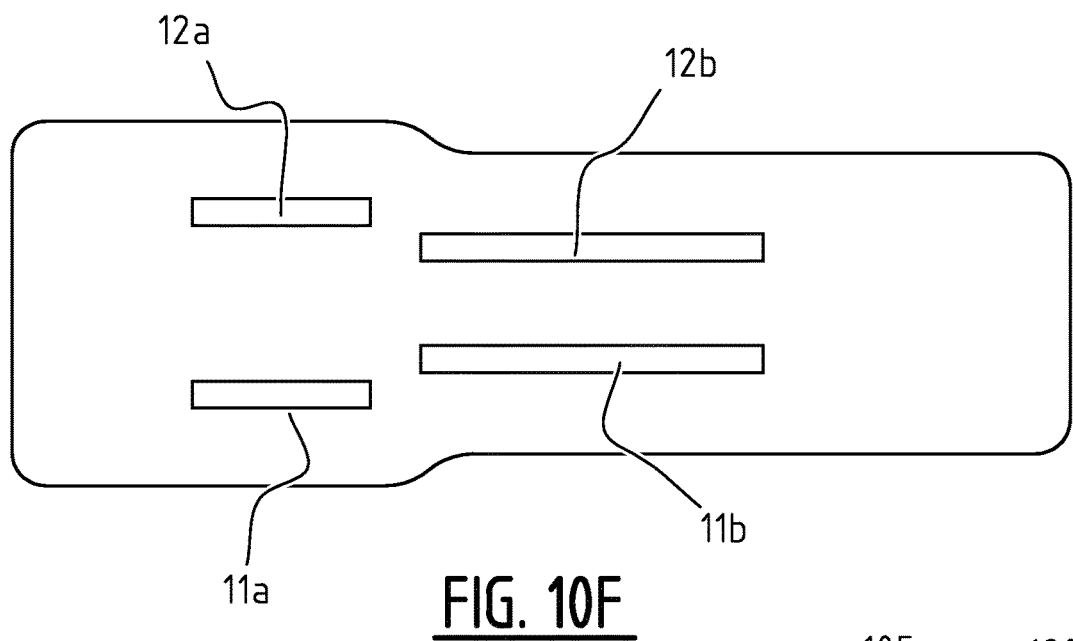
Figure 10G:
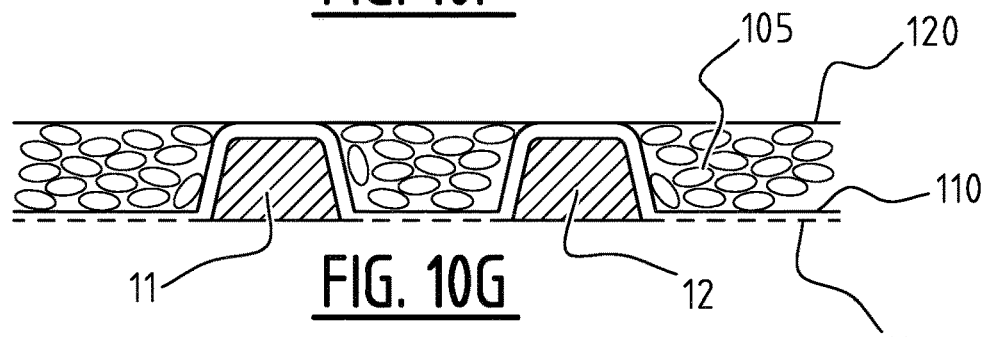
Figure 10H:
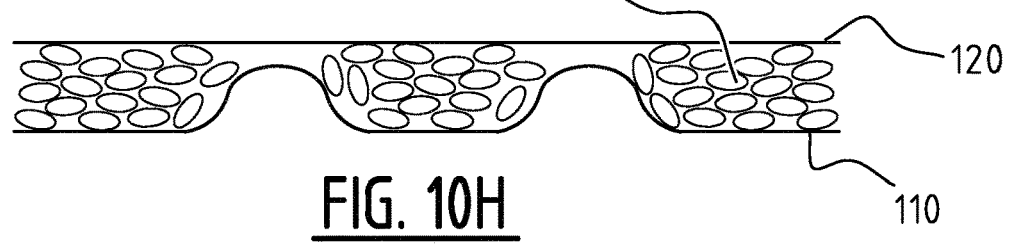

Advantageously, suction may be used to apply the absorbent material. In particular a surface 15 of said rotating member 10 may be provided with a pattern with suction zones 13, 13' and non-suction zones 11, 12; 11', 12'. The first sheet material 110 is shown in FIG. 10 in a transparent manner to reveal the suction and non-suction zones of the rotating member 10. The suction zones 13, 13' may be provided with holes, and the non-suction zones 11, 12; 11', 12' are formed of closed material. For example, the non-suction zones 11, 12; 11', 12' may be provided with inserts as shown in FIG. 10E. As shown in FIG. 10E, the inserts 11, 12; 11', 12', may have a trapezoidal cross section. FIG. 10F shows an insert pattern with four non-suction zones 11a, 11b, 12a, 12b per absorbent core. The inserts may be fixed e.g. with screws on the rotating member 10. At an inner area of the rotating member 10 a vacuum is applied, see VACUUM 1 in FIG. 10. The non-suction zones 11, 12; 11', 12' comprise at least a first elongate zone 11, 11' and a second elongate zone 12, 12' extending in a circumferential direction of the rotating member 10. This is shown also in FIG. 10G where a cross section through the absorbent core is shown during the application of the second sheet material 120. FIG. 10H shows the cross section of the absorbent core downstream of rotating member 10.

Use of suction as well as the first and second binder in combination has the advantage of ensuring both a strong bond between the layers and a desired distribution of absorbent material.

Figure 11A:
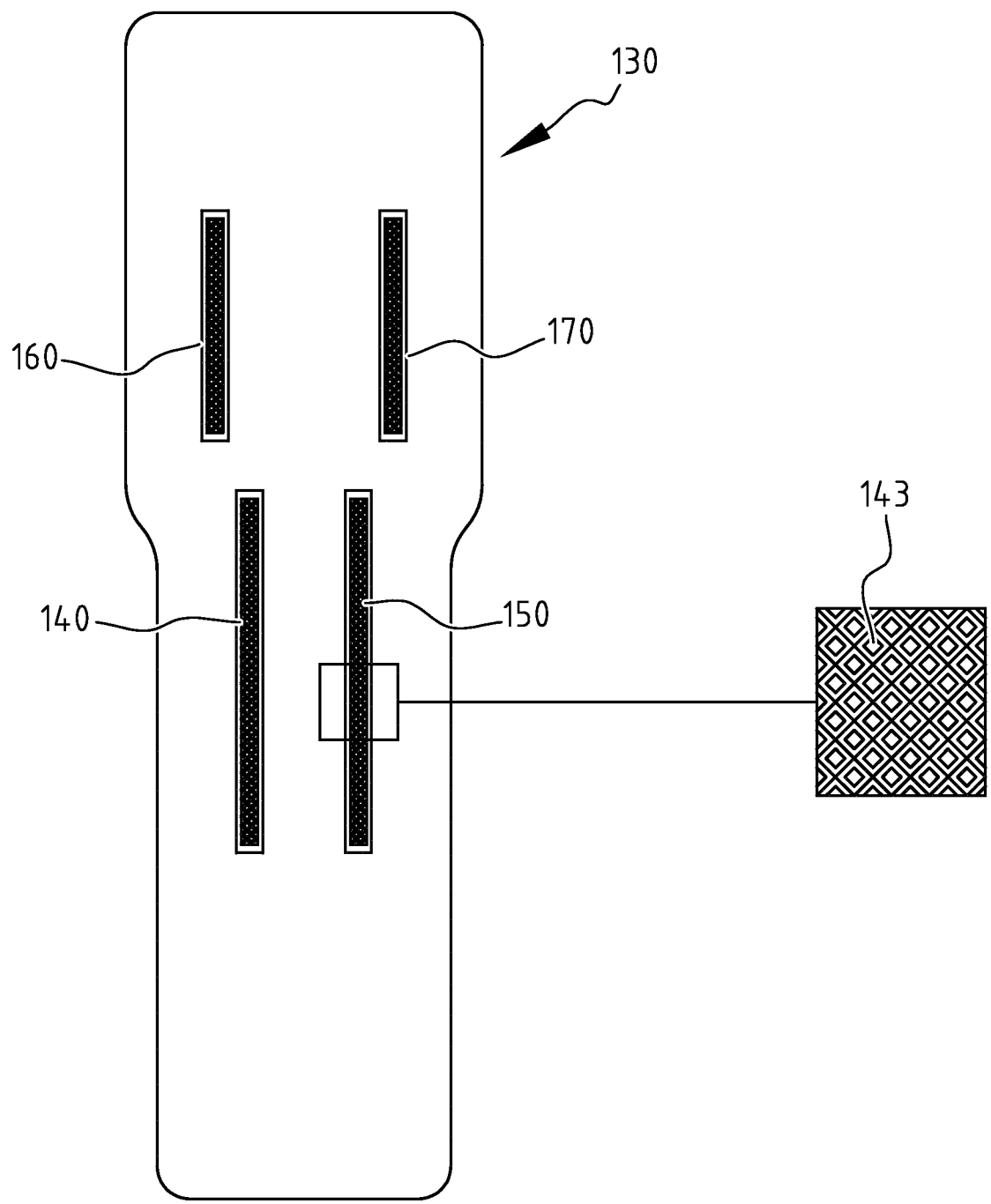
FIG. 11A shows a top view of an exemplary embodiment of an absorbent core with four attachment zones using a first exemplary embodiment of a sealing pattern.

FIG. 11A illustrates an exemplary embodiment of an absorbent core 130 with four attachment zones creating channels 140, 150, 160, 170. In the embodiment of FIG. 11A, the attachment zones are formed by welding the top core wrap sheet 110 to the back core wrap sheet 112. This welding may be done according to a predetermined sealing pattern. In the embodiment of FIG. 11A, the pattern consists of a plurality of discrete shapes 143, here a plurality of squares. Preferably, the discrete shapes 143 have dimensions smaller than 2 mm. Preferably, the distance between adjacent discrete shapes is between 0.5 and 3 mm.

Figure 11B:
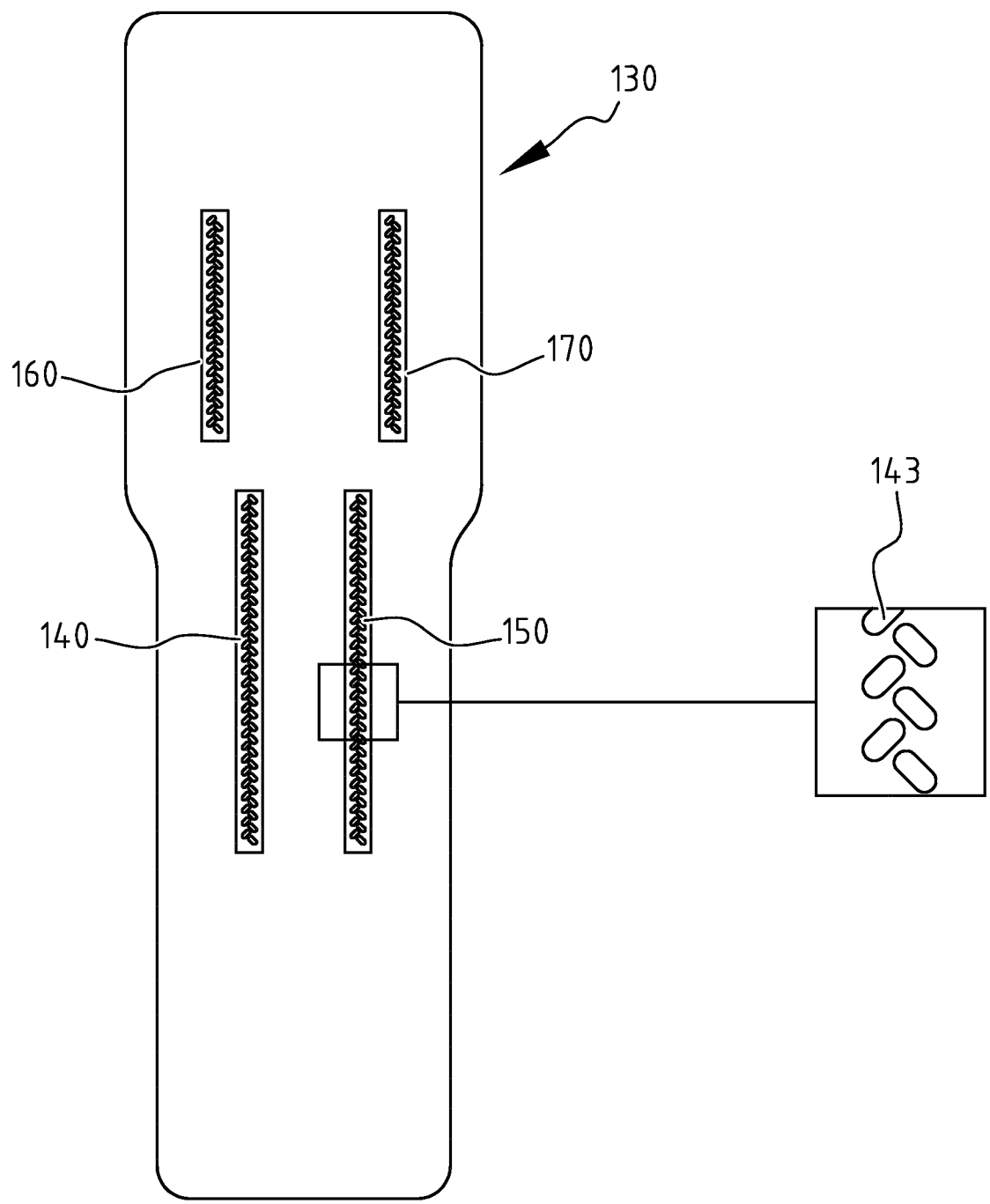
FIG. 11B shows a top view of an exemplary embodiment of an absorbent core with four attachment zones using a second exemplary embodiment of a sealing pattern.

FIG. 11B illustrates another exemplary embodiment of a sealing pattern that may be used in an embodiment of the invention. Here the pattern consists of a plurality of discrete shapes in the form of rounded elements 143. The rounded elements may have a length dimension between 0.5 mm and 5 mm, and a width dimension between 0.5 mm and 5 mm. Preferably, the discrete shapes are equally distributed in the attachment zones.

Figure 11C:
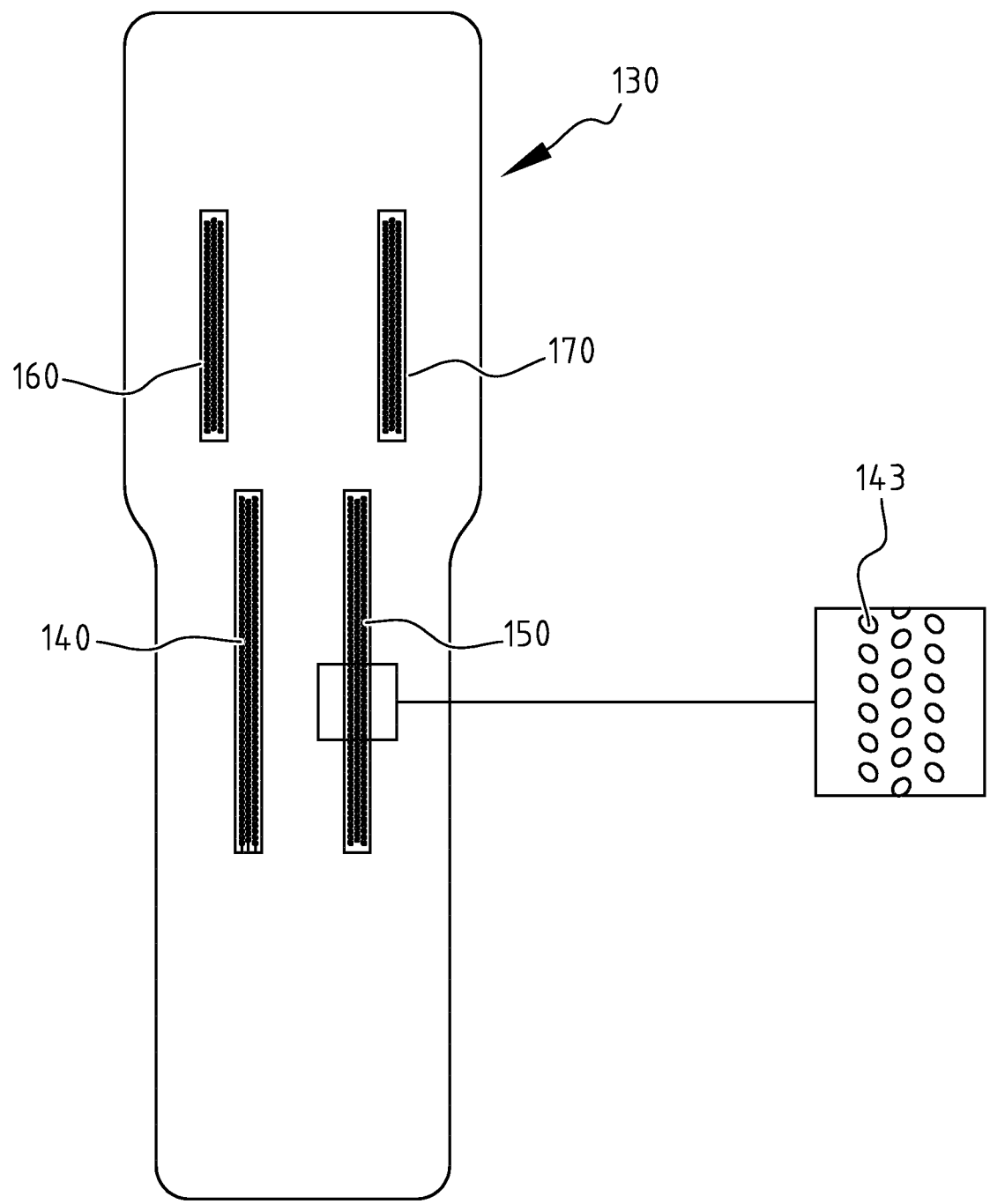
FIG. 11C shows a top view of an exemplary embodiment of an absorbent core with four attachment zones using a third exemplary embodiment of a sealing pattern.

FIG. 11C illustrates yet another embodiment where the sealing pattern consists of discrete shapes which are rounded. In this embodiment, three columns of rounded discrete elements 143 are used for each attachment zone 140, 150, 160, 170.

Figure 11D:
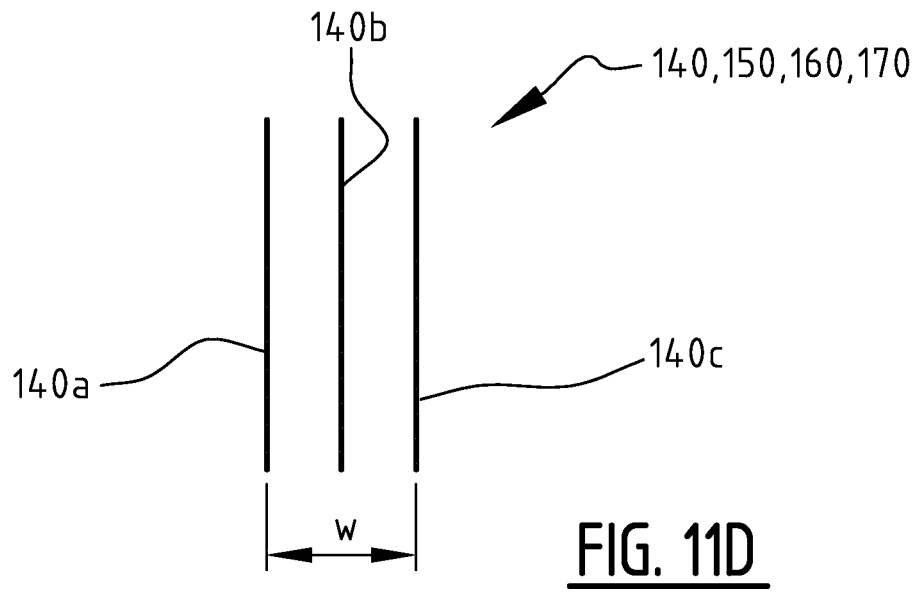
FIG. 11D illustrates a fourth exemplary embodiment of a possible sealing pattern.

FIG. 11D illustrates another exemplary embodiment of an attachment zone for creating a channel 140, 150, 160, 170. In this embodiment, the attachment zone is formed by a plurality of continuous line-shaped attachments 140a, 140b, 140c. The number of lines used may vary, and may be e.g. two lines or more than three adjacent lines. Preferably, the distance w between a first line 140a and a last line 140c is at least 1 mm, more preferably at least 2 mm, even more preferably more than 4 mm.

Figure 11E:
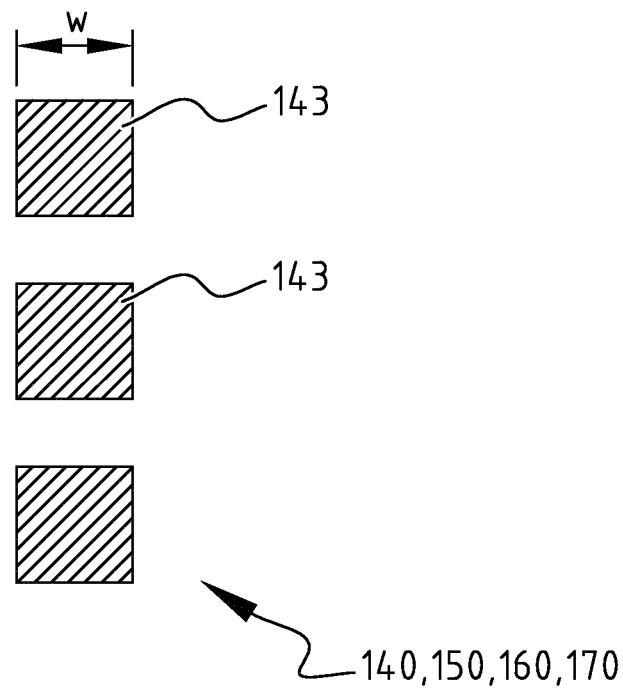
FIG. 11E illustrates a fifth exemplary embodiment of a possible sealing pattern.

In the exemplary embodiment of FIG. 11E, the attachment zones creating channels 140, 150, 160, 170 may be formed of a plurality of discrete elements 143, wherein each discrete element has a width w which covers the entire width w of the attachment zone.

Figure 12:
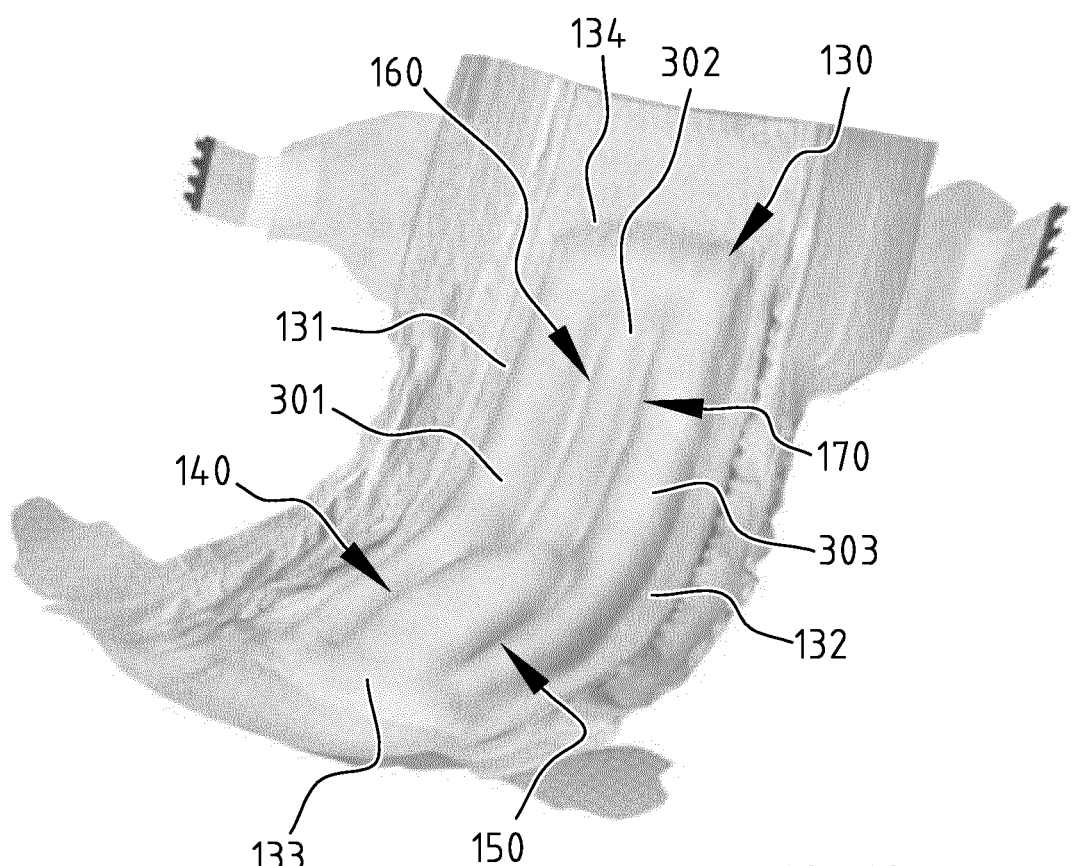
FIG. 12 is a perspective view of an exemplary embodiment of a diaper in a wetted state.
Figure 13A:
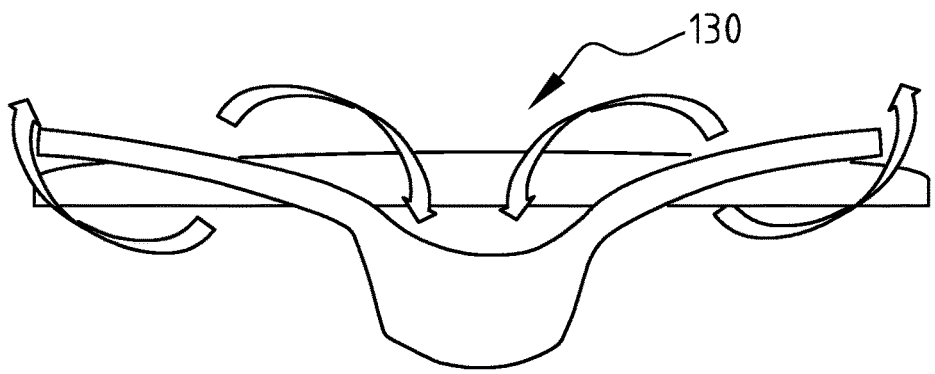
FIGS. 13A and 13B are cross-sectional views illustrating the effect of liquid being absorbed by a traditional absorbent core and liquid being absorbed by an absorbent core according to an exemplary embodiment of the invention, respectively.
Figure 13B:
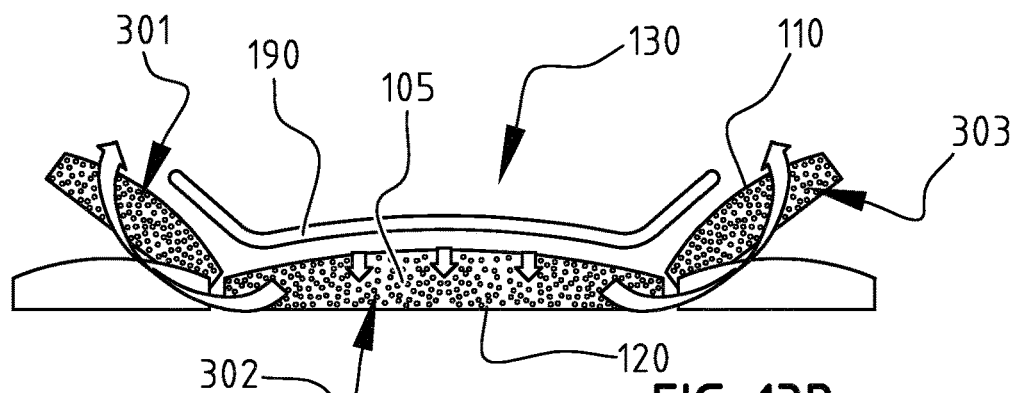

FIG. 13A illustrates an exemplary embodiment of a traditional absorbent core. When a traditional absorbent core absorbs liquid, the core becomes bulky such that the diaper is no longer well adapted to the body. The liquid does not spread evenly but remains in the center of the absorbent core. FIG. 13B illustrates an exemplary embodiment of an absorbent core of the invention. Thanks to the attachment zones and associated channels 140, 150, 160, 170, the liquid is evenly spread, resulting in the formation of tubes 301, 302, 303 which provide a tub shape to the absorbent core 130. Such a tub shape adapts perfectly to the body. Further, compared to prior art solutions, the liquid is kept in an improved manner absorbed in the absorbent core 130, and the risk on leakage is reduced. Also, because of the creation of the channels 140, 150, 160, 170, the liquid is absorbed faster. FIG. 12 shows a perspective view of a diaper in the wetted state. FIG. 12 clearly illustrates the formation of three tubes 301, 302, 303 giving the diaper a tub shape which is well adapted to the body.

Figure 14:
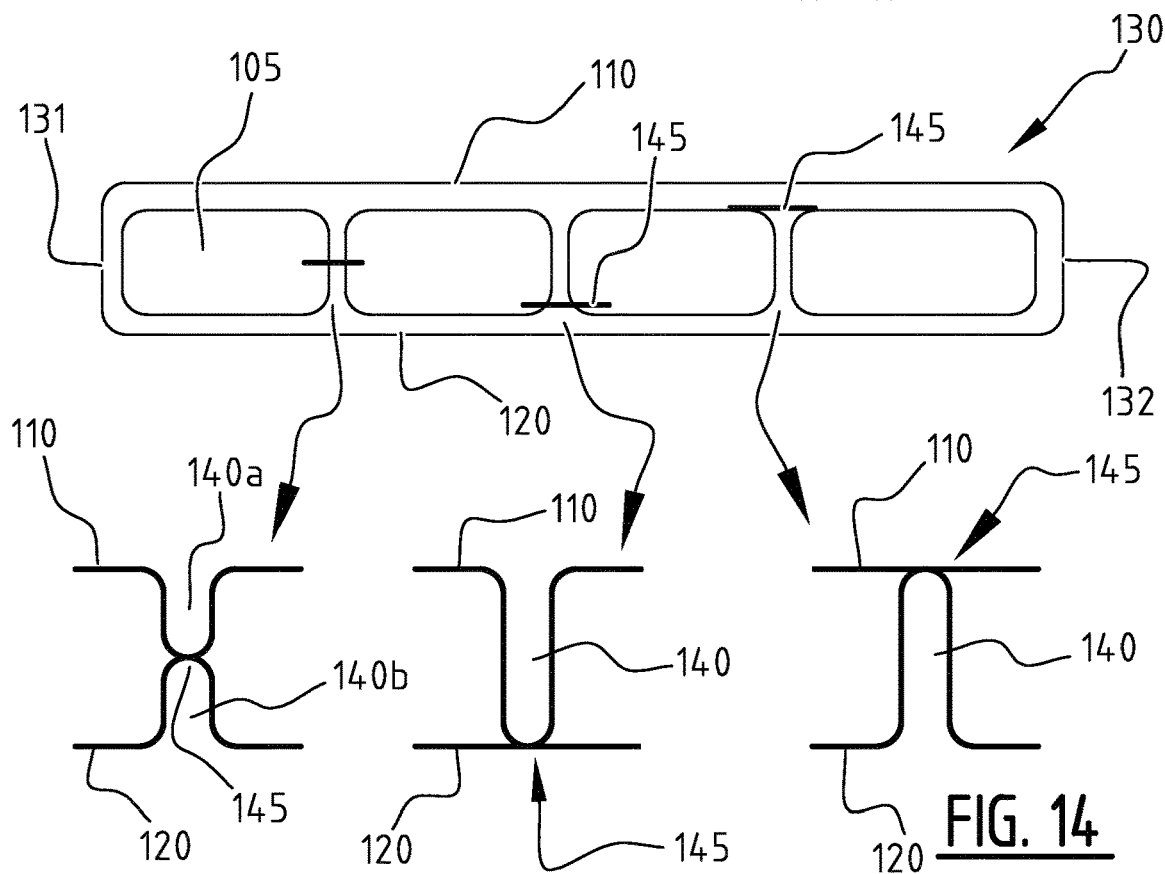
FIG. 14 illustrates a schematic cross-section of an absorbent core, wherein three possible locations are indicated for the attachment zones.

FIG. 14 illustrates an absorbent core 130 comprising an absorbent material 105 between a top core wrap sheet 110 and a back core wrap sheet 120. The absorbent core has a first and second longitudinal edge 131, 132. The absorbent core 130 is provided with a plurality of attachment zones 145. FIG. 14 illustrates that the attachment zones 145 may be positioned at different locations. As illustrated on the left in FIG. 14, the attachment zone may be positioned more or less centrally such that an upper channel portion 140a and a lower channel portion 140b is formed. In an alternative embodiment, the attachment zone 145 may be positioned at the bottom such that an upper channel 140 is created, see the example in the middle of FIG. 14. According to yet another embodiment, the attachment zone 145 may be located at the top, such that the channel 140 is formed below top core wrap sheet 110. The skilled person understands that any variants thereof are also possible, as long as the attachment zones allow the formation of channels upon wetting of the absorbent core 130.

Although the method is illustrated for two channels, the skilled person understands that the method can be adapted for forming three, four or more channels, and in particular for manufacturing any one of the absorbent articles disclosed in the present application.

FIGS. 15A-15X, 16A-16S, 17A-17V and 18A-F illustrate multiple advantageous positions for the attachment zones in an absorbent core according to the invention.

Figure 15A:
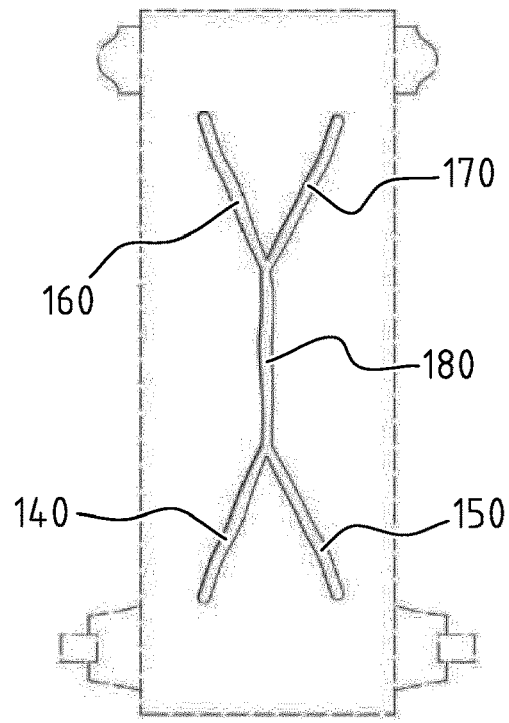
FIGS. 15A-15X illustrate exemplary embodiments of an absorbent core according to the invention.

According to the exemplary embodiment of FIG. 15A the plurality of attachment zones comprises a first attachment zone 140, a second attachment zone 150, a third attachment zone 160 and a fourth attachment zone 170, and a central attachment zone 180. The first and second attachment zones 140 diverge from the central attachment zone 180 in the crotch region in the direction of a rear transverse edge of absorbent core. The third and fourth attachment zone 160, 170 diverge from the central attachment zone 180 in the crotch region in the direction of a front transverse edge of absorbent core.

Figure 15B:
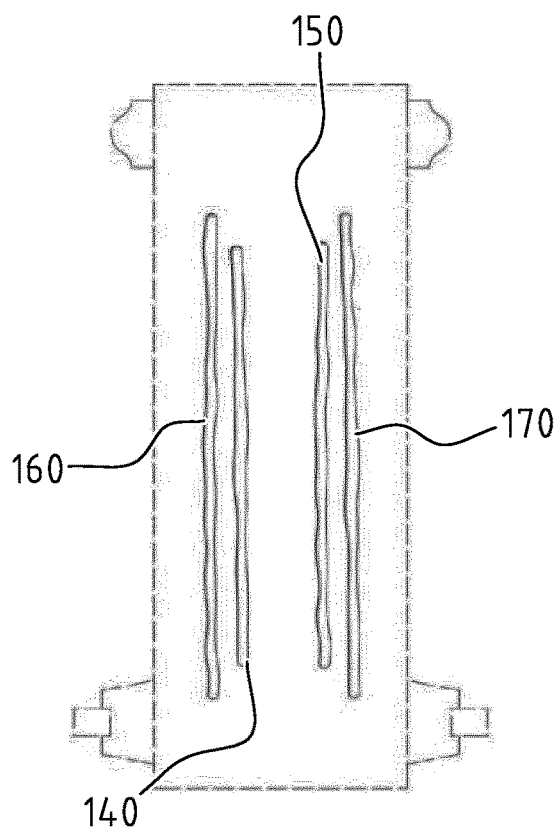

According to the exemplary embodiment of FIG. 15B the plurality of attachment zones comprises a first attachment zone 140, a second attachment zone 150, a third attachment zone 160 and a fourth attachment zone 170. This embodiment is similar to the embodiment of FIG. 2A-2B, with this difference that the outer attachment zones 160, 170 are longer than the inner attachment zones 140, 150.

Figure 15C:
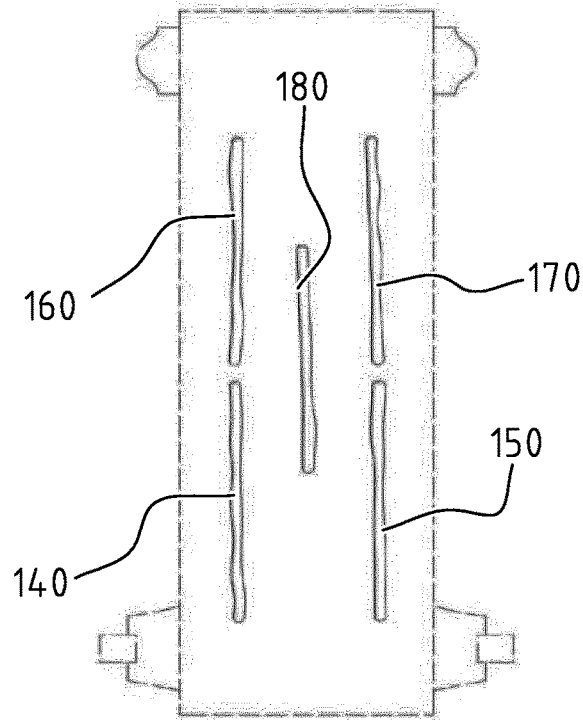

According to the exemplary embodiment of FIG. 15C the plurality of attachment zones comprises a first attachment zone 140, a second attachment zone 150, a third attachment zone 160 and a fourth attachment zone 170, and a central attachment zone 180. The first and third attachment zones 140, 160 are aligned in the longitudinal direction. Also, the second and fourth attachment zones 150, 170 are aligned and extend substantially parallel to the first and third attachment zones 140, 160.

Figure 15D:
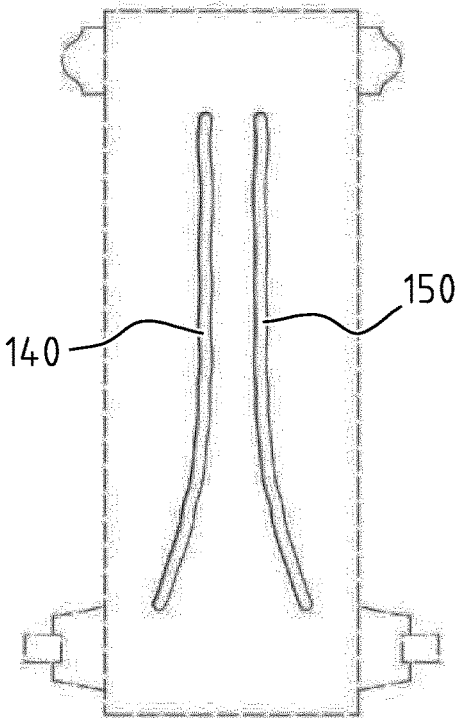

According to the exemplary embodiment of FIG. 15D the plurality of attachment zones comprises a first attachment zone 140 and a second attachment zone 150. The first and second attachment zones 140 are substantially parallel in the crotch region and diverge in the direction of a front transverse edge of absorbent core.

Figure 15E:
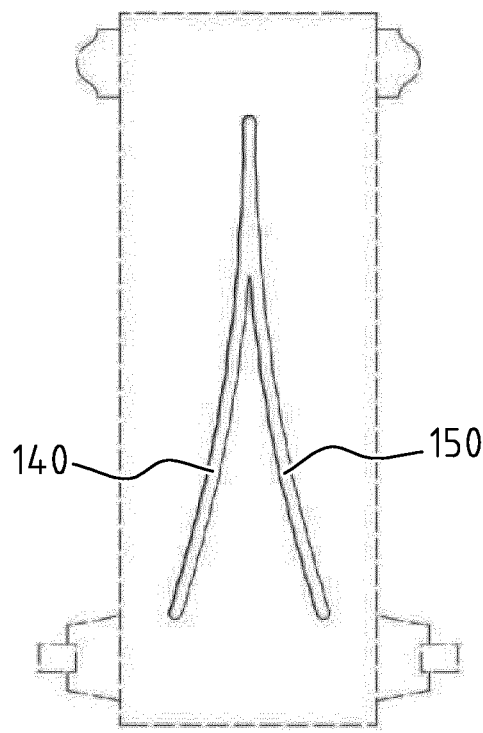

According to the exemplary embodiment of FIG. 15E the plurality of attachment zones comprises a first attachment zone 140 and a second attachment zone 150. The first and second attachment zones 140 partially overlap in the crotch region and diverge in the direction of a front transverse edge of absorbent core.

Figure 15F:
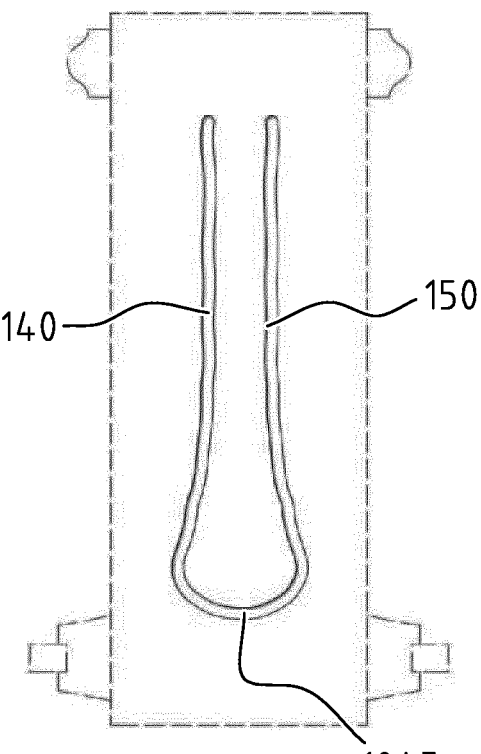

According to the exemplary embodiment of FIG. 15F the plurality of attachment zones comprises a first longitudinal attachment zone 140 and a second longitudinal attachment zone 150 which are interconnected by an attachment portion 1045 in a front part of the absorbent core. In that manner any leakage via the front part can be reduced or avoided.

Figure 15G:
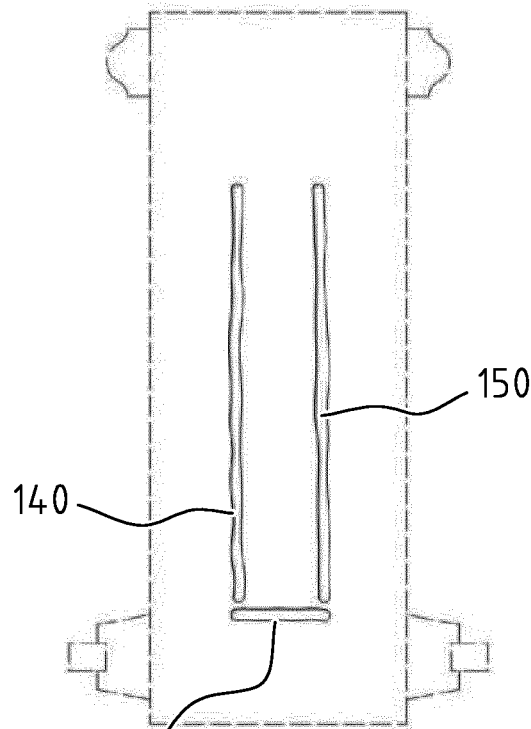

According to the exemplary embodiment of FIG. 15G the plurality of attachment zones comprises a first longitudinal attachment zone 140, a second longitudinal attachment zone 150, and a transverse attachment zone 1045 in a front part of the absorbent core. The transverse attachment zone 1045 substantially connects a front end of first longitudinal attachment zone 140 and a front end of second longitudinal attachment zone 150

Figure 15H:
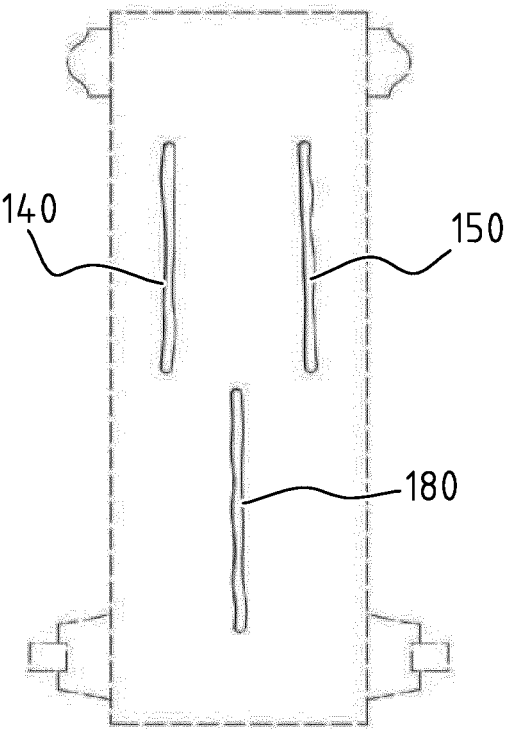

According to the exemplary embodiment of FIG. 15H the plurality of attachment zones comprises a first longitudinal attachment zone 140, a second longitudinal attachment zone 150, a central longitudinal attachment zone 180. The first and second longitudinal attachment zones 140, 150 extend adjacent to each other from the crotch region to a rear transverse edge of the absorbent core.

The central longitudinal attachment zone 180 extends from the crotch region in the direction of the front transverse edge of the absorbent core.

Figure 15I:
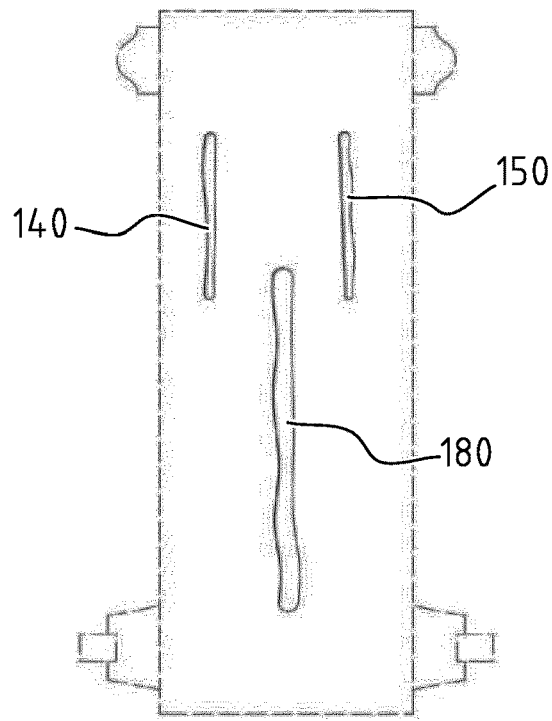

The exemplary embodiment of FIG. 15I is similar to the embodiment of FIG. 15H, with this difference that the central attachment zone 180 extends also from the crotch region in the direction of the rear transverse edge, partially in between the first and second attachment zone 140, 150.

Figure 15J:
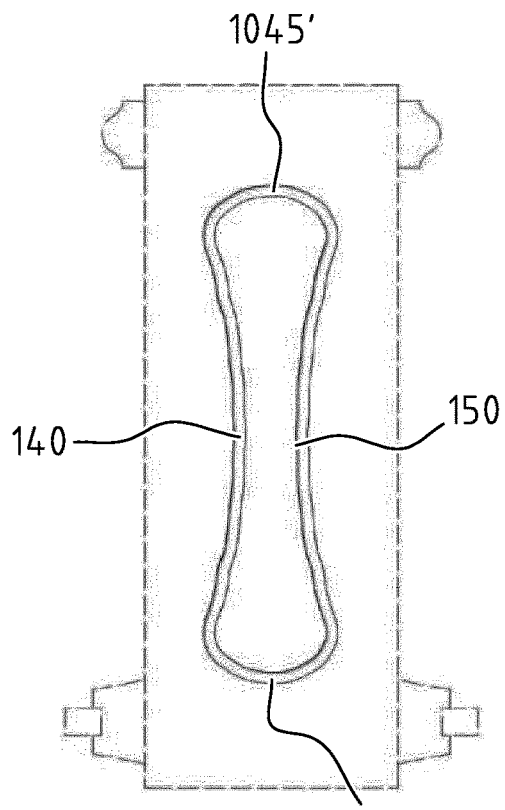

According to the exemplary embodiment of FIG. 15J the plurality of attachment zones comprises a first longitudinal attachment zone 140 and a second longitudinal attachment zone 150 which are interconnected by an attachment portion 1045 in a front part of the absorbent core and an attachment portion 1045' in a rear part of the absorbent core. In that manner any leakage via the front and rear part can be reduced or avoided.

Figure 15K:
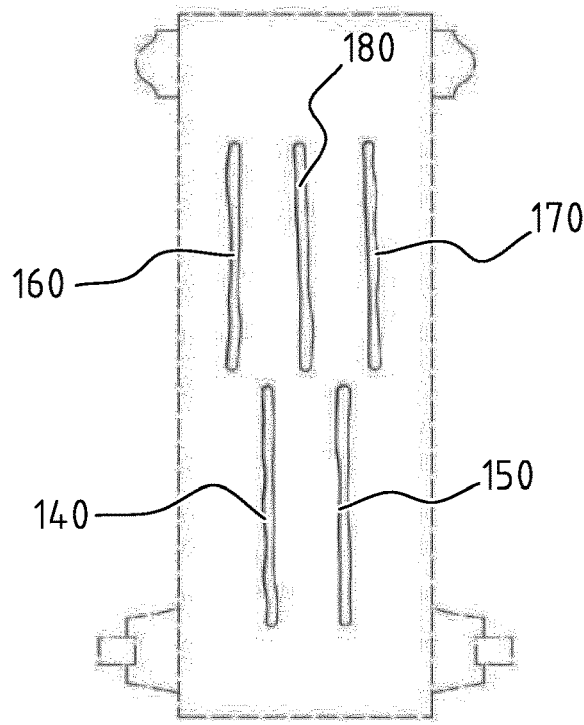

According to the exemplary embodiment of FIG. 15K the plurality of attachment zones comprises a first attachment zone 140, a second attachment zone 150, a third attachment zone 160 and a fourth attachment zone 170, and a central attachment zone 180. The first and second attachment zones 140, 150 extend adjacent to each other from a crotch region in the direction the front transverse edge. Also, the third and fourth attachment zones 160, 170, as well as the central attachment zone extend adjacent to each other from a crotch region in the direction the rear transverse edge. In that manner the distribution of liquid in the rear part of the absorbent core can be further enhanced.

Figure 15L:
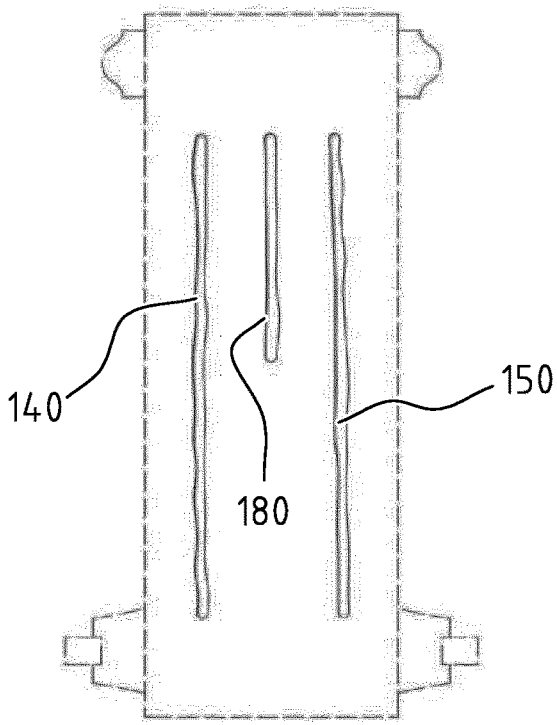

According to the exemplary embodiment of FIG. 15L the plurality of attachment zones comprises a first longitudinal attachment zone 140, a second longitudinal attachment zone 150, and a central longitudinal attachment zone 180. The first and second longitudinal attachment zones 140, 150 extend adjacent to each other over at least 60% of the length of the absorbent core. The central longitudinal attachment zone 180 extends between the first and second attachment zones 140, 150, from the crotch region in the direction of the rear transverse edge of the absorbent core.

Figure 15M:
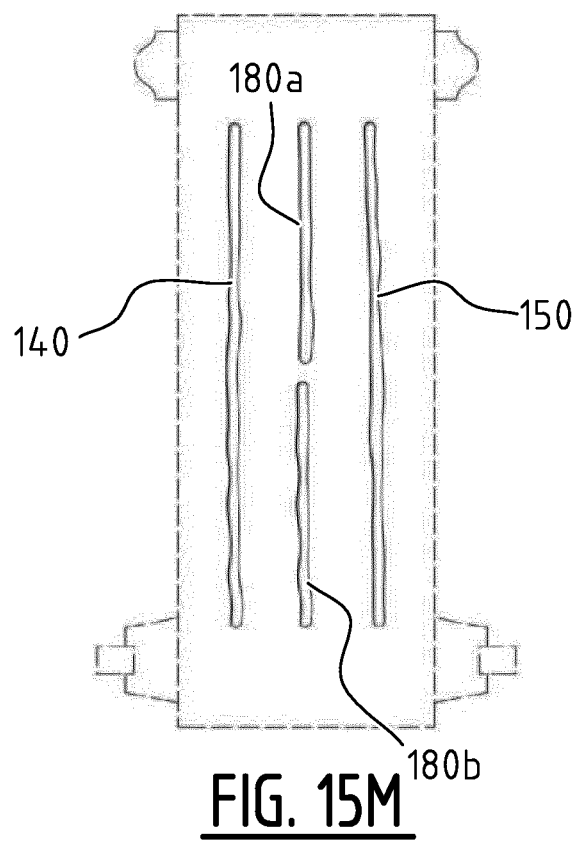

According to the exemplary embodiment of FIG. 15M the plurality of attachment zones comprises a first longitudinal attachment zone 140, a second longitudinal attachment zone 150, a central rear longitudinal attachment zone 180a, and a central front longitudinal attachment zone 180b. The first and second longitudinal attachment zones 140, 150 extend adjacent to each other over at least 60% of the length of the absorbent core. The central rear and front longitudinal attachment zones 180a, 180b extends between the first and second attachment zones 140, 150, in a rear and front part of the absorbent core, respectively.

Figure 15N:
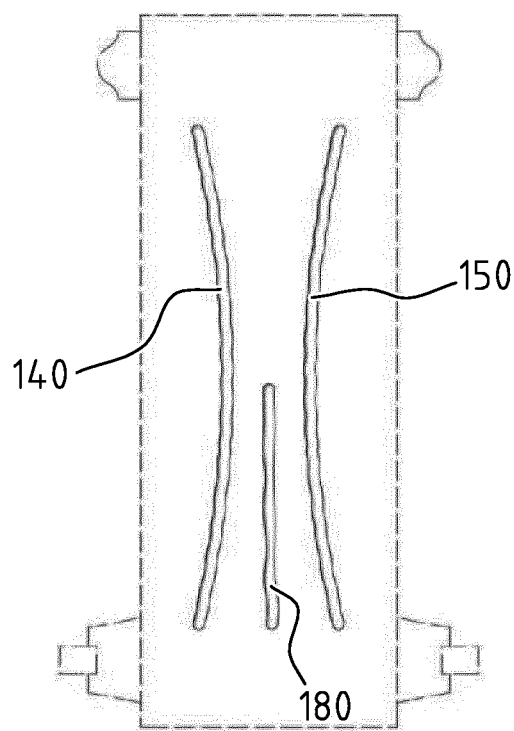

According to the exemplary embodiment of FIG. 15N the plurality of attachment zones comprises a first attachment zone 140, a second attachment zone 150, and a central attachment zone 180. The first and second attachment zones 140 diverge from the crotch region in the direction of a front and rear transverse edge of absorbent core. The central attachment zone is provided in between the first and second attachment zone 140, 150, mainly in a front portion of the absorbent core.

Figure 15O:
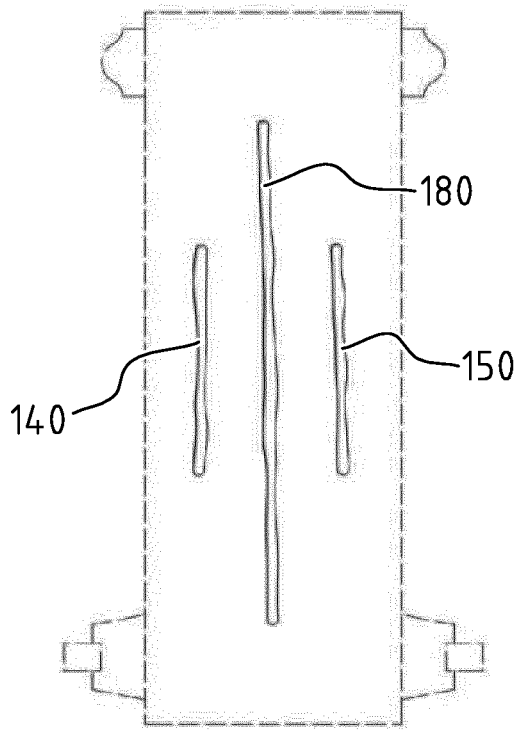

According to the exemplary embodiment of FIG. 15O the plurality of attachment zones comprises a first longitudinal attachment zone 140, a second longitudinal attachment zone 150, and a central longitudinal attachment zone 180. The first and second longitudinal attachment zones 140, 150 extend adjacent and parallel to each other in the crotch region. The central longitudinal attachment zone 180 extends between the first and second attachment zones 140, 150, over at least 60% of the length of the absorbent core.

Figure 15P:
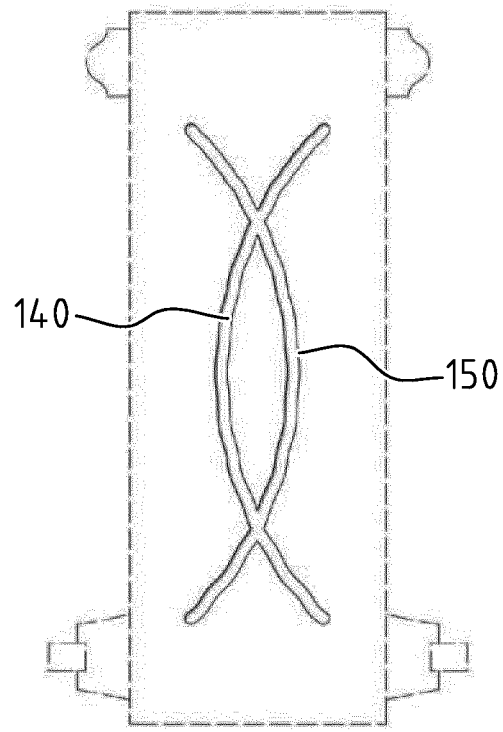

According to the exemplary embodiment of FIG. 15P the plurality of attachment zones comprises a first attachment zone 140 and a second attachment zone 150. The first and second attachment zones 140, 150 extend from the crotch region in the direction of a front and rear transverse edge of absorbent core, and are curved such that the first and second attachment zones 140, 150 cross each other at a first crossing point in a front part of the absorbent core and in a second crossing point in the rear part of the absorbent core.

Figure 15Q:
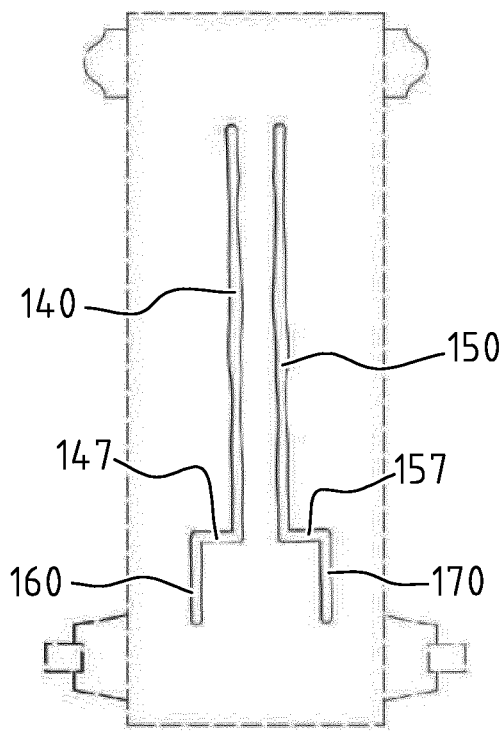

According to the exemplary embodiment of FIG. 15Q the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge, and are interconnected via transverse attachment portions 147, 157 to third and fourth attachment zone 160, 170 extending from the crotch region to the front transverse edge, respectively.

Figure 15R:
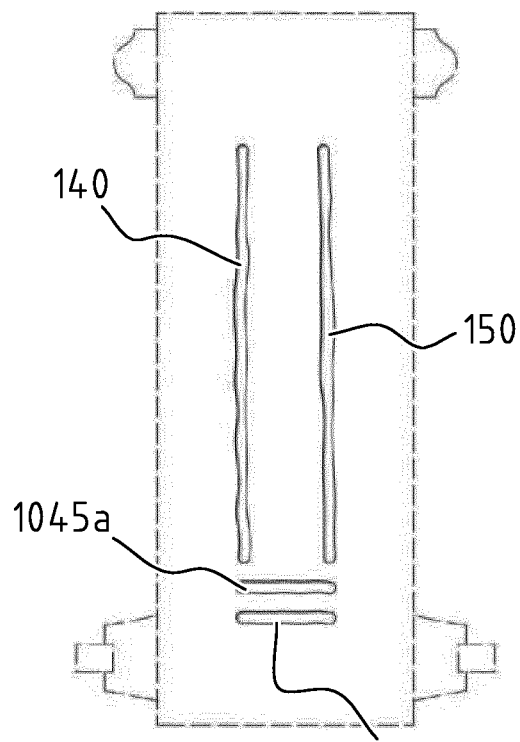

The exemplary embodiment of FIG. 15R is similar to the embodiment of FIG. 15G with this difference that two parallel transverse attachment zones 1045a and 1045b are provided in the front region of the absorbent core.

Figure 15S:
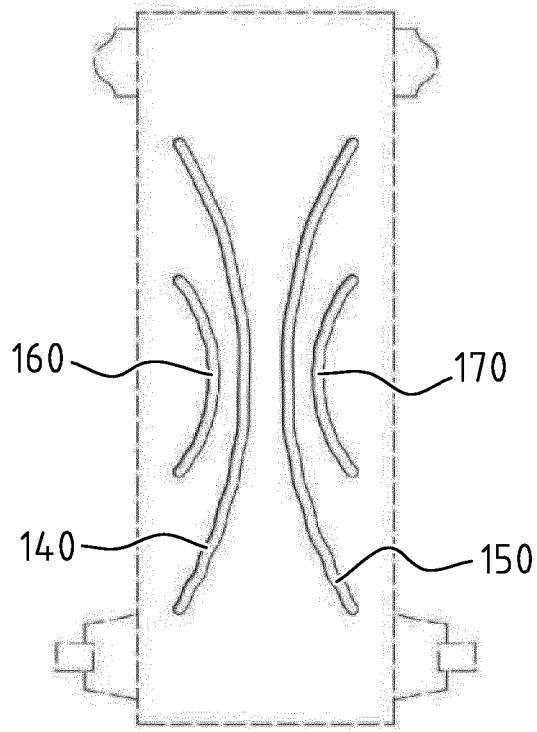

According to the exemplary embodiment of FIG. 15S the plurality of attachment zones comprises a first attachment zone 140, a second attachment zone 150, a third attachment zone 160 and a fourth attachment zone 170. The first and second attachment zones 140, 150 diverge from the crotch region in the direction of a front and rear transverse edge of absorbent core. The third and fourth attachment zones 160, 170 are located outwardly of the first and second attachment zones 140, 150, are shorter than the first and second attachment zones 140, 150, and also diverge from the crotch region in the direction of a front and rear transverse edge of absorbent core. In that manner, in the wetted state, a plurality of tubes is created, wherein the tubes are smaller in a center of the crotch region and gradually widen in the direction of the front and rear transverse edge of the absorbent core. In that manner the shape of the tub which is formed in the wetted state can be further improved to fit well to the body.

Figure 15T:
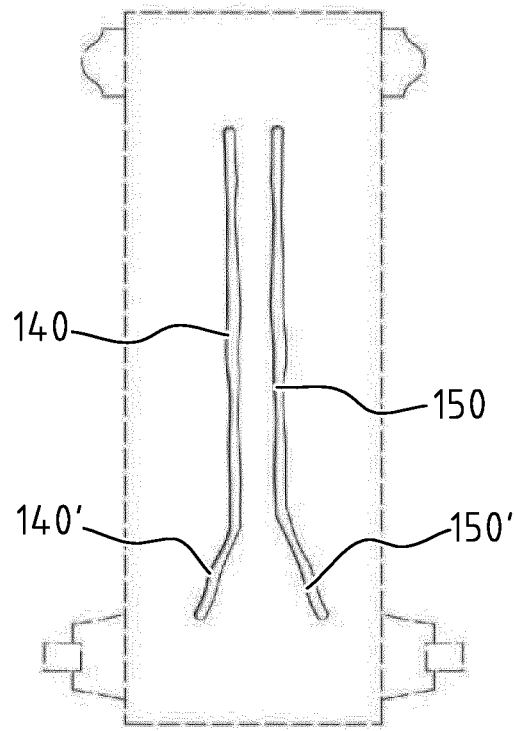

According to the exemplary embodiment of FIG. 15T the plurality of attachment zones comprises a first longitudinal attachment zone 140 and a second longitudinal attachment zone 150, wherein front end portions 140', 150' thereof diverge in the direction of the front transverse edge of the absorbent core.

Figure 15U:
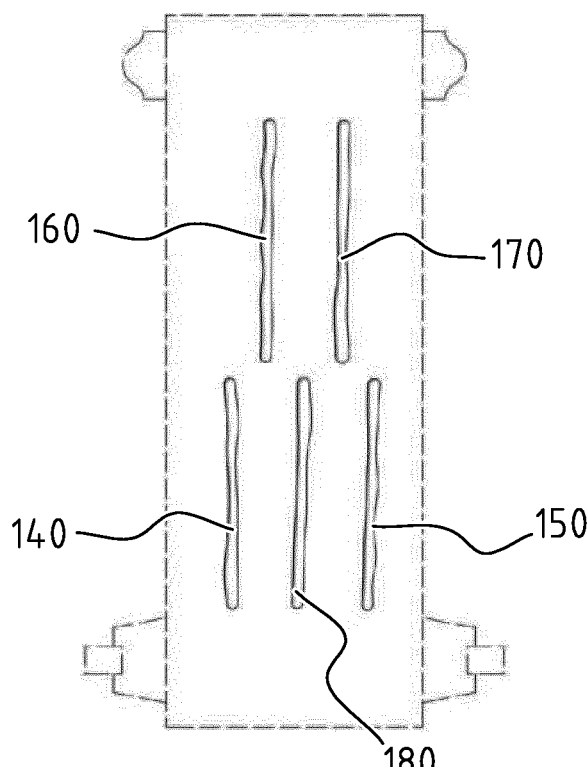

According to the exemplary embodiment of FIG. 15U the plurality of attachment zones comprises a first longitudinal attachment zone 140, a second longitudinal attachment zone 150, a third longitudinal attachment zone 160 and a fourth longitudinal attachment zone 170, and a central longitudinal attachment zone 180. The first and second attachment zones 140, 150, as well as the central attachment zone 180 extend adjacent to each other from a crotch region in the direction the front transverse edge. Also, the third and fourth attachment zones 160, 170 extend adjacent to each other from a crotch region in the direction the rear transverse edge. In that manner the distribution of liquid in the front part of the absorbent core can be further enhanced.

Figure 15V:
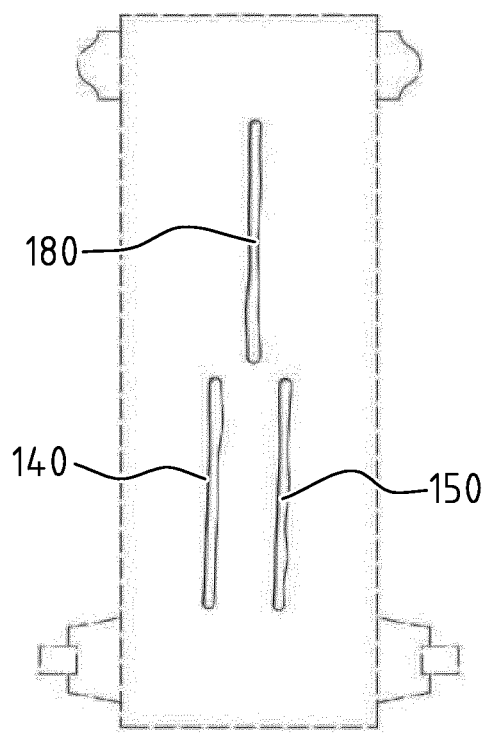

According to the exemplary embodiment of FIG. 15V the plurality of attachment zones comprises a first longitudinal attachment zone 140, a second longitudinal attachment zone 150, and a central longitudinal attachment zone 180. The first and second attachment zones 140, 150 extend adjacent to each other from a crotch region in the direction the front transverse edge. The central attachment zone 180 extends from a crotch region in the direction the rear transverse edge.

Figure 15W:
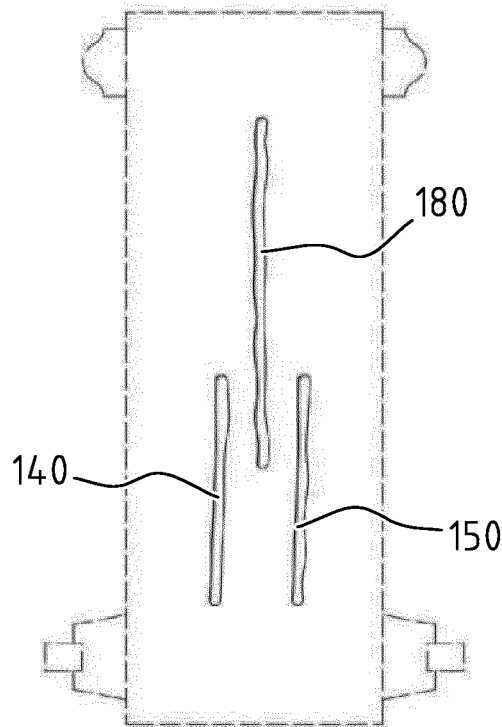

The exemplary embodiment of FIG. 15W is similar to the embodiment of FIG. 15V with this difference that the central attachment zone 180 extends partially in between the first and the second attachment zone 140, 150.

Figure 15X:
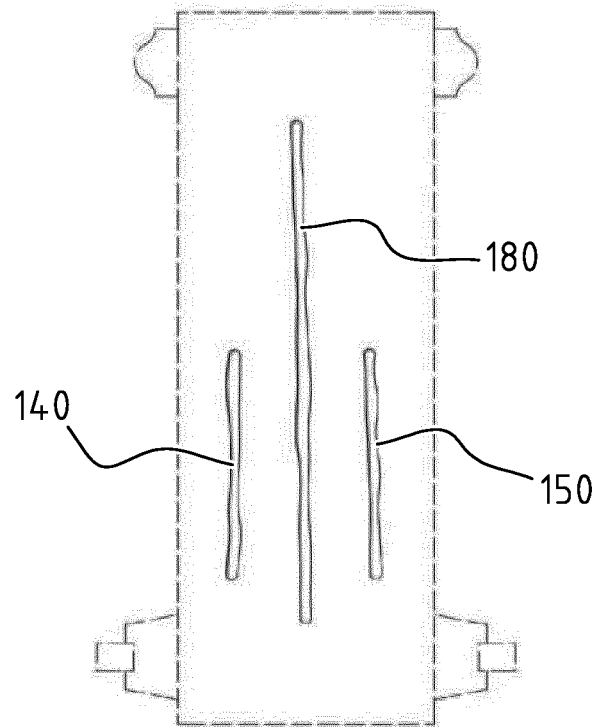

The exemplary embodiment of FIG. 15X is similar to the embodiment of FIG. 15V with this difference that the central attachment zone 180 extends all the way in between the first and the second attachment zone 140, 150 in the direction of the front transverse edge.

Figure 16A:
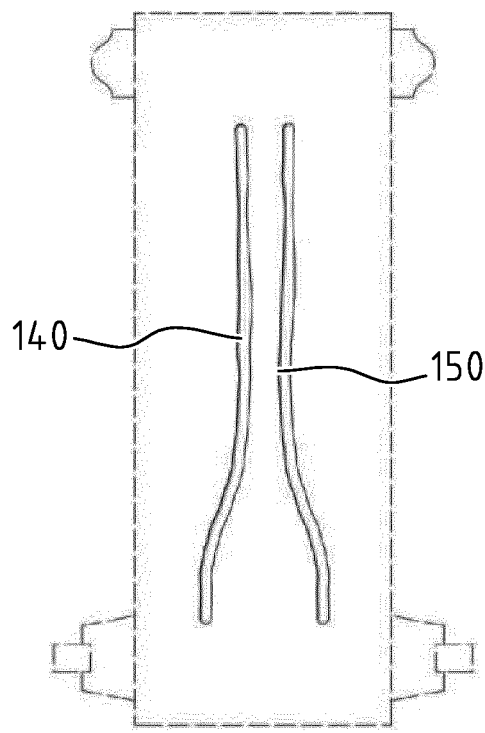
FIGS. 16A-16S illustrate other exemplary embodiments of an absorbent core according to the invention.

According to the exemplary embodiment of FIG. 16A the plurality of attachment zones comprises a first attachment zone 140 and a second attachment zone 150. The first and second attachment zones 140 are substantially parallel in a rear part of the crotch region, whilst the transverse distance between the first and second attachment zones gradually increases in the direction of a front transverse edge of absorbent core.

Figure 16B:
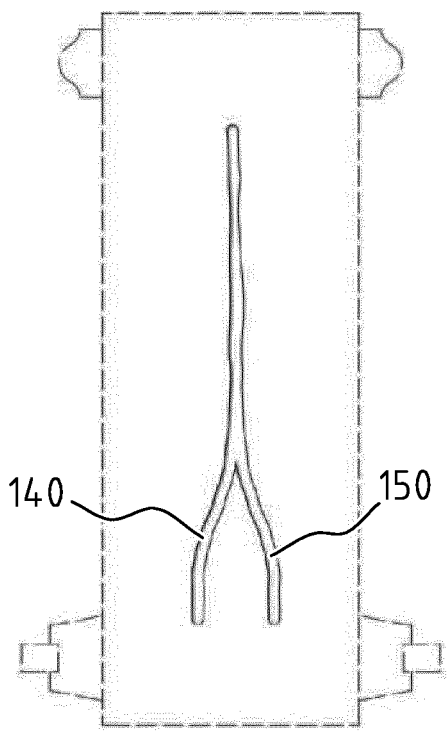

According to the exemplary embodiment of FIG. 16B the plurality of attachment zones comprises a first attachment zone 140 and a second attachment zone 150. The first and second attachment zones 140 partially overlap in a rear part of the crotch region, whilst the transverse distance between the first and second attachment zones gradually increases in the direction of a front transverse edge of absorbent core.

Figure 16C:
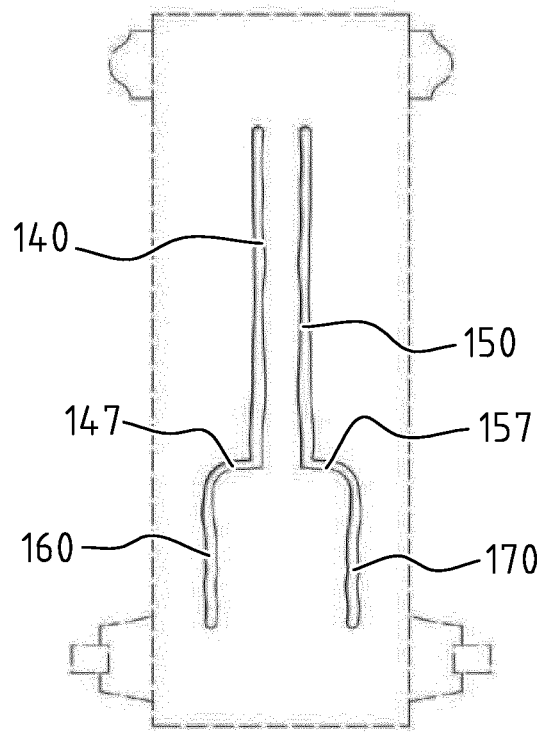
Figure 16D:
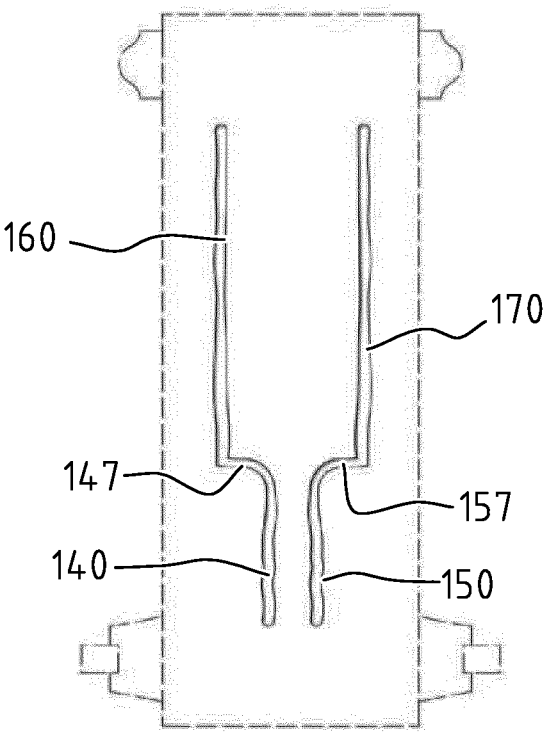
Figure 16E:
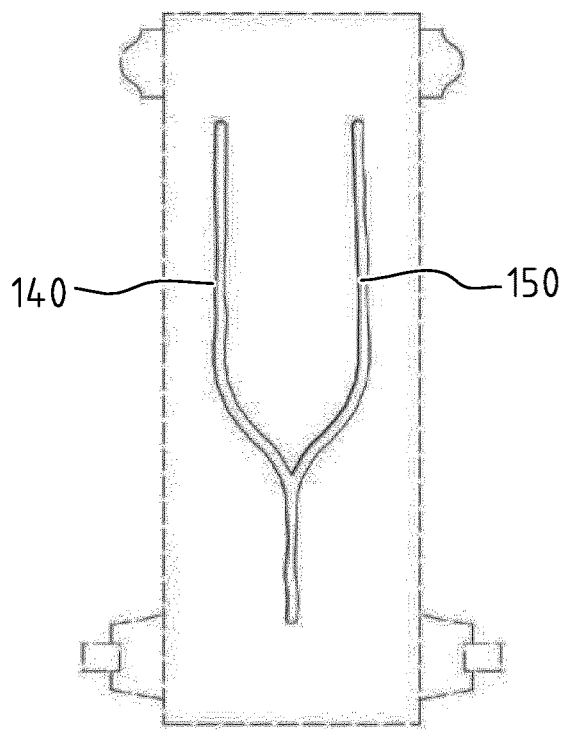

According to the exemplary embodiment of FIGS. 16C and 16D the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge, and are interconnected via transverse attachment portions 147, 157 to third and fourth attachment zone 160, 170 extending from the crotch region to the front transverse edge, respectively. In FIG. 16C the distance between the first and second attachment zones is smaller than the distance between the third and fourth attachment zones, whilst in FIG. 16D the distance between the first and second attachment zones is bigger than the distance between the third and fourth attachment zones. The embodiment of FIG. 16E is similar to the embodiment of FIG. 16D with this difference that the third and fourth attachment zones overlap in a front portion of the absorbent core.

Figure 16F:
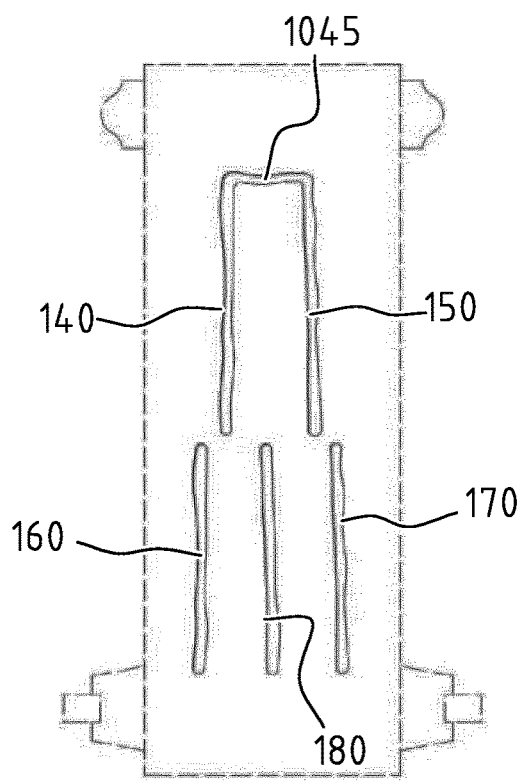

The embodiment of FIG. 16F is similar to the embodiment of FIG. 15U with this difference that the third and fourth longitudinal attachment zones 160, 170 are interconnected at their rear end by a transverse attachment zone 1045.

Figure 16G:
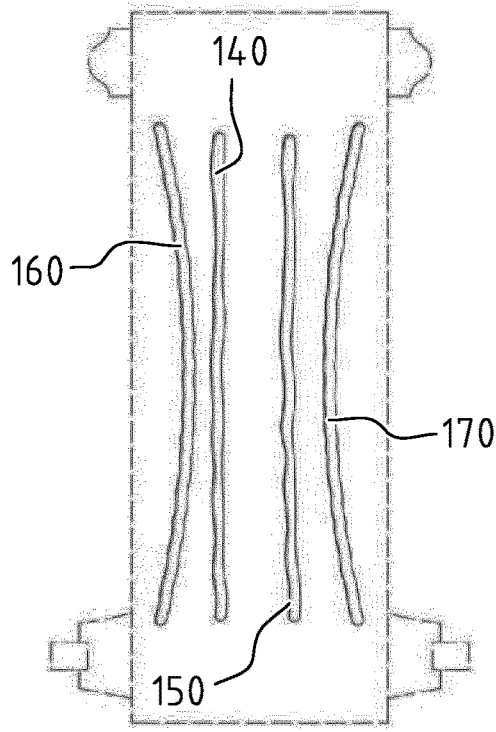

The embodiment of FIG. 16G is similar to the embodiment of FIG. 15B with this difference that the third and fourth longitudinal attachment zones 160, 170 have end portions which diverge outwardly in the direction of the front transverse edge and the rear transverse edge of the absorbent core.

Figure 16H:
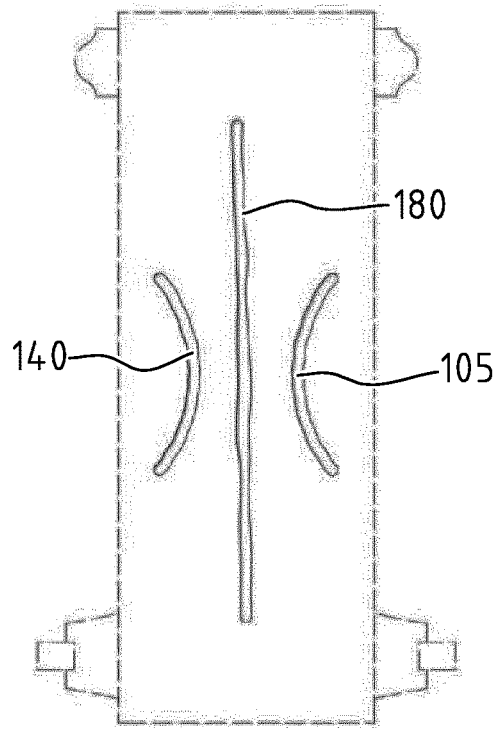

The embodiment of FIG. 16H is similar to the embodiment of FIG. 15O with this difference that the first and second attachment zones 140, 150 have end portions which diverge outwardly in the direction of the front transverse edge and the rear transverse edge of the absorbent core.

Figure 16I:
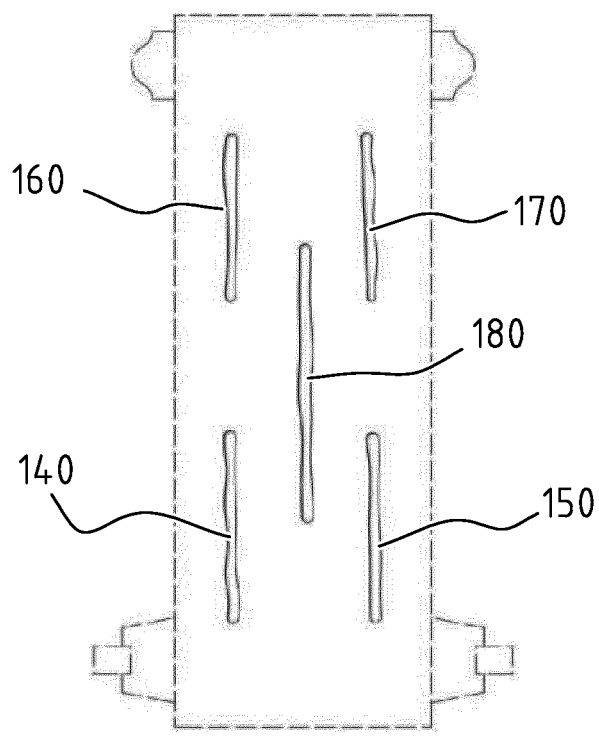

The embodiment of FIG. 16I is similar to the embodiment of FIG. 15C with this difference that the first, second, third and fourth attachment zones 140, 150, 160, 170 are shorter such that in a central part of the crotch region only central attachment zone 180 is present.

Figure 16J:
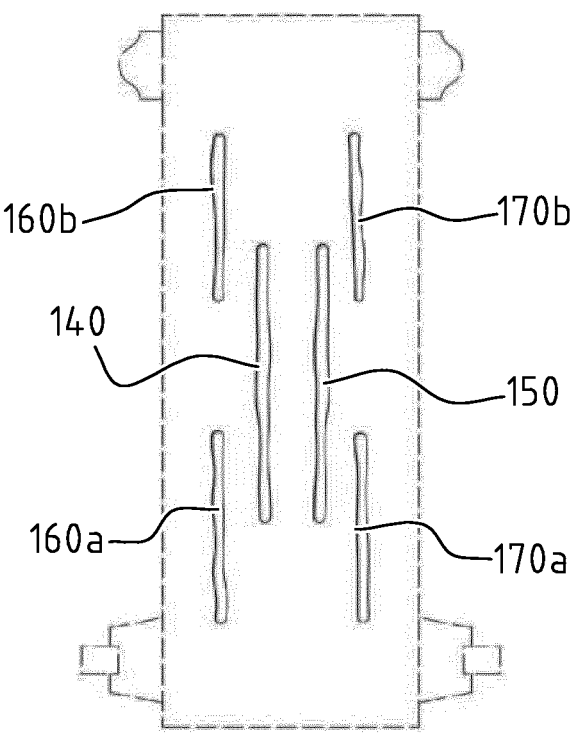

The embodiment of FIG. 16J is similar to the embodiment of FIG. 16I with this difference that the two central attachment zones 180 are provided between first and third attachment zones 140, 160 and second and fourth attachment zones 150, 170.

Figure 16K:
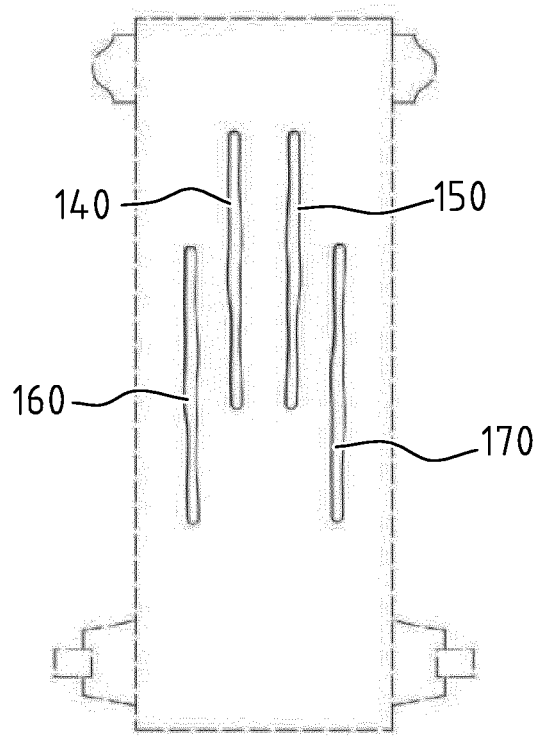
Figure 16L:
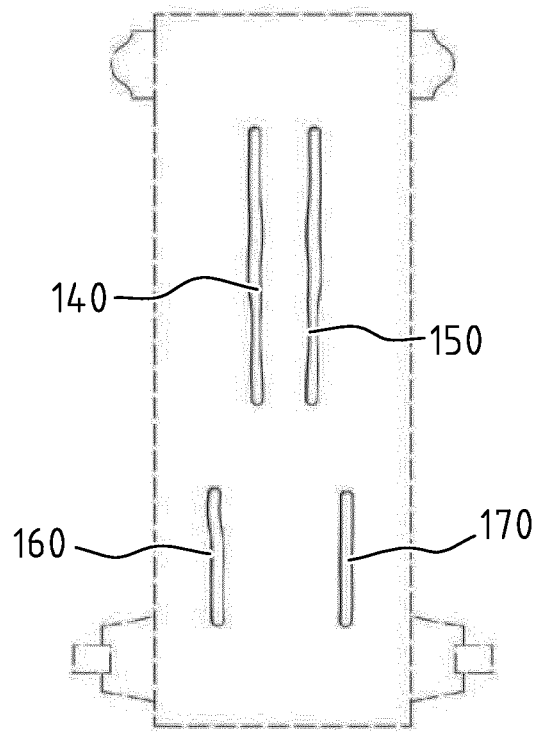

The embodiments of FIGS. 16K and 16L the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the front transverse edge. The third and fourth attachment zone 160, 170 extend from the crotch region to the rear transverse edge. The distance between the first and second attachment zones 140, 150 is bigger than the distance between the third and fourth attachment zones 160, 170. In FIG. 16K the third and fourth attachment zones 160, 170 extend partially between the first and second attachment zones 140, 150, whilst in FIG. 16L, seen in the longitudinal direction, the third and fourth attachment zones 160, 170 are at a distance of the first and second attachment zones 140, 150.

Figure 16M:
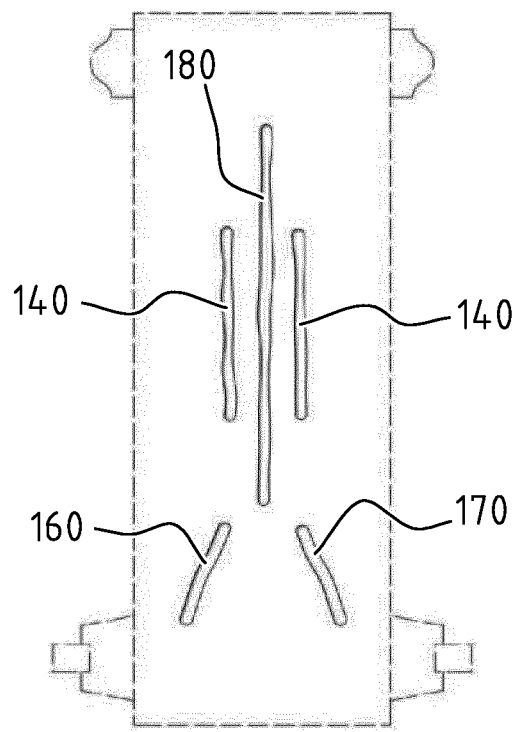
Figure 16N:
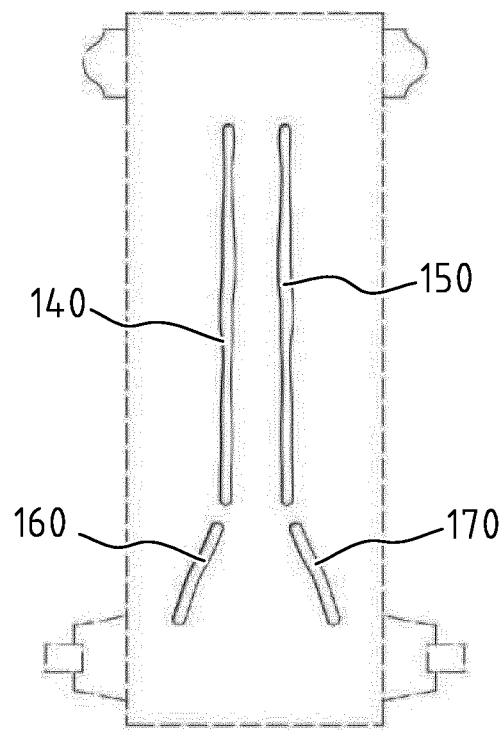
Figure 16O:
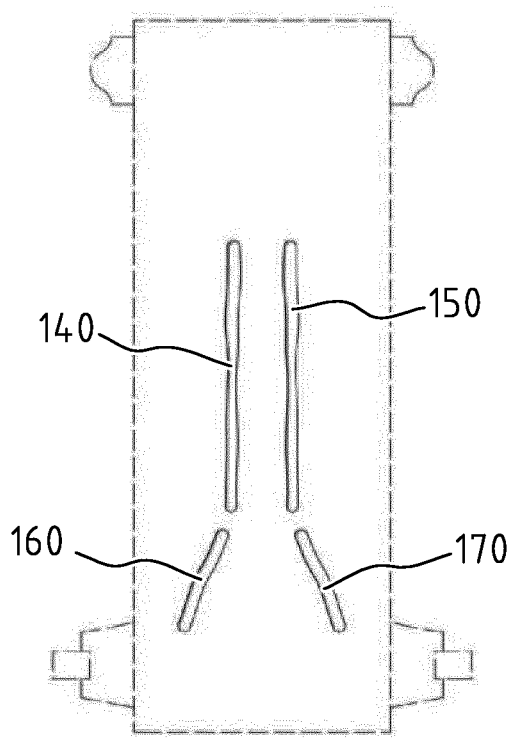

In the embodiments of FIGS. 16M, 16N and 16O the plurality of attachment zones comprises a first longitudinal attachment zone 140, a second longitudinal attachment zone 150, and outwardly diverging attachment zones 160, 170 in a front portion of the absorbent core. In FIG. 16M, additionally a central attachment zone 180 is provided between the first longitudinal attachment zone 140 and the second longitudinal attachment zone 150.

Figure 16P:
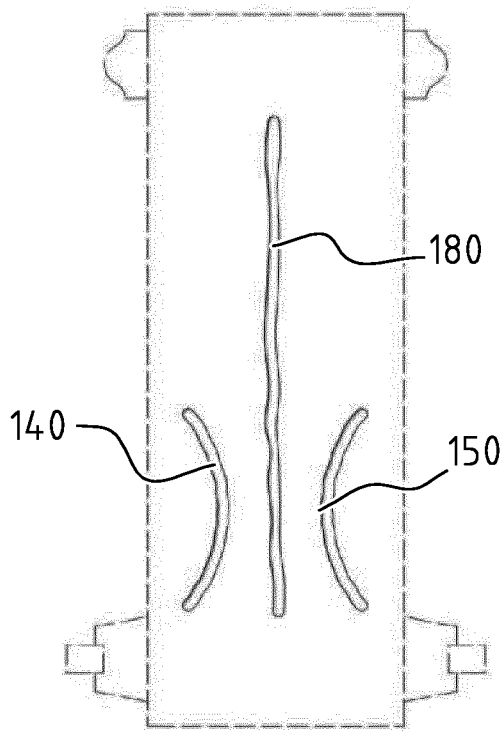

FIG. 16P is similar to the embodiment of FIG. 16H with this difference that first and second attachment zones are provided more to the front of absorbent core.

Figure 16Q:
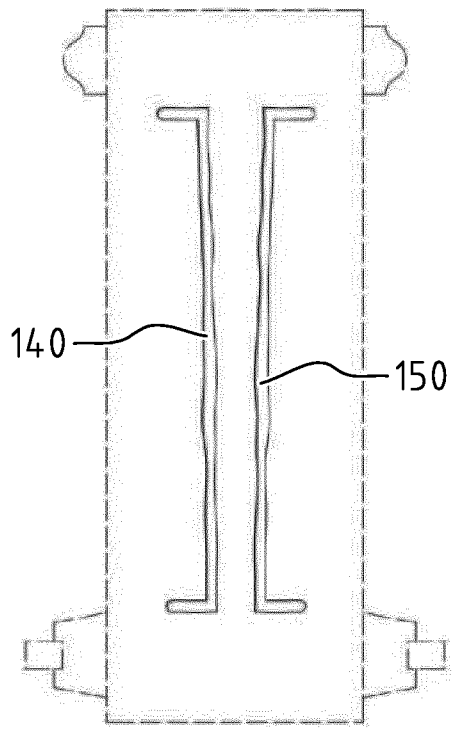

In the embodiment of FIG. 16Q the plurality of attachment zones comprises a first longitudinal attachment zone 140 and a second longitudinal attachment zone 150 which extend over at least 60% of the length of the absorbent core. The first longitudinal attachment zone 140 and the second longitudinal attachment zone 150 are each provided at a front end and at a rear end with an outwardly directed transverse portion. In that manner leakage risks at the front and rear parts of the absorbent core can be further reduced.

Figure 16R:
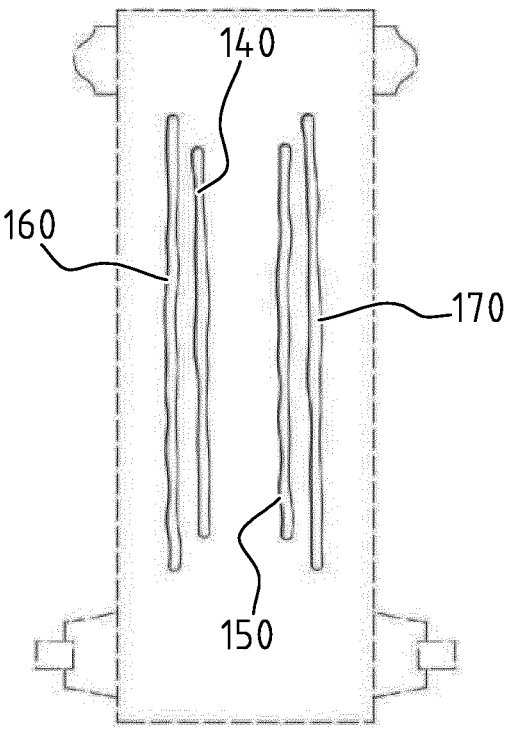

FIG. 16R is similar to the embodiment of FIG. 15B.

Figure 16S:
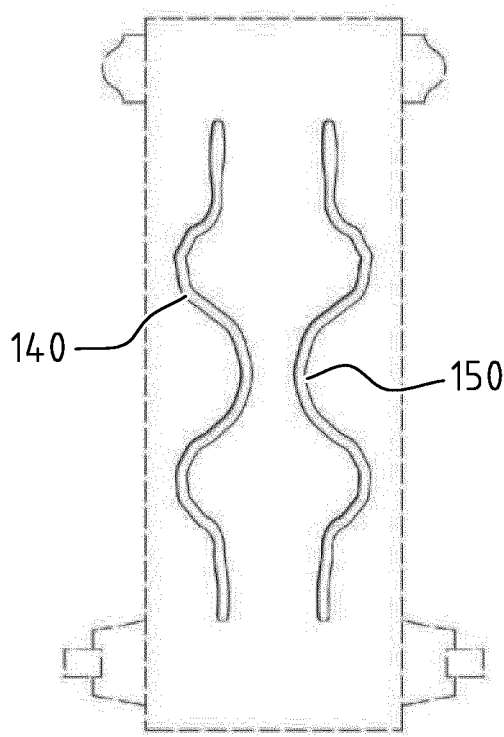

In the embodiment of FIG. 16S the plurality of attachment zones comprises a first undulated attachment zone 140 and a second undulated attachment zone 150 each extending over at least 60% of the length of the absorbent core. The undulations will increase the length of the channels 140, 150, further improving the liquid distribution in the absorbent core.

FIGS. 17A-17V and FIGS. 18A-18G illustrate yet other exemplary embodiments of an absorbent core according to the invention.

Figure 17A:
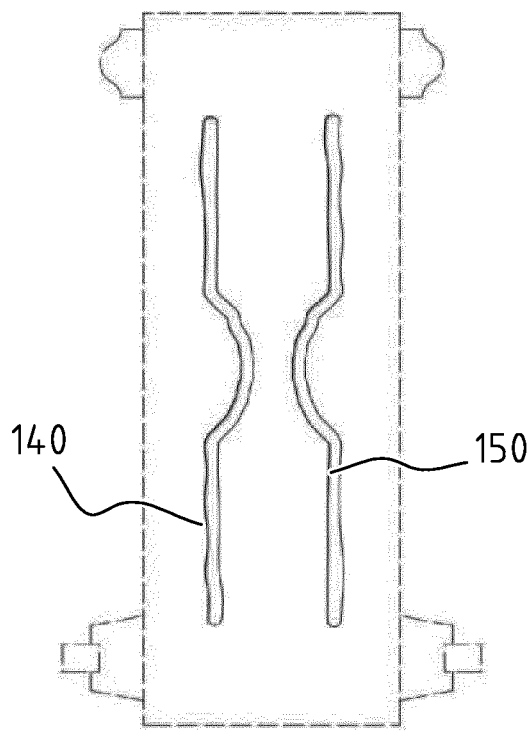
FIGS. 17A-17V illustrate yet other exemplary embodiments of an absorbent core according to the invention.
Figure 17B:
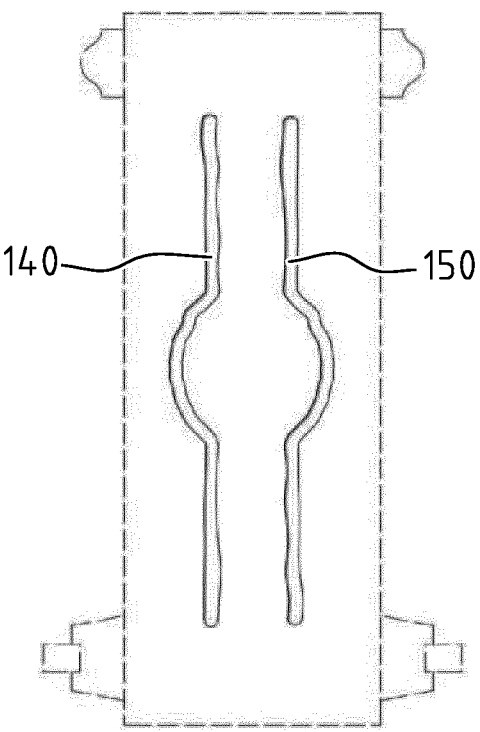
Figure 17C:
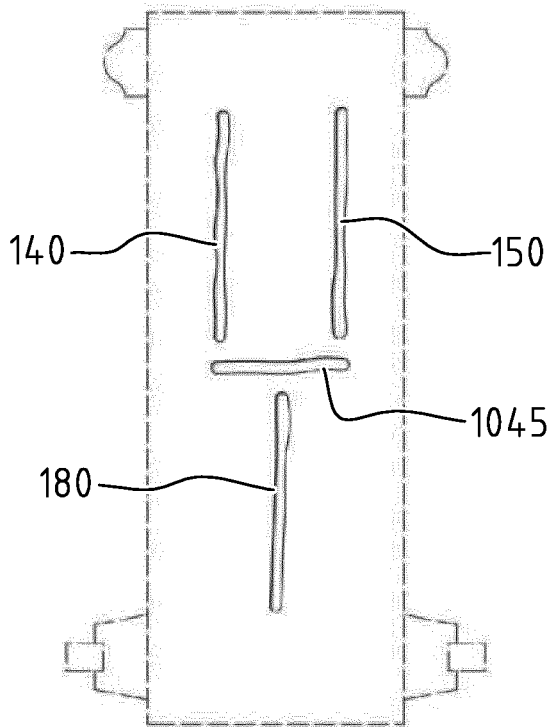
Figure 17D:
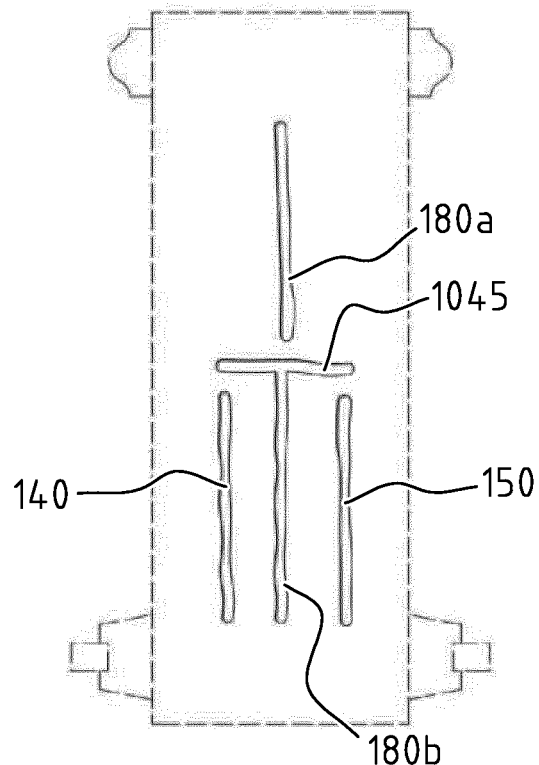
Figure 17E:
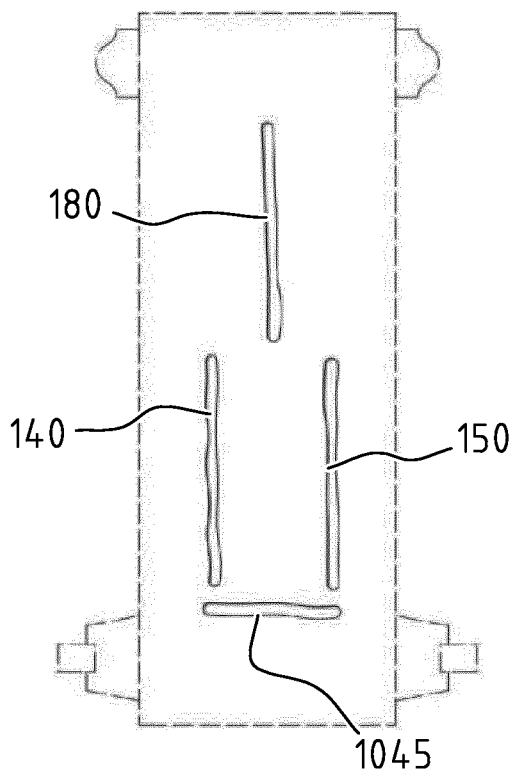
Figure 17F:
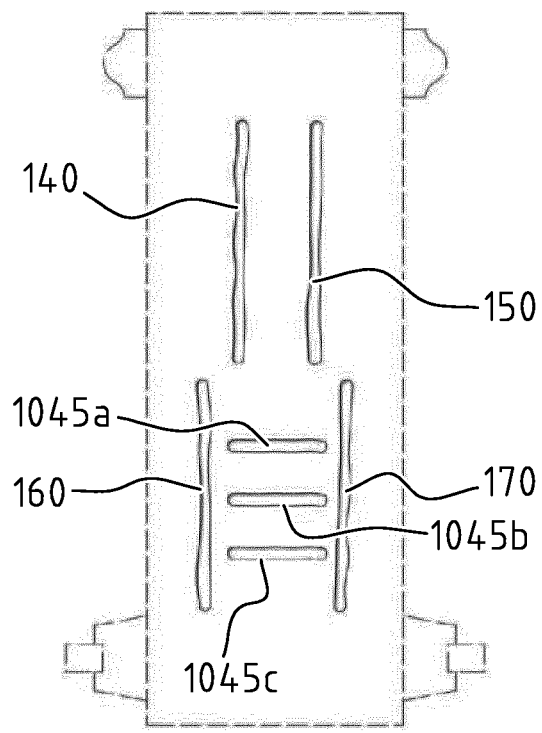
Figure 17G:
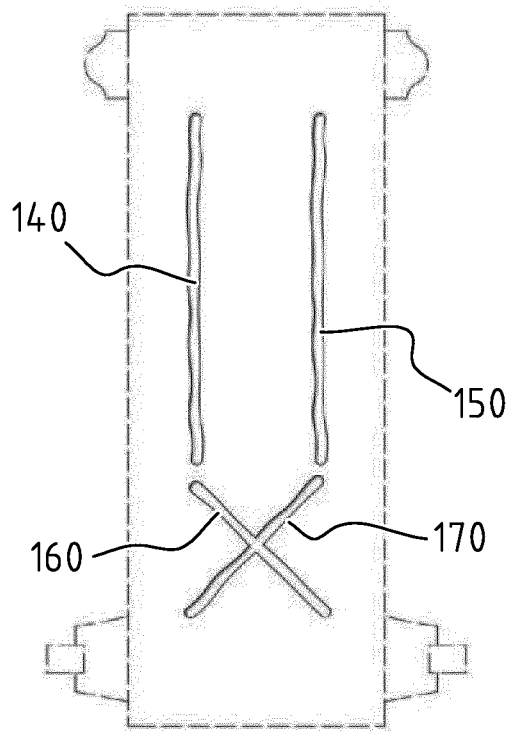
Figure 17H:
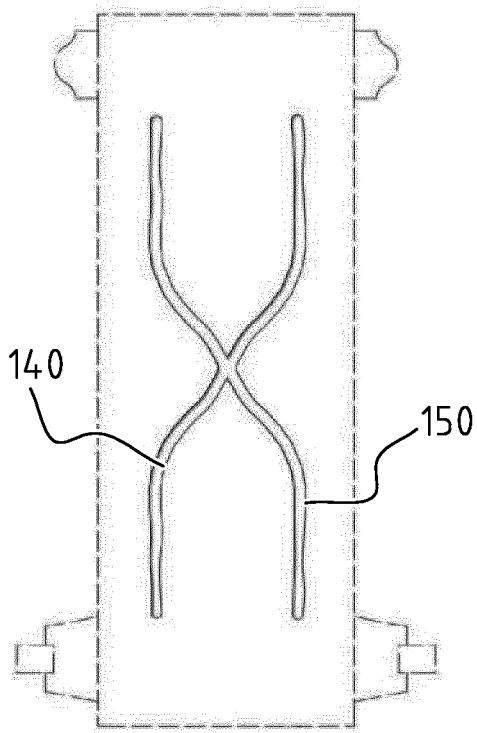
Figure 17I:
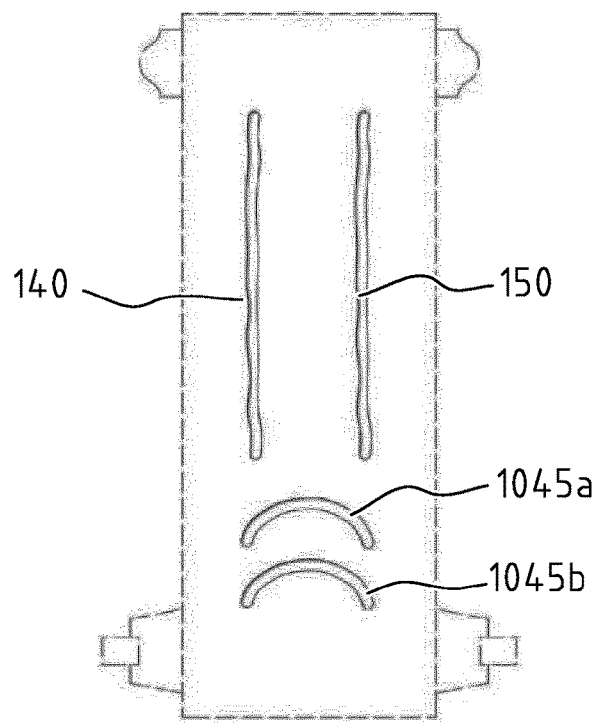
Figure 17J:
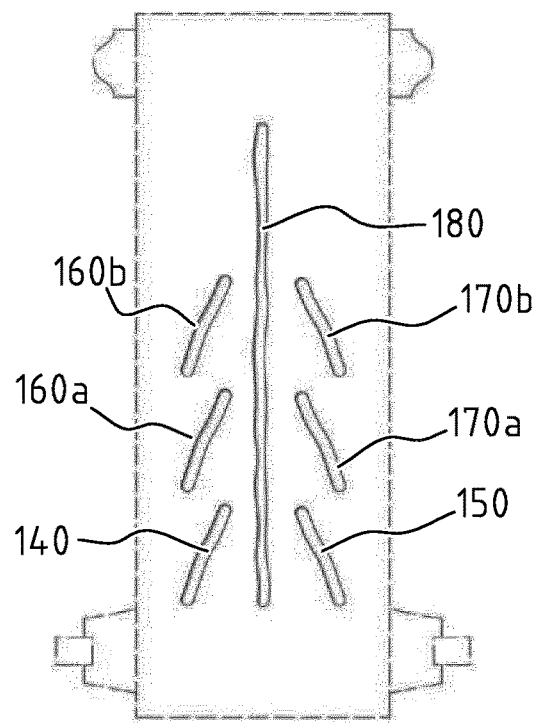
Figure 17K:
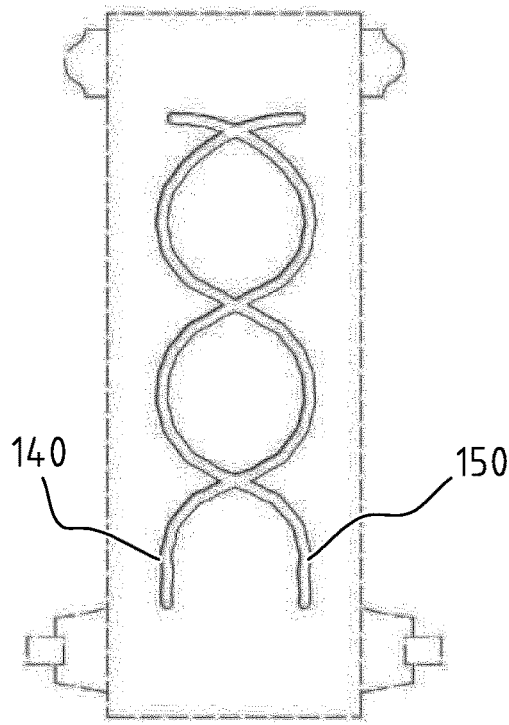
Figure 17L:
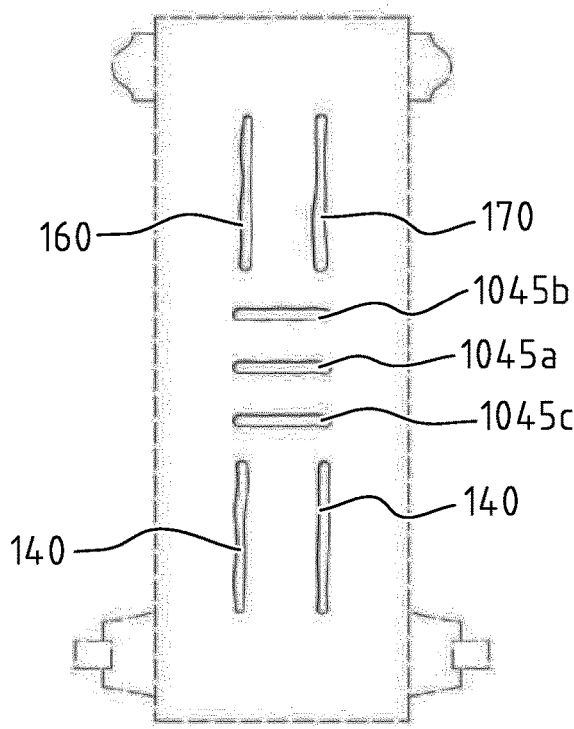
Figure 17M:
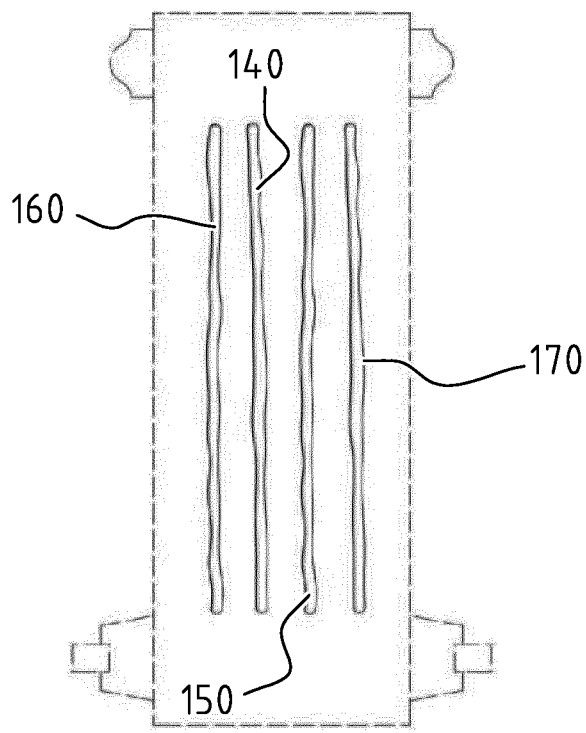
Figure 17N:
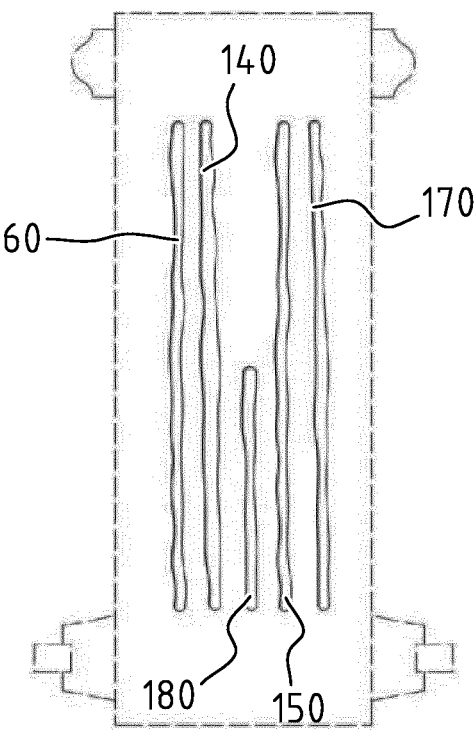
Figure 17O:
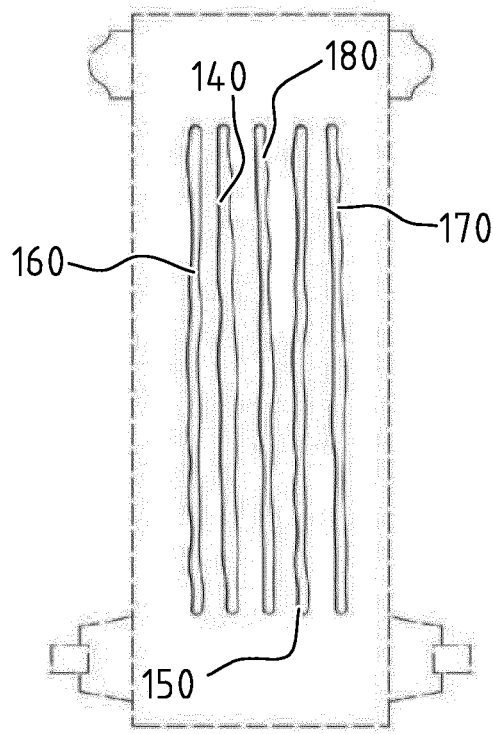
Figure 17P:
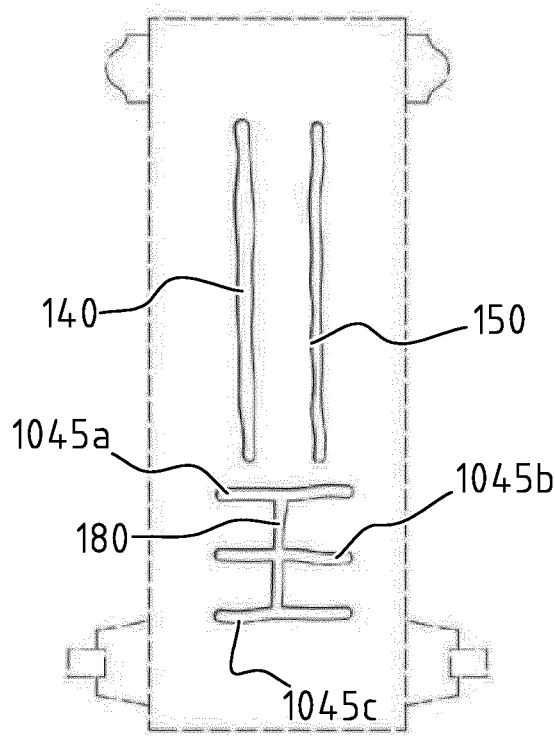
Figure 17Q:
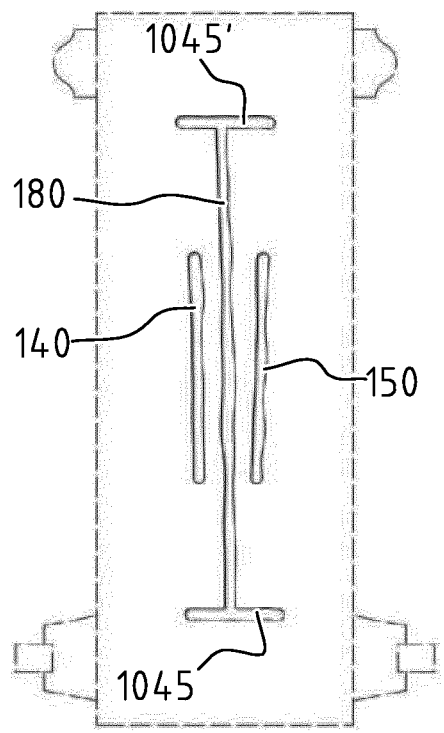
Figure 17R:
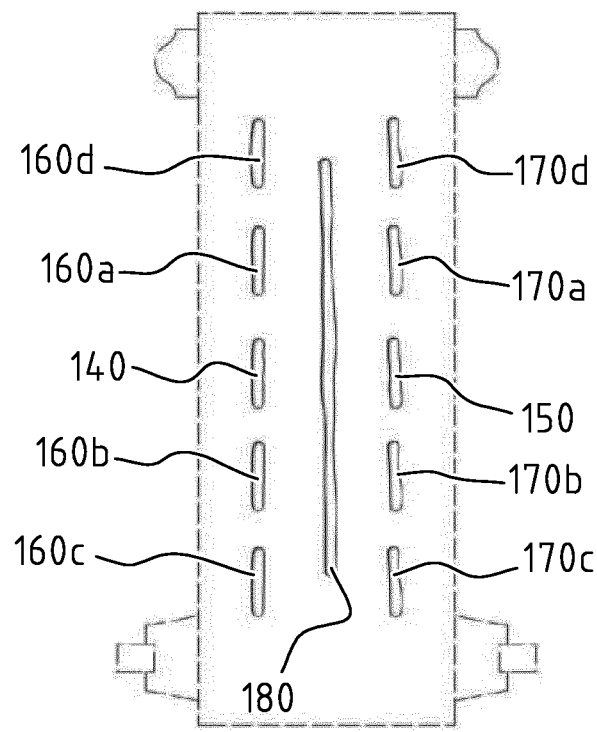
Figure 17S:
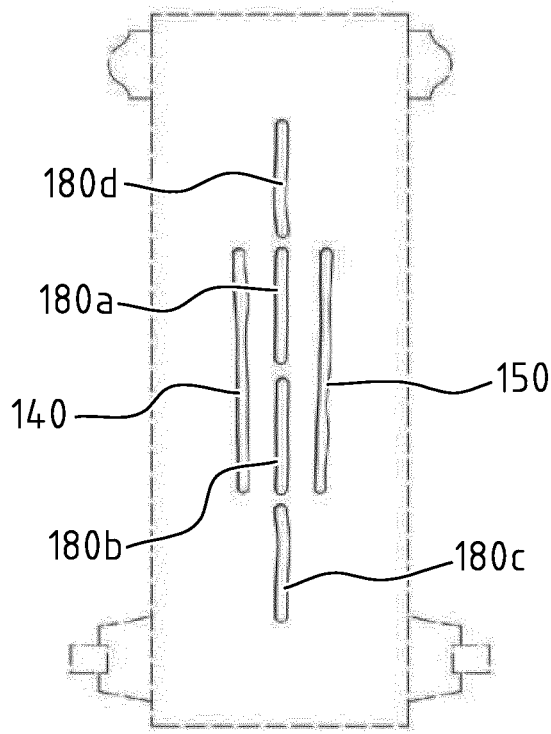
Figure 17T:
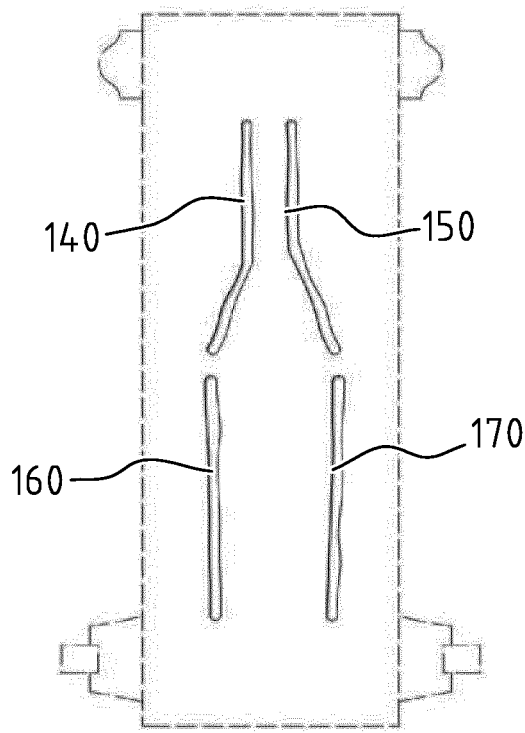
Figure 17U:
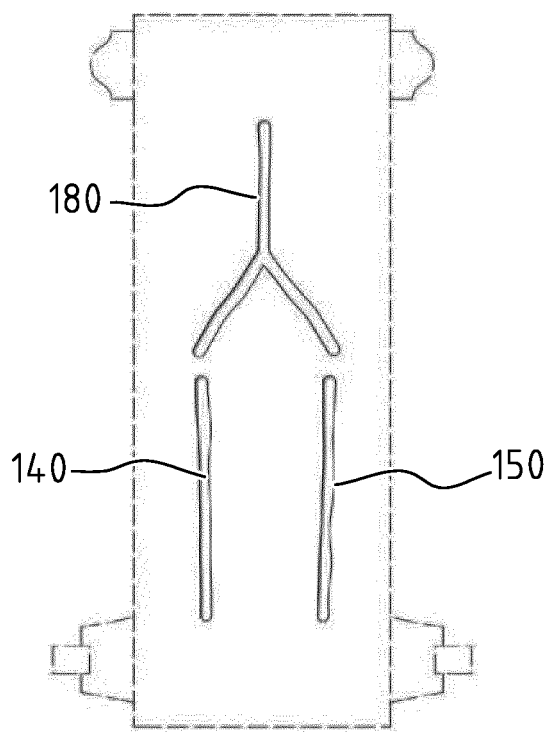
Figure 17V:
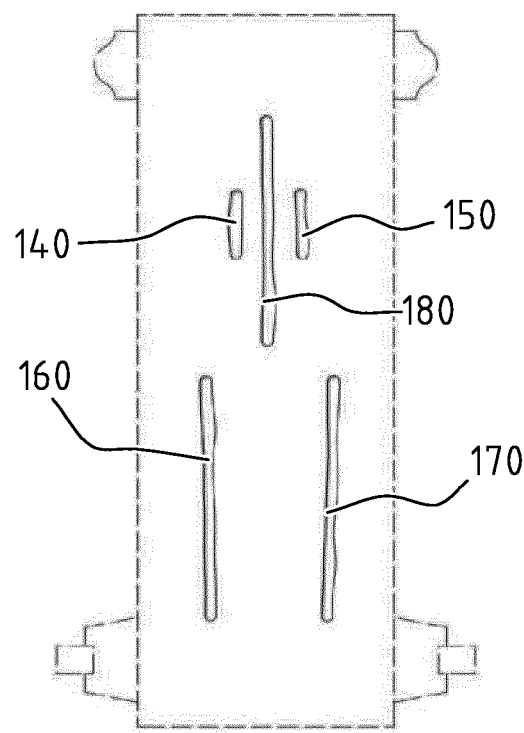

FIGS. 17A, 17B, 17H and 17K illustrate that the first and second attachment zones 140, 150 may comprise curved portions. FIGS. 17C, 17D, 17E, 17F, 17G, 17J, 17L, 17M, 17N, 17O, 17P, 17Q, 17R, 17S, 17T, 17U, 17V illustrate that various patterns are possible with one or more longitudinal sections 140, 150, 160, 170, 180, and/or one or more inclined sections 160, 170, 160a, 160b, 170a, 170b and/or one or more transverse sections 1045, 1045a, 1045b, 1045c. FIG. 17I illustrates that also curved transverse sections 1045a, 1045b may be used.

Figure 18E:
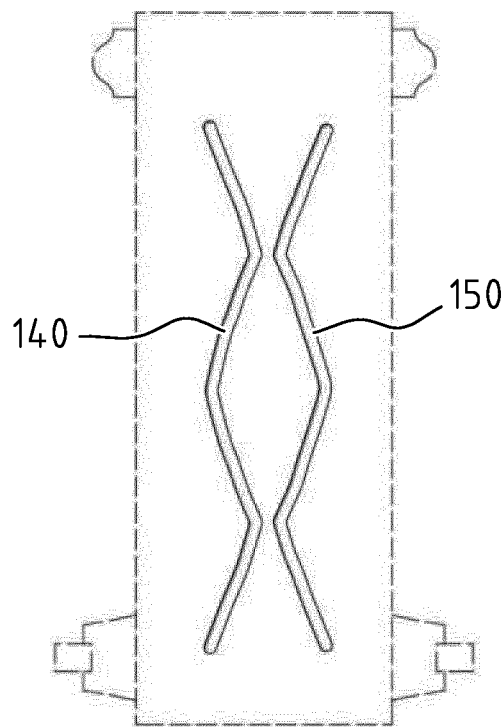
Figure 18F:
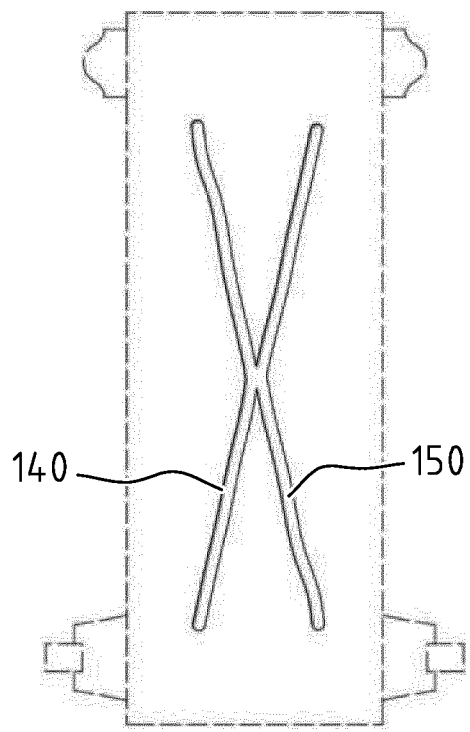
Figure 18G:
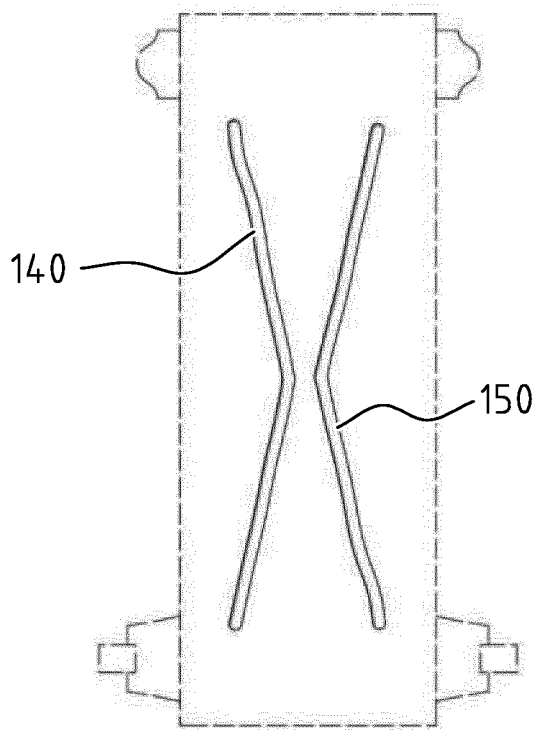

FIGS. 18A-18G illustrate further embodiments. In FIG. 18A the first to fourth attachment zones are similar to the first to fourth attachment zones of FIG. 16I, but instead of a central rectilinear attachment zone, there is provided an oval attachment zone 180 in the crotch region, between the first and second attachment zone 140, 150 and the third and fourth attachment zone 160, 170. FIGS. 18B, 18C, 18D illustrate that various patterns are possible with one or more longitudinal sections and/or one or more inclined sections and/or one or more transverse sections as described before. FIGS. 18E, 18F, 18G illustrate that the first and second attachment zones 140, 150 may comprise various rectilinear sections which are oriented at an angle with respect to the longitudinal direction of the absorbent core.

FIGS. 19A-19D illustrate further embodiments wherein the absorbent core is provided with at least a first attachment zone 140, wherein in said first attachment zone 141 said top core wrap sheet is attached to said back core wrap sheet along an attachment which extends, seen in a transverse and/or longitudinal direction of the absorbent core, over a transverse and/or longitudinal distance which is at least 1 mm, preferably at least 2 mm, more preferably at least 3 mm, most preferably at least 4 mm; and/or said top core wrap sheet is attached to said back core wrap sheet along a discontinuous attachment at a plurality of locations at a distance of each other, seen in the transverse and/or longitudinal direction of the absorbent core; such that upon wetting of the absorbent material, a first channel is created at said first attachment zone 140.

Figure 19A:
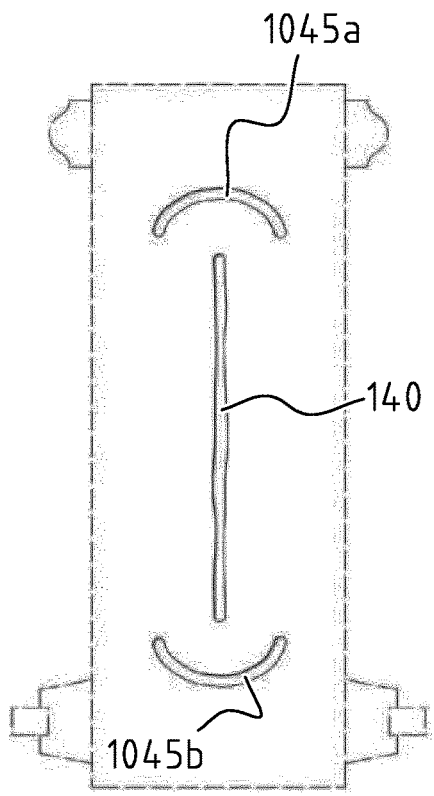
FIGS. 19A-19D illustrate yet other exemplary embodiments of an absorbent core according to the invention.
Figure 19B:
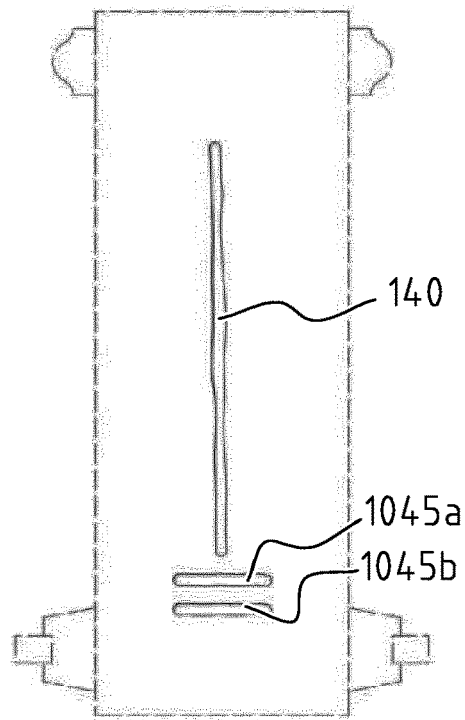
Figure 19C:
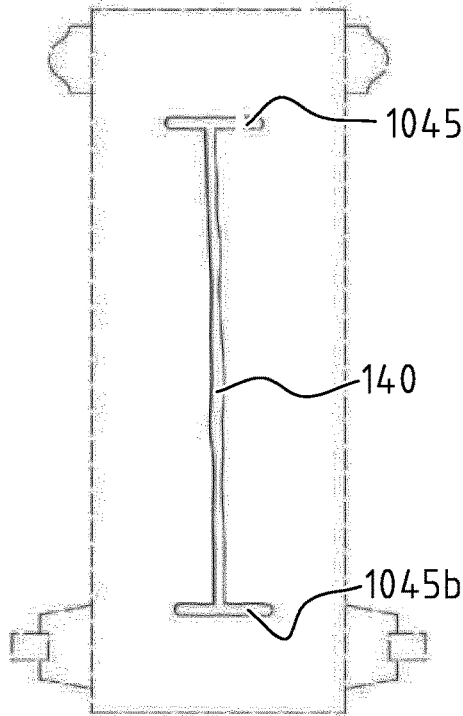
Figure 19D:
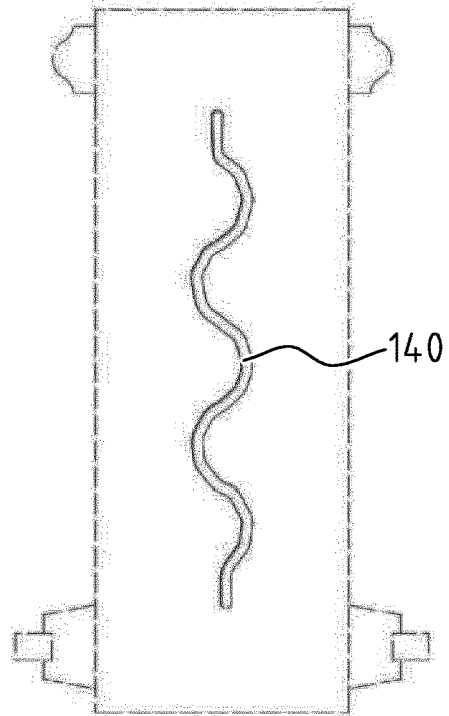

In the embodiment of FIG. 19A, a single longitudinal attachment zone 140 is illustrated, along with a first and second transversal attachment zone 1045a, 1045b which are positioned at either end of the longitudinal attachment zone 140. The first and second transversal attachment zone 1045a, 1045b are illustrated as curved zones, but it is clear to the skilled person that the first and/or second transversal attachment zone may also be provided as straight zones. In the embodiment of FIG. 19B, a single longitudinal attachment zone 140 is illustrated, along with a first and second transversal attachment zone 1045*a*, 1045*b* which are positioned between the attachment zone 140 and the first transversal edge of the absorbent core. In addition to, or alternative to the embodiment of FIG. 19B the first and second transversal attachment zones 1045*a*, 1045*b* may be positioned between the attachment zone 140 and the second transversal edge of the absorbent core. In other words, it is clear to the skilled person that e.g. a third and/or fourth transversal attachment zone may be added. In the embodiment of FIG. 19C, a single longitudinal attachment zone 140 is illustrated, along with a first and second transversal attachment zone 1045*a*, 1045*b* which are positioned at either side of the longitudinal attachment zone 140. Although the transversal attachment zones 1045*a*, 1045*b* are illustrated to be connected to the longitudinal attachment zone 140, it is clear to the skilled person that other embodiments exist wherein the transversal attachment zones 1045*a*, 1045*b* are not connected to the longitudinal attachment zone 140. In the embodiment of FIG. 19D, a single longitudinal attachment zone 140 is illustrated. The illustrated longitudinal attachment zone 140 comprises curved sections, however, in addition or alternatively the longitudinal attachment zone 140 may comprise straight sections. It is clear to the skilled person that any of the earlier described embodiments related to at least two longitudinal attachment zones, or any combination thereof may be applied to the embodiments wherein the absorbent core comprises a single longitudinal attachment zone.

Since liquid may in many cases not be distributed evenly or symmetrically, it may be advantageous to include at least one attachment zone through which liquid may go from the first and second channels 140, 150 and vice-versa. This will allow a good distribution over the entire absorbent core as well as an improved formation of the channels and the tub-shape upon swelling of the absorbent core.

In the embodiments of FIGS. 20A-20W, 20Z, 21G-21M, 21O-21T, 21V-21X, 21Z, 22D-22M, 22R-22Z, 23A-23L, this is achieved with a transversal attachment zone 1045 connecting the front ends of longitudinal attachment zones 140, 150. As will be clear from the figures, the presence of such a transversal attachment zone 1045 does not preclude the elements mentioned in conjunction with the previous figures, such as the presence of a central attachment zone 180 and/or variations of the length, position and/or shape of longitudinal attachment zones 140, 150. The figures furthermore show that the presence of such a transversal attachment also does not preclude the presence of third and fourth longitudinal attachment zones 160, 170, or of transversal attachment zones 147, 157 which connect the longitudinal attachment zones 140, 150 to the further longitudinal attachment zones 160, 170. Furthermore, the figures show that the transversal attachment zone 1045 need not be straight: it may be rounded as in for example FIGS. 20A-20D, rounded at the edges only as for example in FIGS. 20E-20H, or take another shape.

Figure 20A:
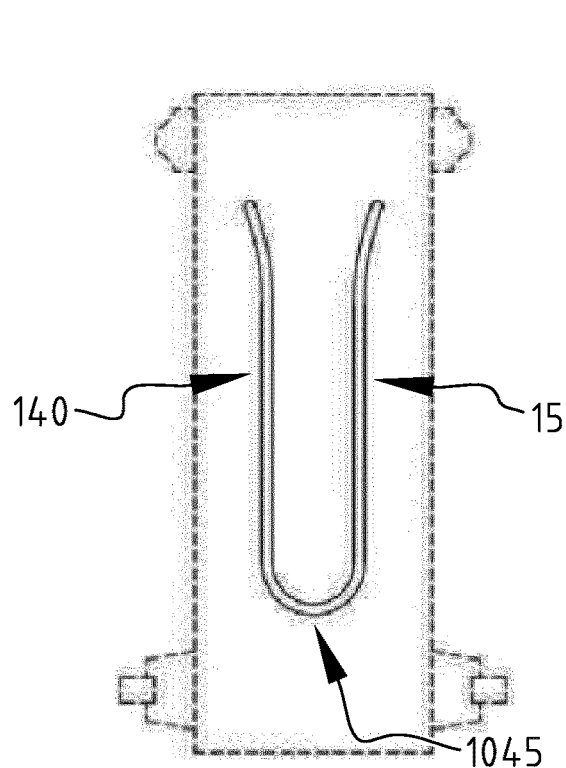
FIGS. 20A-20Z illustrate yet other exemplary embodiments of an absorbent core according to the invention.
Figure 20B:
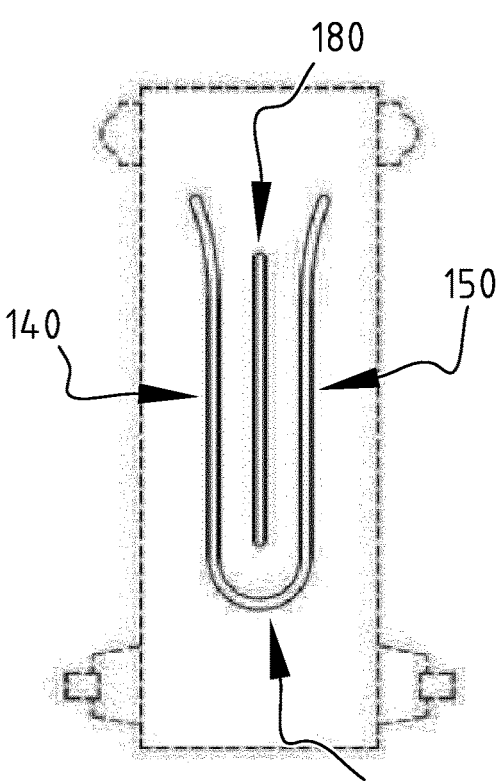
Figure 20C:
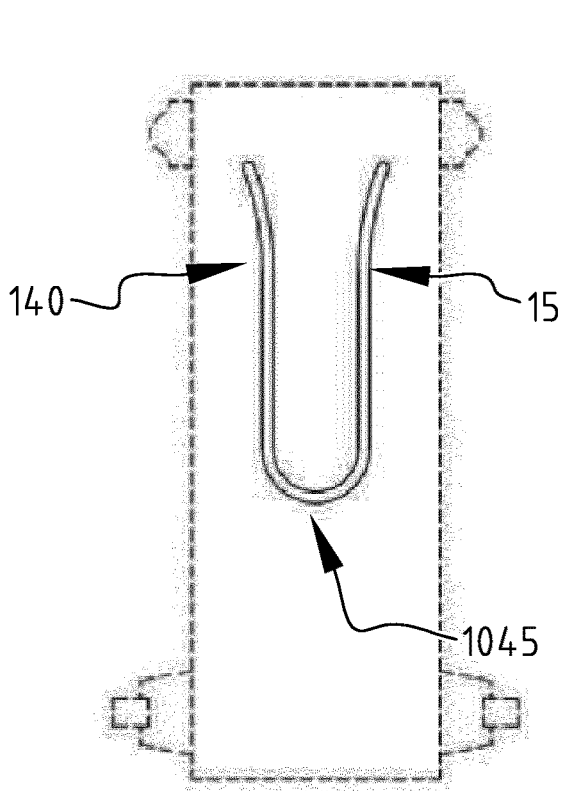
Figure 20D:
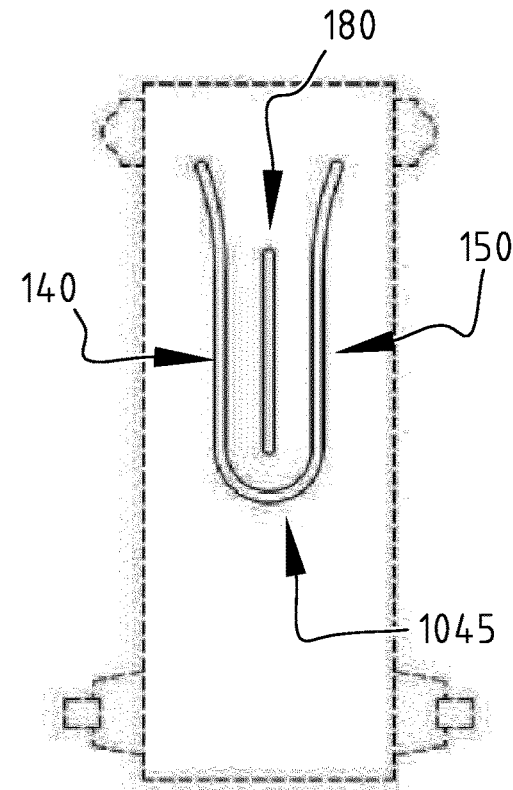
Figures 20E, 20F:
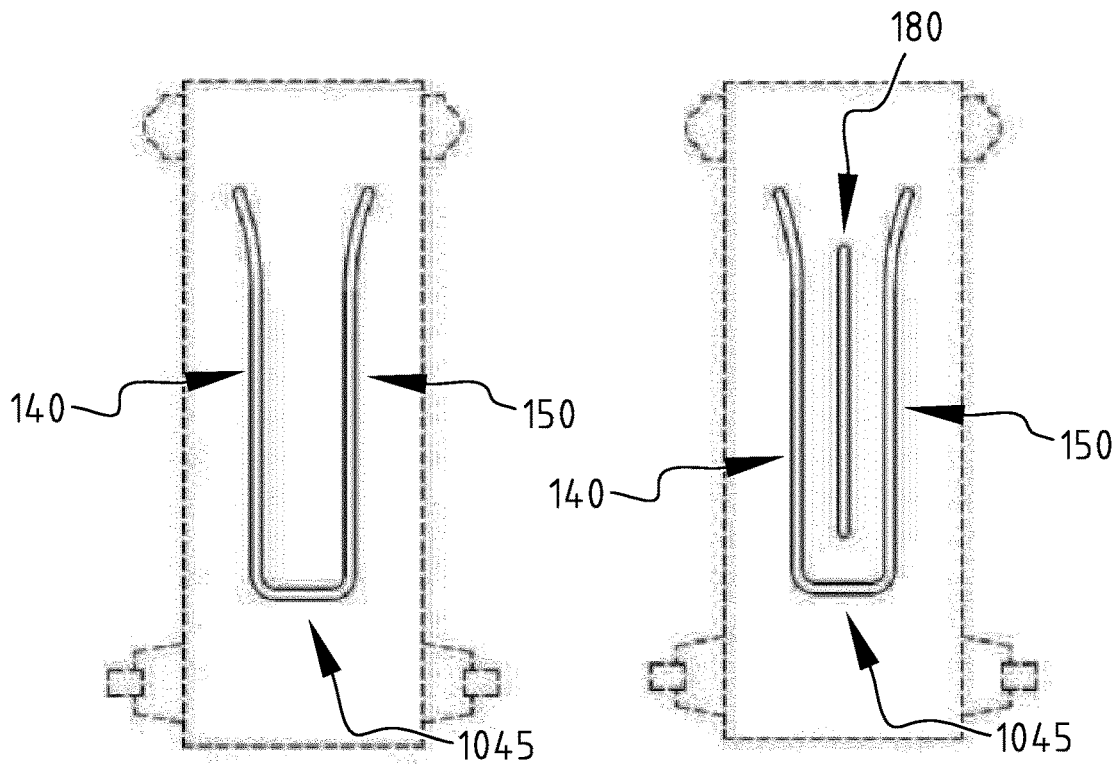
Figures 20G, 20H:
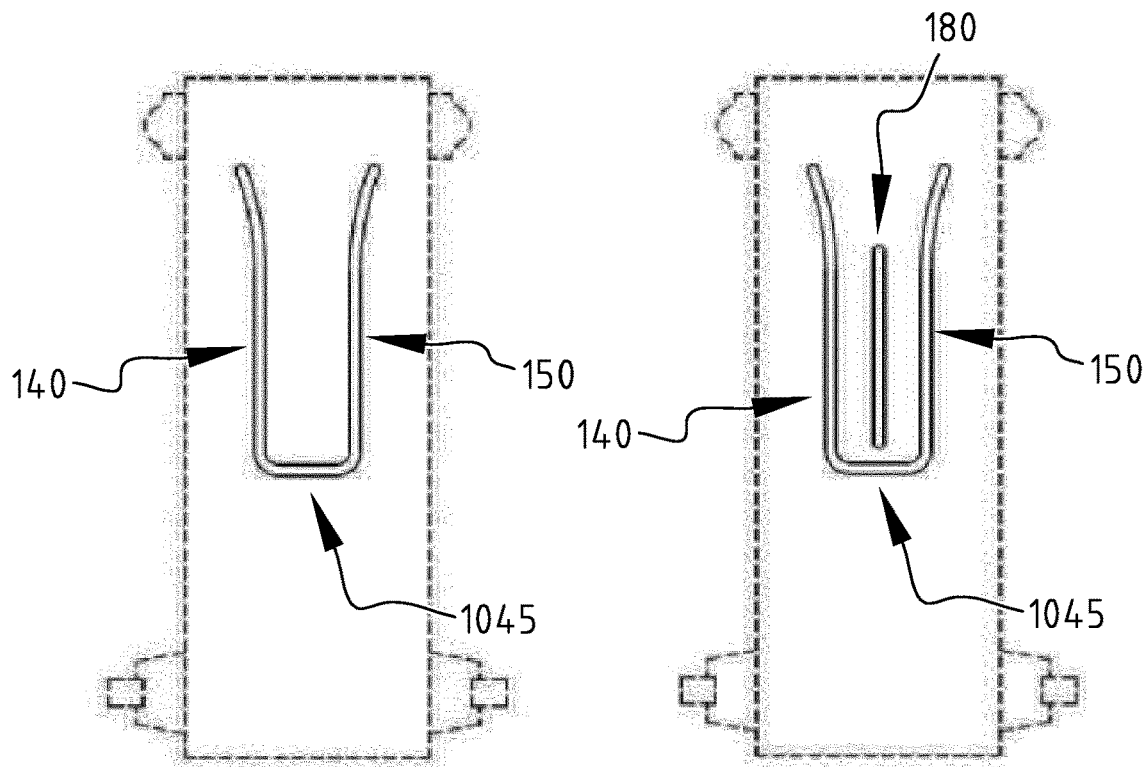
Figure 20I:
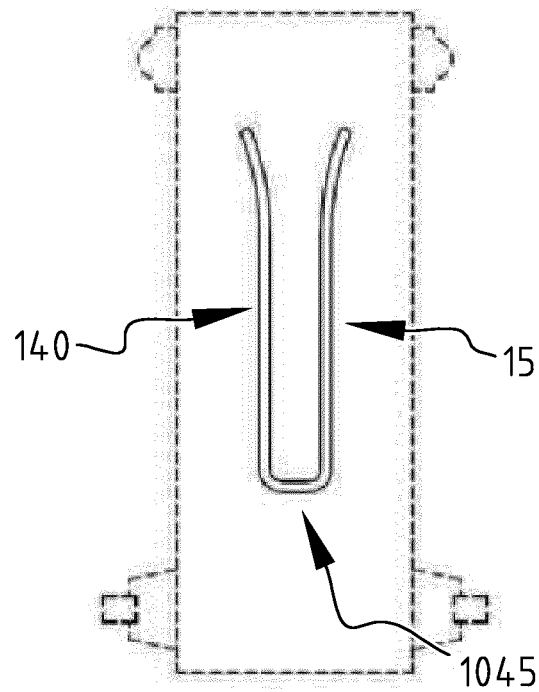
Figure 20J:
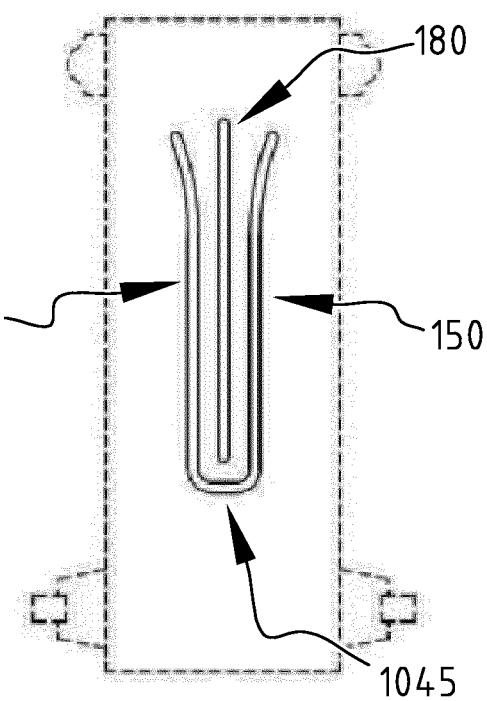
Figure 20K:
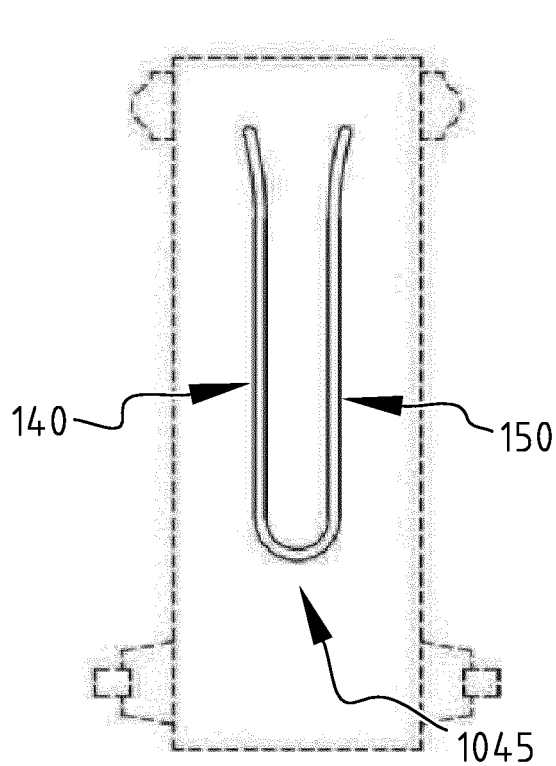
Figure 20L:
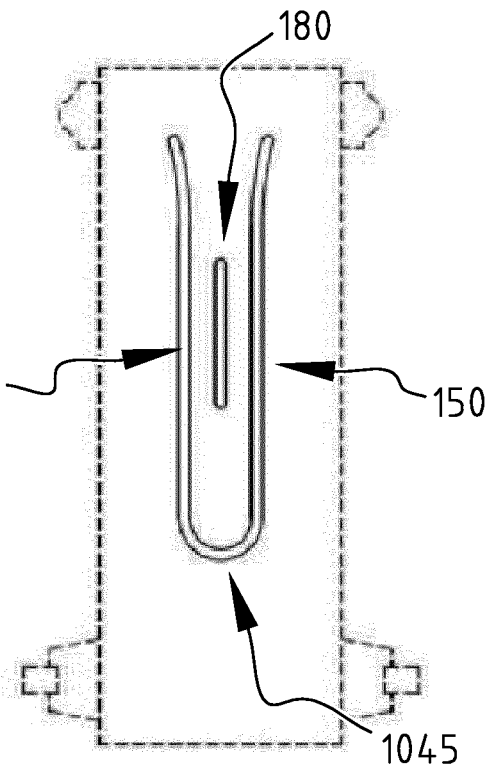
Figure 20M:
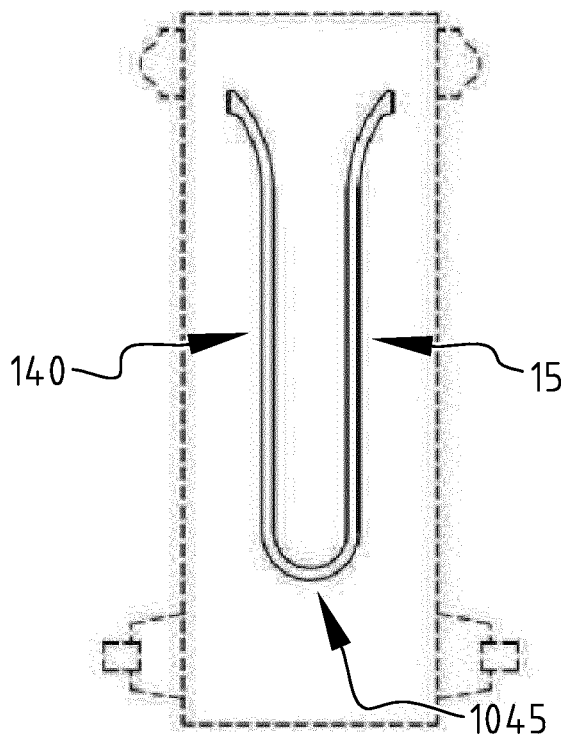
Figure 20N:
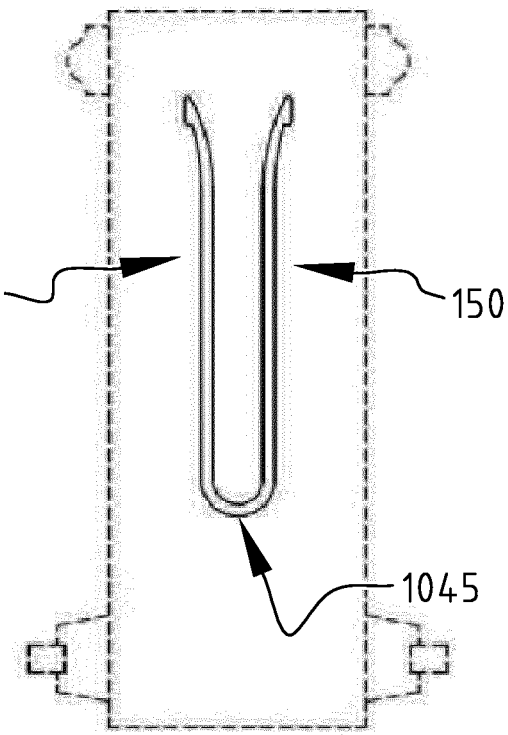
Figure 20O:
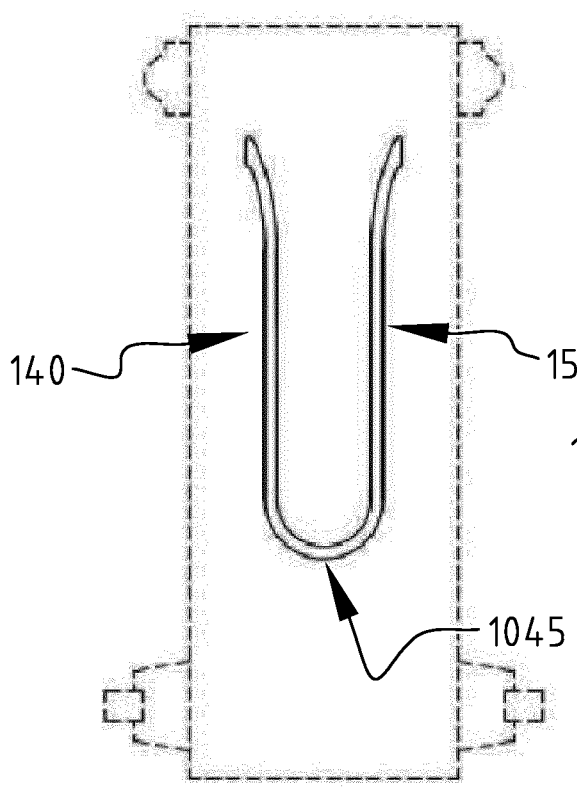
Figure 20P:
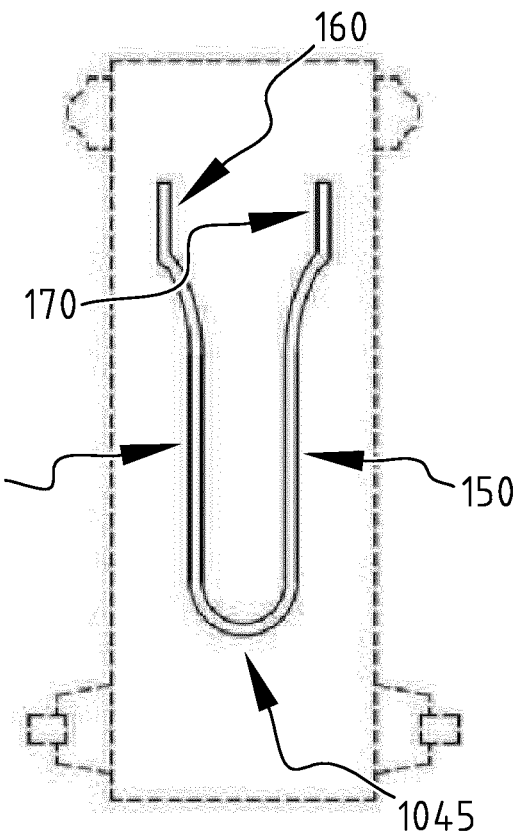
Figure 20Q:
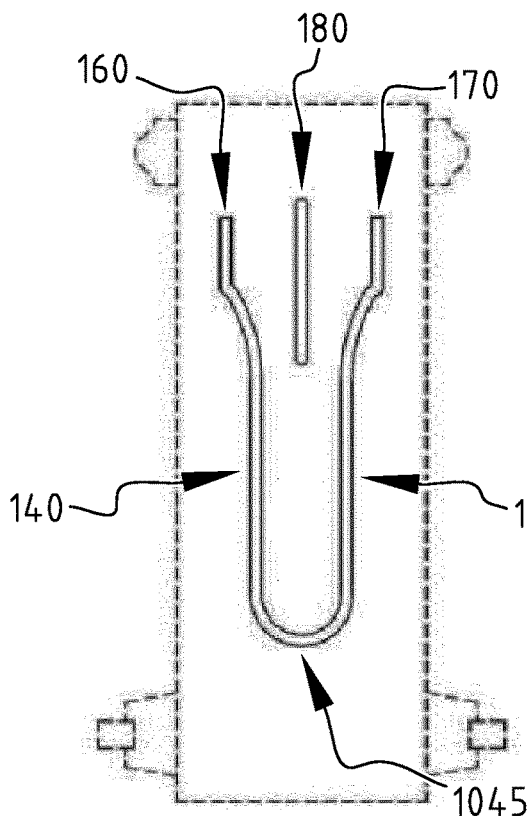
Figure 20R:
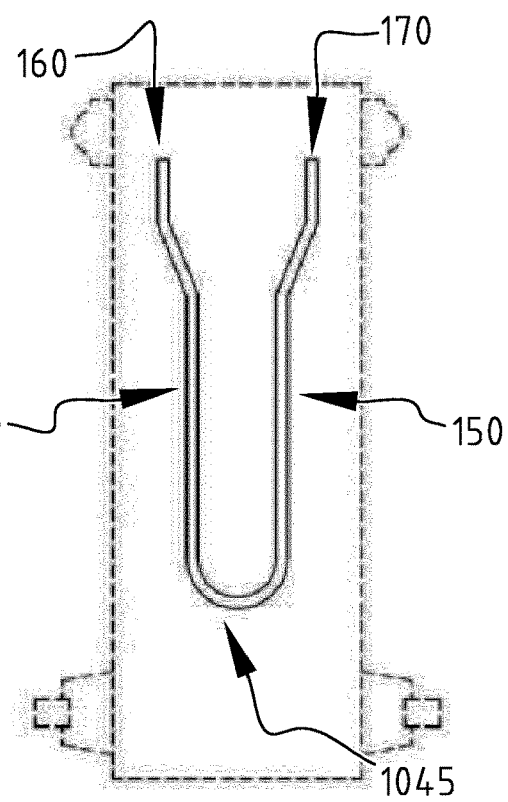
Figure 20S:
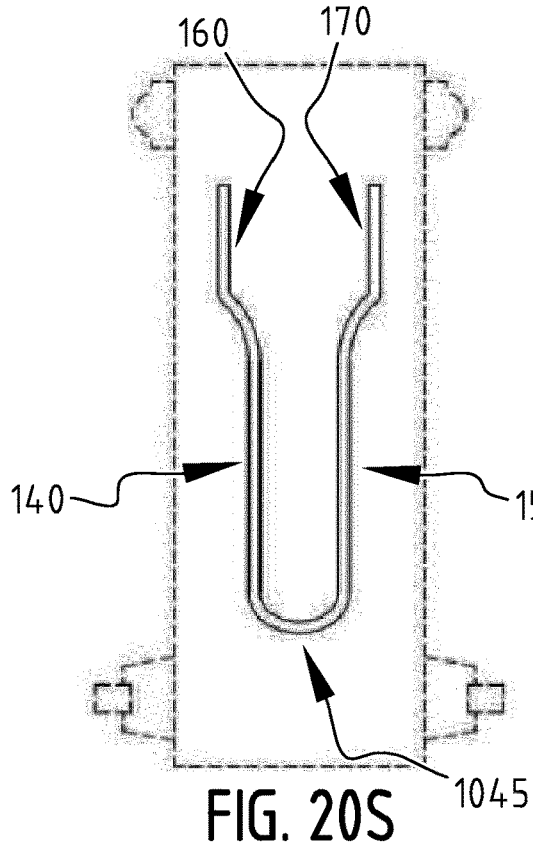
Figure 20T:
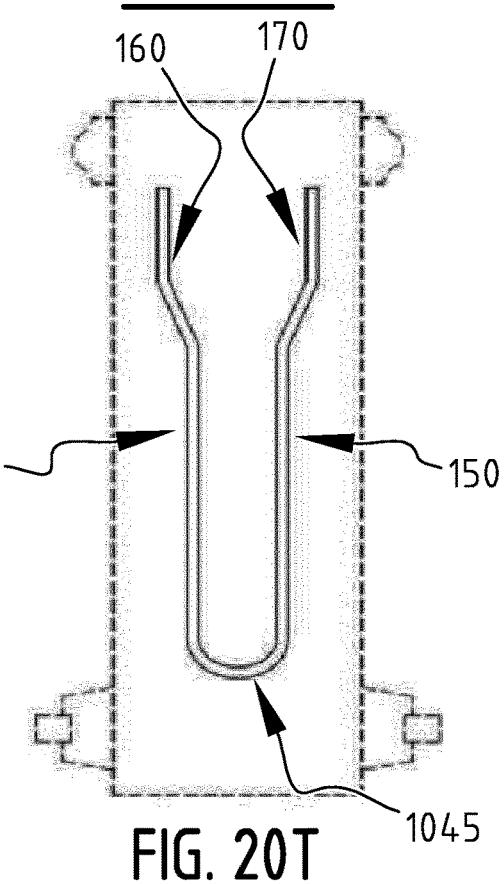
Figure 20U:
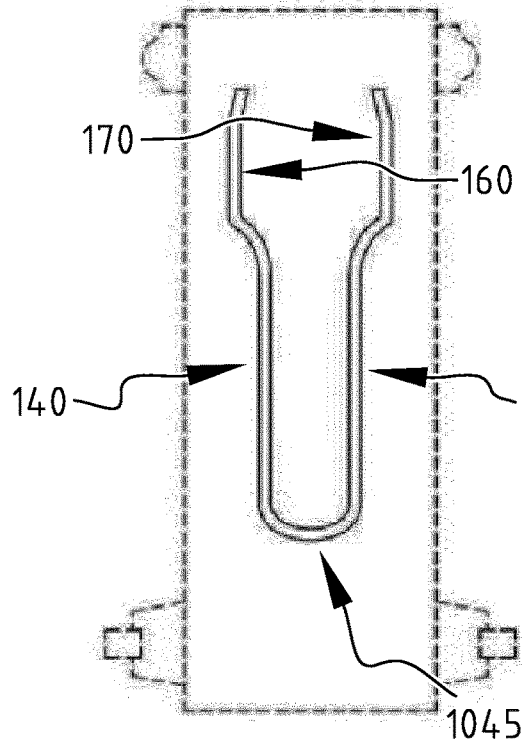
Figure 20V:
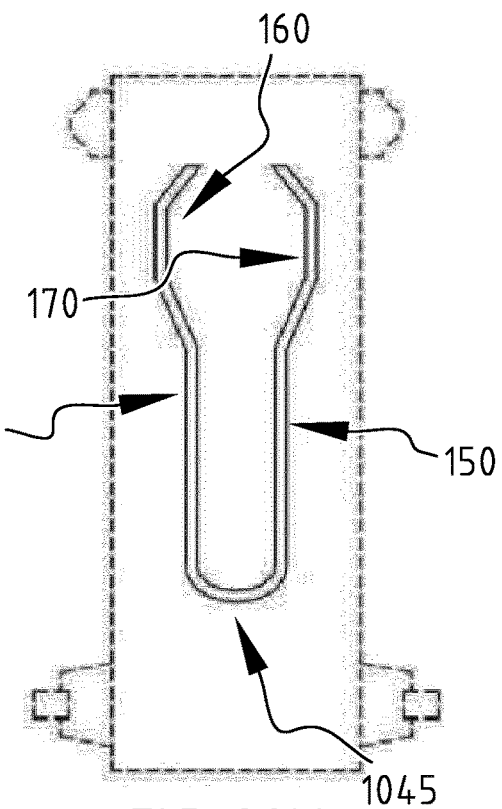
Figure 20W:
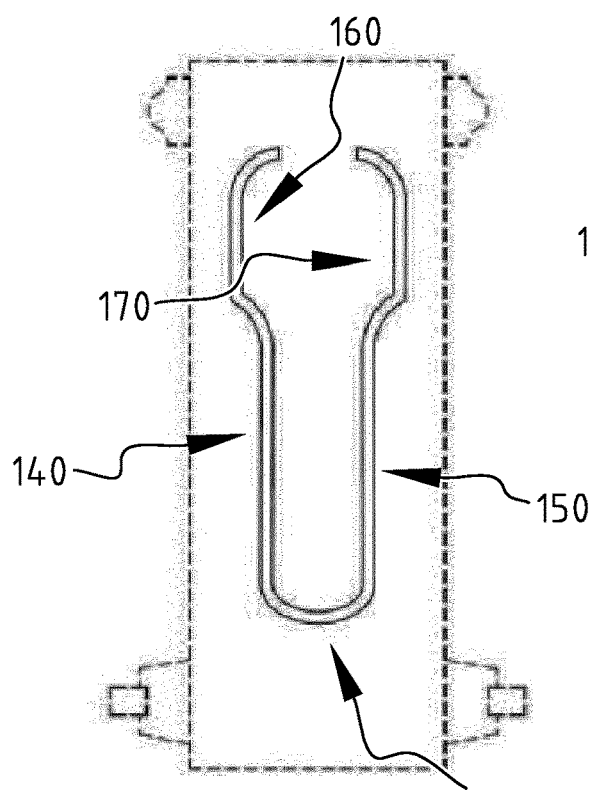
Figure 20X:
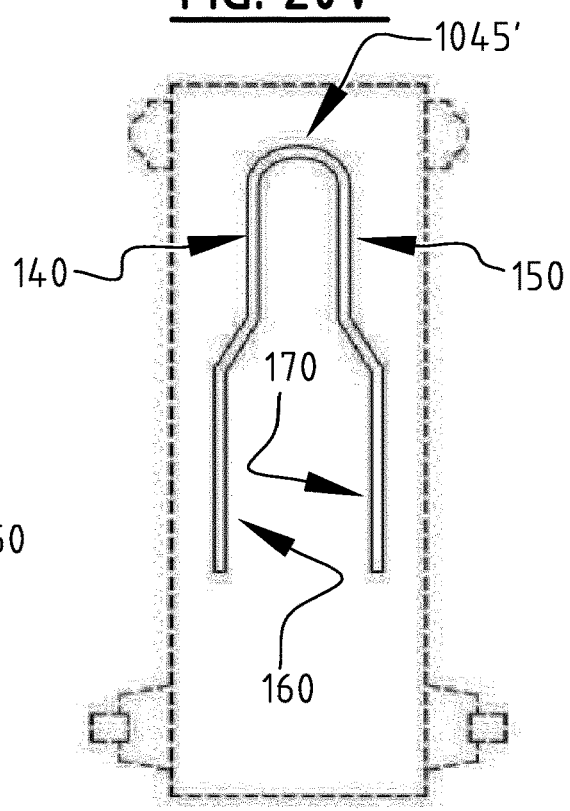
Figure 20Y:
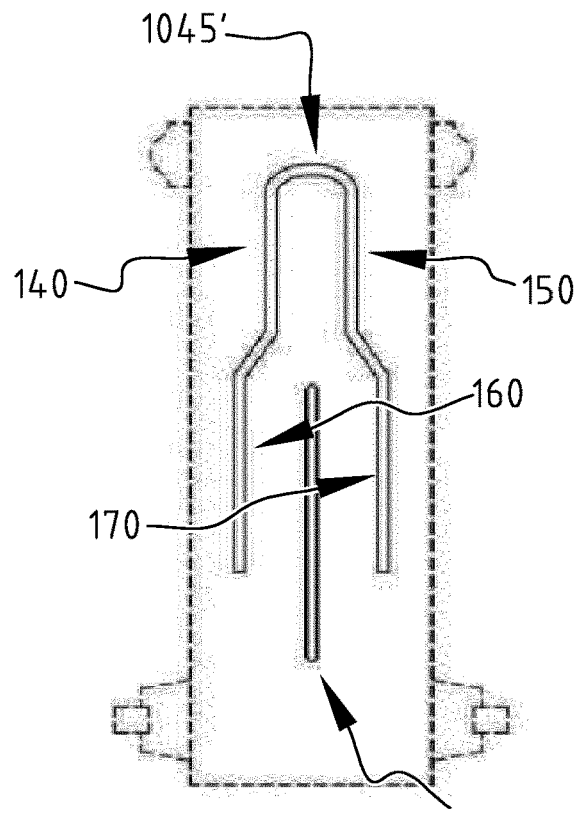
Figure 20Z:
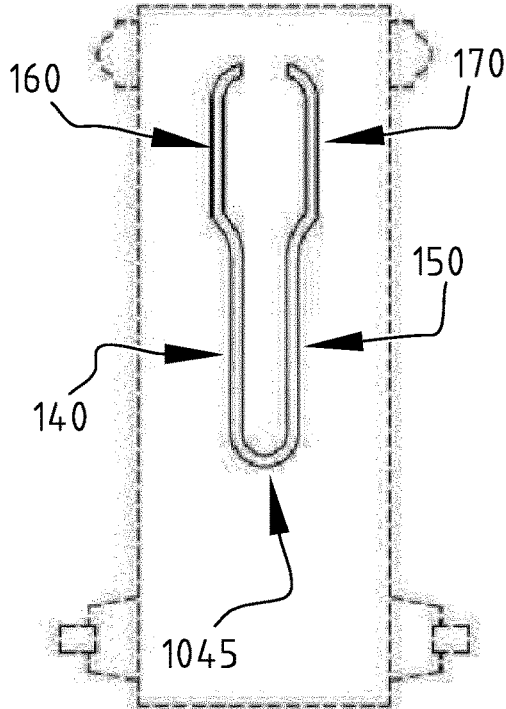
Figure 21A:
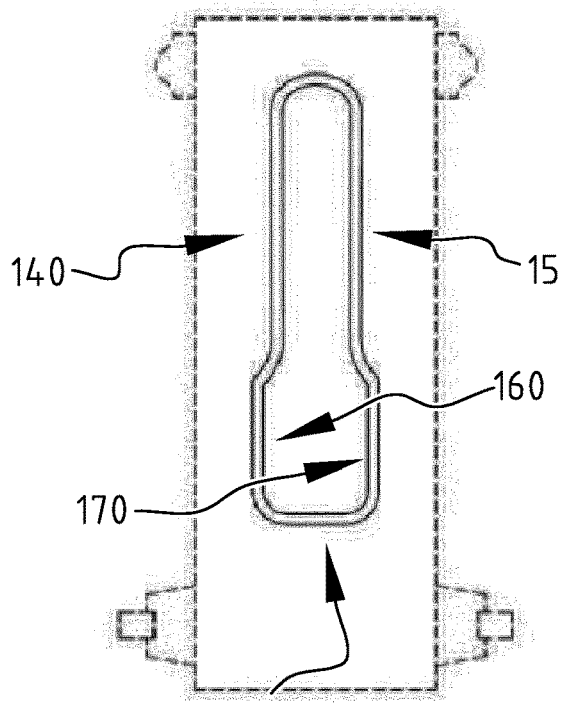
FIGS. 21A-21Z illustrate yet other exemplary embodiments of an absorbent core according to the invention.
Figure 21B:
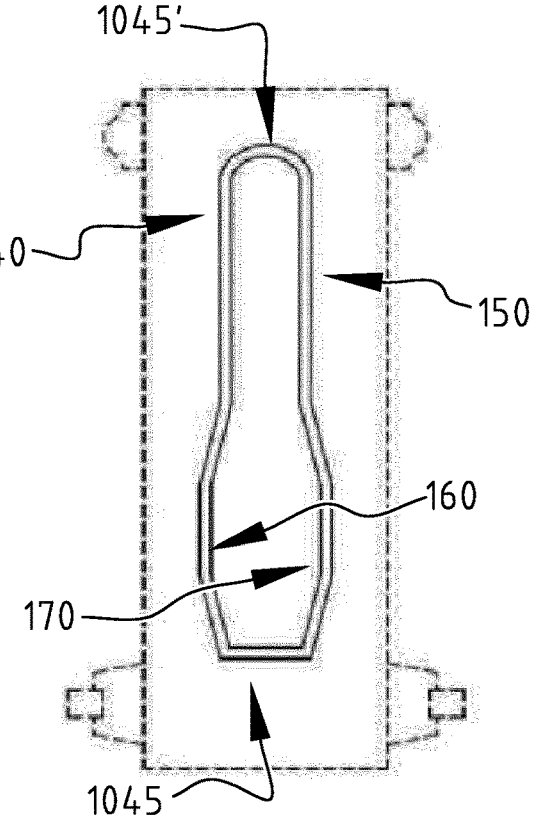
Figure 21C:
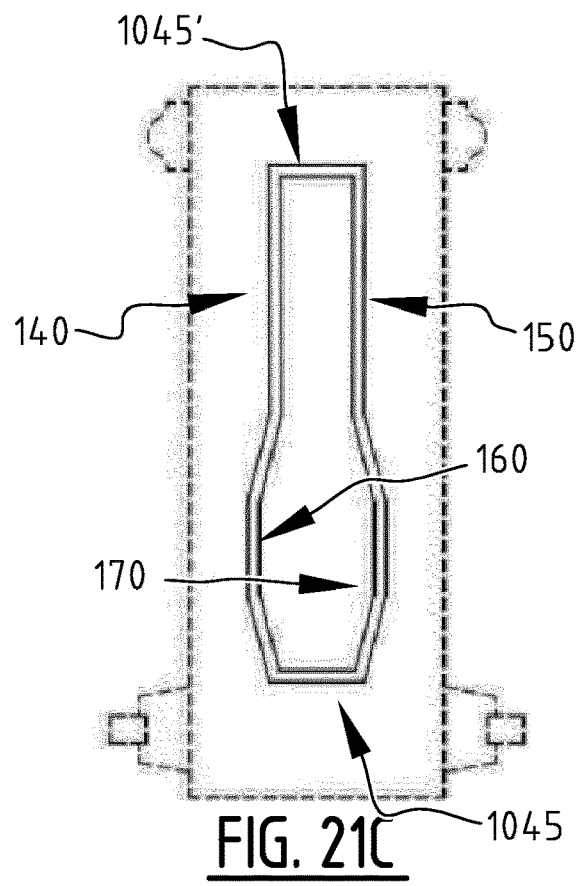
Figure 21D:
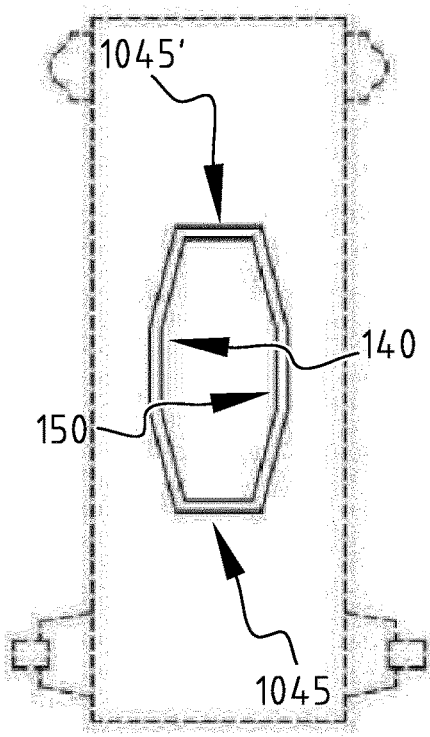
Figure 21E:
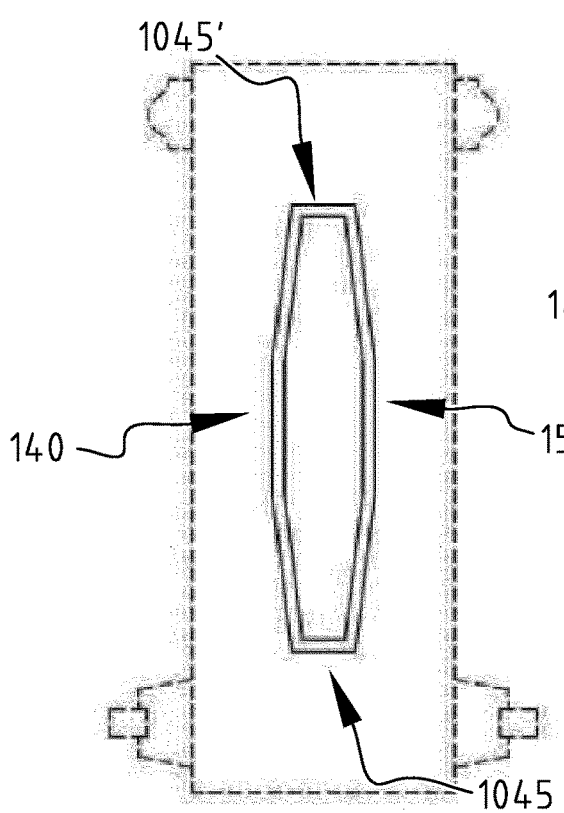
Figure 21F:
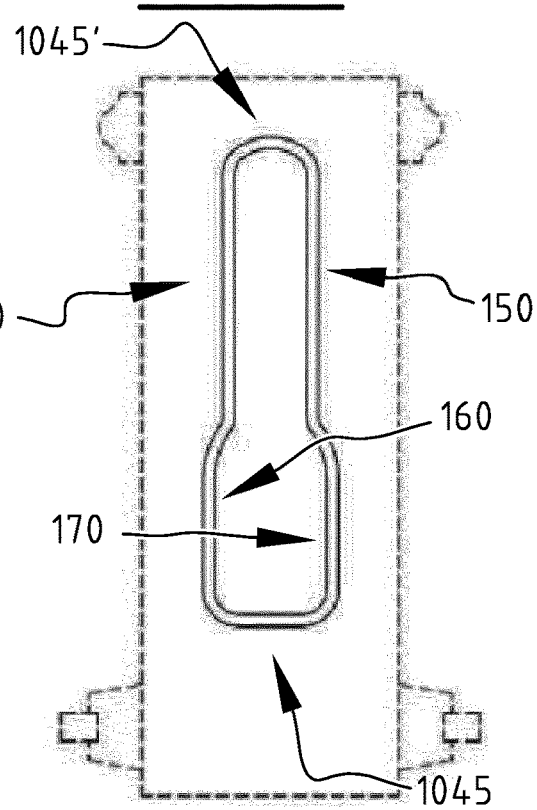
Figure 21G:
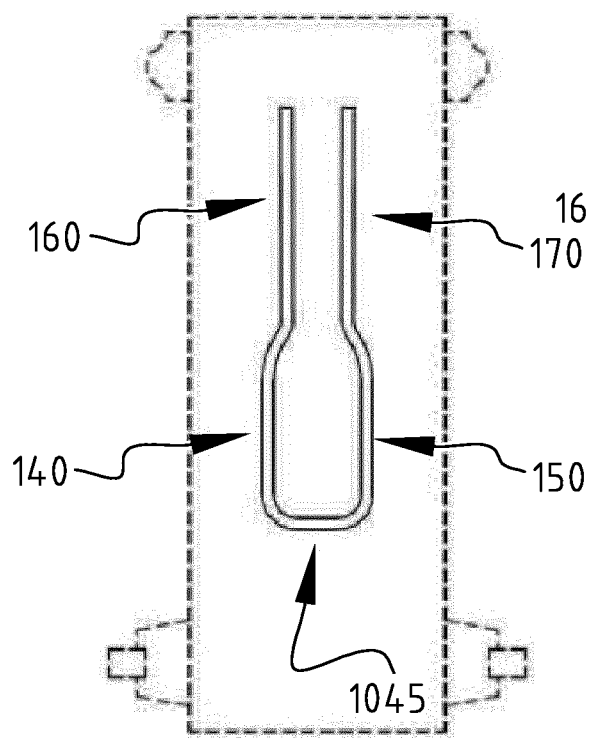
Figure 21H:
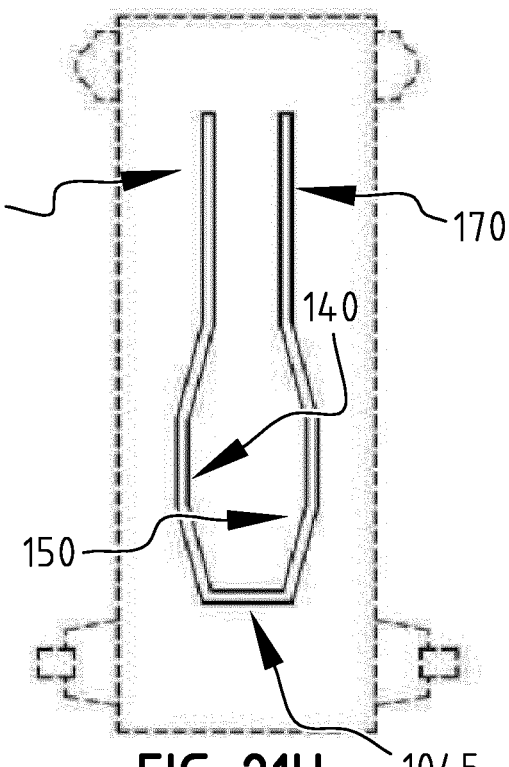
Figure 21I:
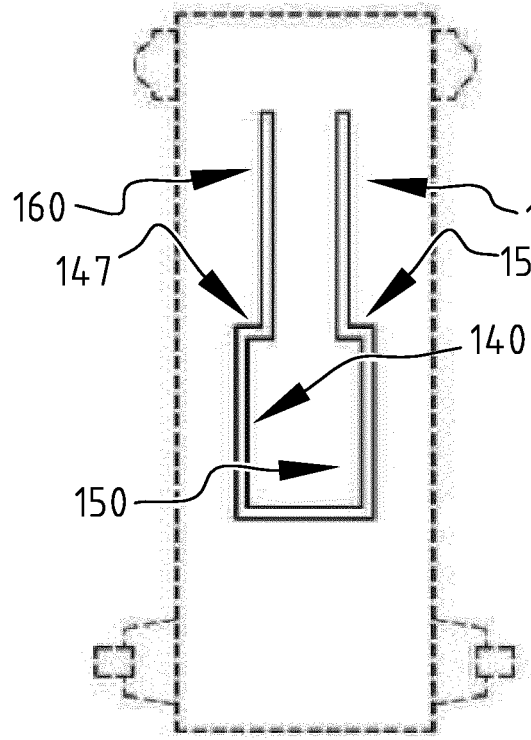
Figure 21J:
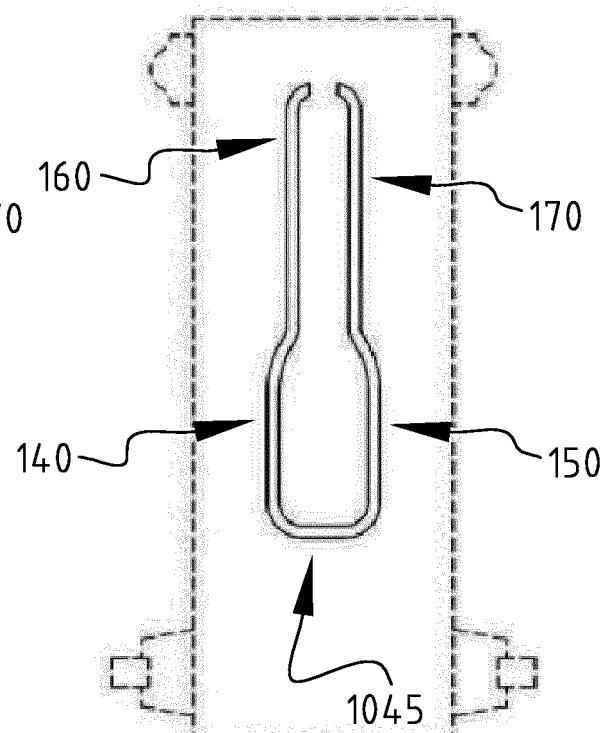
Figure 21K:
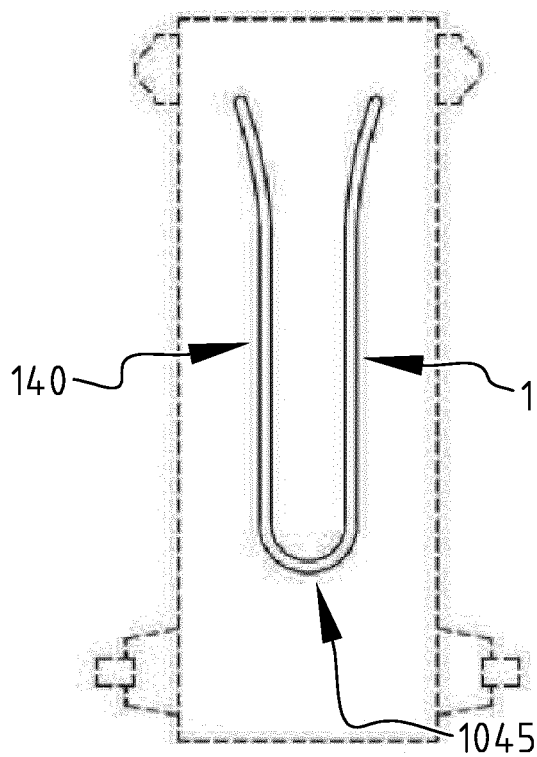
Figure 21L:
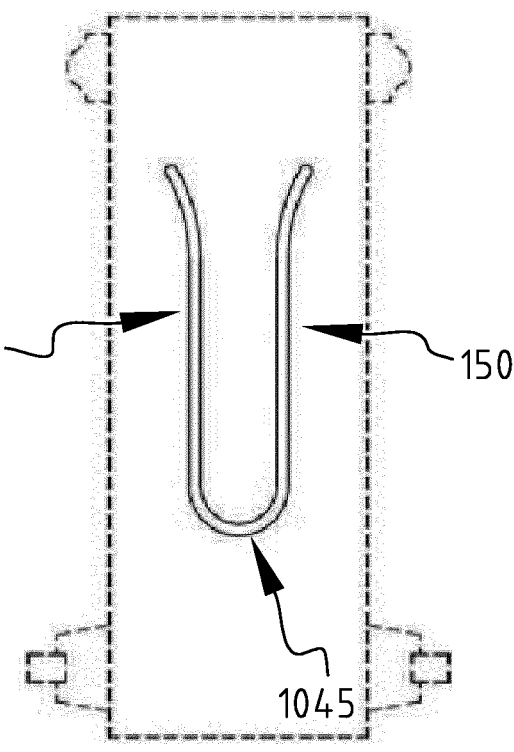
Figure 21M:
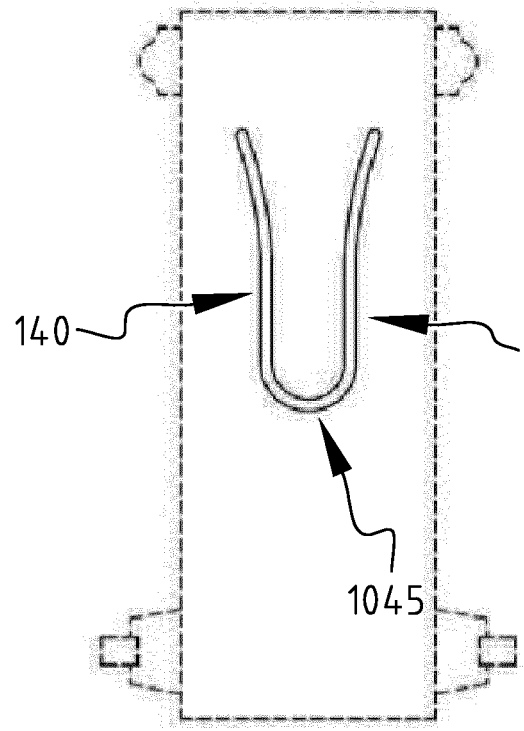
Figure 21N:
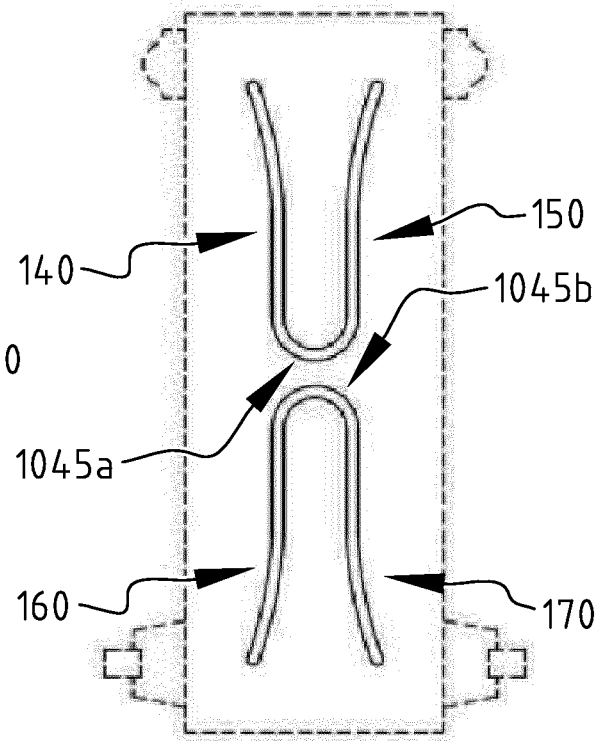
Figure 21O:
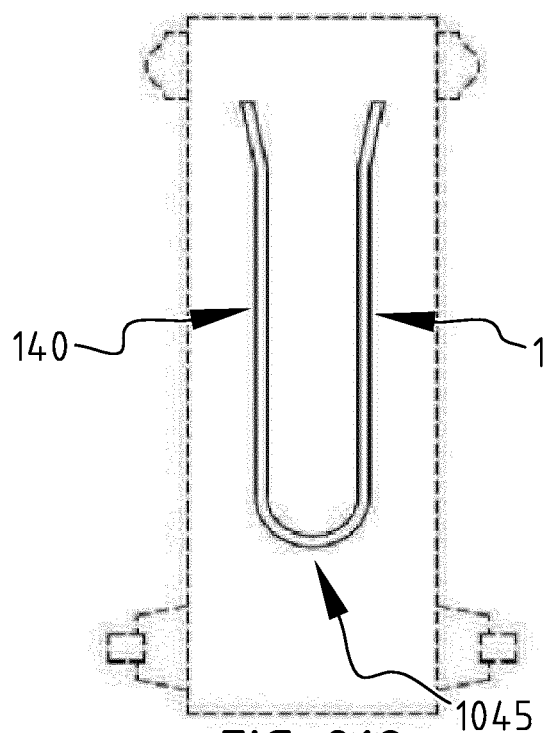
Figure 21P:
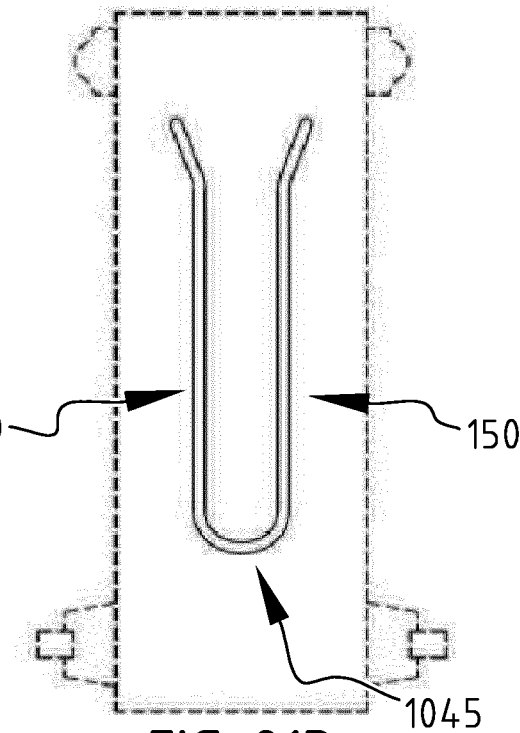
Figure 21Q:
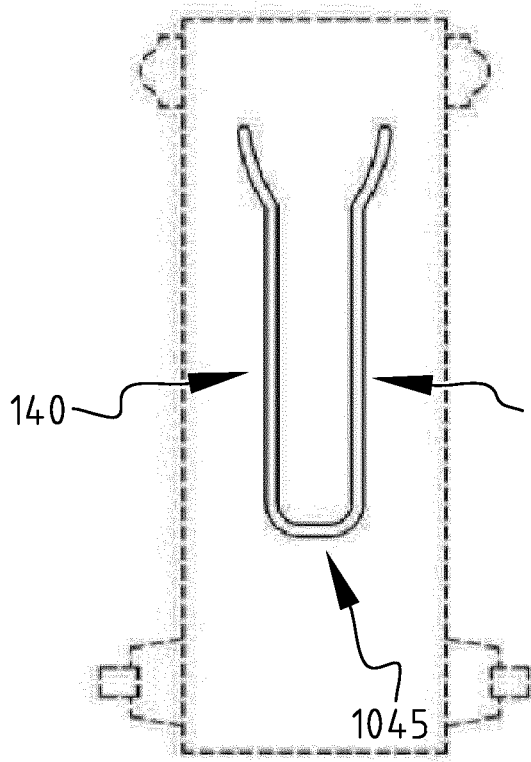
Figure 21R:
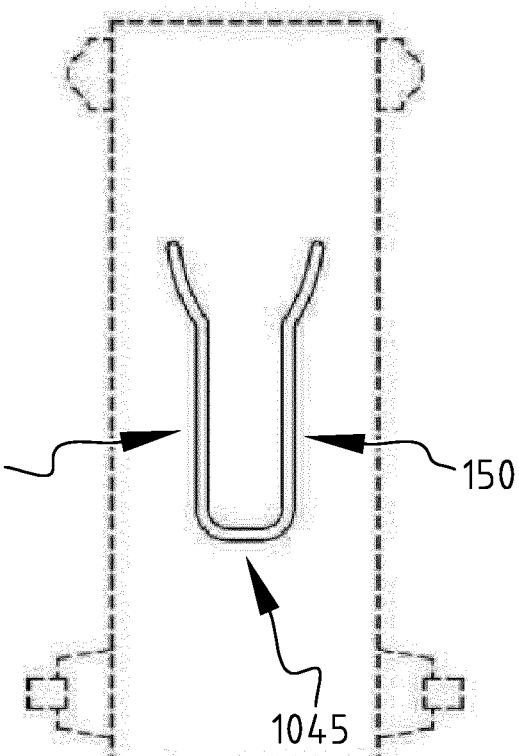
Figures 21S, 21T:
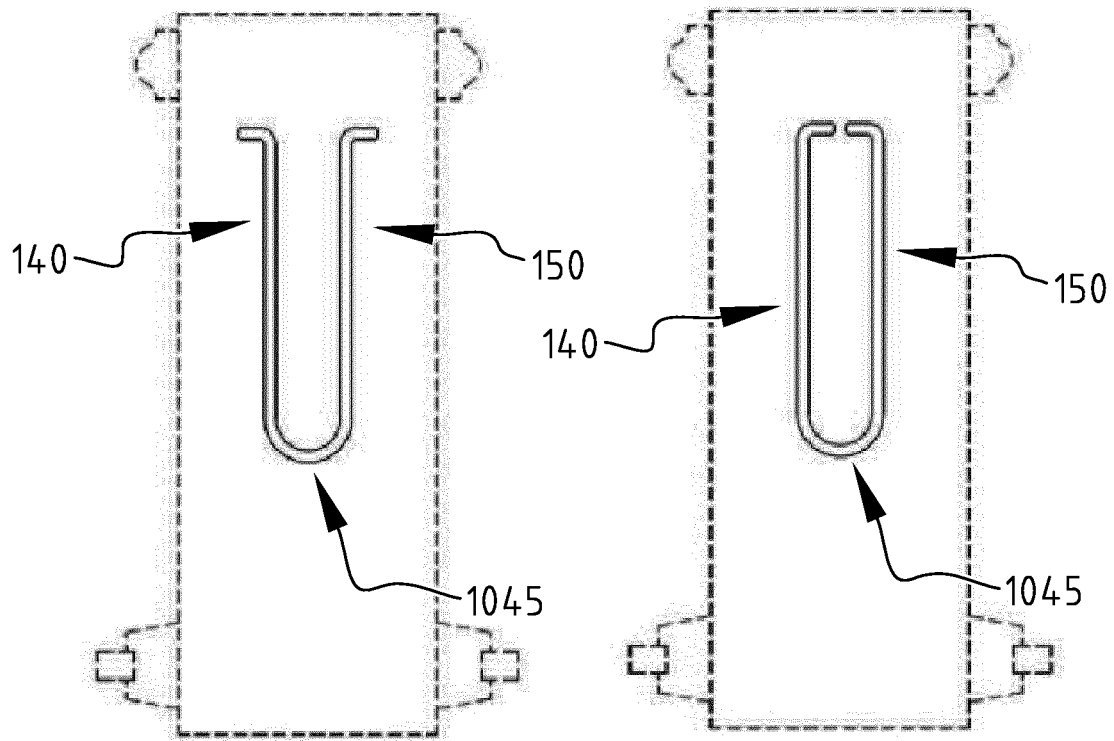
Figures 21U, 21V:
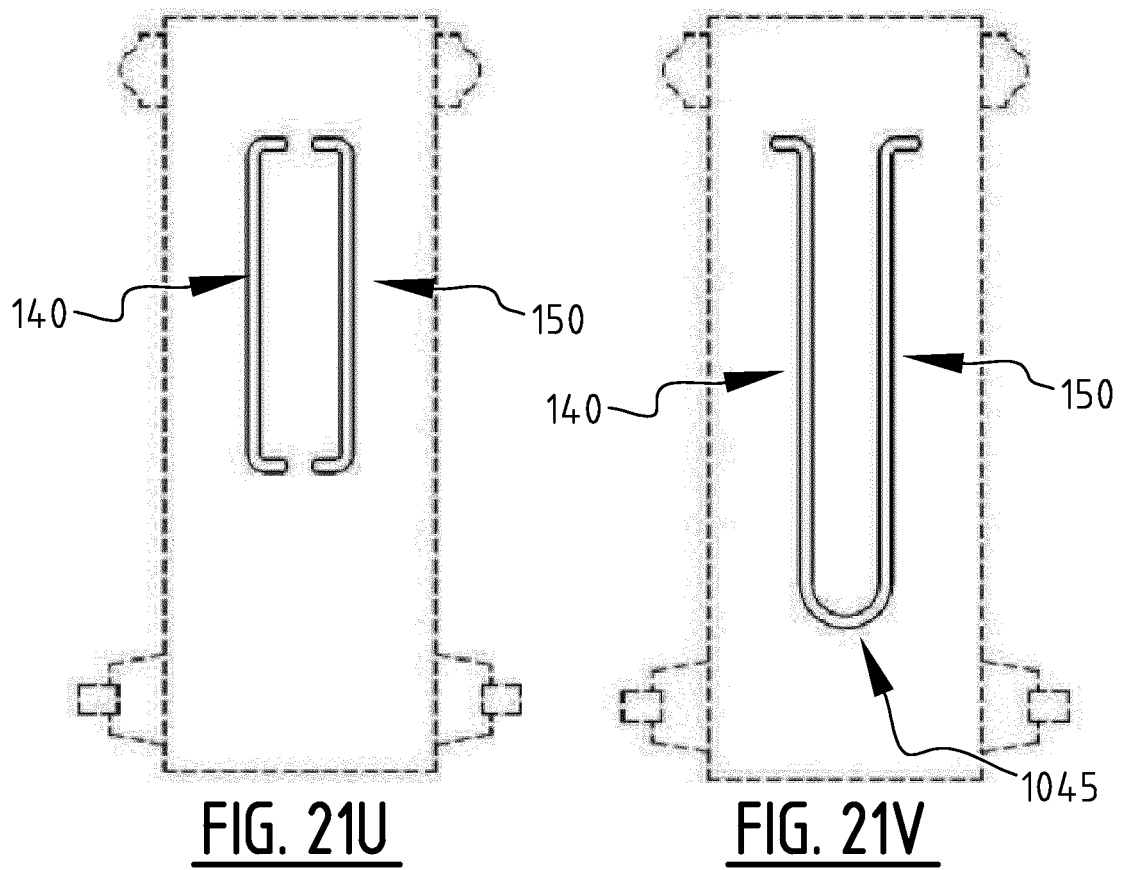
Figure 21W:
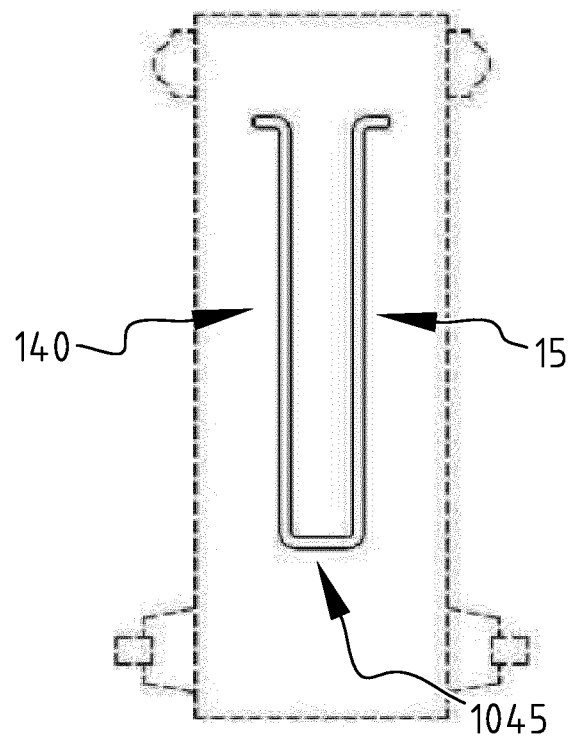
Figure 21X:
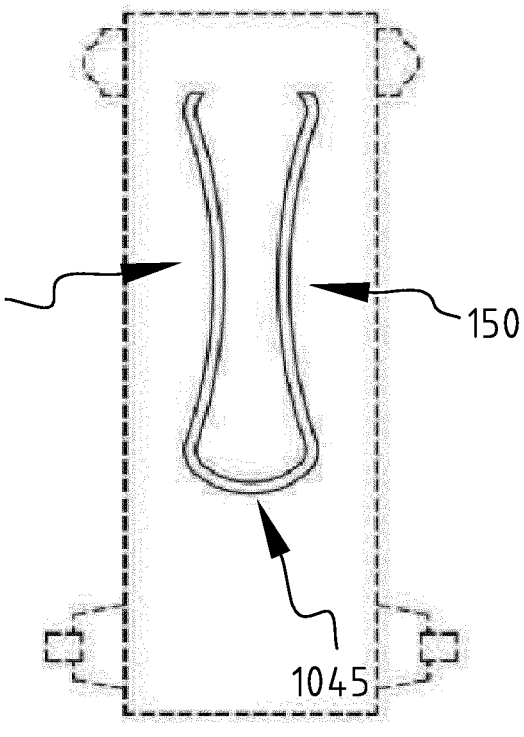
Figure 21Y:
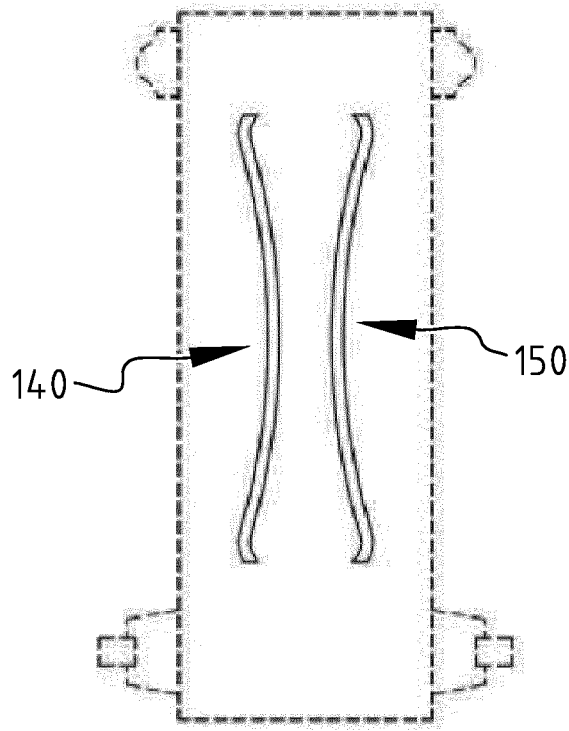
Figure 21Z:
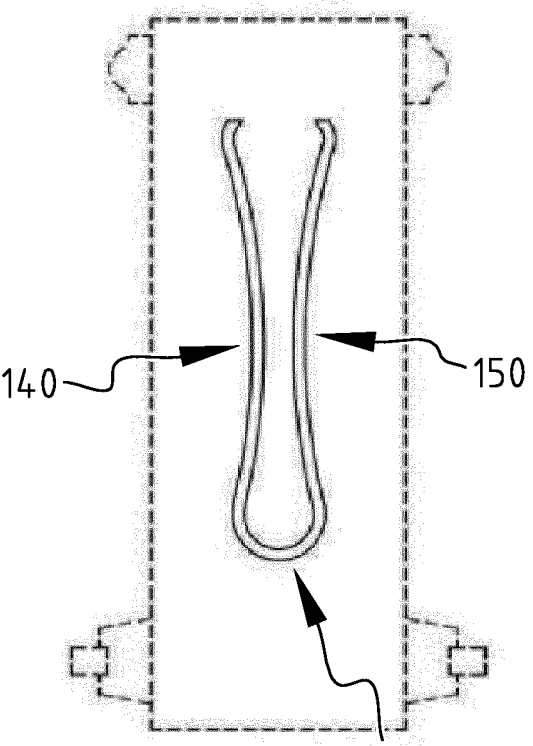
Figure 22A:
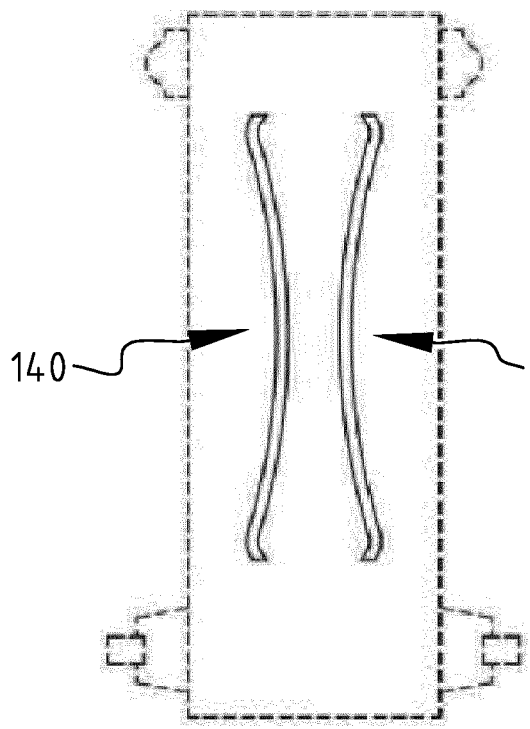
FIGS. 22A-22Z illustrate yet other exemplary embodiments of an absorbent core according to the invention.
Figure 22B:
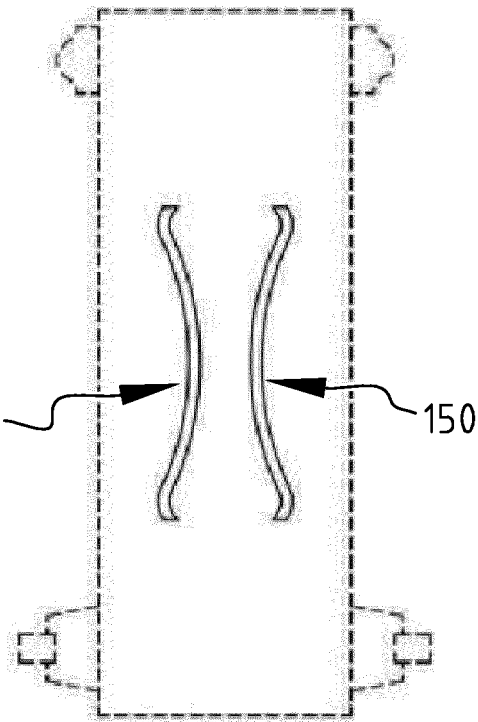
Figure 22C:
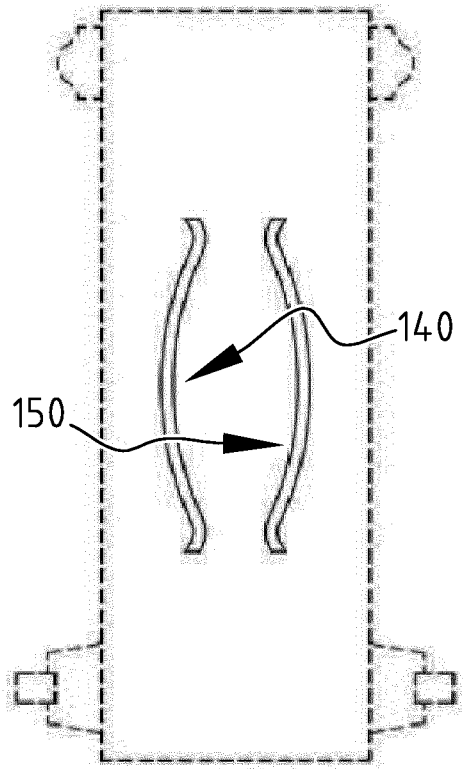
Figure 22D:
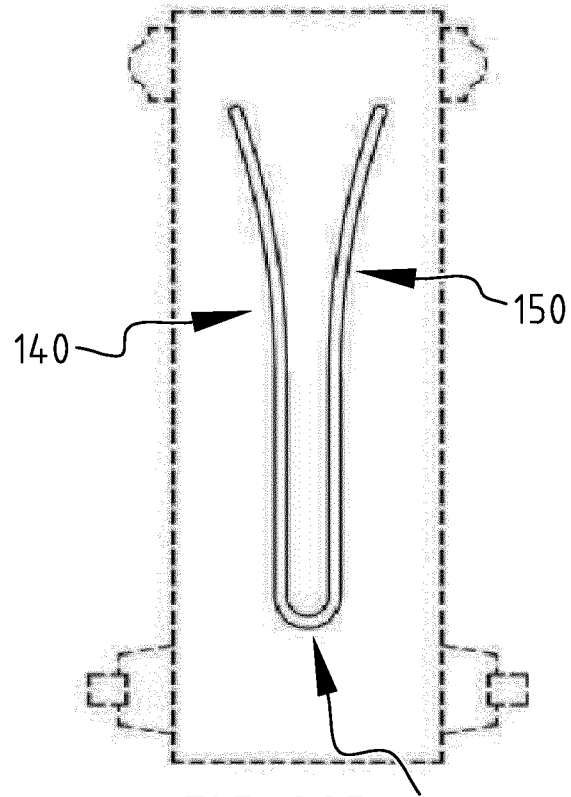
Figure 22E:
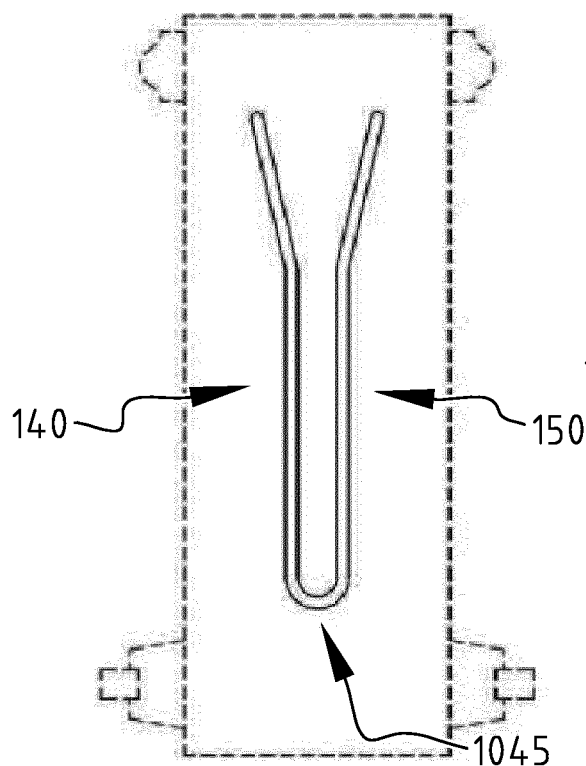
Figure 22F:
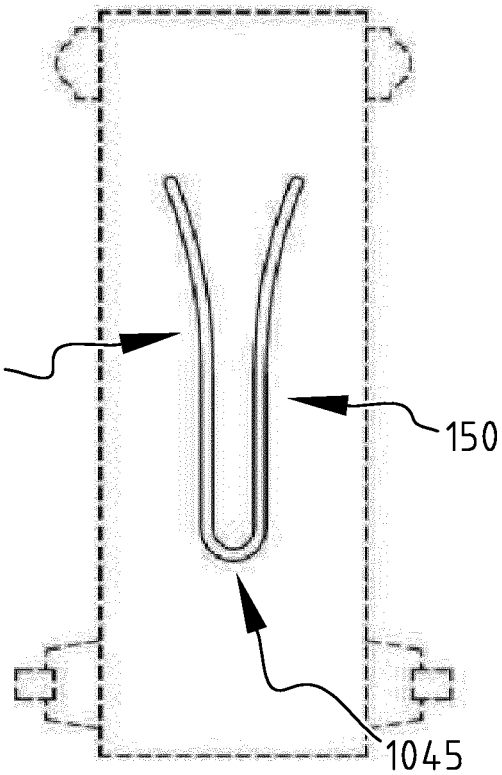
Figure 22G:
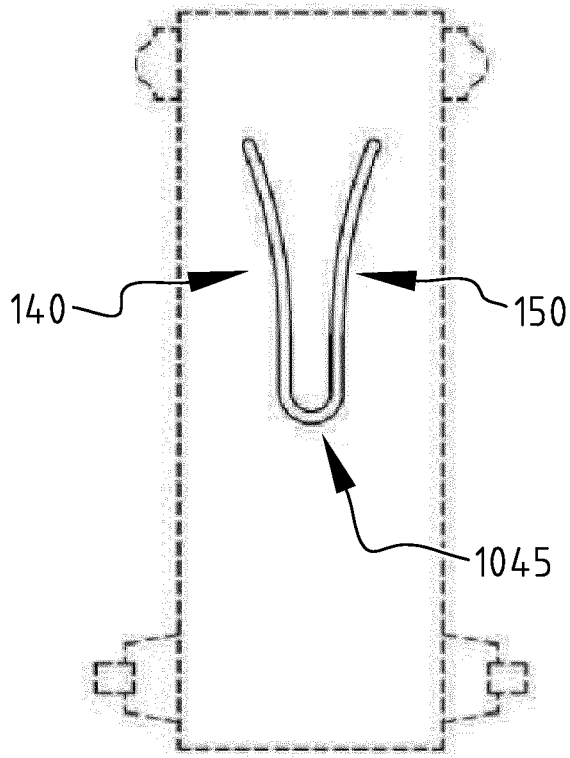
Figure 22H:
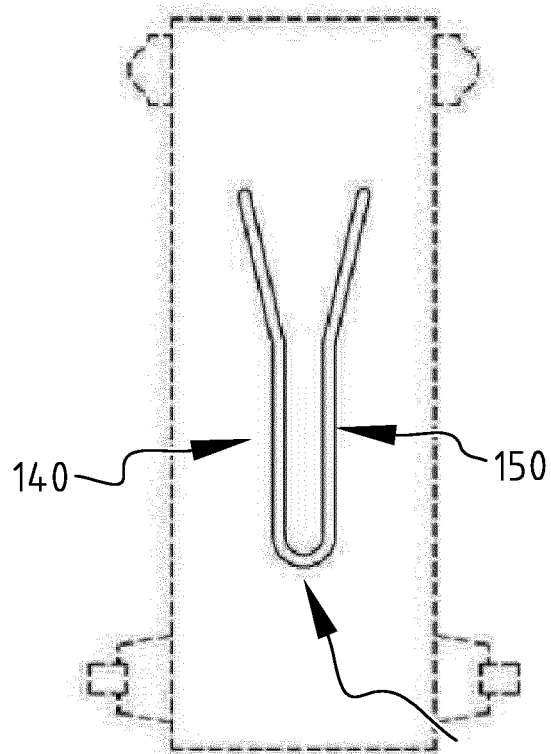
Figure 22I:
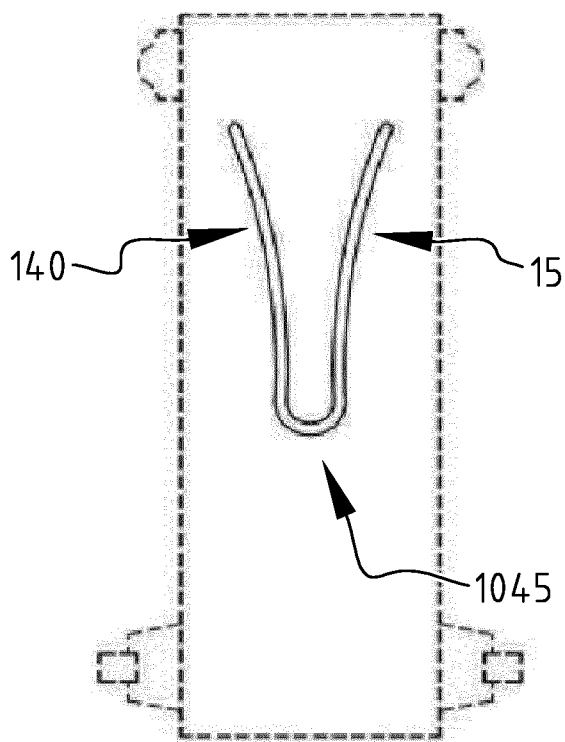
Figure 22J:
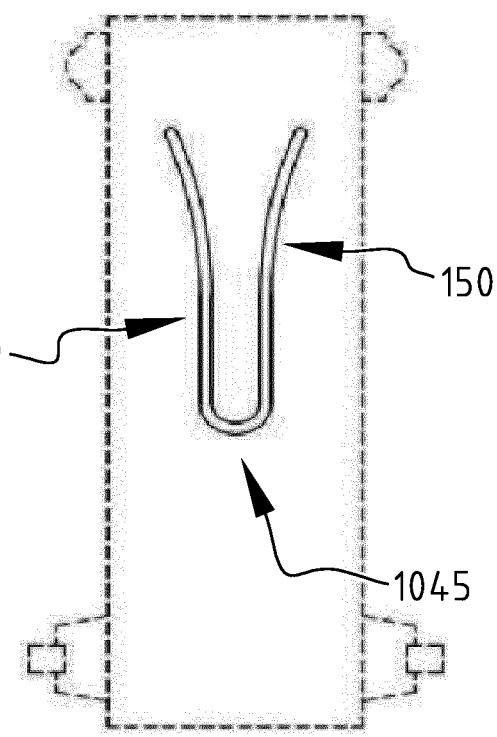
Figure 22K:
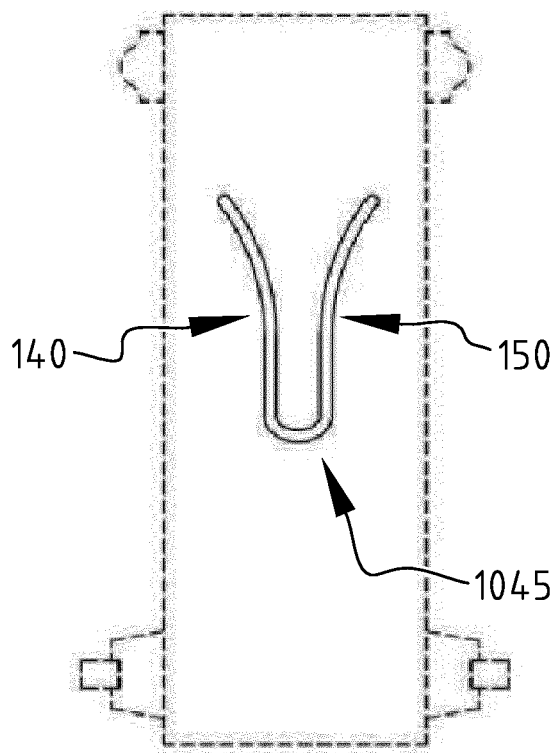
Figure 22L:
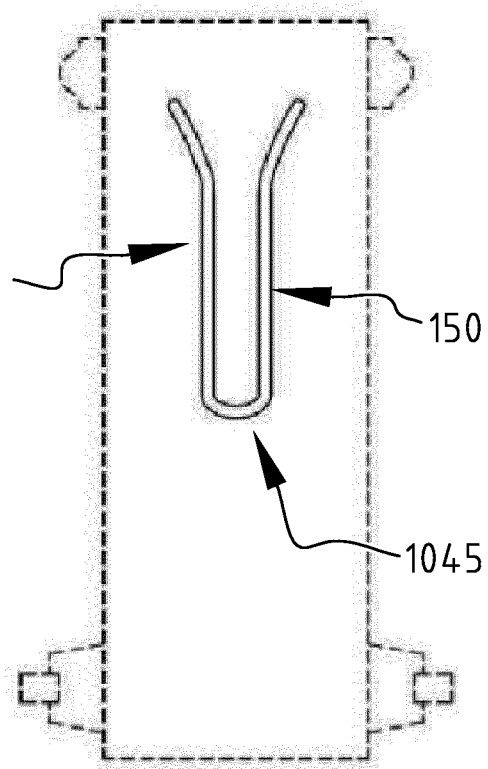
Figure 22M:
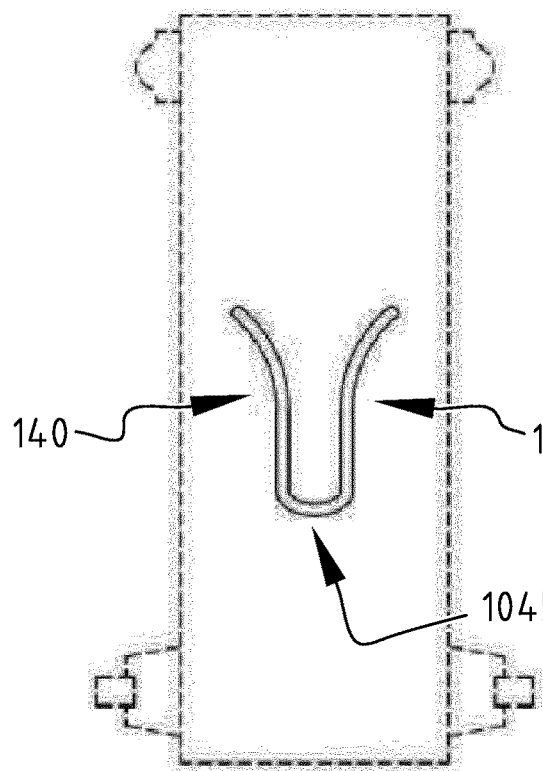
Figure 22N:
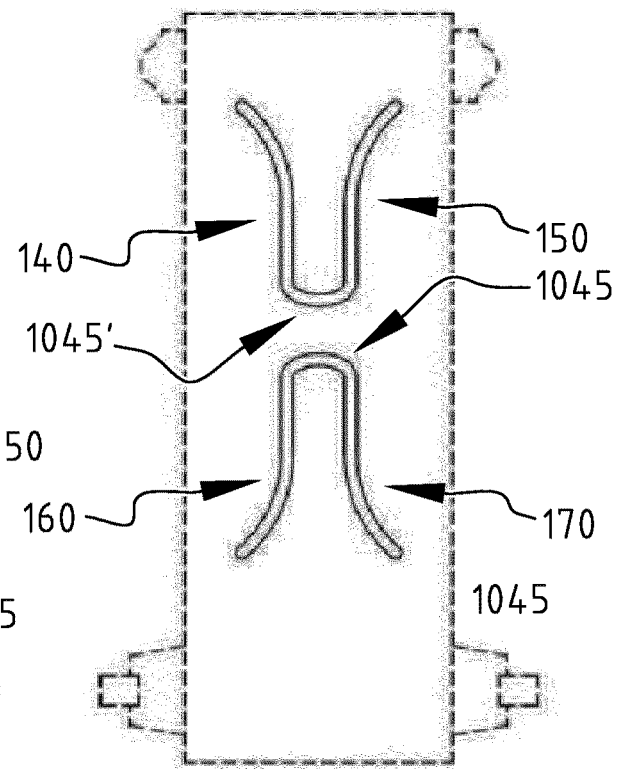
Figure 22O:
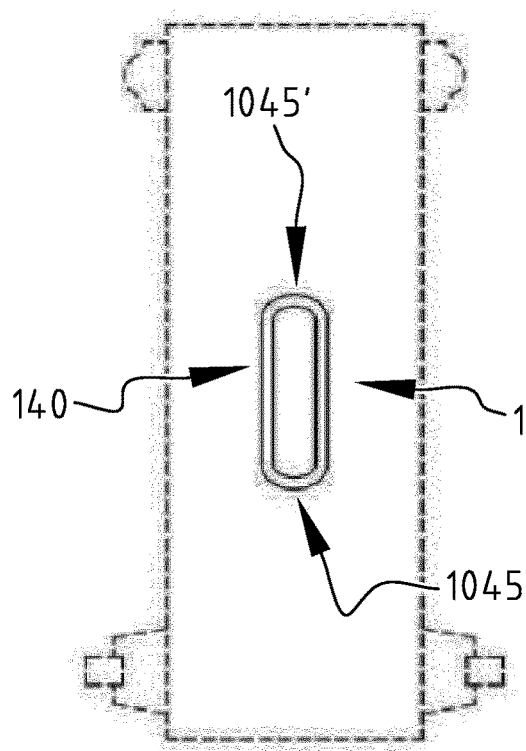
Figure 22P:
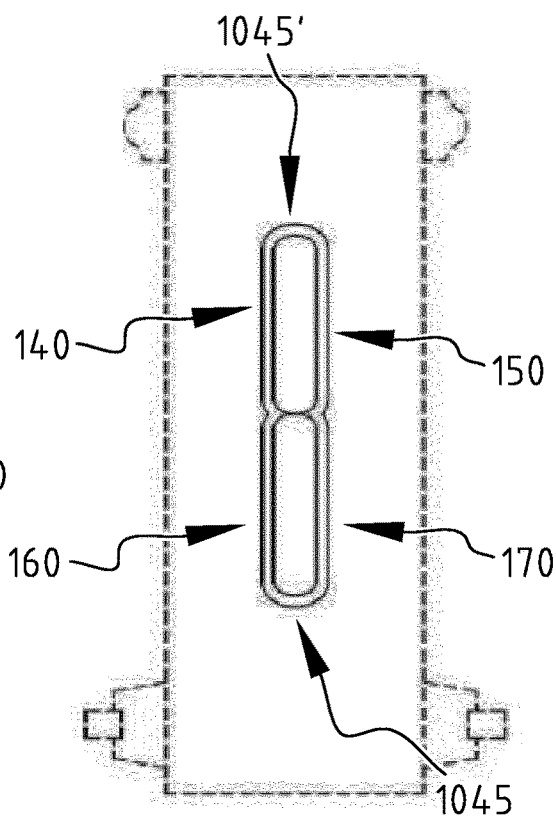
Figures 22Q, 22R:
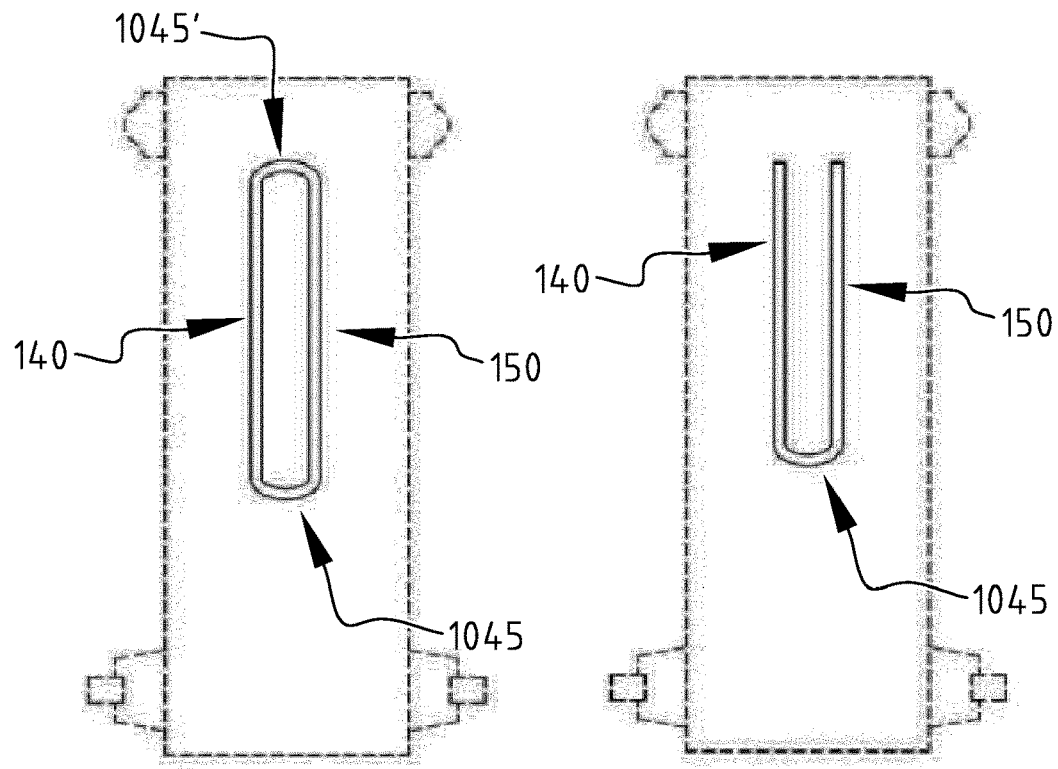
Figures 22S, 22T:
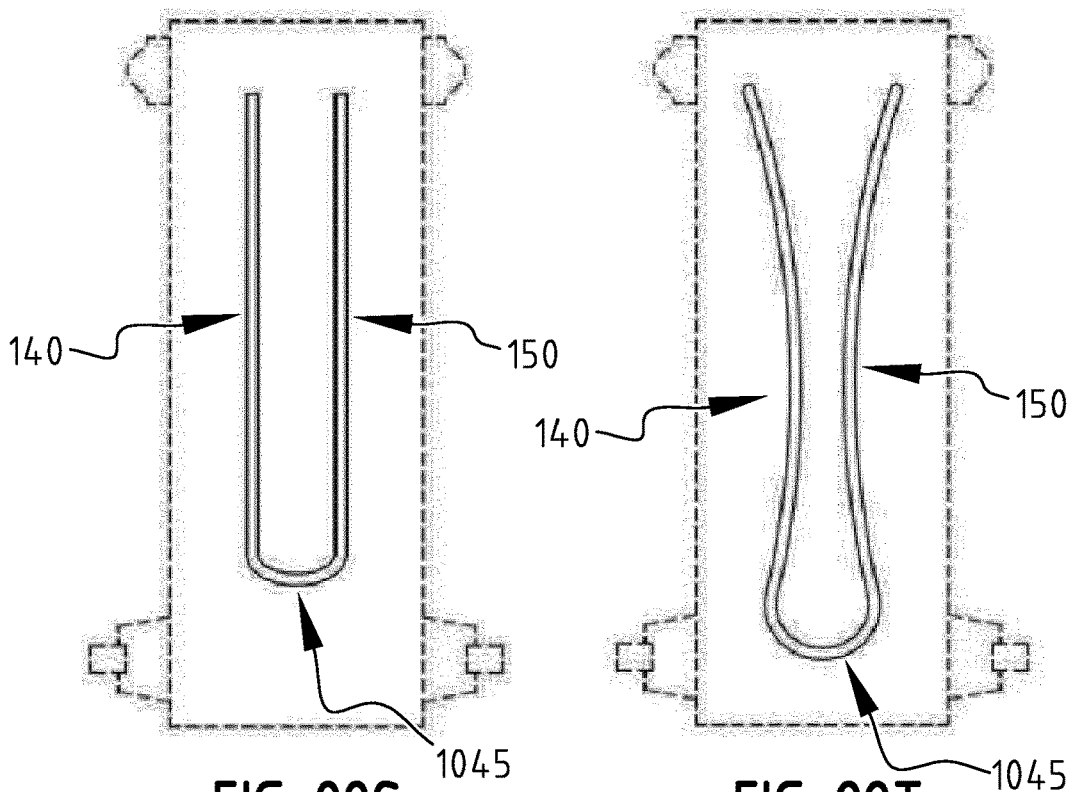
Figures 22U, 22W:
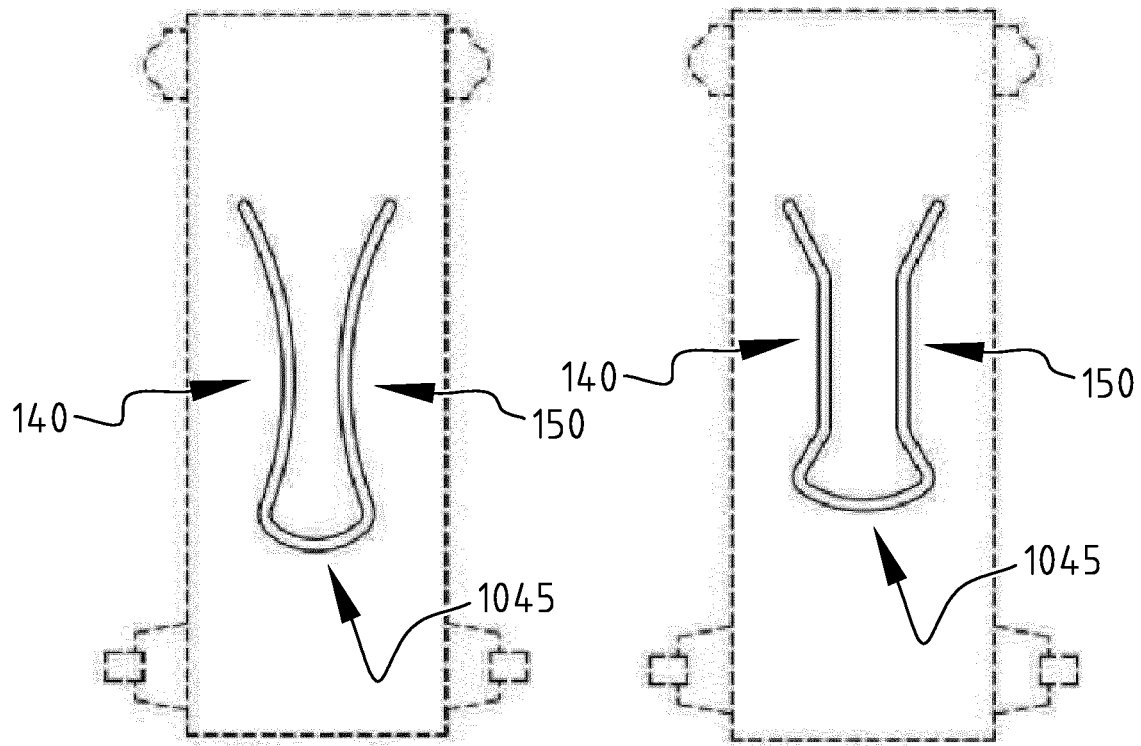
Figures 22V, 22X:
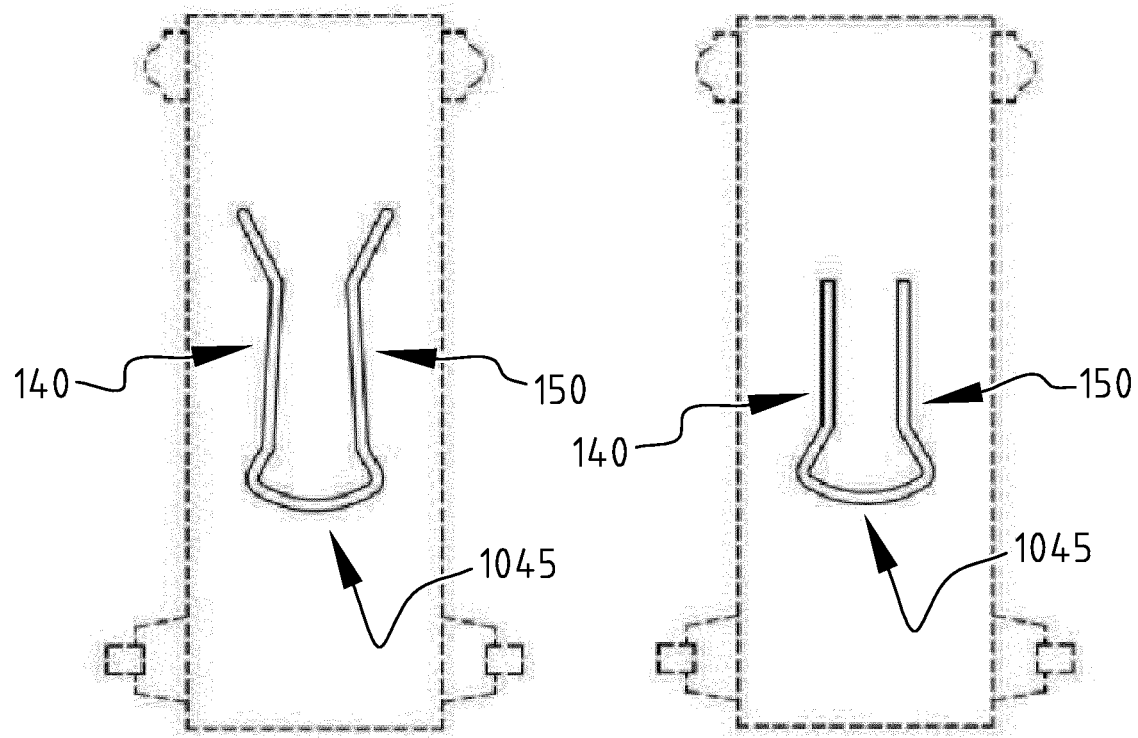
Figure 22Y:
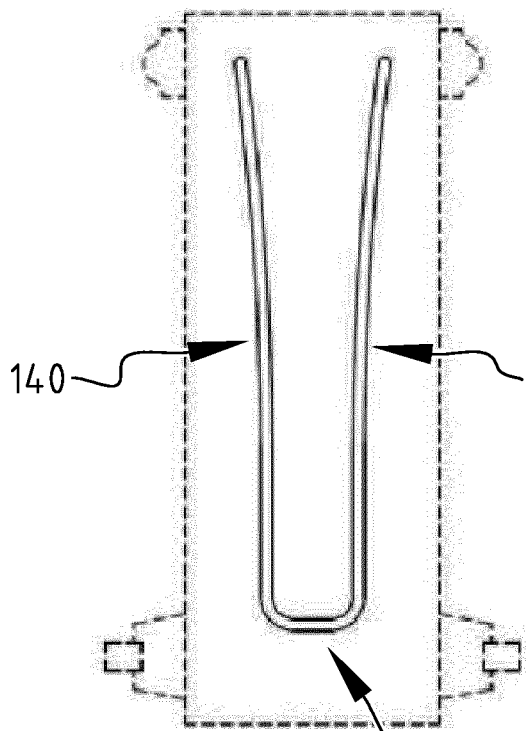
Figure 22Z:
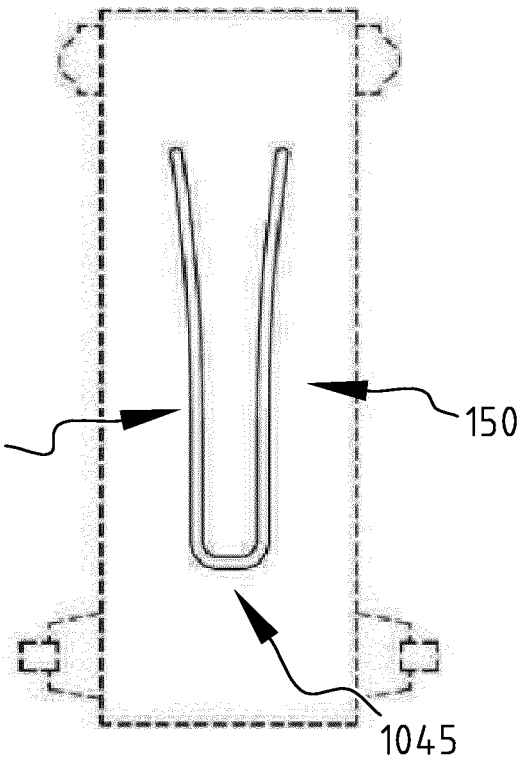

In the embodiments of FIGS. 20X-20Y, a transversal attachment zone 1045' connects the back ends of longitudinal attachment zones 140, 150. In the embodiments of FIGS. 21A-21F, 22O-22Q, 23M-23P, there are two transversal attachment zones 1045 and 1045', respectively connecting the front and back ends of the longitudinal attachment zones 140, 150, 160, 170. In the embodiments of FIGS. 21N, 22N, 23U and 23V, there are two longitudinal attachment zones 140, 150 positioned toward the back side of the absorbent core which are connected by a transversal attachment zone 1045' at their front ends, as well as two longitudinal attachment zones 160, 170 positioned toward the front side of the absorbent core which are connected by a transversal attachment zone 1045 at their back ends.

Figure 23A:
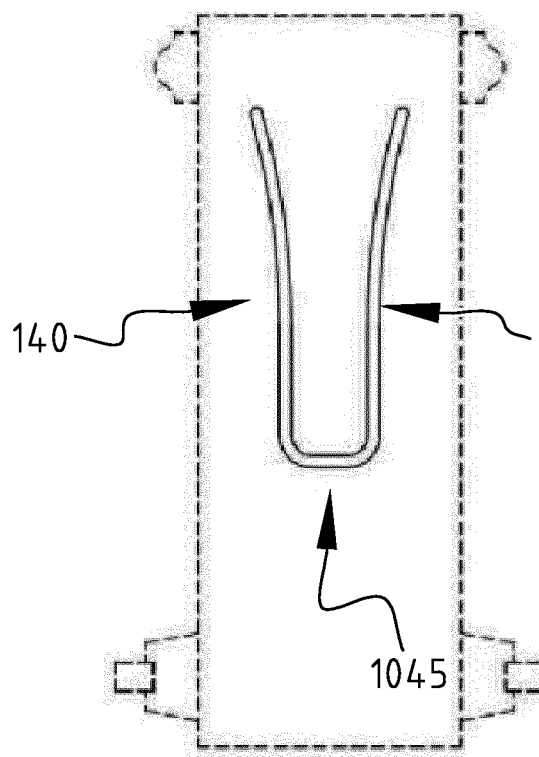
FIGS. 23A-23V illustrate yet other exemplary embodiments of an absorbent core according to the invention.
Figure 23B:
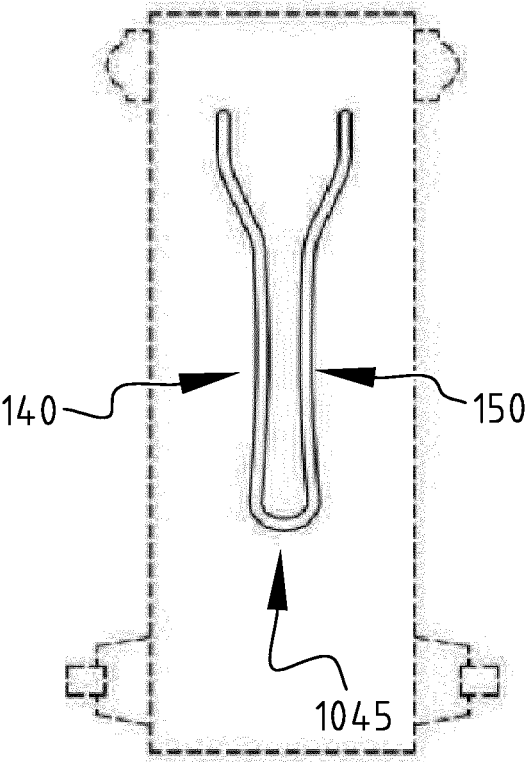
Figure 23C:
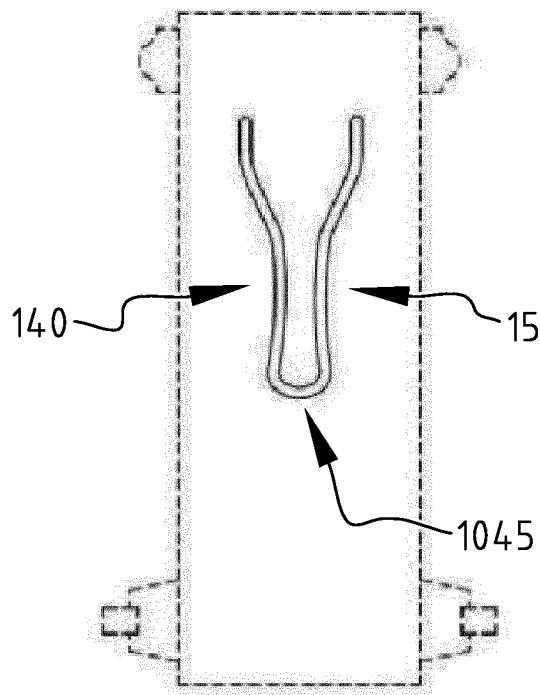
Figure 23D:
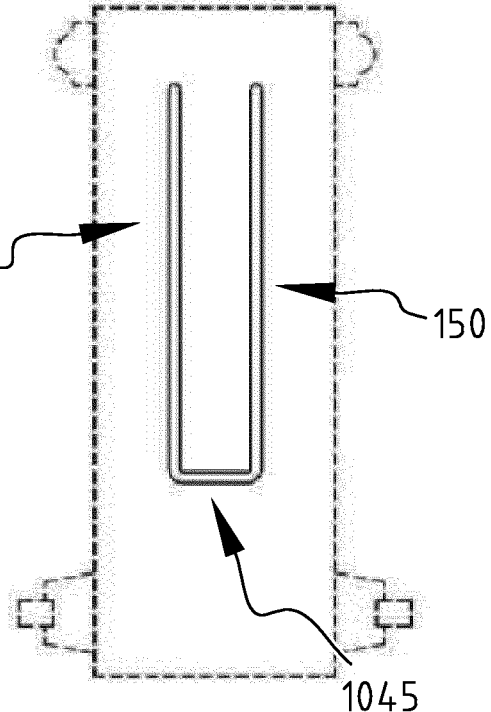
Figure 23E:
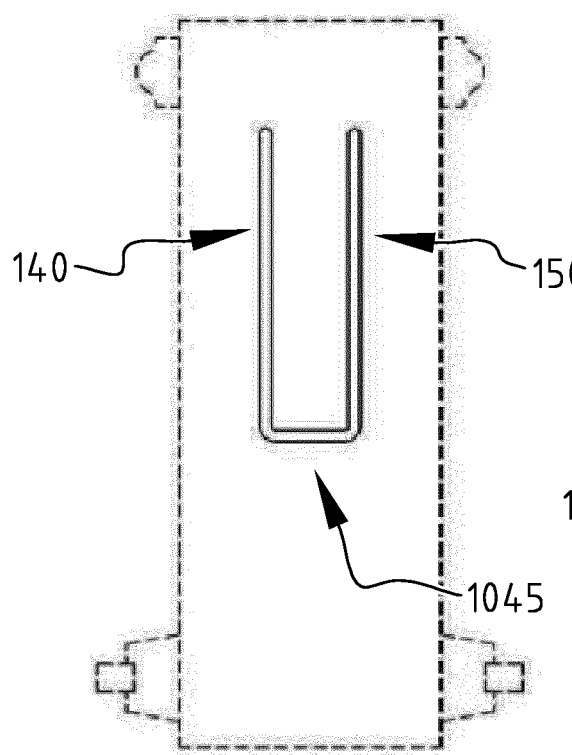
Figure 23F:
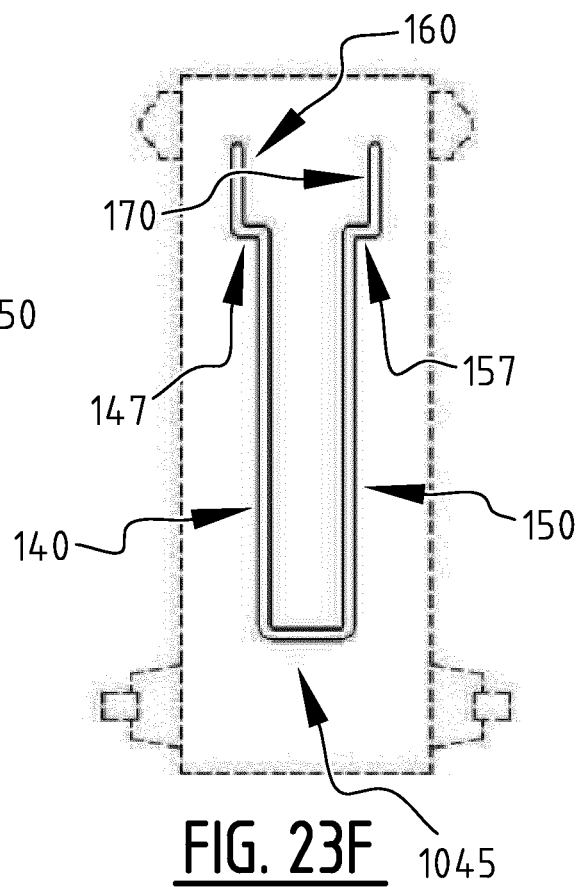
Figure 23G:
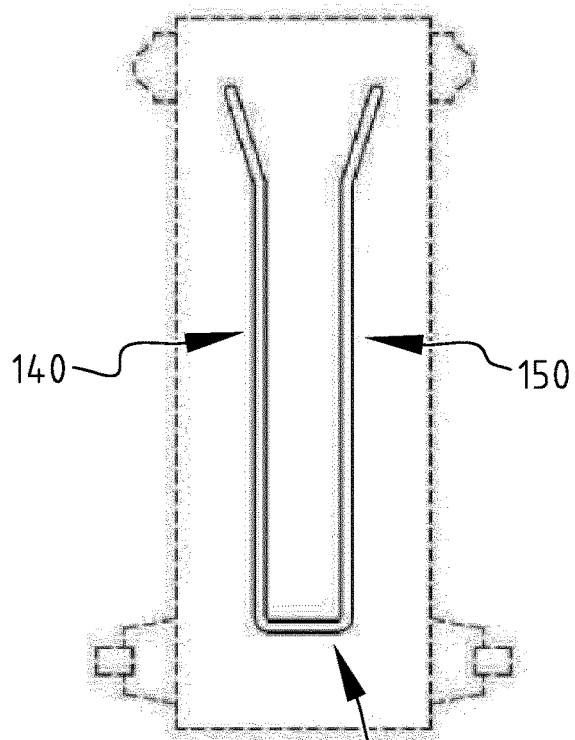
Figure 23H:
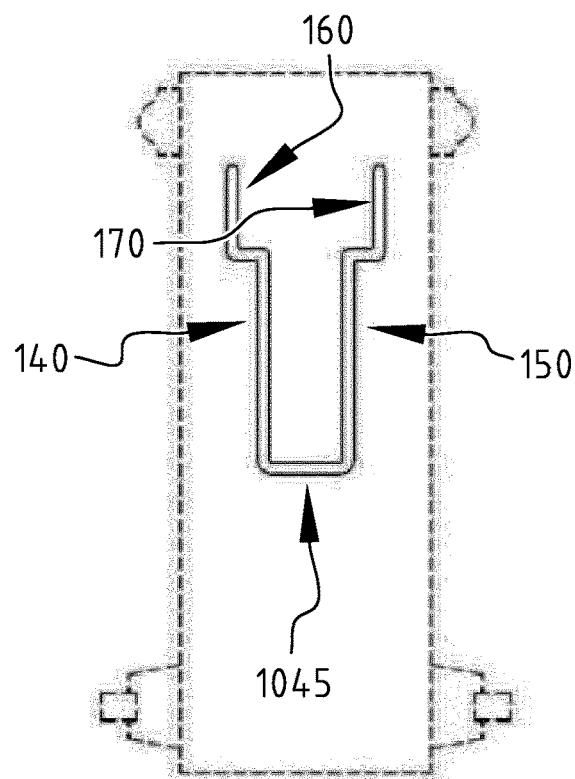
Figure 23I:
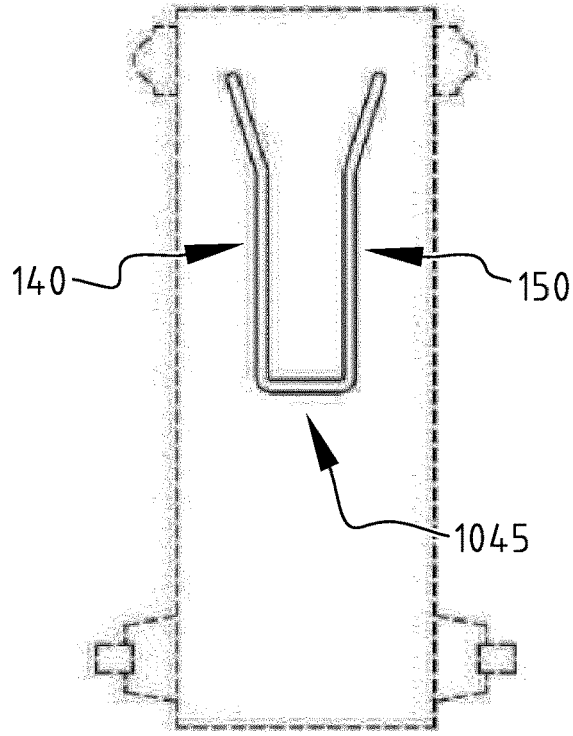
Figure 23J:
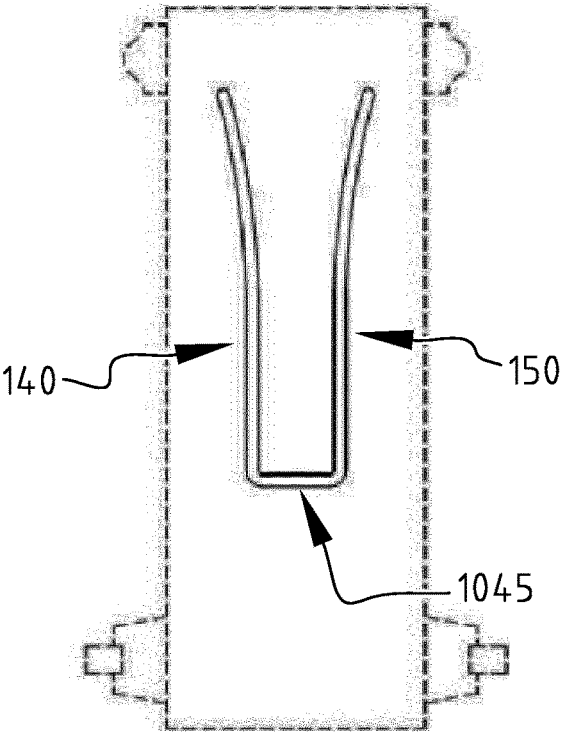
Figure 23K:
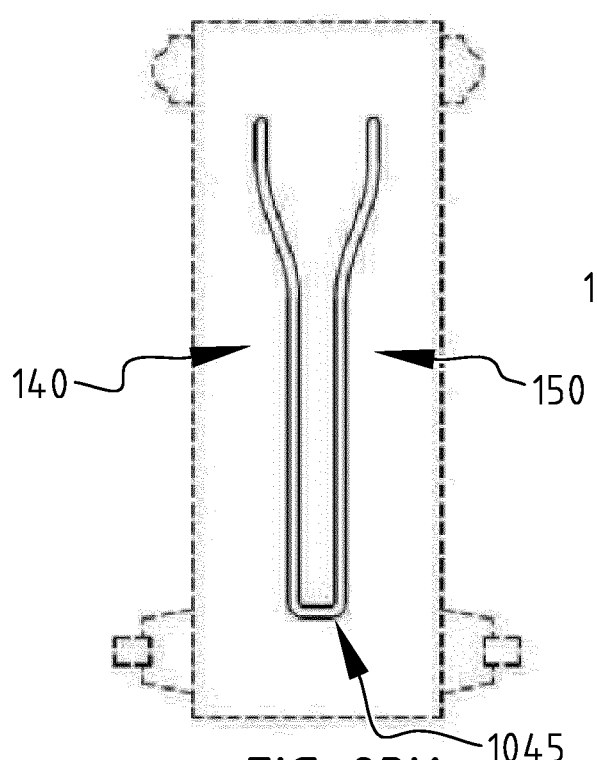
Figure 23L:
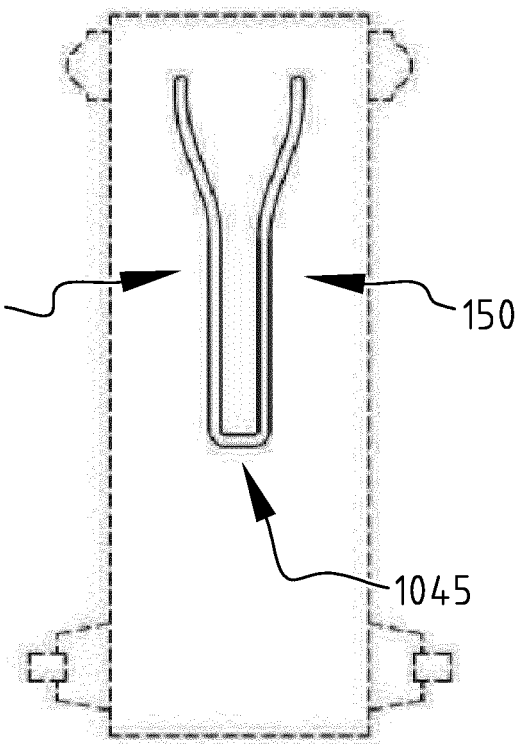
Figure 23M:
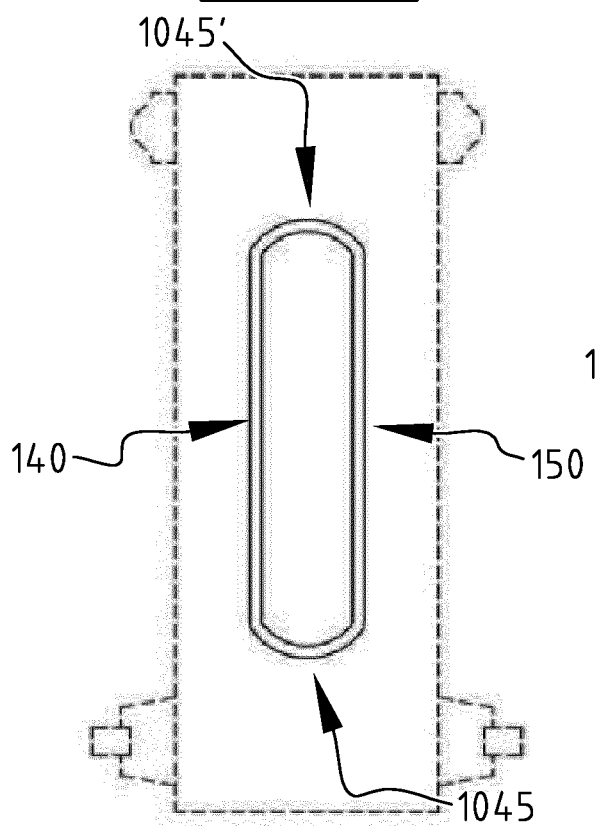
Figure 23N:
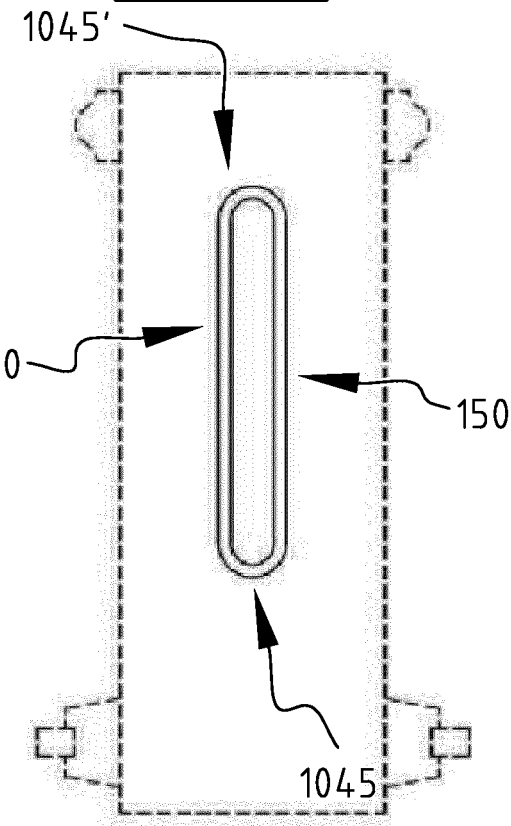
Figure 23O:
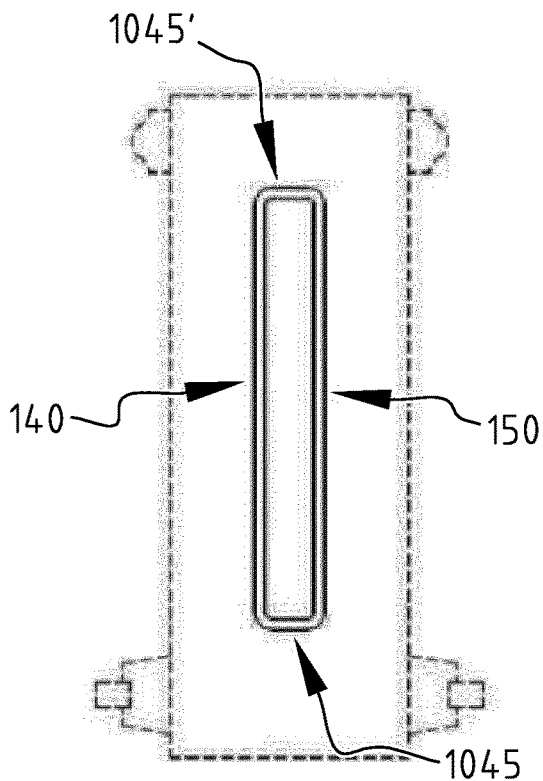
Figure 23P:
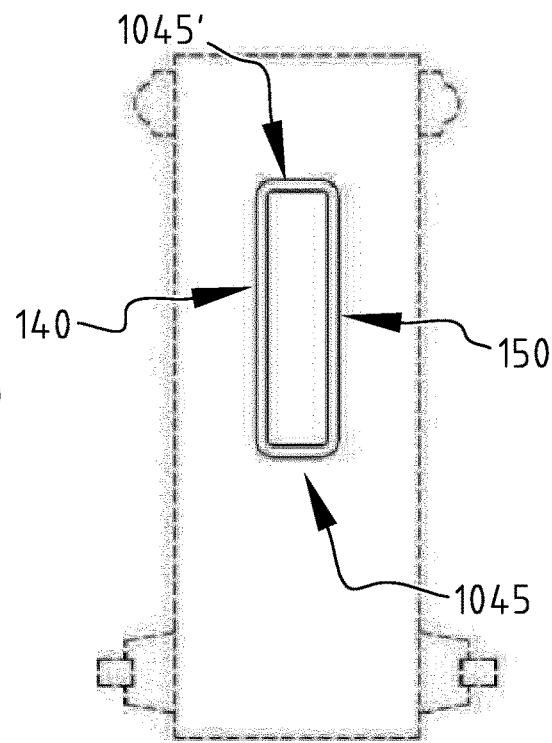
Figure 23Q:
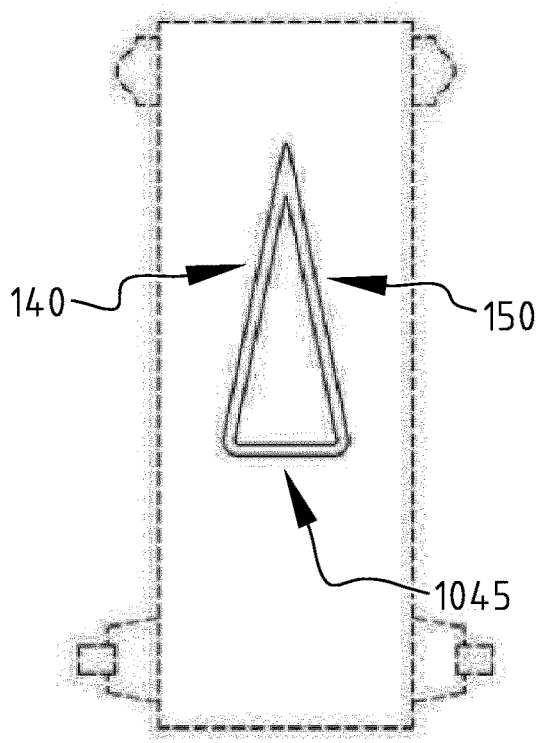
Figure 23R:
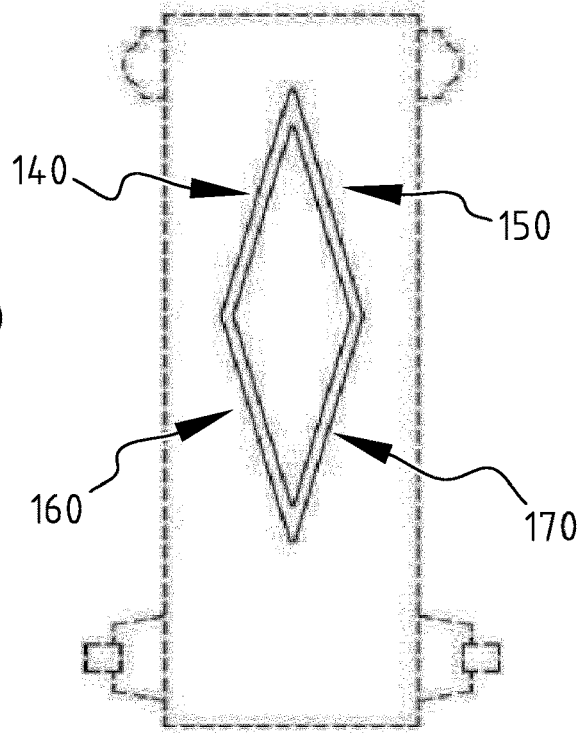
Figures 23S, 23T:
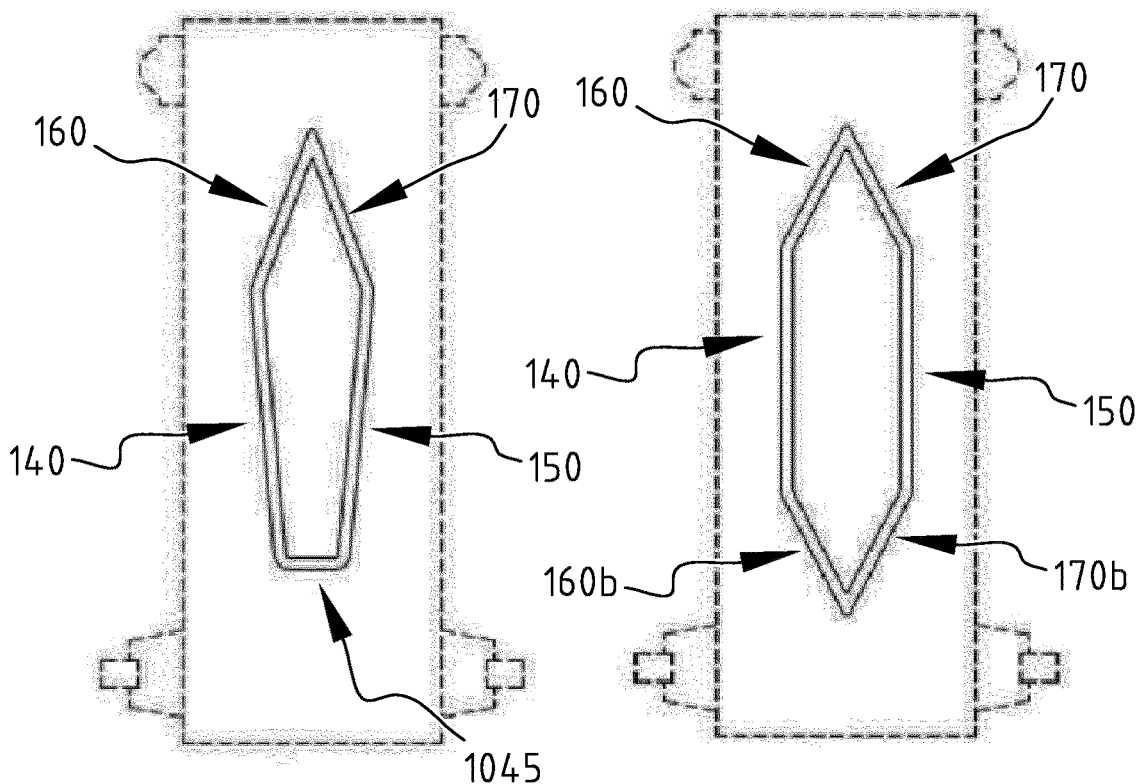
Figures 23U, 23V:
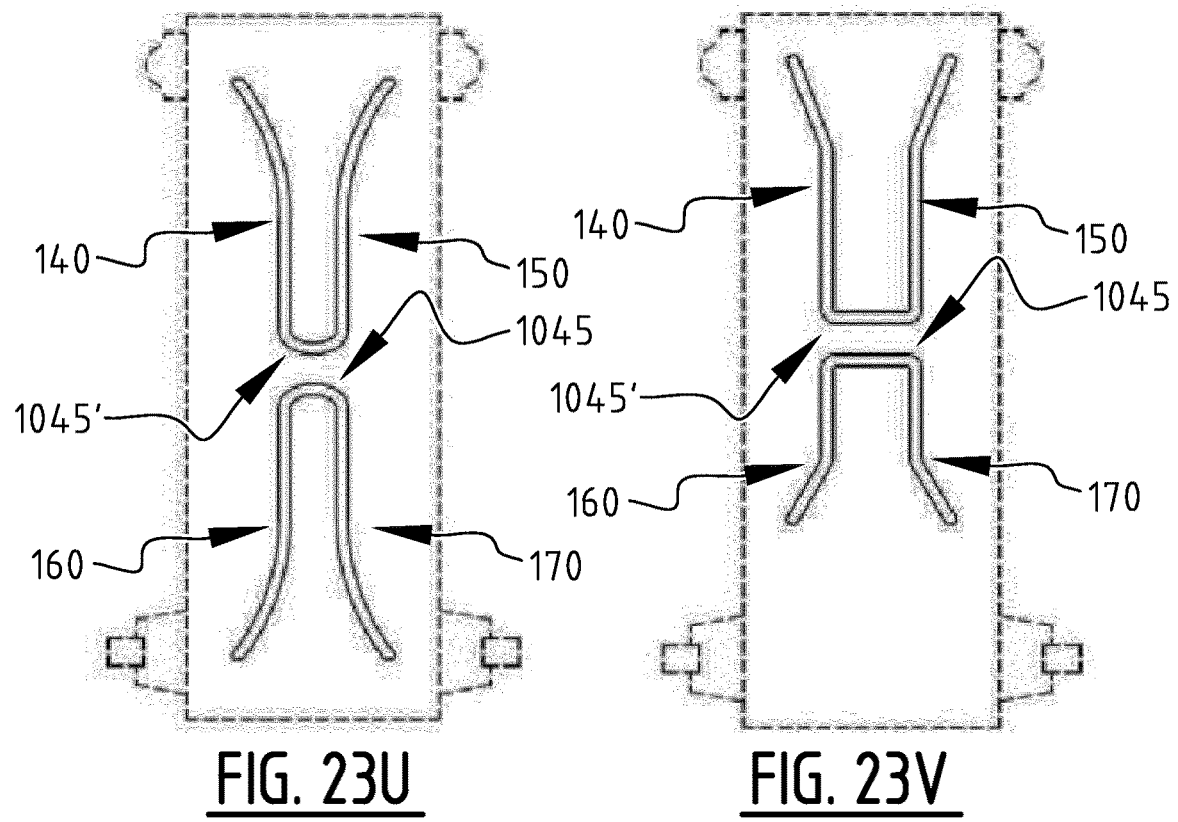

The connecting between the longitudinal channels need not be done with a transversal channel, but may also be achieved by shaping the longitudinal channels in a specific way. For example, in the embodiment of FIG. 23R, the four longitudinal attachment zones 140, 150, 160, 170 collectively form a diamond shape. Likewise, in the embodiment of FIG. 23T, six longitudinal attachment zones 140, 150, 160*a*, 170*a*, 160*b*, 170*c* are so connected as to form an elongated hexagon shape. Combinations of these two methods of connecting channels are also possible. In the embodiment of FIG. 23Q, the longitudinal attachment zones 140, 150 are connected at their front ends by a transversal attachment zone 1045 and converge to meet at their back ends. In the embodiment of FIG. 23S, longitudinal attachment zones 140 and 150 are connected by a transversal attachment zone 1045, while longitudinal attachment zones 160, 170, which are connected to zones 140, 150 respectively, converge at their back ends. The skilled person will be capable of envisaging other combinations and variations of the depicted embodiments.

The advantageous effect may be achieved even in cases wherein the longitudinal attachment zones are not directly connected, but merely approach each other in certain places. For example, in the embodiments of FIG. 20Z, 21J, 21T, the front ends of longitudinal attachment zones 140, 150 are connected by transversal attachment zone 1045, and the back ends of longitudinal attachment zones 160, 170 are shaped such that they approach one another. In other embodiments, such as the ones of FIG. 21U, 21Y, 22A-22C, the longitudinal attachment zones 140, 150, 160, 170 approach one another either at the ends or along their path, and this may, depending on the specific configuration, be sufficient to allow for liquid to go from one channel to another.

FIGS. 25A-25Z and FIGS. 26A-26T illustrate embodiments in which the dimensions of the longitudinal attachments zones 140, 150, 160, 170, 180 in the longitudinal direction have been reduced as compared to previously illustrated embodiments. Regarding the illustrated configurations of the shorter longitudinal attachments zones 140, 150, 160, 170, central attachments zones 180, 180*a*, 180*b*, 180*c* and transversal attachment zones 1045, 1045*a*, 1045*b*, 1045*c* as illustrated in FIGS. 25A-25Z and FIGS. 26A-26T, it is clear to the skilled person that the above described technical considerations and advantages in view of longer longitudinal attachments zones 140, 150, 160, 170, central attachments zones 180, 180*a*, 180*b*, 180*c* and transversal attachment zones 1045, 1045*a*, 1045*b*, 1045*c* as illustrated in the previous figures apply in a similar way, mutatis mutandis.

Figure 24A:
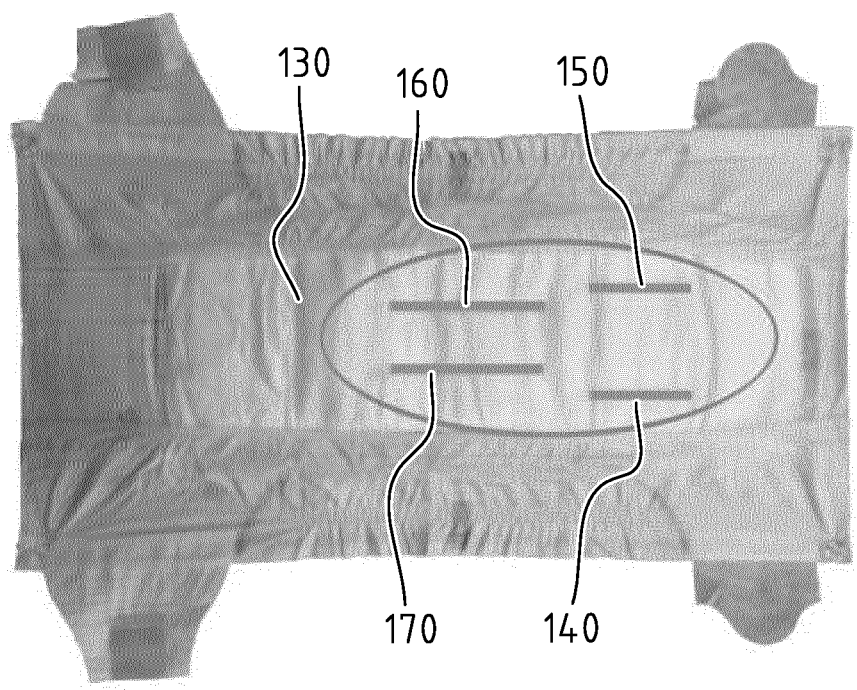
FIGS. 24A-24C are photographs of an exemplary embodiment of a diaper in a dry and wetted state.
Figure 24B:
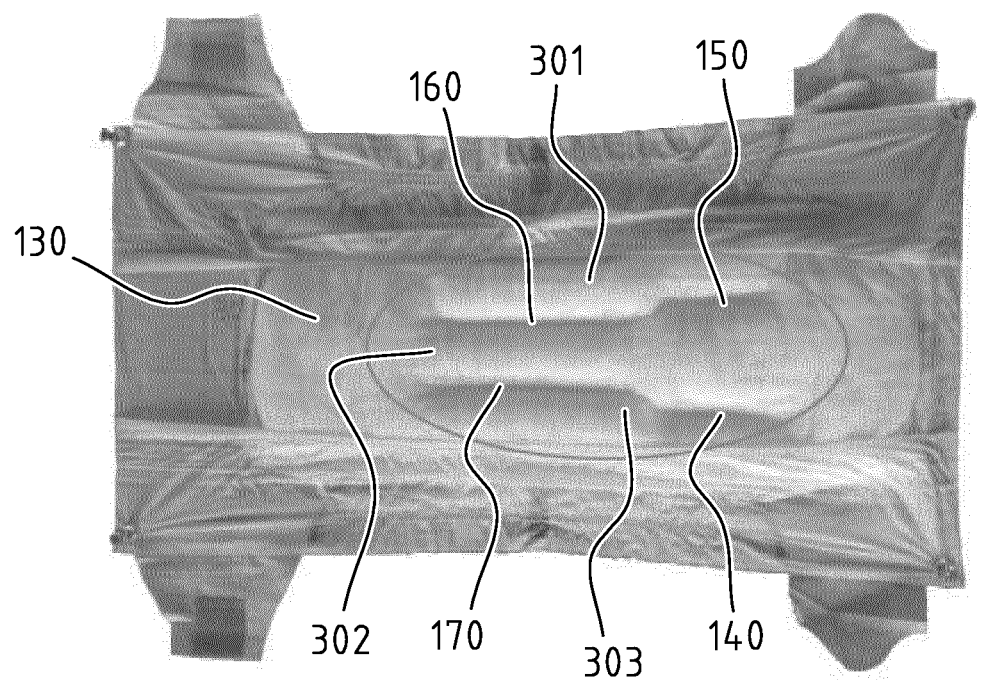
Figure 24C:
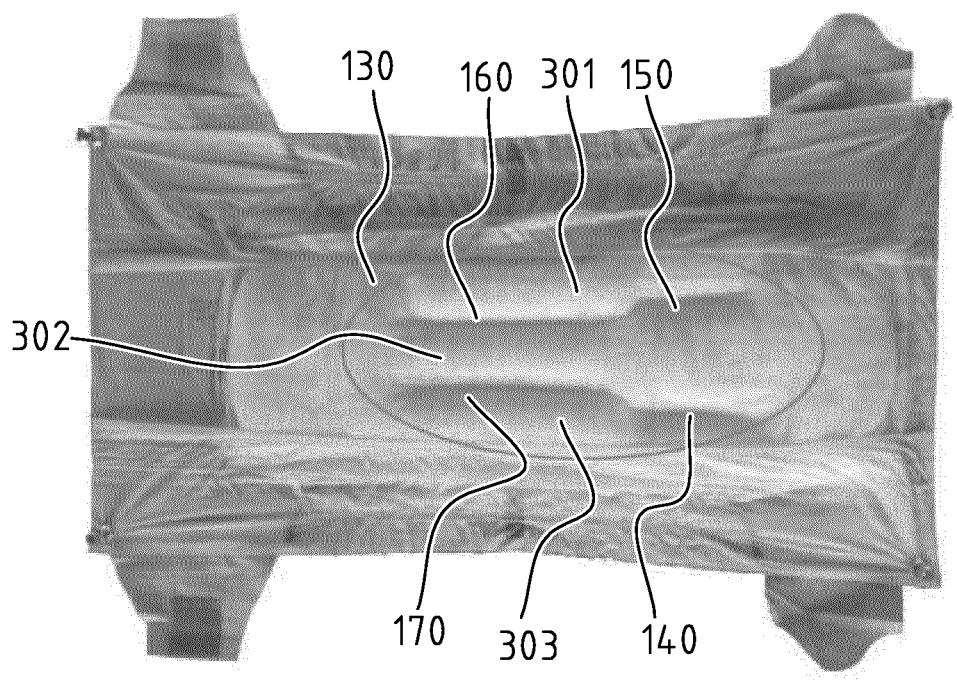
Figure 25A:
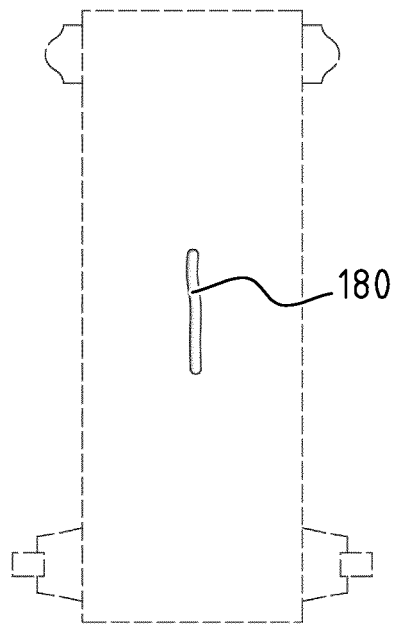
FIGS. 25A-25Z illustrate yet other exemplary embodiments of an absorbent core according to the invention.
Figure 25B:
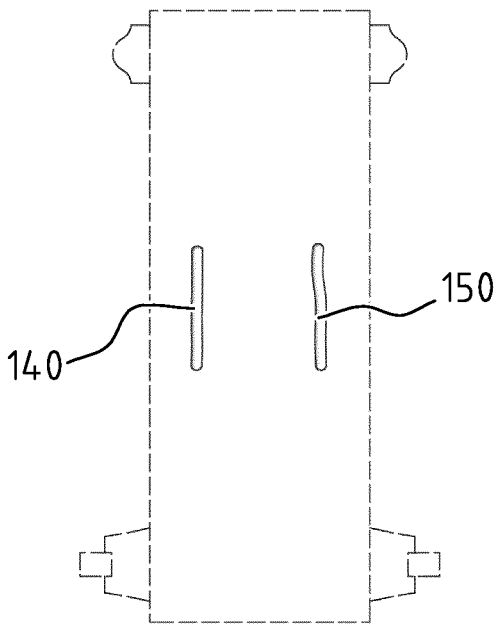
Figure 25C:
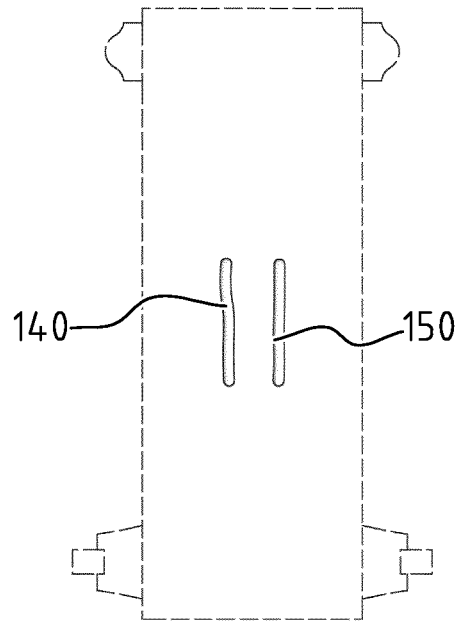
Figure 25D:
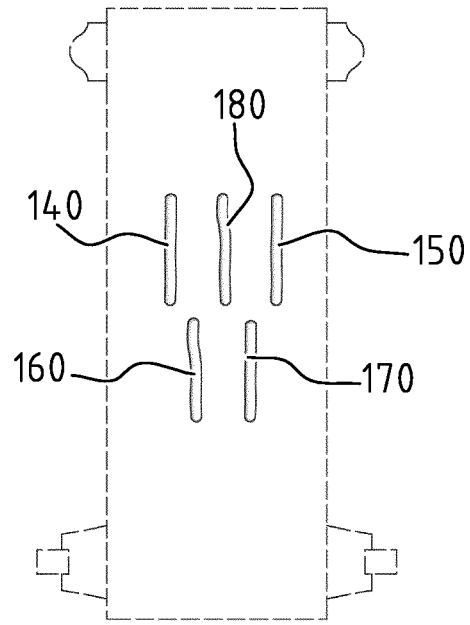
Figure 25E:
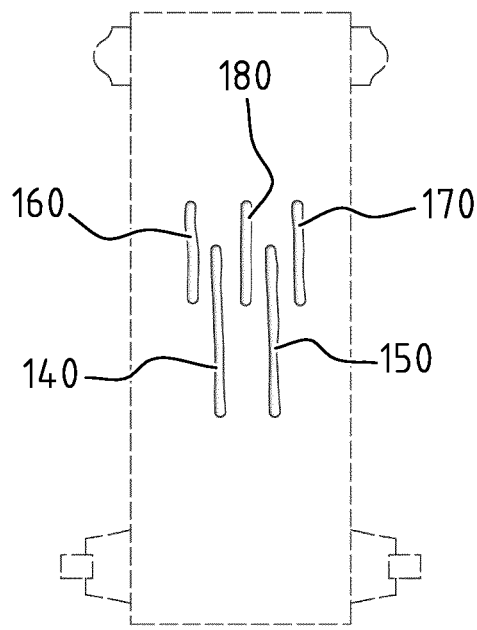
Figure 25F:
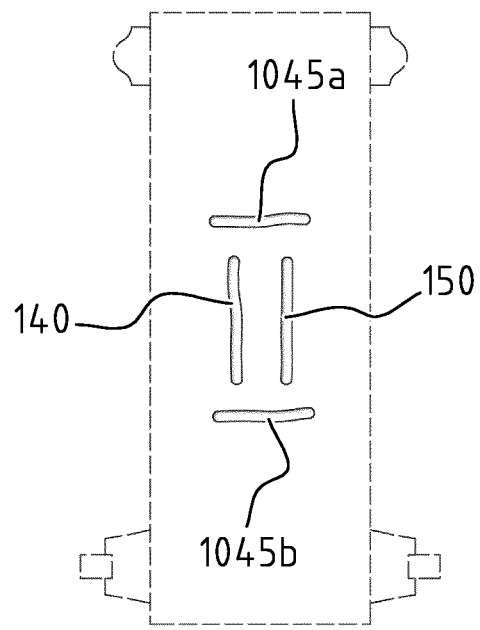
Figure 25G:
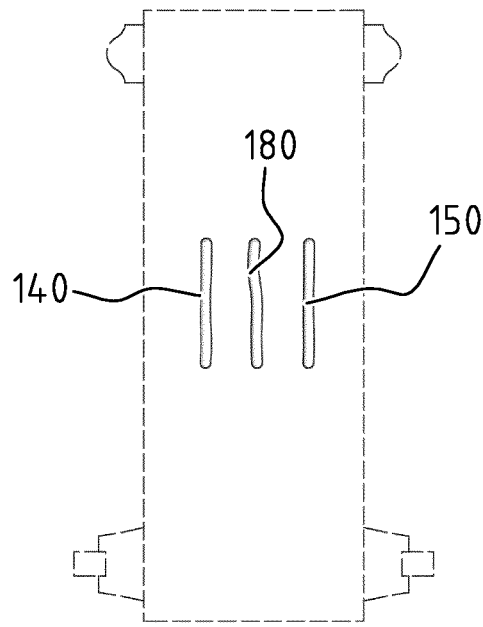
Figure 25H:
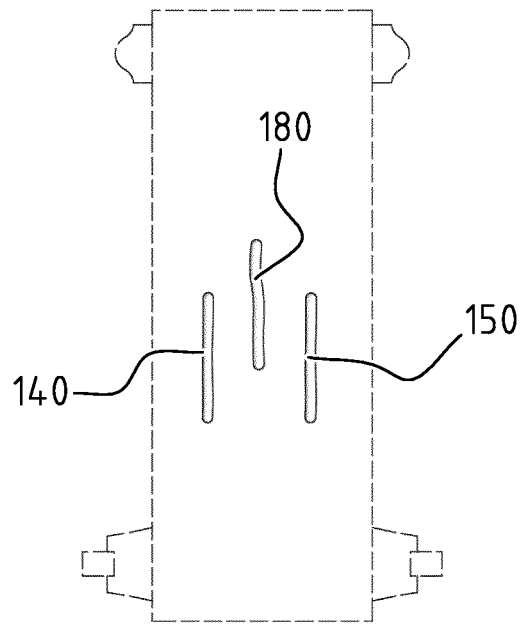
Figure 25I:
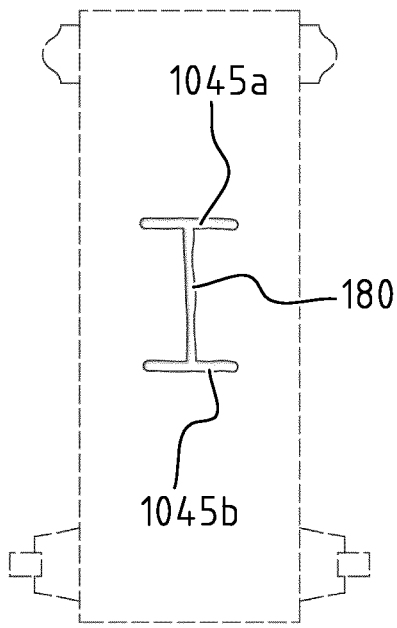
Figure 25J:
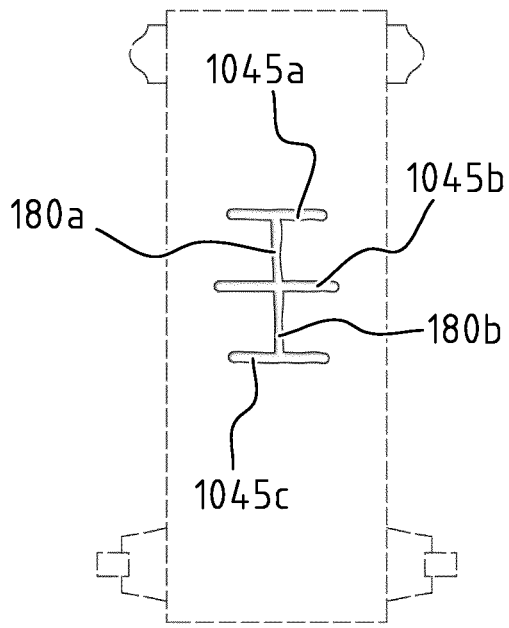
Figure 25K:
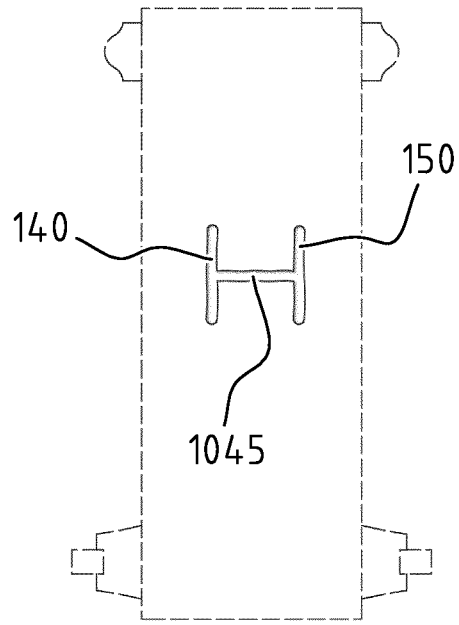
Figure 25L:
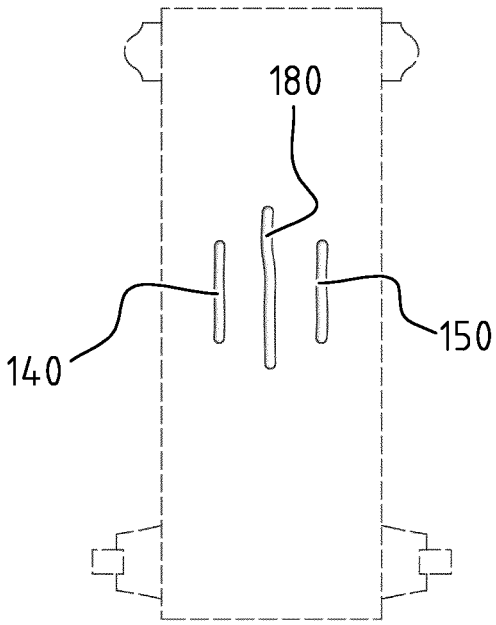
Figure 25M:
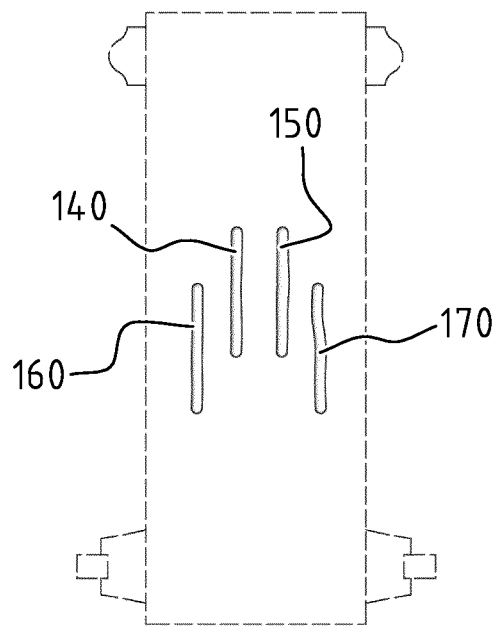
Figure 25N:
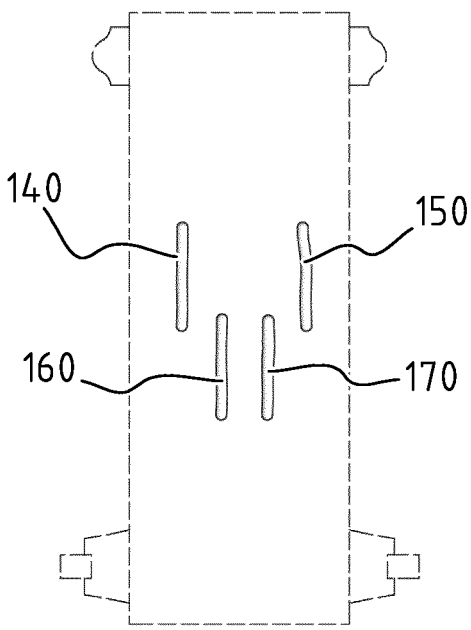
Figure 25O:
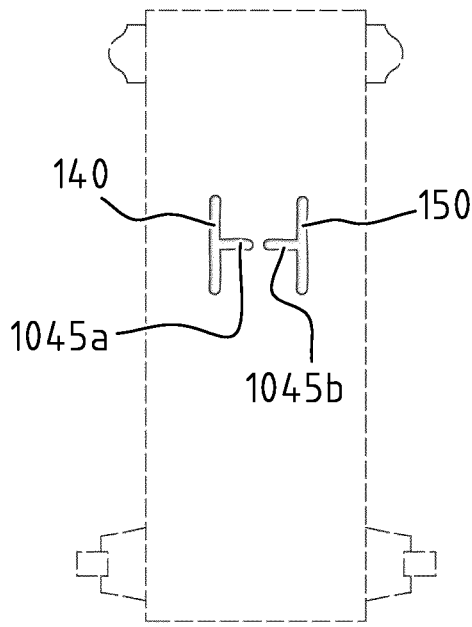
Figure 25P:
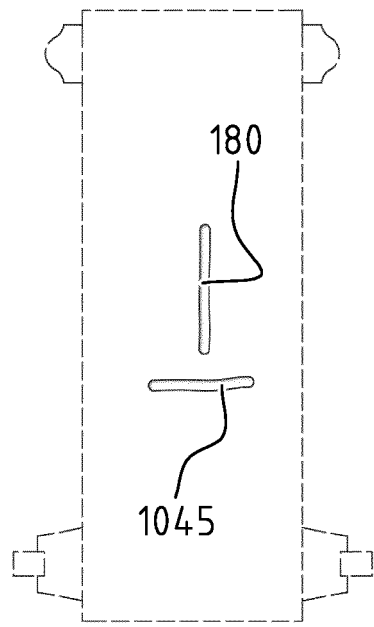
Figure 25Q:
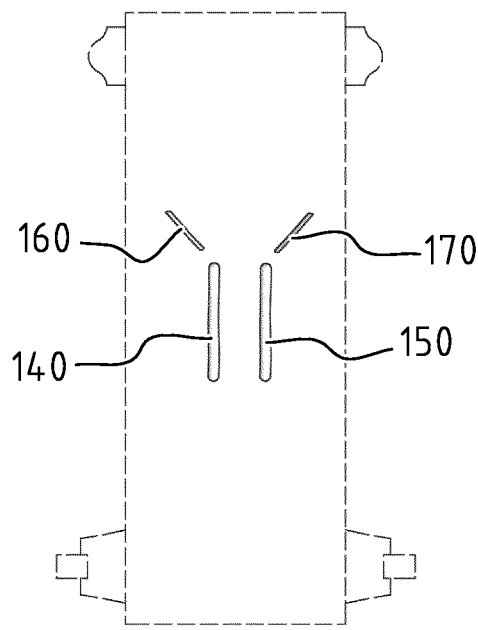
Figure 25R:
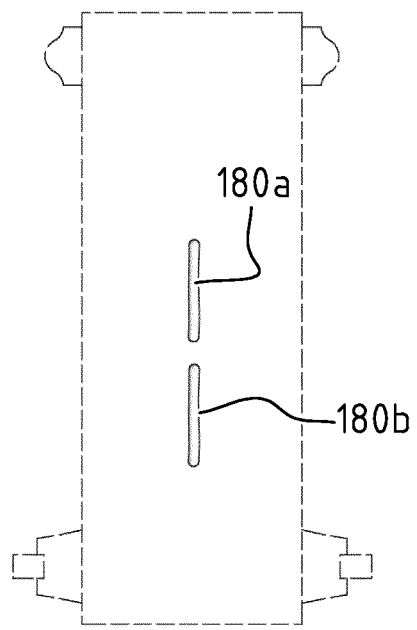
Figure 25S:
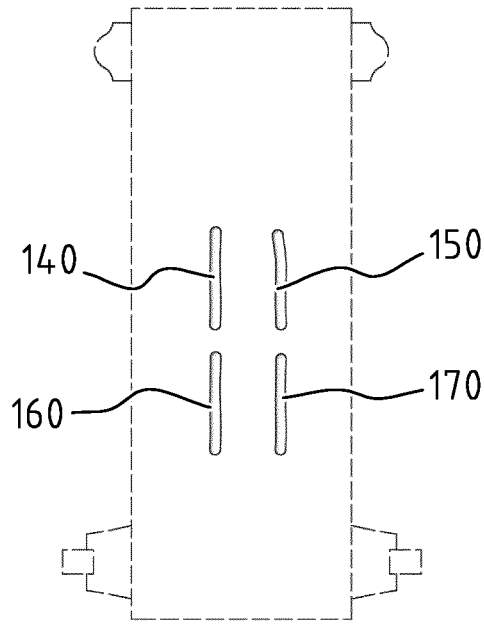
Figure 25T:
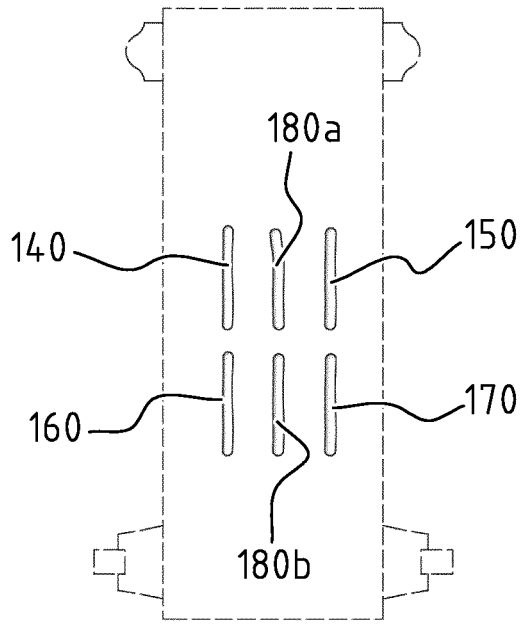
Figure 25U:
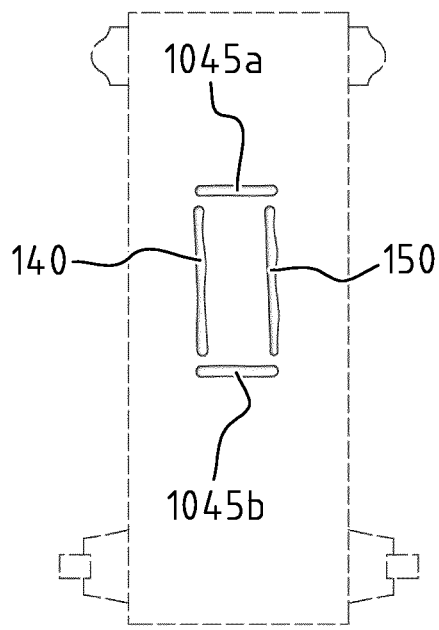
Figure 25V:
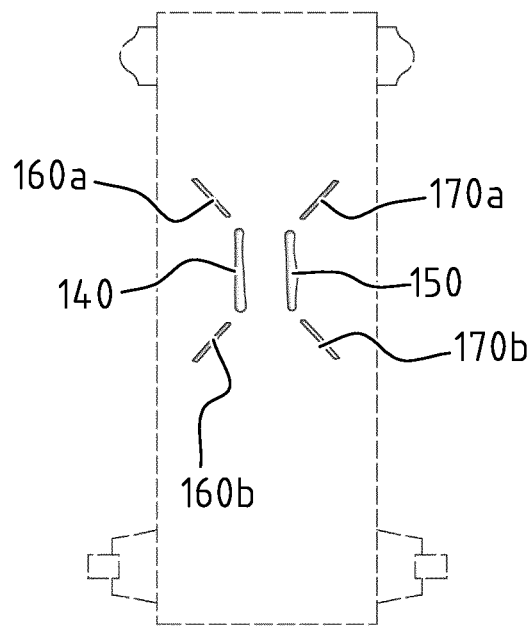
Figure 25W:
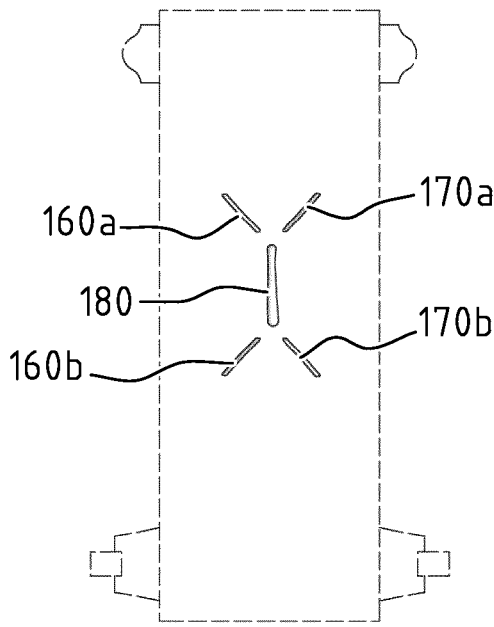
Figure 25X:
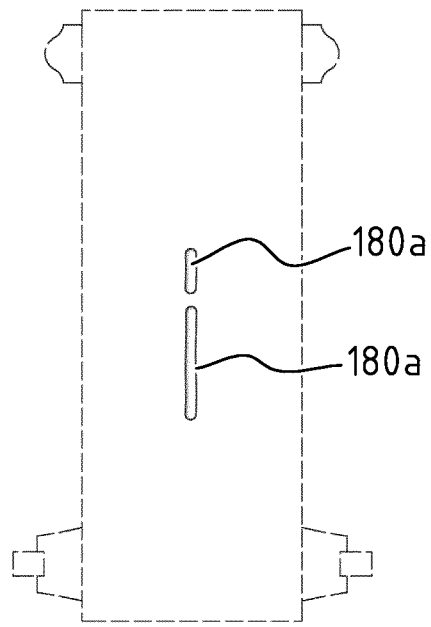
Figure 25Y:
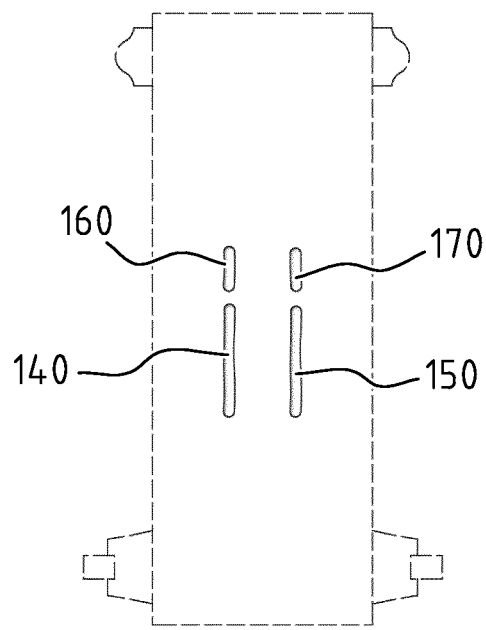
Figure 25Z:
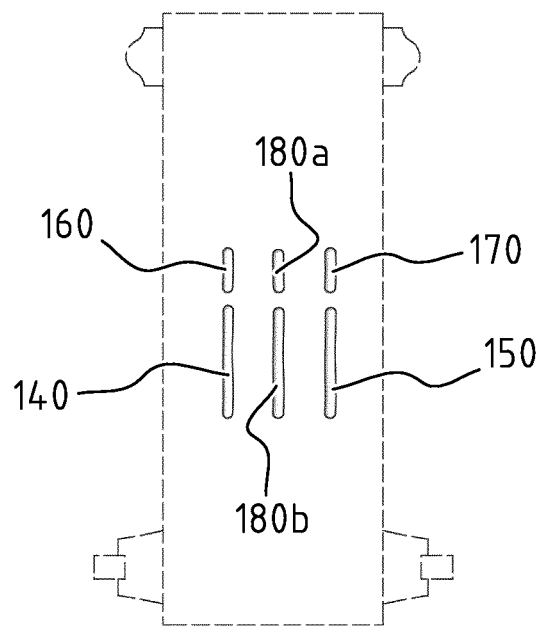
Figure 26A:
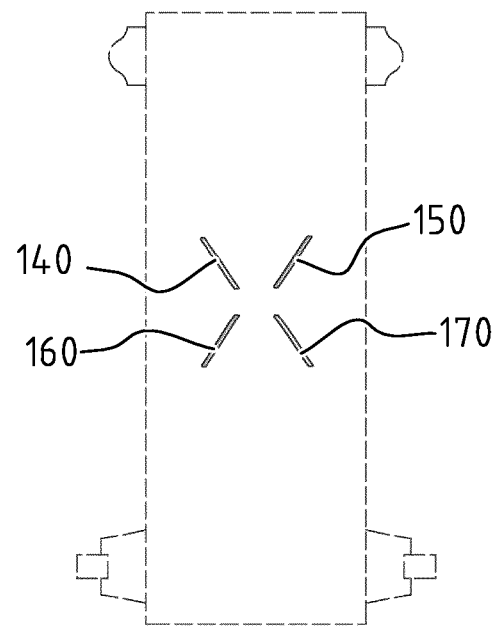
FIGS. 26A-26T illustrate yet other exemplary embodiments of an absorbent core according to the invention.
Figure 26B:
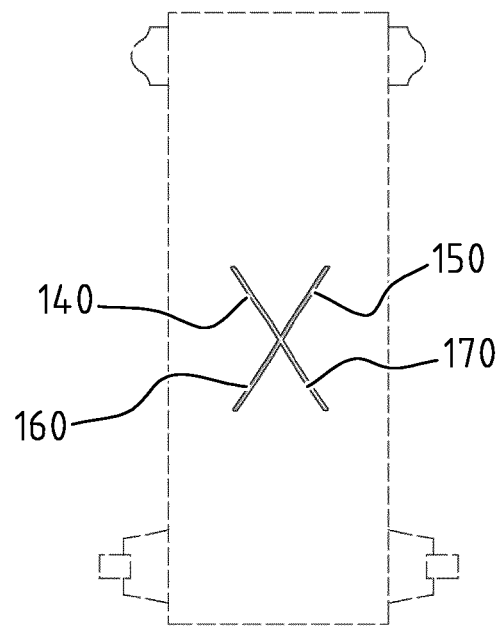
Figure 26C:
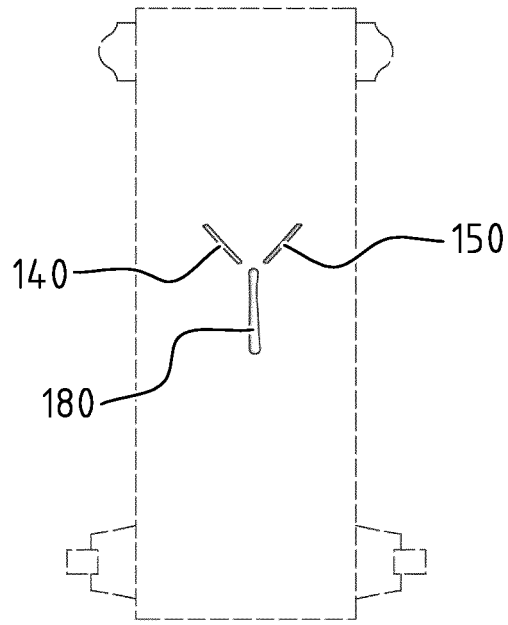
Figure 26D:
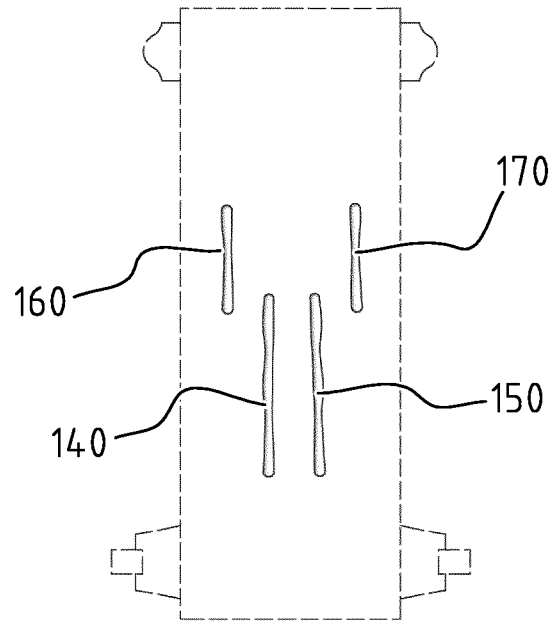
Figure 26E:
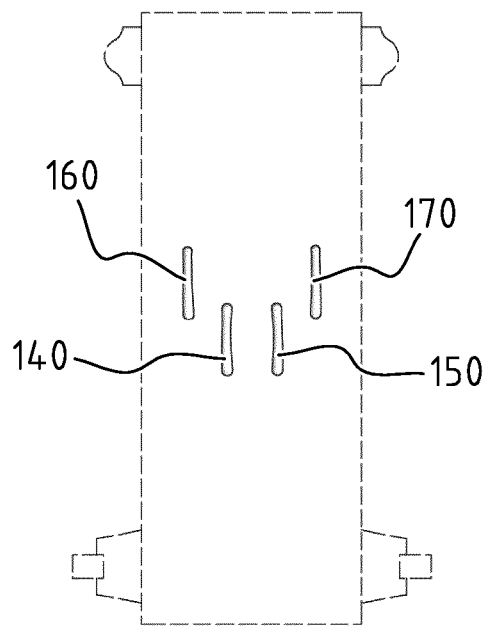
Figure 26F:
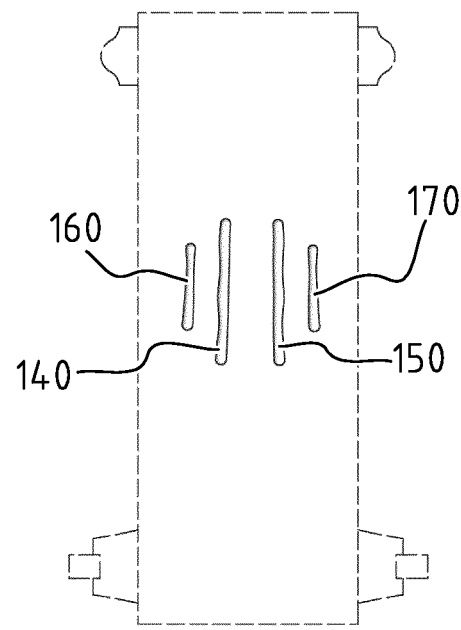
Figure 26G:
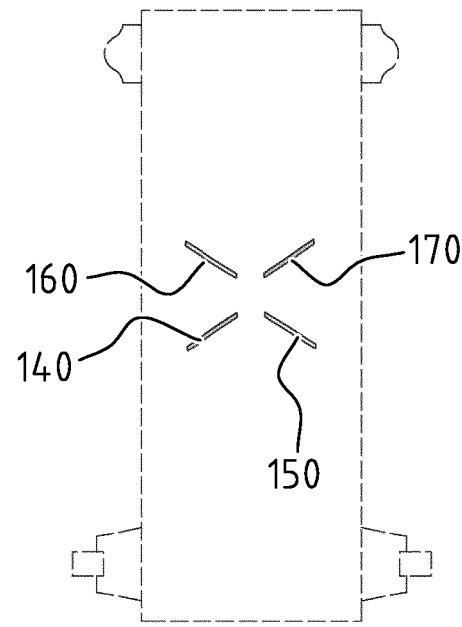
Figure 26H:
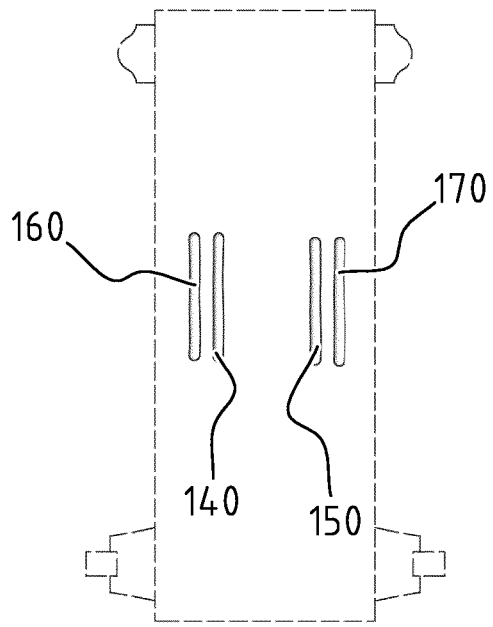
Figure 26I:
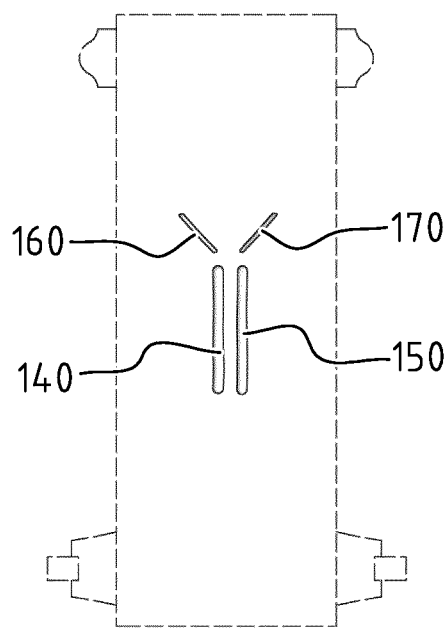
Figure 26J:
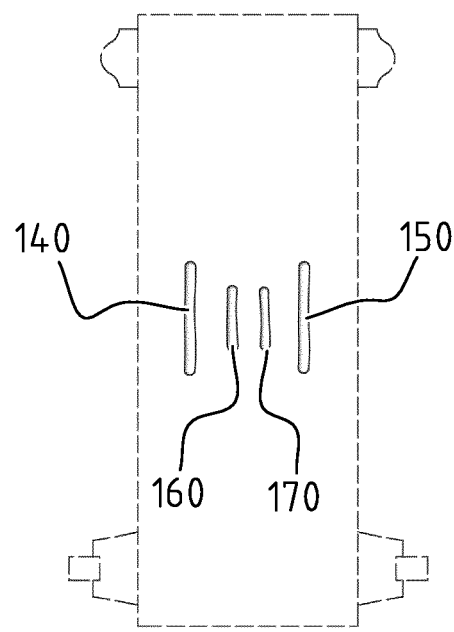
Figure 26K:
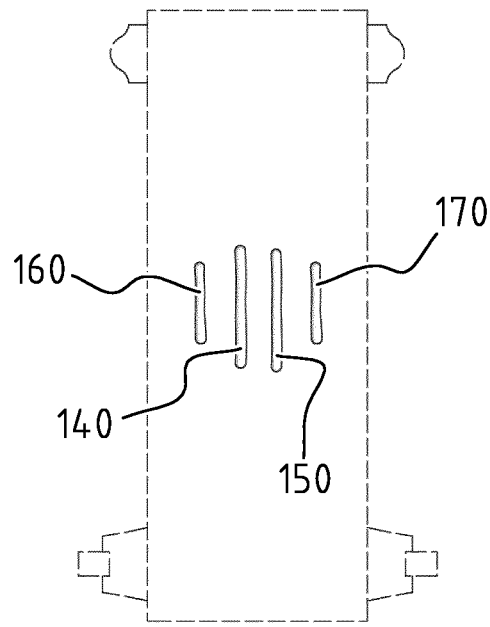
Figure 26L:
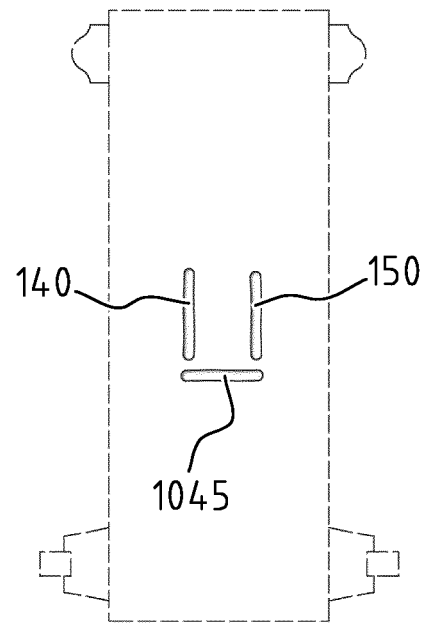
Figure 26M:
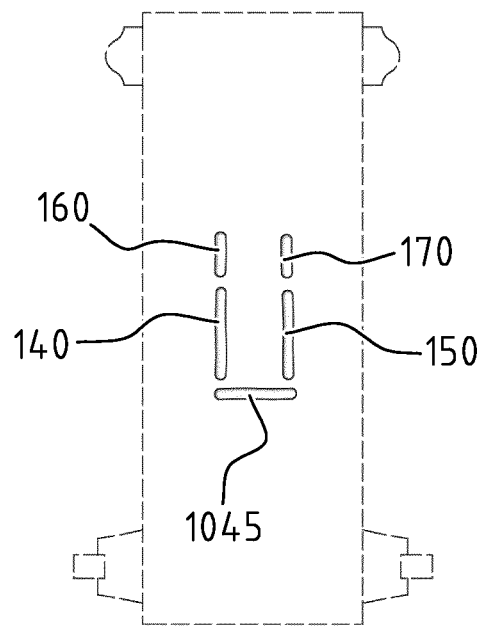
Figure 26N:
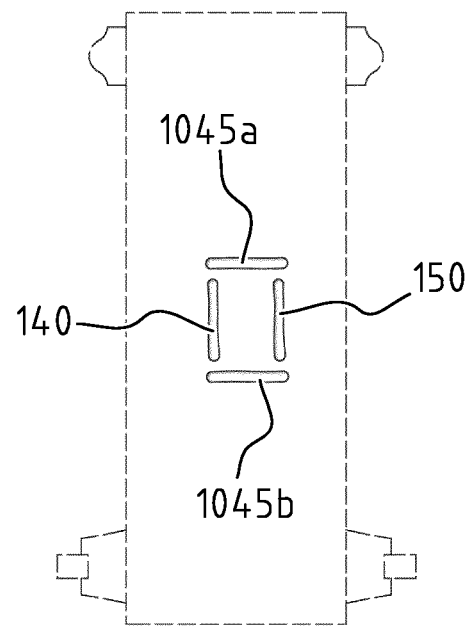
Figure 26O:
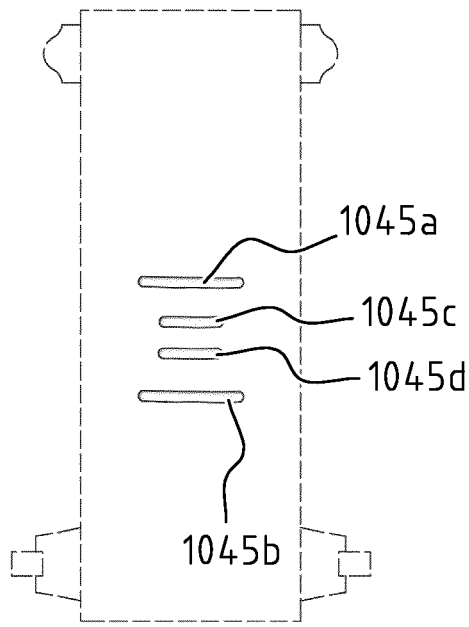
Figure 26P:
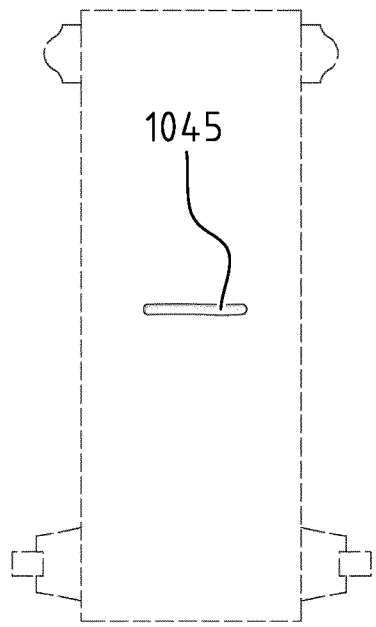
Figure 26Q:
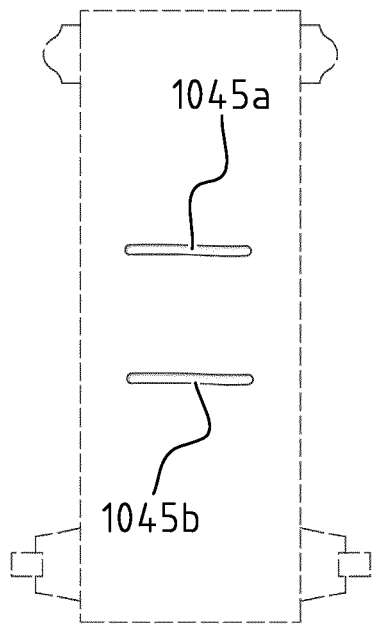
Figure 26R:
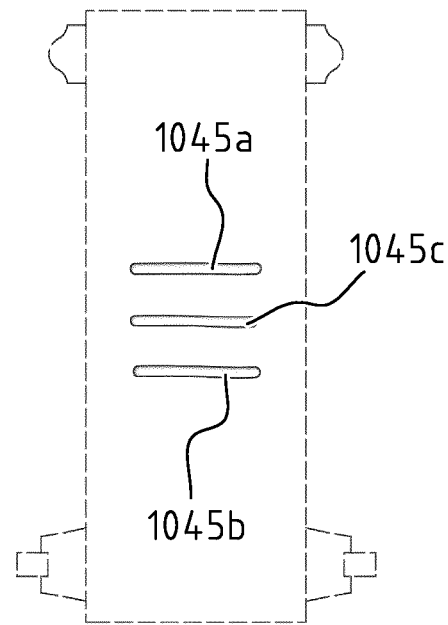
Figure 26S:
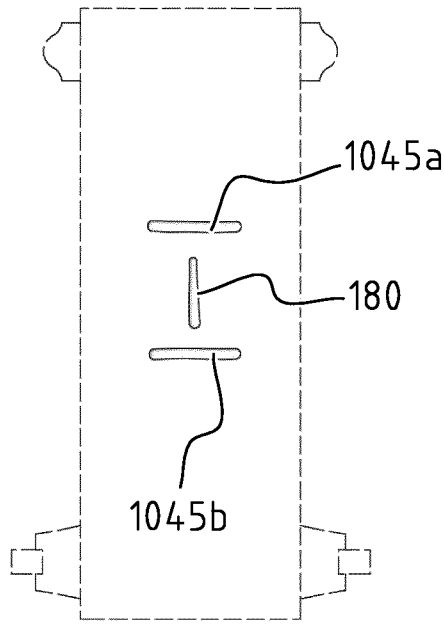
Figure 26T:
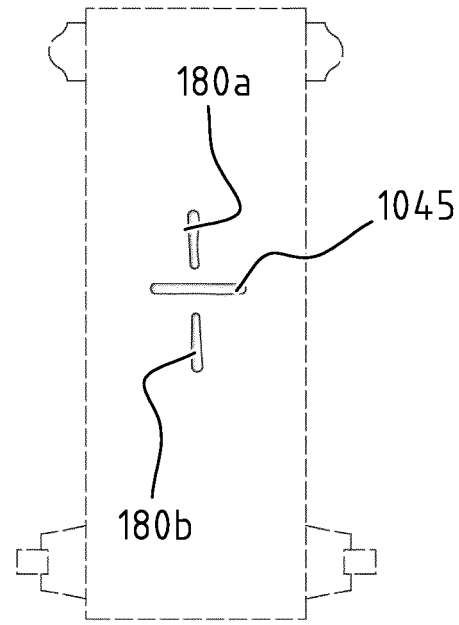

In addition to the perspective view as shown in FIG. 12, FIGS. 24A-C are photographs representing an absorbent article comprising an exemplary embodiment of an absorbent core of the invention. FIG. 24A illustrates the absorbent article when the absorbent core is in a dry state, whereas FIGS. 24B and 24C illustrate the absorbent article when the absorbent core is in a wetted state. In FIG. 24A attachments zones 140, 150, 160 and 170 wherein substantially no absorbent material is present, can be distinguished. However, in the illustrated photograph 24A the attachment zones 140, 150, 160 and 170 have been slightly darkened in order to better illustrate the position thereof, since due to quality restraints of the photograph 24A a part of this visual information has been lost. FIGS. 24B and 24C are photographs of the absorbent article in a wetted state, wherein tubes 301, 302, 303 have formed, which leads to the attachment zones 140, 150, 160 and 170 becoming more visible as channels. Thanks to the attachment zones and associated channels 140, 150, 160 and 170 the liquid is evenly spread, resulting in the formation of tubes 301, 302, 303 which provide a tub shape to the absorbent core 130. Such a tub shape adapts perfectly to the body and can be seen, at least partially, in FIG. 24C where the absorbent article is not attached to a bottom surface at the corners of the absorbent article, which is the case in FIGS. 24A and 24B. Further, compared to prior art solutions, the liquid is kept in an improved manner absorbed in the absorbent core 130, and the risk on leakage is reduced. Also, because of the creation of the channels 140, 150, 160, 170, the liquid is absorbed faster.

Whilst the principles of the invention have been set out above in connection with specific embodiments, it is to be understood that this description is merely made by way of example and not as a limitation of the scope of protection which is determined by the appended claims.

The invention claimed is:
1. An absorbent article comprising
a liquid pervious topsheet,
a liquid impervious backsheet, and
an absorbent core comprising an absorbent material between a top core wrap sheet and a back core wrap sheet,
said absorbent core being positioned in between said topsheet and said backsheet,
wherein the absorbent core is provided with at least one attachment zone between the top core wrap sheet and the back core wrap sheet,
wherein a first binder is arranged on one of the top core wrap sheet and the back core wrap sheet in a first area between the top core wrap sheet and the back core wrap sheet at a specified distance from the at least one attachment zone, wherein the first area comprises a plurality of substantially parallel, longitudinal first stripes; and a second binder is arranged on the other of the top core wrap sheet and the back core wrap sheet in a second area between the top core wrap sheet and the back core wrap sheet, wherein the first area is substantially complementary to the second area.

2. The absorbent article of claim 1, wherein the first binder is different from the second binder.

3. The absorbent article of claim 1, wherein the attachment between the top core wrap sheet and the back core wrap sheet in the at least one attachment zone is a permanent attachment; and wherein the absorbent core is configured such that, in a wetted state of the absorbent material, the absorbent material extends over the at least one attachment zone.

4. The absorbent article of claim 1, wherein a position and/or shape of one or more of the at least one attachment zone is indicated by a distinguishable color and/or colored pattern.

5. The absorbent article of claim 4, wherein the distinguishable color and/or colored pattern is provided on at least one of the top sheet, the top core wrap sheet, the backsheet and the back core wrap sheet or wherein the position and/or shape of one or more of the of the at least one attachment zone is indicated by a printed ink layer.

6. The absorbent article of claim 1, wherein, outside of the at least one attachment zone the absorbent core has a maximum thickness; wherein at least one attachment zone extends through at least 90% of the maximum thickness of the absorbent core, more preferably through 100% of the thickness of the absorbent core, such that in the at least one attachment zone substantially no absorbent material is present between the top core wrap sheet and the back core wrap sheet.

7. The absorbent article of claim 1, wherein an attachment between the top core wrap sheet and the back core wrap sheet in the at least one attachment zone is any one of the following or a combination thereof: pressure bonding, thermal bonding, sonic bonding, chemical bonding, adhesive.

8. The absorbent article of claim 1, wherein the absorbent material comprises cellulosic fluff pulp.

9. The absorbent article of claim 1, wherein the second area includes the at least one attachment zone.

10. The absorbent article of claim 1, wherein the first binder is the same as the second binder, and a transition zone is distinguishable between the first area and the second area.

11. The absorbent article of claim 1, wherein the first binder is arranged as a layer having a first thickness and the second binder is arranged as a layer having a second thickness which is different from the first thickness, preferably higher than the first thickness.

12. The absorbent article of claim 1, wherein in said at least one attachment zone said top core wrap sheet is attached to said back core wrap sheet through a semi-permanent attachment configured to release after having been in contact with liquid.

13. The absorbent article of claim 1, wherein the absorbent material is substantially fluffless.

14. The absorbent article of claim 1, wherein substantially no absorbent material is present in the at least one attachment zone.

15. The absorbent article of claim 1, wherein the at least one attachment zone has a first width and a first length, and wherein the second area comprises a plurality of substantially parallel, longitudinal second stripes having a second width and a second length, wherein the second width is larger than the first width and the second length is larger than the first length.

* * * * *